(12) United States Patent
Nathanson et al.

(10) Patent No.: US 11,377,451 B2
(45) Date of Patent: Jul. 5, 2022

(54) COMPOSITIONS AND METHODS FOR TREATING CANCER

(71) Applicant: The Regents of the University of California, Oakland, CA (US)

(72) Inventors: David A. Nathanson, Los Angeles, CA (US); Michael E. Jung, Los Angeles, CA (US); Jonathan Tsang, Los Angeles, CA (US); Lorenz Urner, Los Angeles, CA (US); Peter M. Clark, Los Angeles, CA (US); Timothy F. Cloughesy, Calabasas, CA (US); Gyudong Kim, Seoul (KR)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/475,144

(22) Filed: Sep. 14, 2021

(65) Prior Publication Data

US 2022/0064177 A1    Mar. 3, 2022

Related U.S. Application Data

(63) Continuation of application No. PCT/US2020/022743, filed on Mar. 13, 2020.

(60) Provisional application No. 62/904,241, filed on Sep. 23, 2019, provisional application No. 62/819,322, filed on Mar. 15, 2019.

(51) Int. Cl.
*C07D 491/14*    (2006.01)
*C07D 491/056*    (2006.01)
*C07D 239/95*    (2006.01)
*C07D 239/94*    (2006.01)
*C07D 405/04*    (2006.01)

(52) U.S. Cl.
CPC ....... *C07D 491/056* (2013.01); *C07D 239/94* (2013.01); *C07D 239/95* (2013.01); *C07D 405/04* (2013.01); *C07B 2200/05* (2013.01)

(58) Field of Classification Search
CPC .. C07D 491/14; C07D 407/04; C07D 239/94; A61K 31/519; A61K 31/517
USPC .......... 544/251, 255; 514/266.24, 266.4, 267
See application file for complete search history.

(56) References Cited

U.S. PATENT DOCUMENTS

| | | | |
|---|---|---|---|
| 5,747,498 A | 5/1998 | Schnur et al. | |
| 6,835,735 B2 | 12/2004 | Lee et al. | |
| 7,521,456 B2 | 4/2009 | Allen et al. | |
| 8,916,574 B2 | 12/2014 | Wang et al. | |
| 2003/0045537 A1 | 3/2003 | Lee et al. | |
| 2020/0290978 A1 | 9/2020 | Nathanson et al. | |

FOREIGN PATENT DOCUMENTS

| | | |
|---|---|---|
| CN | 1854130 B | 4/2011 |
| CN | 105017163 A | 11/2015 |
| CN | 106432202 A | 2/2017 |
| GB | 2033894 A | 5/1980 |
| WO | WO-2008046242 A1 | 4/2008 |
| WO | WO-2012127012 A1 | 9/2012 |
| WO | WO-2016/100347 A2 | 6/2016 |
| WO | WO-2017/116680 A1 | 7/2017 |
| WO | WO-2017/117680 A1 | 7/2017 |
| WO | WO-2019/067543 A1 | 4/2019 |
| WO | WO-2020/190765 A2 | 9/2020 |

OTHER PUBLICATIONS

Ha, et. al., Bulletin of the Korean Chemical Society (2005), 26(6), 959-965. (Year: 2005).*
"18F-FDG PET and osimertinib in evaluating glucose utilization in patients with EGFR activated recurrent glioblastoma," Clinical Trials (13 pages) (Feb. 26, 2019).
Chilin et al., "Exploring epidermal growth factor receptor (EGFR) inhibitor features: the role of fused dioxygenated rings on the quinazoline scaffold," J Med Chem, 53(4): 1862-1866 (2010).
Clark et al., "Emerging approaches for targeting metabolic vulnerabilities in malignant glioma," Curr Neurol Neurosci Rep, 16(2): 1-10 (2016).
Ellingson et al., "Multiparametric MR-PET imaging predicts pharmacokinetics and clinical response to GDC-0084 in patients with recurrent high-grade glioma," Clin Can Res, 26(13): 3135-3144 (2020).
Goldenberg et al., "Assessments of tumor metabolism with CEST MRI," NMR Biomed, 31 (10): e3943 (2019).
International Preliminary Report on Patentability for International Application No. PCT/US2020/022743 dated Sep. 16, 2021.
International Search Report and Written Opinion for International Application No. PCT/US2021/051023 dated Dec. 21, 2021.
International Search Report and Written Opinion for International Application No. PCT/US2021/051024 dated Dec. 14, 2021.
International Search Report and Written Opinion for International Application No. PCT/US2021/051338 dated Nov. 24, 2021.
Lopez-Gines et al., "Association of chromosome 7, chromosome 10 and EGFR gene amplification in glioblastoma multiforme," Clin Neuropathol. 24(5): 209-218 (2005).
Sakka et al., "Discovery of novel EGFR inhibitors: in silico study and 3D-pharmacophore model generation," Journal of Computational Methods in Molecular Design, 3(2): 10-25 (2013).

(Continued)

*Primary Examiner* — Jeffrey H Murray
(74) *Attorney, Agent, or Firm* — Foley Hoag LLP; David P. Halstead; Lucas P. Watkins

(57) ABSTRACT

The present disclosure relates to compounds, compositions and methods for treating cancer, including compounds that are capable of penetrating the blood brain barrier to modulate the activity of EGFR tyrosine kinase. The disclosure further relates to methods of treating cancer in the brain, including glioblastoma and other EGFR mediated cancers. The disclosure further relates to methods of treating cancers such as glioblastoma and other EGFR mediated cancers that have been determined to have altered glucose metabolism in the presence of inhibitors. The present disclosure also provides methods of administering to a subject a glucose metabolism inhibitor and a cytoplasmic p53 stabilizer.

22 Claims, 85 Drawing Sheets

Specification includes a Sequence Listing.

(56) References Cited

OTHER PUBLICATIONS

Tsang et al., "DDIS-17. Development of brain-penetrant EGFR inhibitors for CNS malignancies," Neuro-Oncol, 21(6) (2019).
Abida et al., "An updated review: newer quinazoline derivatives under clinical trial," International Journal of Pharmaceutical & Biological Archive, 2(6):1651-1657 (2011).
Asif, "Chemical characteristics, synthetic methods, and biological potential of quinazoline and quinazolinone derivatives," International Journal of Medicinal Chemistry, (2014).
Assefa et al., "3D-QSAR and molecular docking studies of 4-anilinoquinazoline and 4-anilinoquinoline epidermal growth factor receptor (EGFR)," Journal of Computer-Aided Molecular Design, 17(8):475-493 (2003).
Burris, "Dual kinase inhibition in the treatment of breast cancer: initial experience with the EGFR-ErbB-2 inhibitor lapatinib," The Oncologist, 9(3):10-15 (2004).
CAS Registry No. 1207969-28-7 (Mar. 4, 2010).
CAS Registry No. 1348957-85-6 (Dec. 5, 2011).
CAS Registry No. 1348971-95-8 (Dec. 5, 2011).
CAS Registry No. 1348975-63-2 (Dec. 5, 2011).
CAS Registry No. 1349202-84-1 Dec. 5, 2011).
CAS Registry No. 1349618-58-1 (Dec. 6, 2011).
CAS Registry No. 886446-50-0 (Jun. 1, 2006).
CAS Registry No. 886446-54-4 (Jun. 1, 2006).
CAS Registry No. 886446-55-5 (Jun. 1, 2006).
CAS Registry No. 886446-56-6 (Jun. 1, 2006).
CAS Registry No. 886446-57-7 (Jun. 1, 2006).
CAS Registry No. 886446-58-8 (Jun. 1, 2006).
CAS Registry No. 886446-73-7 (Jun. 1, 2006).
Chen et al., "Elucidating inhibitory models of the inhibitors of epidermal growth factor receptor by docking and 3D-QSAR," Bioorganic & Medicinal Chemistry, 12: 2409-2417 (2004).
Chilin et al., "Exploring epidermal growth factor receptor (EGFR) inhibitor features: the role of fused dioxygenated rings on the quinazoline scaffold," Journal of Medicinal Chemistry, 53(4):1862-1866 (2010).
Chilin et al., "Exploring Epidermal Growth Factor Receptor (EGFR) Inhibitor Features: The Role of Fused Dioxygenated Rings on the Quinazoline Scaffold," Journal of Medicinal Chemistry, 53: 1862-1866 (2010).
Clark et al., "Emerging approaches for targeting metabolic vulnerabilities in malignany glioma," Current Neurology and Neuroscience Reports, 16(2):17 (2016).
Desiniotis et al., "Advances in the design and synthesis of prazosin derivatives over the last ten years," Expert Opinion on Therapeutic Targets, 15(12):1405-1418 (2011).
Extended European Search Report for EP Application No. EP 18860554 dated Mar. 3, 2021.
Garofalo et al., "Design, synthesis, and DNA-binding of N-alkyl(anilino)quinazoline derivatives," Journal of Medicinal Chemistry, 53(22):8089-8103 (2010).
Ghosh et al., "PI3k-AKT pathway negatively controls EGFR-dependent DNA-binding activity of Stat3 in glioblastoma multiforme cells," Oncogene, 24(49):7290 (2005).
Giannopolou et al., "An in vitro study, evaluating the effect of sunitinib and/or lapatinib on two glioma cell lines," Investigational New Drugs, 28(5):554-560 (2010).
Gupta et al., "Targeting the epidermal growth factor receptor: exploring the potential of novel inhibitor N-(3-Ethynylphenyl)-6, 7-bis (2-methoxyetjoxy) quinolin-4-amine using docking and molecular dynamics simulation," Protein and Peptide Letters, 19(9):955-968 (2012).
Ha et al., "Design and Synthesis of Novel Epidermal Growth Factor Receptor Kinase Inhibitors," Bull. Korean Chem. Soc., 26(6):959-965 (2005).
Haghighijoo et al., "A reapid and convinient method for synthesis of anilinoquinazoline: an improved synthesis of erlotinib derivatives," Trends in Pharmaceutical Sciences, 1 (3):173-178 (2015).
Harris et al., "Selective alkylation of a 6, 7-dihydroxyquinazoline," Tetrahedron Letters, 46(45):7715-7719(2005).
Hennequin et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., 45: 1300-1312 (2002).
International Preliminary Report on Patentability for International Application No. PCT/US2018/052858 dated Apr. 9, 2020.
International Search Report and Written Opinion for International Application No. PCT/US2018/052858 dated Jan. 15, 2019.
International Search Report and Written Opinion for International Application No. PCT/US2020/022743 dated Oct. 22, 2020.
Jafari et al., "Quinazolinone and quinazoline derivatives: recent structures with potent antimicrobial and cytotoxic activities," Research in Pharmaceutical Sciences, 11(1):1 (2016).
Lee et al. "7-Substituted-[1,4]dioxano[2,3-g]quinazolines as inhibitors of epidermal growth factor receptor kinase," Arch. Pharm. Pharm. Med. Chem., 335(10): 487-494 (2002).
Lee et al., "1,4-Dioxane-fused 4-anilinoquinazoline as inhibitors of epidermal growth factor receptor kinase," Archiv de Parmazie: An International Journal Pharmaceutical and Medicinal Chemistry, 334(11):357-360 (2001).
Mai et al., "Cytoplasmic p53 couples oncogene-driven glucose metabolism to apoptosis and is a therapeutic target in glioblastoma," Nature Medicine, 23:1342-1351 (2017).
Mai et al., "Cytoplasmic p53 couples oncogene-driven glucose metabolism to apotosis and is a therapeutic target in gliblastoma," Nat Med, 23(11):1342-1351 (2017).
Narla et al., "4-(3'-Bromo-4'hydroxylphenyl)-amino-6,7-dimethoxyquinazoline: a novel quinazoline derivative with potent cytotoxic activity against human glioblastoma cells," Clinical Cancer Research, 4(6):1405-1414 (1998).
Narla et al., "Inhibition of human glioblastoma cell adhesion and invasion by 4-(4'-hydroxylphenyl)-amino-6,7-dimethoxyquinazoline (WHI-P131) and 4-(3'-bromo-4'hydroxylphenyl)-amino-6, 7-dimethoxyquinazoline (WHI-P154)," Clinical Cancer Research, 4(10):2463-2471 (1998).
Nathanson, "Mechanisms of evading targeted treatments in GBM: Functional diagnostics to predict outcome to targeted therapy," Department of Molecular & Medical Pharmacology Society of Neuro-Oncology Sunrise Session, Nov. 23, 2019.
Ryan et al., "ZD6474—a novel inhibitor of VEGFR and EGFR tyrosine kinase activity," British Journal of Cancer, 92(1):S6-S13 (2005).
Shen et al., "Autophagy inhibition induces enhanced proapoptotic effects of ZD6474 in glioblastoma," British Journal of Cancer, 109(1):164 (2013).
Shi et al., "Facile synthesis of novel perfluorocarbon-modulated 4-anilinoquinazoline analogues," Chinese Journal of Chemistry, 35(11):1693-1700 (2017).
Tsang et al., "Development of a Potent Brain-Penetrant EGFR Tyrosine Kinase Inhibitor against Malignant Brain Tumors," ACS Med. Chem Lett. (2020).
Wang et al., "The role of Myc and let-7a in glioblastoma, glucose metabolism and response to therapy," Archives of Biochemistry and Biophysics, 84-92 (2015).
Wedge et al., "ZD4190: an orally active inhibitor of vascular endothelial growth factor signaling with broad-spectrum antitumor efficacy," Cancer Research, 60(4):970-975 (2000).
Xu et al., "Synthesis and bioactivity of 6, 7-Dimethoxy-Quinazoline-4-Arylamine derivatives," Chinese Pharmaceutical Journal—Beijing, 42(22):1748 (2007).
Zeng et al. "Discovery and evaluation of clinical candidate AZD3759, a potent, oral active, central nervous system-penetrant, epidermal growth factor receptor tyrosine kinase inhibitor," Journal of Medicinal Chemistry, 58(20): 8200-8215 (2015).
Zhu et al., "EGFR tyrosine kinase inhibitor AG1478 inhibits cell proliferation and arrests cell cycle in nasopharyngeal carcinoma cells," Cancer letters, 169(1):27-32 (2001).

* cited by examiner

FIG. 21A
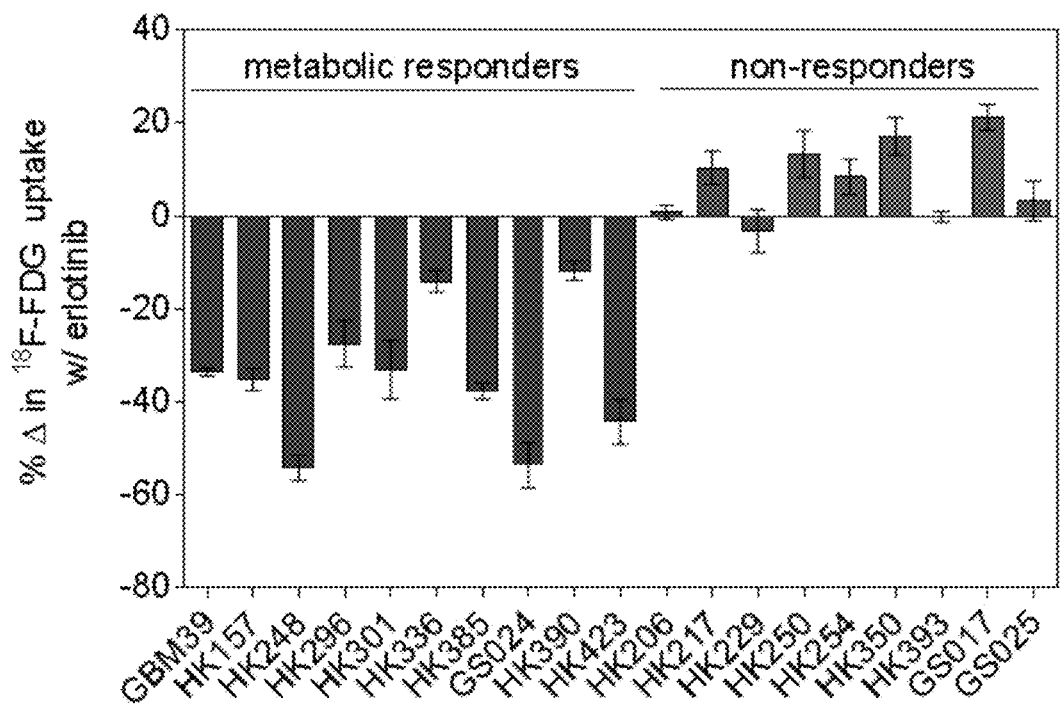
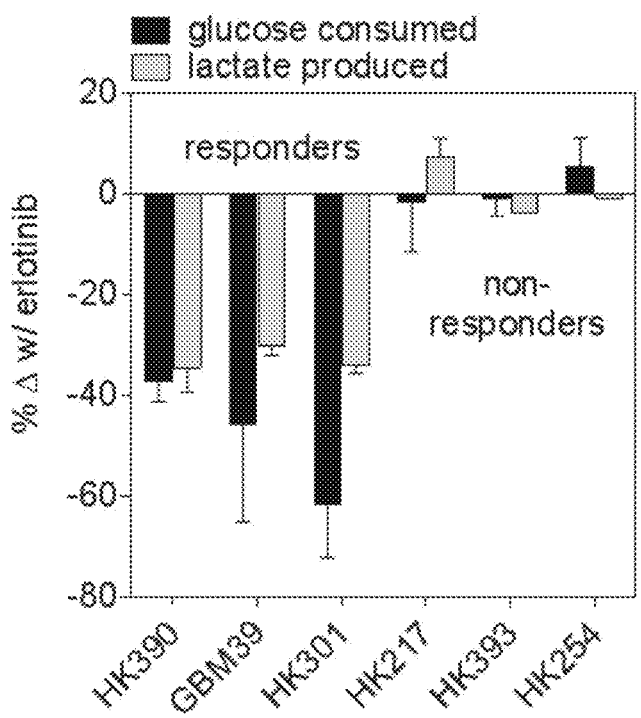
FIG. 21B

| GENE A | GENE B | P-VALUE | LOG ODDS RATIO | ASSOCIATION |
|---|---|---|---|---|
| EGFR | TP53 | <0.001 | -1.383 | Mut. Excl. |
| MDM2 | TP53 | <0.001 | -2.547 | Mut. Excl. |
| CDKN2A | TP53 | <0.001 | -1.403 | Mut. Excl. |
| EGFR | CDKN2A | 0.004 | .703 | Co-occurance |
| MDM2 | CDK2NA | <0.001 | -2.138 | Mut. Excl. |

*Only significant interactions are shown*

$^{18}$F-FDG PET Tumor 1 (white circle)

$^{18}$F-FDG PET Tumor 2 (white circle)

1.  JCN068S

2.

3.  JCN083S

4.

5.

6.  JCN082S

COMPOSITIONS AND METHODS FOR TREATING CANCER

RELATED APPLICATIONS

This application is a continuation of PCT/US2020/022743, filed Mar. 13, 2020, which claims the benefit of U.S. Provisional Application Nos. 62/819,322, filed Mar. 15, 2019, and 62/904,241, filed Sep. 23, 2019, the contents of which are fully incorporated by reference herein.

STATEMENT OF GOVERNMENT SUPPORT

This invention was made with government support under Grant Numbers CA151819, CA211015, CA213133, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 12, 2021, is named UCH-17701_SL.txt and is 3,782 bytes in size.

BACKGROUND

Glioblastoma (glioblastoma multiforme; GBM) accounts for the majority of primary malignant brain tumors in adults. Amplification and mutation of the epidermal growth factor receptor (EGFR) gene is a signature genetic abnormality encountered in GBM (Sugawa, et al. (1990) *Proc. Natl. Acad. Sci.* 87: 8602-8606; Ekstrand, et al. (1992) *Proc. Natl. Acad. Sci.* 89: 4309-4313). A range of potential therapies that target EGFR or its mutant constitutively active form, ΔEGFR, including tyrosine kinase inhibitors (TKIs), monoclonal antibodies, vaccines, and RNA-based agents, are currently in development or in clinical trials for the treatment of GBM. However, to date their efficacy in the clinic has so far been limited by both upfront and acquired drug resistance (Taylor, et al. (2012) *Curr. Cancer Drug Targets.* 12:197-209). A major limitation is that current therapies such as erlotinib, lapatinib, gefitinib and afatinib are poorly brain penetrant (Razier, et al. (2010) *Neuro-Oncology* 12:95-103; Reardon, et al. (2015) *Neuro-Oncology* 17:430-439; Thiessen, et al. (2010) *Cancer Chemother. Pharmacol.* 65:353-361).

Molecular targeted therapies have revolutionized cancer treatment and paved the path for modern precision medicine. However, despite well-defined actionable genetic alterations, targeted drugs have failed in glioblastoma (GBM) patients. This is in large part due to insufficient CNS penetration of most targeted agents to levels necessary for tumor kill; potentially evoking robust adaptive mechanisms to drive therapeutic resistance. While drug combinations that inhibit both the primary lesion and the compensatory signaling pathway(s) are appealing, these combination therapy strategies have been hampered by enhanced toxicities leading to subthreshold dosing of each drug.

An alternative therapeutic approach targets an oncogenic driver to modify an important functional property for tumor survival, rendering cells vulnerable to an orthogonal second hit[6]. This "synthetic lethal" strategy may be particularly attractive when the oncogene-regulated functional network(s) intersect with tumor cell death pathways. In a certain example, oncogenic signaling drives glucose metabolism to suppress intrinsic apoptosis and promote survival. Inhibition of oncogenic drivers with targeted therapies can trigger the intrinsic apoptotic machinery as a direct consequence of attenuated glucose consumption. The intertwined nature of these tumorigenic pathways may present therapeutic opportunities for rational combination treatments, however, this has yet to be investigated.

In view of the foregoing, there remains a clinical need for brain penetrant chemotherapeutics for the treatment of glioblastoma and other cancers.

SUMMARY OF THE INVENTION

In one aspect, the present disclosure provides compounds of Formula I or Formula I*:

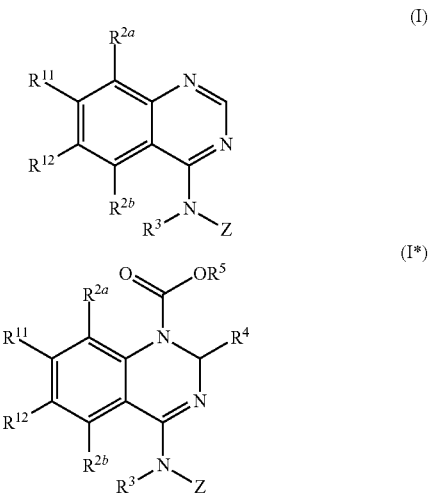

or a pharmaceutically acceptable salt thereof, wherein:
Z is aryl or heteroaryl;
$R^{2a}$ and $R^{2b}$ are each independently selected from hydrogen, alkyl, halo, CN, and $NO_2$;
$R^3$ is hydrogen, alkyl, or acyl;
$R^4$ is alkoxy;
$R^5$ is alkyl; $R^7$ and $R^8$ are, each independently, selected from hydrogen, alkyl, such as alkoxyalkyl, aralkyl, or arylacyl;
$R^{11}$ is hydrogen, alkyl, halo, CN, $NO_2$, $OR^7$, cycloalkyl, heterocyclyl, aryl or heteroaryl; and
$R^{12}$ is hydrogen, alkyl, halo, CN, $NO_2$, $OR^8$, cycloalkyl, heterocyclyl, aryl or heteroaryl; or
$R^{11}$ and $R^{12}$ taken together complete a carbocyclic or heterocyclic ring.

In certain aspects, the present disclosure provides methods of inhibiting EGFR or ΔEGFR, comprising administering to a subject an amount of a compound of the disclosure.

In certain aspects, the present disclosure provides methods of treating cancer comprising administering to a subject in need of a treatment for cancer an amount of a compound of the disclosure. In some embodiments, the cancer is glioblastoma multiforme.

In certain aspects, the present disclosure provides methods of treating cancer comprising administering to a subject a glucose metabolism inhibitor and a cytoplasmic p53 stabilizer, wherein the glucose metabolism inhibitor is a compound of the disclosure. In some embodiments, the cancer is glioblastoma multiforme.

In certain aspects, the present disclosure provides methods of making compounds of Formula I or Formula I*.

BRIEF DESCRIPTION OF THE DRAWINGS

FIGS. 21A-21F depict the inhibition of EGFR-driven glucose metabolism induces minimal cell death but primes GBM cells for apoptosis. FIG. 21A depicts percent change in $^{18}$F-FDG uptake after 4 hours of erlotinib treatment relative to vehicle in 19 patient-derived GBM gliomaspheres. "Metabolic responders" (blue) are samples that show a significant decrease in $^{18}$F-FDG uptake relative to vehicle, whereas "non-responders" (red) show no significant decrease. FIG. 21B depicts percent change in glucose consumption and lactate production with 12 hours of erlotinib treatment relative to vehicle. Measurements are made using Nova Biomedical BioProfile Analyzer. FIG. 21C depicts Annexin V staining of metabolic responders (blue, n=10) or non-responders (red, n=9) after treatment with erlotinib for 72 hours. FIG. 21D depicts the percent change, relative to vehicle control, in priming as determined by cytochrome c release following exposure to each BH3 peptide (BIM, BID, or PUMA) in metabolic responders or non-responders treated with erlotinib for 24 hours. FIG. 21E depicts Left: Immunoblot of whole cell lysate of HK301 cells overexpressing GFP control or GLUT1 and GLUT3 (GLUT1/3). Right: Changes in glucose consumption or lactate production of HK301-GFP or HK301-GLUT1/3 after 12 hours of erlotinib treatment. Values are relative to vehicle control. FIG. 21F depicts using HK301-GFP or HK301-GLUT1/3 cells. Erlotinib concentration for all experiments was 1 µM. Comparisons were made using two-tailed unpaired Student's t-test. Data represent means±s.e.m. values of three independent experiments. *p<0.05, p<0.01, *p<0.001, ****p<0.0001.

FIG. 22A depicts immunoblot of indicated proteins in two responders (HK301 and HK336) expressing CRISPR/CAS9 protein with control guide RNA (sgCtrl) or p53 guide RNA (p53KO). FIG. 22B depicts the percent change, relative to vehicle control, in priming as determined by cytochrome c release following exposure to BIM peptide in sgCtrl and p53KO cells treated with erlotinib for 24 hours. FIG. 22C depicts immunoblot of indicated proteins in HK301 sgCtrl, p53KO, p53KO+p53$^{cyto}$, and p53KO+p53$^{wt}$. FIG. 22D depicts that immunofluorescence of p53 protein combined with DAPI staining to reveal protein localization in HK301 sgCtrl, p53KO+p53$^{cyto}$, and p53KO+p53$^{wt}$ (scale bars=20 µm). Gliomaspheres were first disassociated to single cell and adhered to the 96-well plates using Cell-Tak (Corning) according to manufacturer instructions. Adhered cells were then fixed with ice-cold methanol for 10 min then washed three times with PBS. Cells were then incubated with blocking solution containing 10% FBS and 3% BSA in PBS for 1 hr and subsequently incubated with p53 (Santa Cruz, SC-126, dilution of 1:50) antibody overnight at 4° C. The following day, cells were incubated with secondary antibody (Alexa Fluor 647, dilution 1:2000) for an hour and DAPI staining for 10 min, then imaged using a Nikon TI Eclipse microscope equipped with a Cascade II fluorescent camera (Roper Scientific). Cells were imaged with emissions at 461 nM and 647 nM and then processed using NIS-Elements AR analysis software. FIG. 22E depicts changes in indicated mRNA levels following 100 nM doxorubicin treatment for 24 hrs in HK301 sgCtrl, p53KO, p53KO+p53$^{cyto}$, and p53KO+p53$^{wt}$. Levels were normalized to respective DMSO treated cells. FIG. 22F depicts similar data to 22B but in HK301 sgCtrl, p53KO, p53KO+p53$^{cyto}$, and p53KO+p53$^{wt}$. FIG. 22G depicts similar data to 22E but in HK301 sgCtrl, p53KO, p53KO+p53$^{R175H}$, p53KO+p53$^{R273H}$, and p53KO+p53$^{NES}$. FIG. 22H depicts similar data to 22B and 22F but in HK301 sgCtrl, p53KO, p53KO+p53$^{R175H}$, p53KO+p53$^{R273H}$, and p53KO+p53$^{NES}$. Erlotinib concentration for all experiments was 1 µM. Comparisons were made using two-tailed unpaired Student's t-test. Data represent means±s.e.m. values of three independent experiments. *p<0.05, p<0.01, *p<0.001, ****p<0.0001.

FIG. 23A depicts the immunoprecipitation of p53 in two metabolic responders (HK301 and GBM39) following 24 hours of erlotinib treatment. The immunoprecipitate was probed with the indicated antibodies. Below are respective pre-immunoprecipitation lysates (input). FIG. 23B depicts data similar to 23A but in two non-responders (HK393 and HK254). FIG. 23C depicts data similar to 23A and 23B but in HK301-GFP and HK301-GLUT1/3. To the right are immunoblots for indicated inputs. FIG. 23D depicts HK301 was treated for 24 hours with erlotinib, WEHI-539, or both and immunoprecipitation and immunoblotting was performed as described previously. FIG. 23E depicts annexin V staining of two responders (GBM39 and HK301) and a non-responder (HK393) following 72 hours of treatment with erlotinib, WEHI-539, or both. FIG. 23F depicts annexin V staining of HK301-GFP and HK301-GLUT1/3 following 72 hours of treatment with erlotinib, wehi-539, or both. Erlotinib and WEHI-539 concentrations for all experiments were 1 µM and 5 µM, respectively. Comparisons were made using two-tailed unpaired Student's t-test. Data represent means±s.e.m. values of three independent experiments. *p<0.05, **p<0.01.

FIG. 24A depicts a summary of alterations in EGFR and genes involved in p53 regulation across 273 GBM samples. Genetic alterations in EGFR (amp/mutation) are mutually exclusive to those in p53. As shown, EGFR alterations are on the left side of the table while most alterations in p53 are on the right. FIG. 24B depicts a table indicating the significant associations between alterations in EGFR and genes involved in the p53 pathway. FIG. 24C depicts Annexin V staining of a metabolic responder (left: HK301) and non-responder (right: GS017) treated with varying concentrations of erlotinib, nutlin, and in combination represented as a dose-titration matrix. FIG. 24D depicts the dose-titration of erlotinib and nutlin as described in 24C was conducted across 10 metabolic responders and 6 non-responders, and the synergy score was calculated (see Materials and Methods). FIG. 24E depicts Annexin V staining of HK301-GFP and HK301 GLUT1/3 following 72 hours of treatment with erlotinib, nutlin, or both. FIG. 24F depicts the same as 24E but in HK301-sgCtrl and HK301-p53KO. FIG. 24G depicts HK301 that was treated for 24 hours with erlotinib, nutlin, or in combination Immunoprecipitation was performed with immunoglobulin G control antibody or anti-p53 antibody, and the immunoprecipitate was probed with the indicated antibodies. Below are respective pre-immunoprecipitation lysates (input). All data are representative of at least n=3 independent experiments, mean±SEM. Unless indicated, erlotinib and nutlin concentrations for all experiments were 1 µM and 2.5 µM, respectively. p<0.01, *p<0.001, ****p<0.0001

FIG. 25A depicts the percentage change in $^{18}$F-FDG uptake after 4 hours of erlotinib, 2DG, or pictilisib treatment relative to vehicle in HK393 and HK254. FIG. 25B depicts the percentage change, relative to vehicle control, in priming as determined by cytochrome c release following exposure to BIM peptide in HK393 and HK254 following erlotinib, 2DG, or pictilisib for 24 hours. FIG. 25C depicts data similar to 25B but in HK393 sgCtrl and p53KO. FIG. 25D depicts the immunoprecipitation of p53 in HK393 and HK254 following 24 hours of 2DG or pictilisib treatment. The immunoprecipitate was probed with the indicated antibodies. Below are respective pre-immunoprecipitation lysates (input). FIG. 25E depicts the synergy score of various drugs (erlotinib, 2DG, and pictilisib) in combination with nutlin in HK393 and HK254. FIG. 25F depicts Annexin V staining of HK393 sgCtrl and HK393 p53KO following 72 hours of treatment with 2DG, pictilisib, 2DG+nutlin, or pictilisib+nutlin. Unless indicated, erlotinib, 2DG, pictilisib, and nutlin concentrations for all experiments were 1 µM, 1 mM, 1 µM and 2.5 µM, respectively. Comparisons were made using two-tailed unpaired Student's t-test. Data represent means±s.e.m. values of three independent experiments. *p<0.05, p<0.01, *p<0.001.

FIG. 26A depicts the $^{18}$F-FDG PET/CT imaging of GBM39 intracranial xenografts before and after 15 hours erlotinib treatment (75 mg/kg). FIG. 26B depicts GBM39 intracranial xenografts that were treated with vehicle (n=5), 75 mg/kg erlotinib (n=7), 50 mg/kg Idasanutlin (n=5), or in combination daily (n=12), and tumor burden was assessed at indicated days using secreted gaussia luciferase (see Materials and Methods). FIG. 26C depicts data similar to 26A but in HK393 intracranial xenografts. FIG. 26D depicts data similar to 26B, but in HK393 intracranial xenografts (n=7 for all groups). FIG. 25E depicts the percent survival of 26B. FIG. 26F depicts the percent survival of 26C. FIG. 26G depicts the percent survival of metabolic responder HK336 following indicated treatments for 25 days and then released from drug (n=7 for all groups). FIG. 26H depicts the percent survival of non-responder GS025 following indicated treatments for 25 days and then released from drug (n=9 for all groups). Comparisons for 26B and 26D used data sets from the last measurements and were made using two-tailed unpaired t-test. Data represent means±s.e.m. values. **p<0.01.

FIG. 27A depicts the percent change in $^{18}$F-FDG uptake at indicated times of erlotinib treatment relative to vehicle in two metabolic responders (HK301 and GBM39). FIG. 27B depicts an immunoblot of indicated proteins of a metabolic responder (HK301) and non-responder (HK217) following genetic knockdown of EGFR with siRNA. FIG. 27C depicts the percent change in $^{18}$F-FDG uptake in HK301 and HK217 following genetic knockdown of EGFR. FIG. 27D depicts the change in glucose consumption with 12 hours of erlotinib treatment in three metabolic responders (HK301, GBM39, HK390) and three non-responders (HK393, HK217, HK254). Measurements are made using Nova Biomedical BioProfile Analyzer. FIG. 27E depicts the change in and lactate production with 12 hours of erlotinib treatment in three metabolic responders (HK301, GBM39, HK390) and three non-responders (HK393, HK217, HK254). Measurements are made using Nova Biomedical BioProfile Analyzer. FIG. 27F depicts basal ECAR measurements of two responders (HK301 and GBM39, in blue) and two non-responders (HK217 and HK393, in red) following 12 hours of erlotinib treatment. FIG. 27G depicts change in glutamine consumption following 12 hours of erlotinib treatment, as measured by Nova Biomedical BioProfile Analyzer. Erlotinib concentrations for all experiments were 1 µM. Comparisons were made using two-tailed unpaired Student's t-test. Data represent means±s.e.m. values of three independent experiments. *p<0.05, p<0.01, *p<0.001, ****p<0.0001.

FIG. 28A depicts an immunoblot of indicated proteins following 4 hours of erlotinib treatment in metabolic responders. FIG. 28B depicts an immunoblot of indicated proteins following 4 hours of erlotinib treatment in metabolic non-responders.

FIG. 29A depicts the genetic background across a panel of GBM lines. FIG. 29B depicts fluorescence in situ hybridization (FISH) of HK390, HK336, HK254, and HK393 showing polysomy of EGFR. Fluorescence in situ hybridization (FISH) was performed using commercially available fluorescently labeled dual-color EGFR (red)/CEP 7 (green) probe (Abbott-Molecular). FISH hybridization and analyses were performed on cell lines, following the manufacturer's suggested protocols. The cells were counterstained with DAPI and the fluorescent probe signals were imaged under a Zeiss (Axiophot) Fluorescent Microscope equipped with dual- and triple-color filters.

FIG. 30A depicts an immunoblot of indicated proteins following 24 hours of erlotinib treatment in metabolic responders (GBM39, HK301, and HK336) and non-responders (HK217, HK393, and HK254). FIG. 30B depicts example of dynamic BH3 profiling analysis in a metabolic responder (HK301). Left: Percent cytochrome c release is measured following exposure to various peptides at indicated concentrations. Right: The difference in cytochrome c release between vehicle treated cells and erlotinib treated cells is calculated to obtain the percent priming Erlotinib concentrations for all experiments was 1 μM.

FIG. 31A depicts the change in glucose consumption and lactate production with 12 hours of erlotinib treatment in HK301-GFP and HK301 GLUT1/3. Measurements are made using Nova Biomedical BioProfile Analyzer. FIG. 31B depicts Left: Immunoblot of whole cell lysate of GBM39 cells overexpressing GFP control or GLUT1 and GLUT3 (GLUT1/3). Right: Changes in glucose consumption or lactate production of GBM39-GFP or GBM39-GLUT1/3 after 12 hours of erlotinib treatment. Values are relative to vehicle control. FIG. 31C depicts data similar to 35A but in GBM39-GFP and GBM39-GLUT1/3. Erlotinib concentrations for all experiments was 1 μM. Comparisons were made using two-tailed unpaired Student's t-test. Data represent means±s.e.m. values of three independent experiments. *p<0.05, p<0.01, *p<0.001, ****p<0.0001.

FIG. 32A depicts the percent change in $^{18}$F-FDG uptake following 4 hours of erlotinib treatment in HK301 sgCtrl and p53 KO cells (mean±s.d., n=3). FIG. 32B depicts relative mRNA levels of p53-regulated genes following 24 hours 1 μM erlotinib treatment in or 100 nM doxorubicin treatment in HK301 (metabolic responder). FIG. 32C depicts HK301 cells infected with a p53-luciferase reporter system and p53 activity was measured following 24 hours of 1 μM erlotinib treatment (mean±s.d., n=3). Results are representative of two independent experiments. FIG. 32D depicts Immunoblot of indicated proteins in HK336 sgCtrl, p53KO, p53KO+ p53$^{cyto}$, and p53KO+p53$^{wt}$. FIG. 32E depicts the immunofluorescence of p53 protein combined with DAPI staining to reveal protein localization in HK336 sgCtrl, p53KO+ p53$^{cyto}$, and p53KO+p53$^{wt}$ (scale bars=20 μm). Immunofluorescence was performed as previously described. FIG. 32F depicts changes in indicated mRNA levels following 100 nM doxorubicin treatment for 24 hrs in HK336 sgCtrl, p53KO, p53KO+p53$^{cyto}$, and p53KO+p53$^{wt}$ (mean±s.d., n=3). Levels were normalized to respective DMSO treated cells. FIG. 32G depicts the percent change, relative to vehicle control, in apoptotic priming—as determined by cytochrome c release following exposure to BIM peptide— in HK336 sgCtrl, p53KO, p53KO+p53$^{cyto}$, and p53KO+ p53$^{wt}$ cells treated with erlotinib for 24 hours. (mean±s.d., n=2). Results are representative of two independent experiments. FIG. 32H depicts an immunoblot of indicated proteins in HK301 sgCtrl, p53KO, p53KO+p53$^{R175H}$, p53KO+ p53$^{R273H}$, and p53KO+p53$^{NES}$. FIG. 32I depicts the percent change in priming in HK301 following 24 hours of erlotinib treatment with or without PFTμ pre-treatment (10 μM for 2 hours) (mean±s.d., n=2). Results are representative of two independent experiments.

FIG. 33A depicts the percent change, relative to vehicle control, in priming as determined by cytochrome c release following exposure to BAD and HRK peptides in metabolic responders (HK301 and HK336) or non-responder (HK229) treated with erlotinib. FIG. 33B depicts Left: Immunoprecipitation of p53 in GBM39-GFP and GBM39-GLUT1/3 following 24 hours of erlotinib treatment. The immunoprecipitate was probed with the indicated antibodies. Right: respective pre-immunoprecipitation lysates (input). FIG. 33C depicts Annexin V staining of HK301 (left) and HK336 (right) sgCtrl, p53KO, p53 KO+p53$^{cyto}$, and p53KO+p53$^{wt}$ following 72 hours of treatment with erlotinib, WEHI-539, or combination. FIG. 33D depicts data similar to 33C but in GBM39-GFP and GBM39-GLUT1/3. Erlotinib and WEHI-539 concentrations for all experiments were 1 μM. Comparisons were made using two-tailed unpaired Student's t-test. Data represent means±s.e.m. values of three independent experiments. *p<0.05, p<0.01, *p<0.001.

FIG. 34A depicts the immunoblot of indicated proteins following 24 hours of erlotinib, nutlin or in combination in two metabolic responders (HK301 and GBM39). FIG. 34B depicts Annexin V staining in HK301 and HK217 following genetic knockdown of EGFR and subsequent nutlin treatment for 72 hours. FIG. 34C depicts the detection of BAX oligomerization in HK301-GFP and HK301-GLUT1/GLUT3. Following 24 hours of indicated treatment, cells were harvested and incubated in 1 mM BMH to promote protein cross-linking and immunoblotted with indicated antibodies. Below BAX is immunoblot for cytosolic cytochrome c following cellular fractionation. FIG. 34D depicts the Top: Immunoblot of indicated proteins in HK301-GFP and HK301-HA-BclxL. Bottom: Annexin V staining in HK301-GFP and HK301-HA-BclxL following 72 hours of treatment with erlotinib, nutlin, or combination. FIG. 34E depicts Annexin V staining of HK301 following 72 hours of erlotinib, nutlin or the combination +/− PFTμ pretreatment (10 μM for 2 hours). FIG. 34F depicts Annexin V staining of HK301 sgCtrl, p53KO, p53KO+p53$^{R175H}$, p53KO+p53$^{R273H}$, and p53KO+p53$^{NES}$ following 72 hours of treatment with erlotinib, nutlin, or combination. FIG. 34G depicts data similar to 34F but in HK301 sgCtrl, p53KO, p53KO+p53$^{cyto}$, and p53KO+p53$^{wt}$. Drug concentrations for all experiments are as follows: erlotinib (1 µM), nutlin (2.5 µM). Comparisons were made using two-tailed unpaired Student's t-test. Data represent means±s.e.m. values of three independent experiments. *p<0.05, p<0.01, *p<0.001, ****p<0.0001. FIG. 34H depicts data similar to 34G but in HK336 sgCtrl, p53KO, p53KO+p53$^{cyto}$, and p53KO+p53$^{wt}$. Drug concentrations for all experiments are as follows: erlotinib (1 µM), nutlin (2.5 µM). Comparisons were made using two-tailed unpaired Student's t-test. Data represent means±s.e.m. values of three independent experiments. *p<0.05, p<0.01, *p<0.001, ****p<0.0001.

FIG. 35A depicts the percent change, relative to vehicle control, in priming as determined by cytochrome c release following exposure to BIM peptides in metabolic responder HK301 following 24 hours of erlotinib or 2DG treatment. FIG. 35B depicts Left: Immunoprecipitation of p53 in HK301 following 24 hours of 2DG treatment. The immunoprecipitate was probed with the indicated antibodies. Right: respective pre-immunoprecipitation lysates (input). FIG. 35C depicts OCR and ECAR measurements of HK301 cells following exposure to oligomycin and rotenone. FIG. 35D depicts Annexin V staining in HK301 following 72 hours of treatment with nutlin, erlotinib, 2DG, oligomycin, rotenone as individual agents or in combination with nutlin. FIG. 35E depicts an immunoblot of indicated proteins following 4 hours of erlotinib or pictilisib treatment in two non-responders (HK254 and HK393). FIG. 35F depicts the Immunoprecipitation of p53 in HK254 following 24 hours of pictilisib or 2DG treatment. The immunoprecipitate was probed with the indicated antibodies. Below are respective pre-immunoprecipitation lysates (input). Drug concentrations for all experiments are as follows: erlotinib (1 µM), nutlin (2.5 µM), 2DG (3 mM for HK301 and 1 mM for HK254), oligomycin (1 µM), rotenone (1 µM), and pictilisib (1 µM). Comparisons were made using two-tailed unpaired Student's t-test. Data represent means±s.e.m. values of three independent experiments. ****p<0.0001.

FIG. 36A depicts the brain and plasma concentrations of Idasanutlin at indicated time points (n=2 mice/time point) in non-tumor bearing mice. FIG. 36B depicts the immunohistochemistry (IHC) analysis of p53 expression in intracranial tumor-bearing xenografts following 36 hours Idasanutlin (50 mg/kg) treatment. FIG. 36C depicts the percent change in $^{18}$F-FDG uptake following 15 hours of erlotinib treatment in GBM39 (n=3) and HK393 (n=5) intracranial xenografts. FIG. 36D depicts the change in mice body weight following daily treatment with erlotinib (75 mg/kg) or combined erlotinib (75 mg/kg) and Idasanutlin (50 mg/kg). All treatments were done orally. Data represent means±s.e.m. values of three independent experiments. *p<0.05.

DETAILED DESCRIPTION OF THE INVENTION

Figure 1:
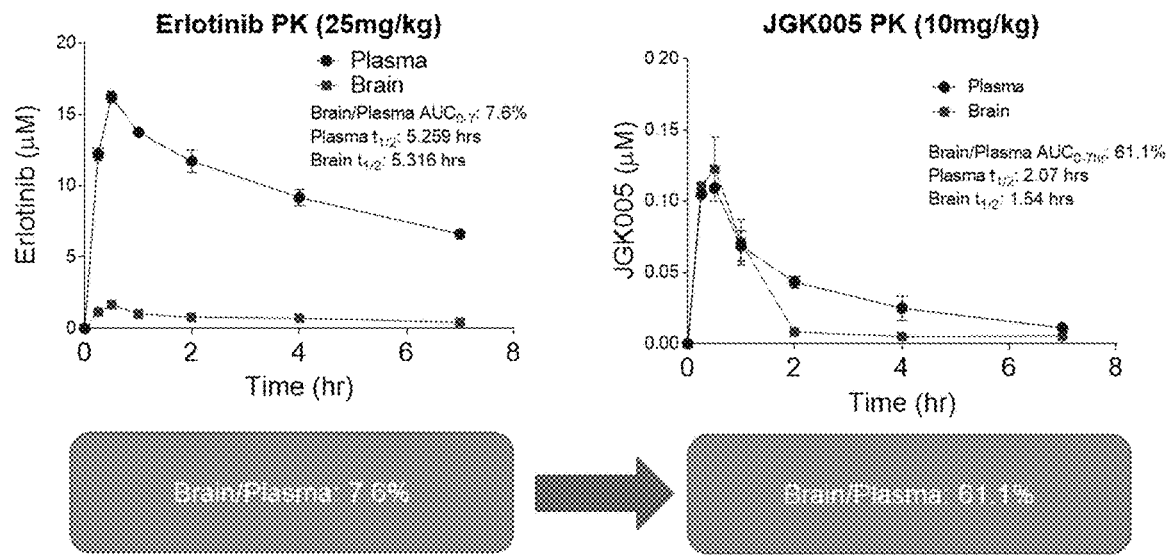
FIG. 1 depicts the oral pharmacokinetics of JGK005 at 10 mg/kg and those of erlotinib at 25 mg/kg. JGK005 has good CNS penetration compared to erlotinib.
Figure 2:
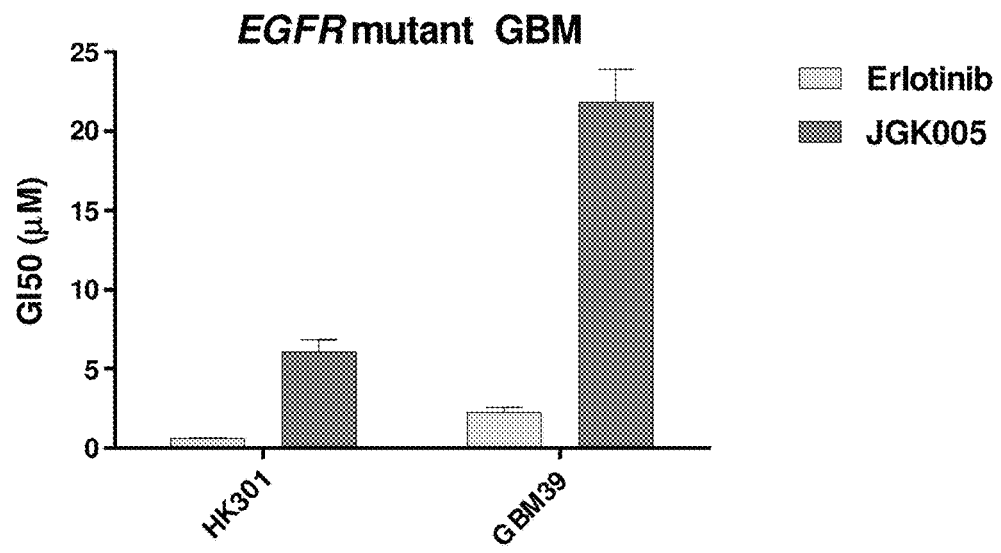
FIG. 2 depicts the activity of erlotinib (left columns) and JGK005 (right columns) against EGFR mutant glioblastomas HK301 and GBM39, respectively. JGK005 has lower activity than erlotinib in both cases.
Figure 3:
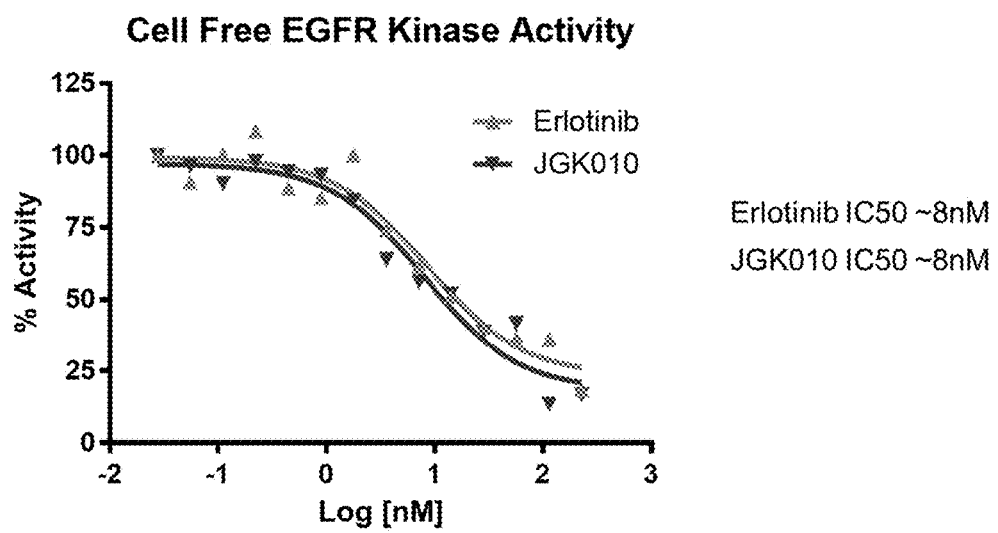
FIG. 3 depicts the cell free EGFR kinase activities of erlotinib and JGK010. Both compounds have an $IC_{50}$ of approximately 8 nM.
Figure 4:
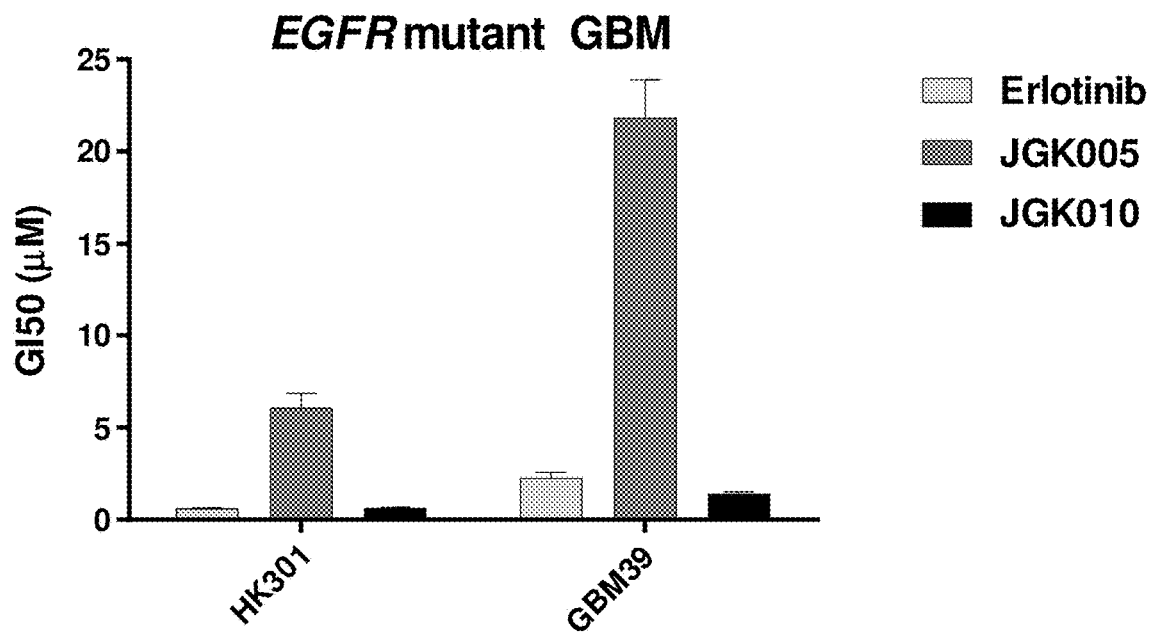
FIG. 4 depicts the potencies of erlotinib (left columns), JGK005 (center columns), and JGK010 (right columns) against HK301 and GBM39 cells.
Figure 5:
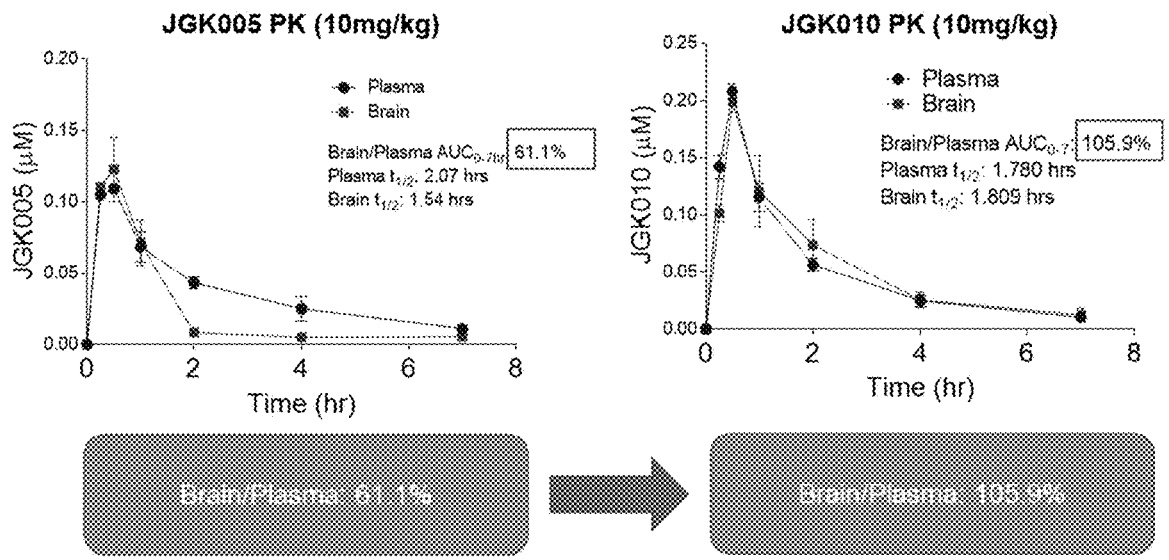
FIG. 5 shows the oral pharmacokinetics of JGK005 at 10 mg/kg and of JGK010 at 10 mg/kg.
Figure 6:
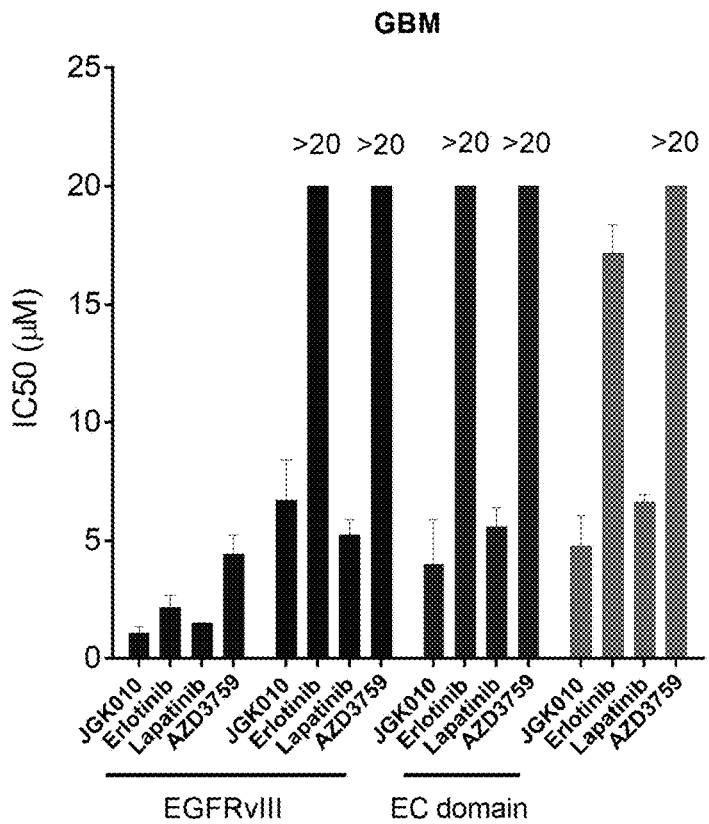
FIG. 6 depicts comparisons of EGFR inhibitors in multiple primary glioblastoma cell lines. Columns 1-4: GBM39 (EGFRvIII), 5-8: GS100 (EGFRwt/EGFRvIII), 9-12: GS017 (A289T), 13-16: GS024 (EGFR polysomy).
Figure 7A:
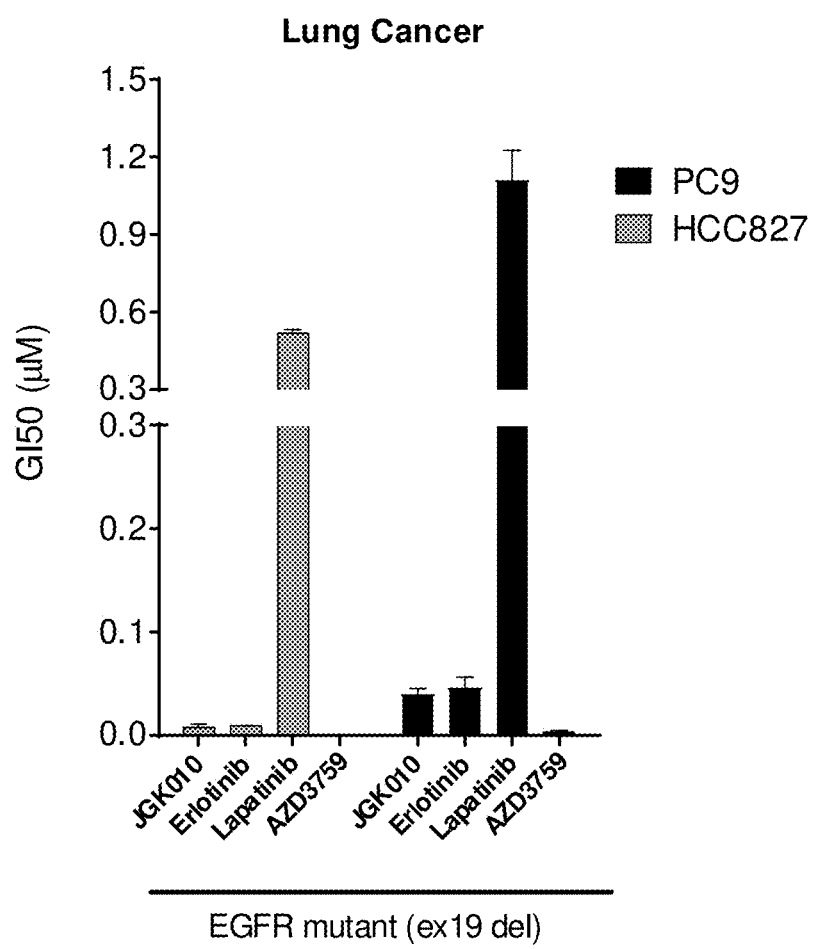
FIG. 7A depicts JGK010 activity in EGFR altered lung cancer.
Figure 7B:
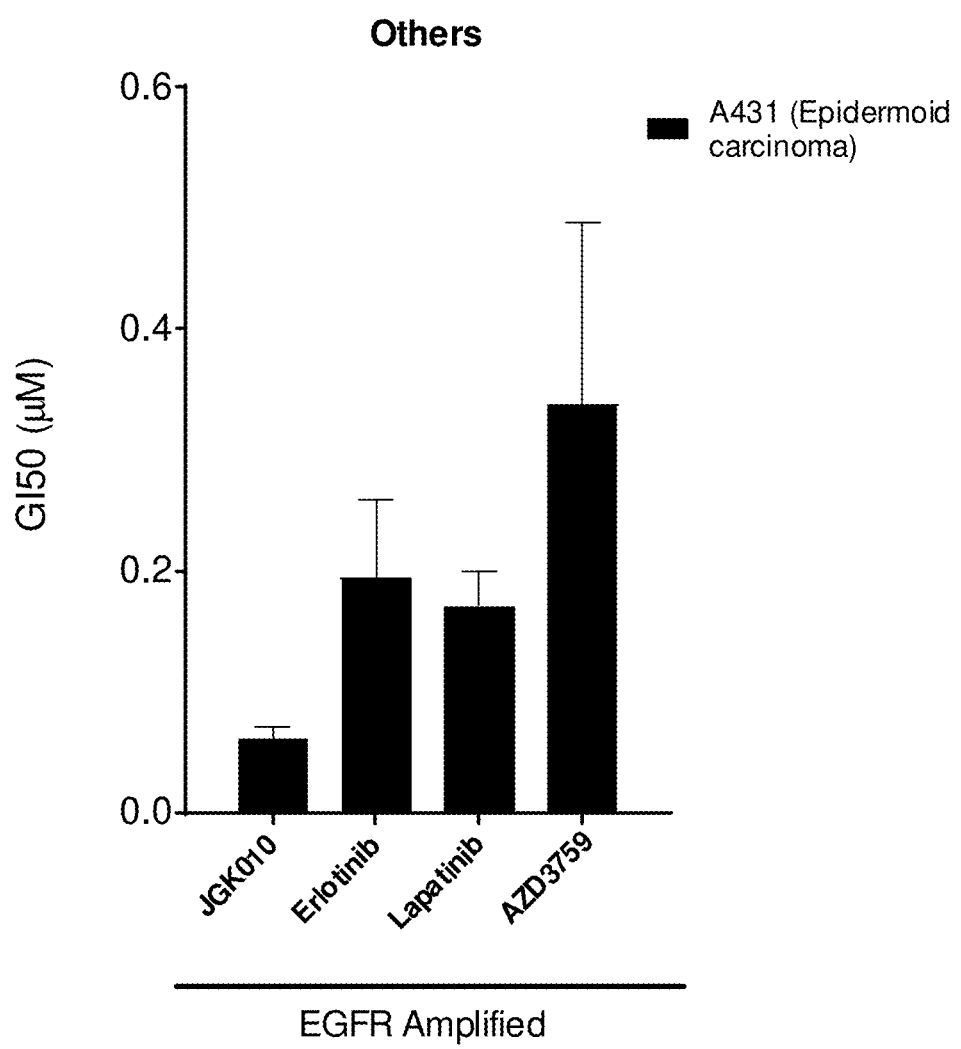
FIG. 7B depicts JGK010 activity in EGFR Amp epidermoid carcinoma.
Figure 8A:
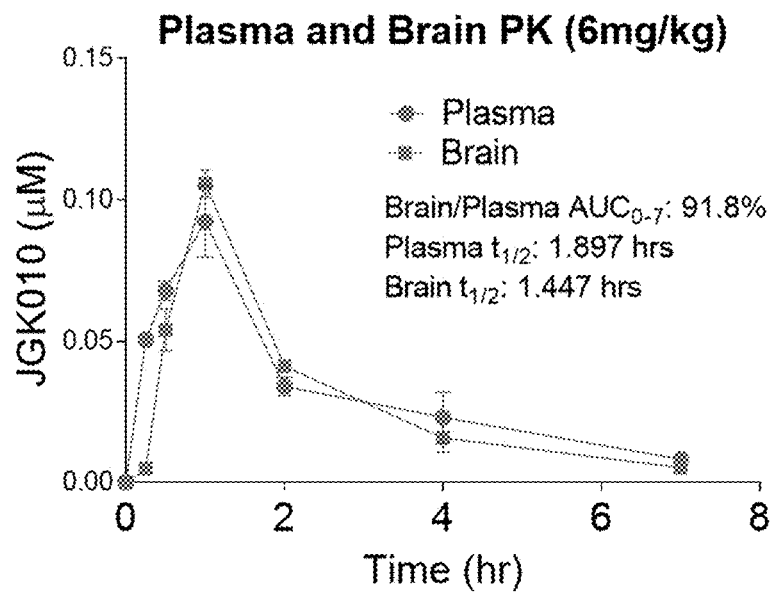
FIG. 8A depicts JGK010 oral pharmacokinetics at 6 mg/kg.
Figure 8B:
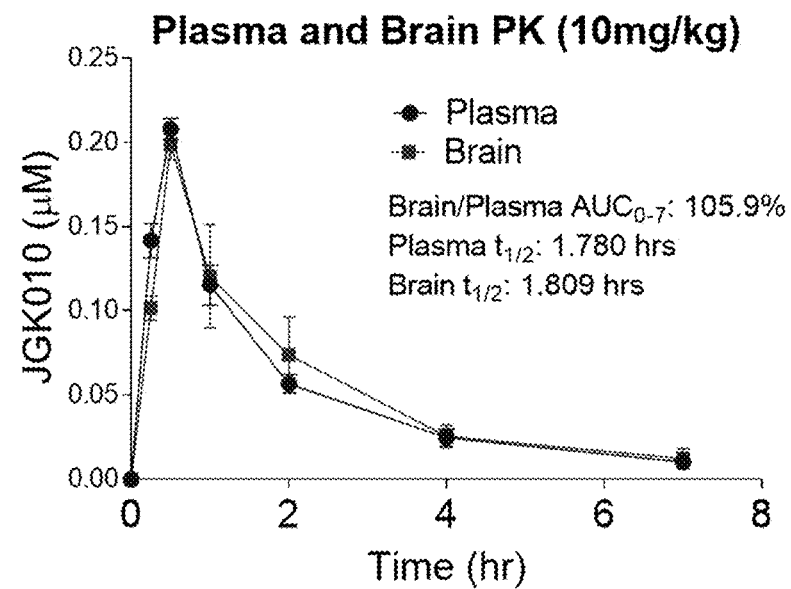
FIG. 8B depicts JGK010 oral pharmacokinetics at 10 mg/kg.
Figure 8C:
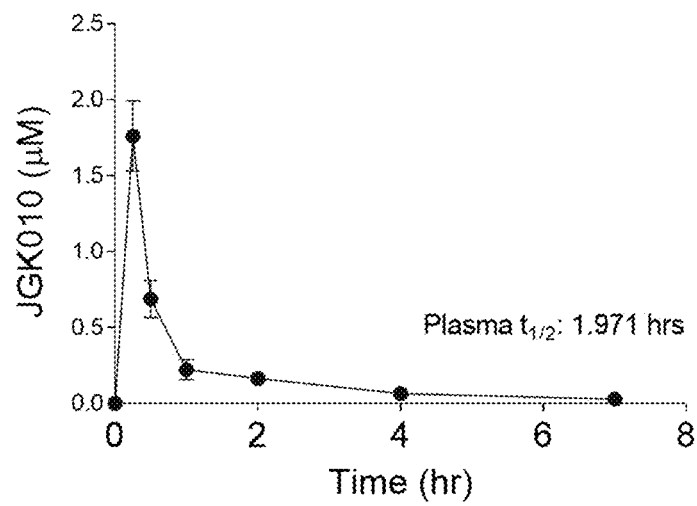
FIG. 8C depicts JGK010 IV pharmacokinetics at 6 mg/kg.
Figure 8D:
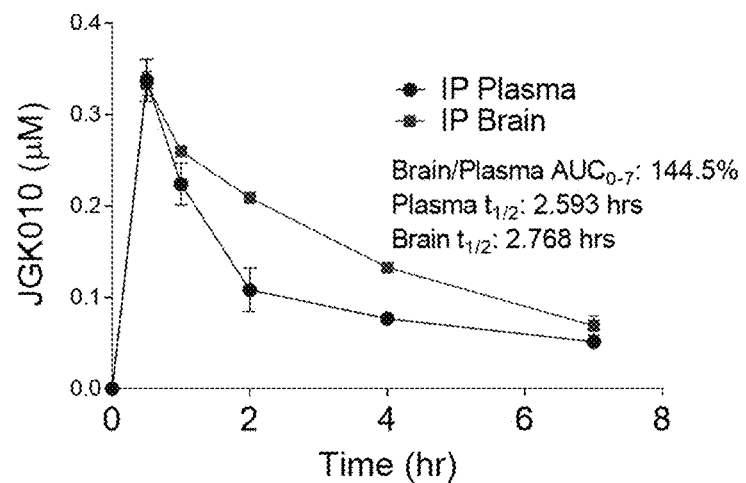
FIG. 8D depicts JGK010 IP pharmacokinetics at 6 mg/kg.
Figure 9:
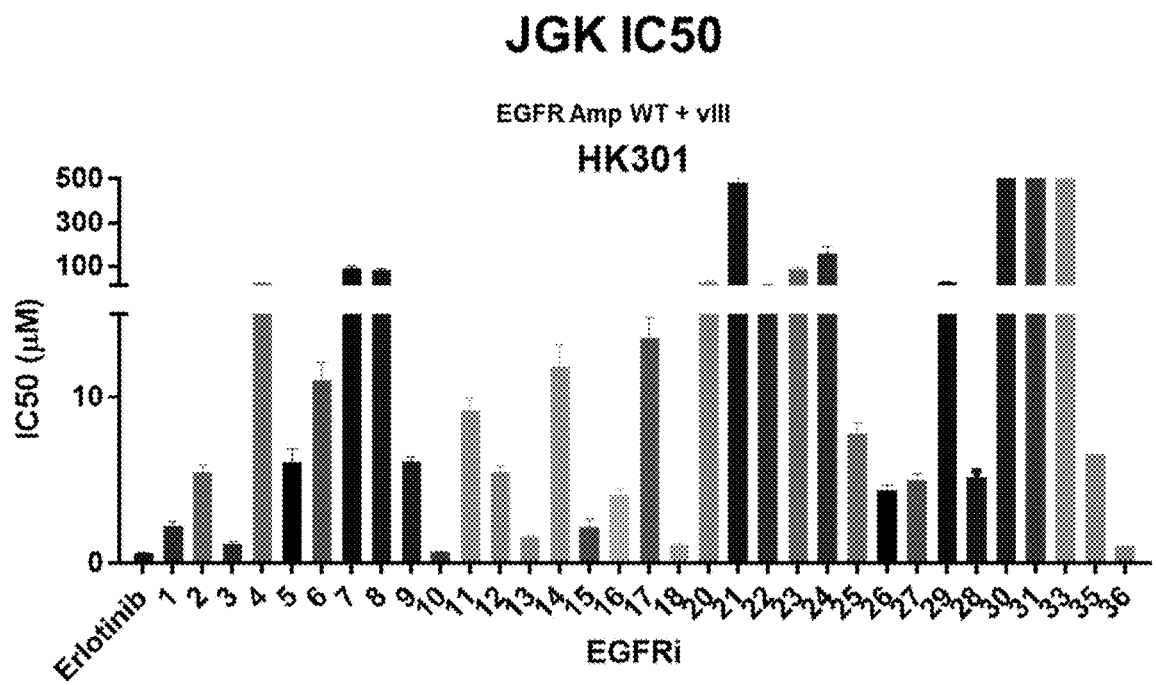
FIG. 9 depicts the activities of erlotinib and exemplary compounds of the disclosure against EGFR Amp WT+vIII HK301.
Figure 10:
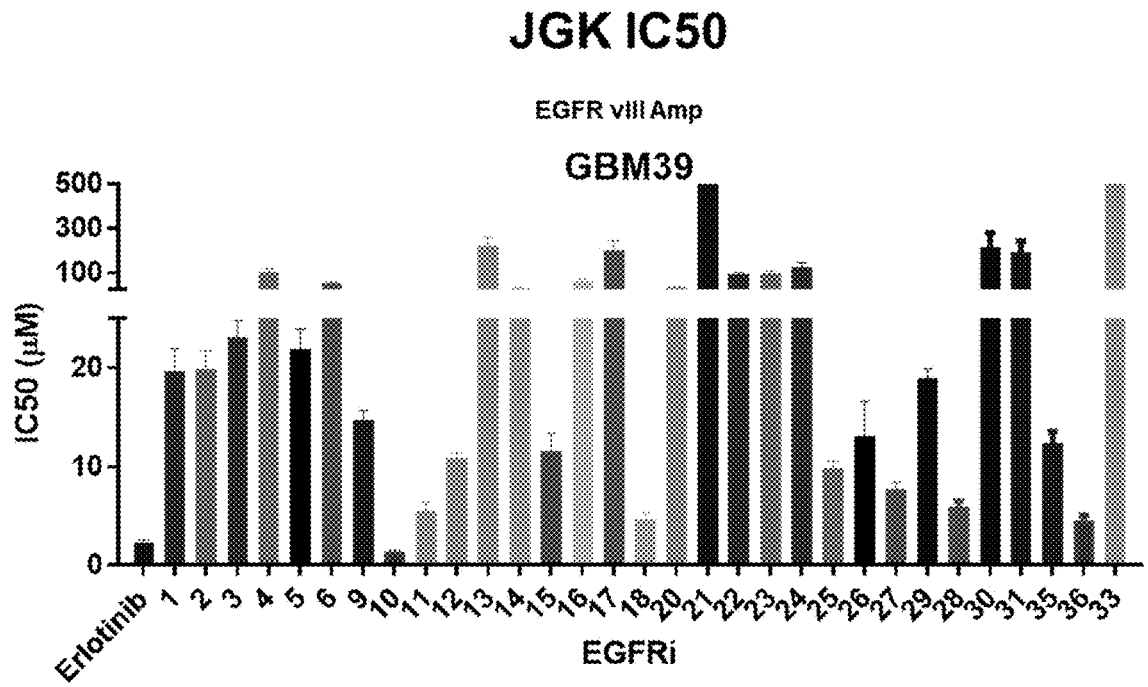
FIG. 10 depicts the activities of erlotinib and exemplary compounds of the disclosure against EGFR vIII Amp GBM 39.
Figure 11:
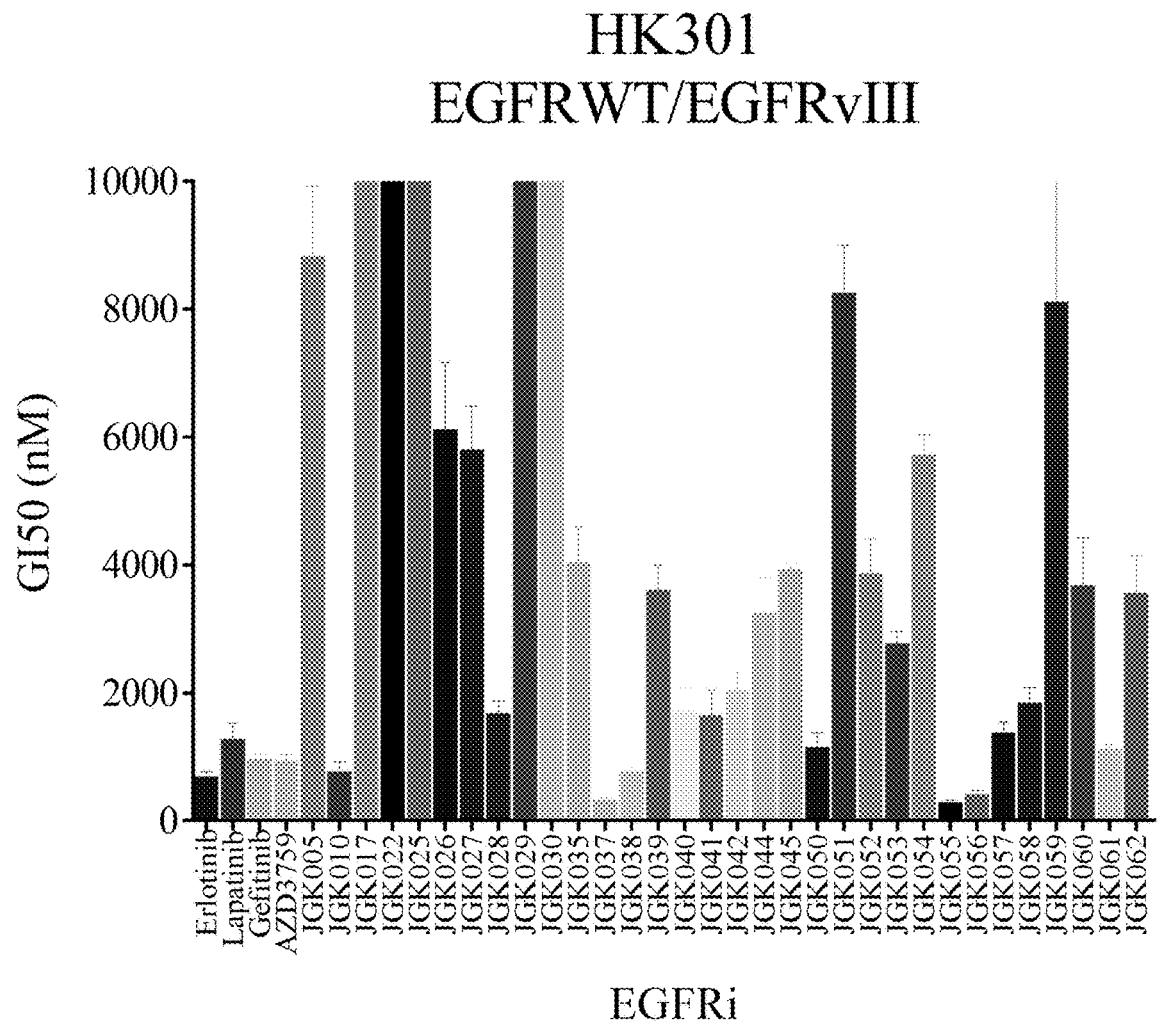
FIG. 11 depicts the activities of erlotinib and exemplary compounds of the disclosure against HK301 cells.
Figure 12:
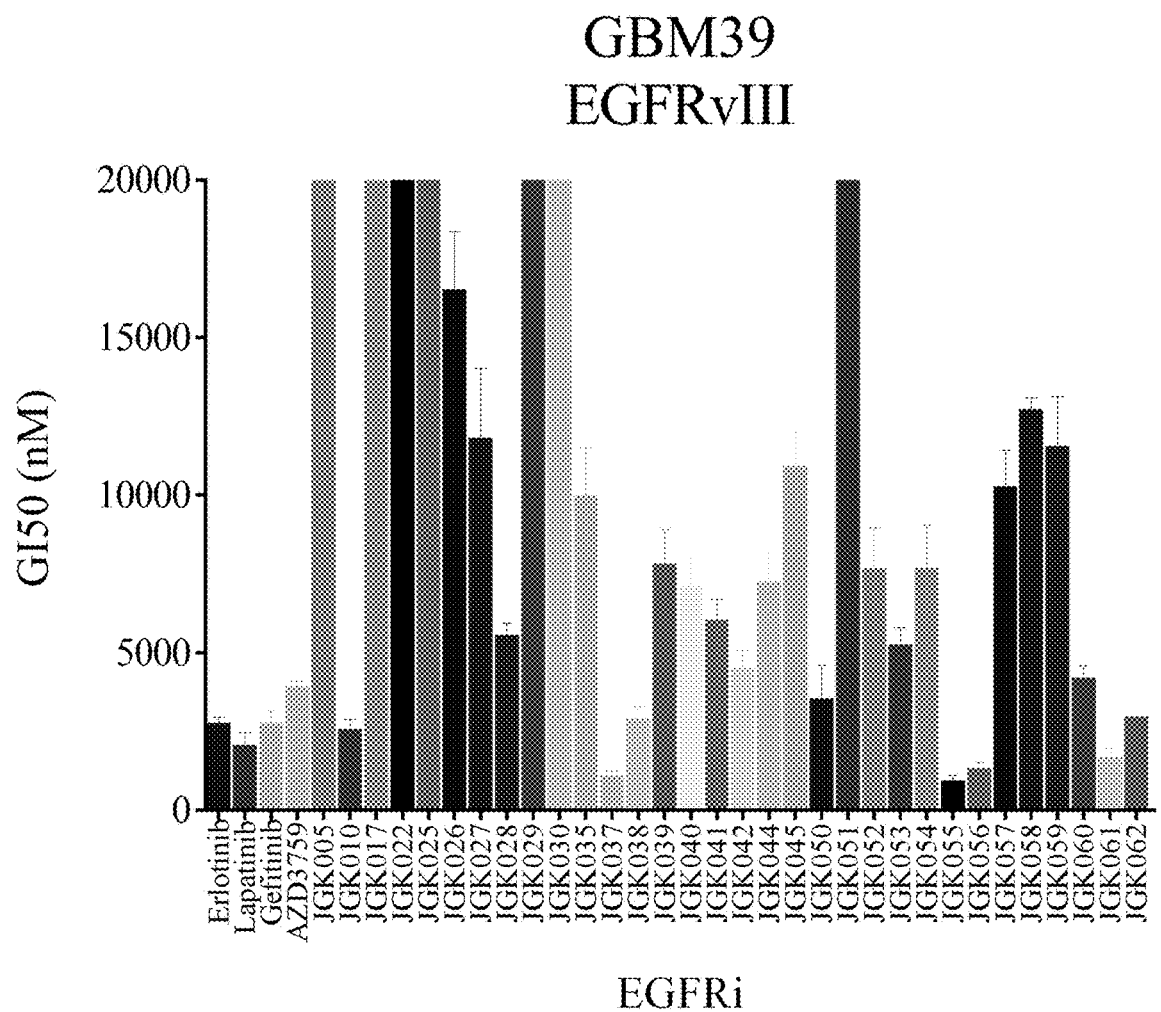
FIG. 12 depicts the activities of erlotinib and exemplary compounds of the disclosure against GBM 39 cells.
Figure 13A:
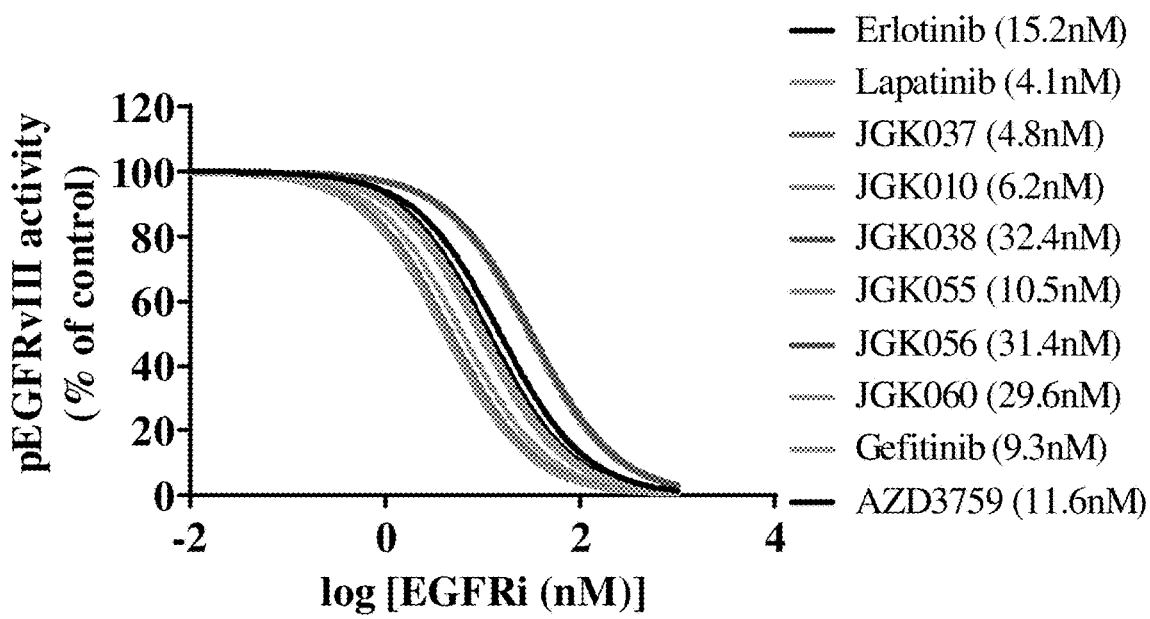
FIG. 13A depicts the phosphor-EGFR vIII inhibition of erlotinib and exemplary compounds of the disclosure.
Figure 13B:
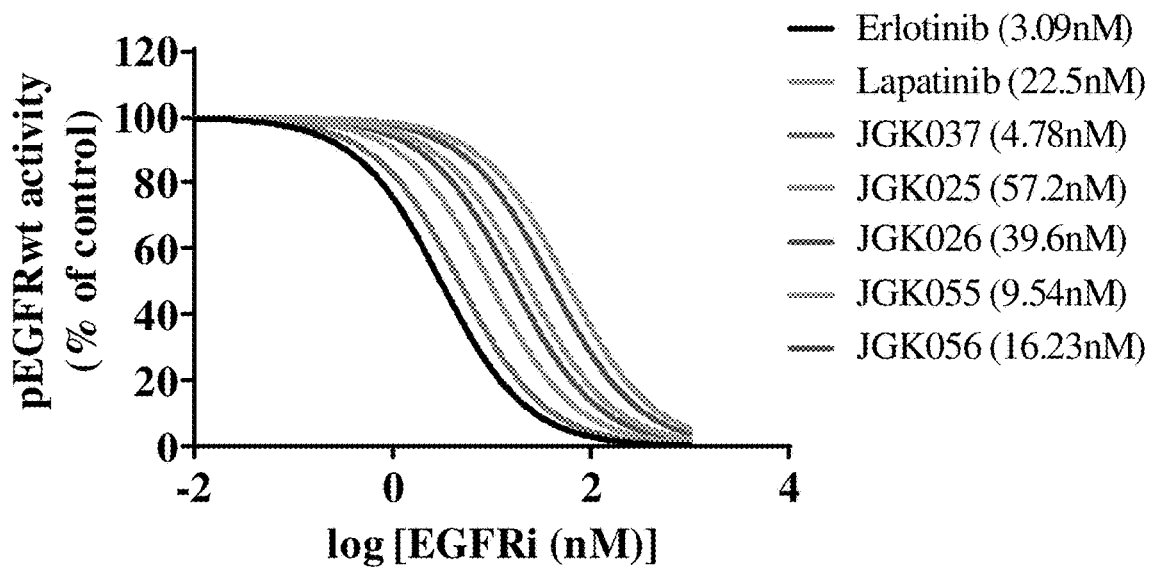
FIG. 13B depicts the phosphor-EGFR vIII inhibition of erlotinib and exemplary compounds of the disclosure.
Figure 14A:
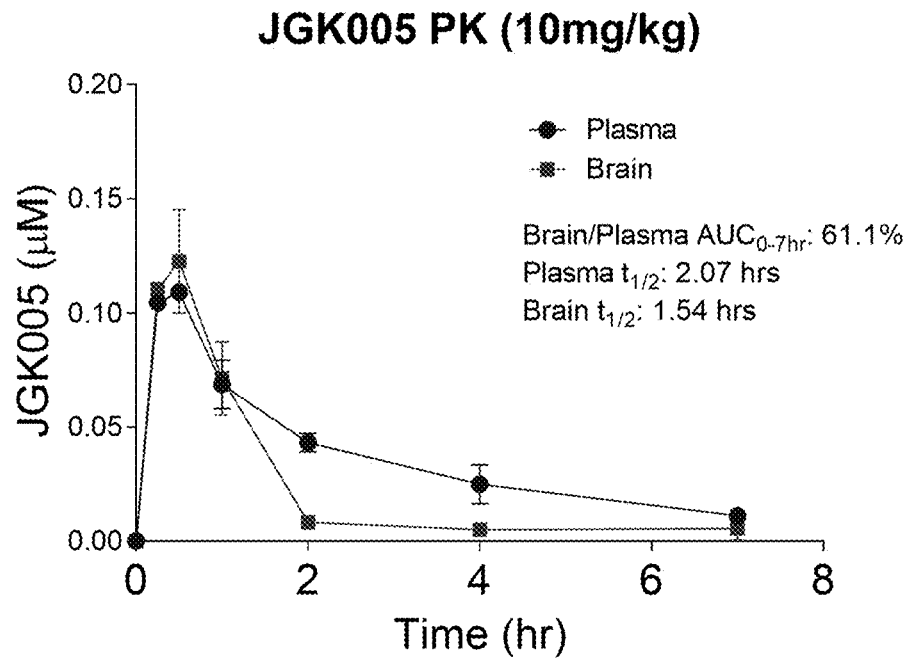
FIG. 14A depicts the pharmacokinetics of JGK005.
Figure 14B:
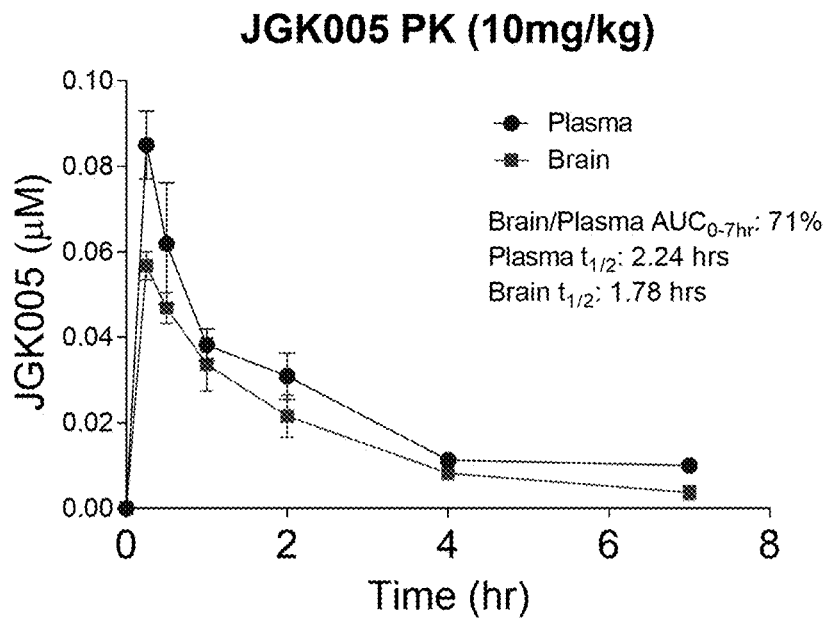
FIG. 14B depicts the pharmacokinetics of JGK005.
Figure 15A:
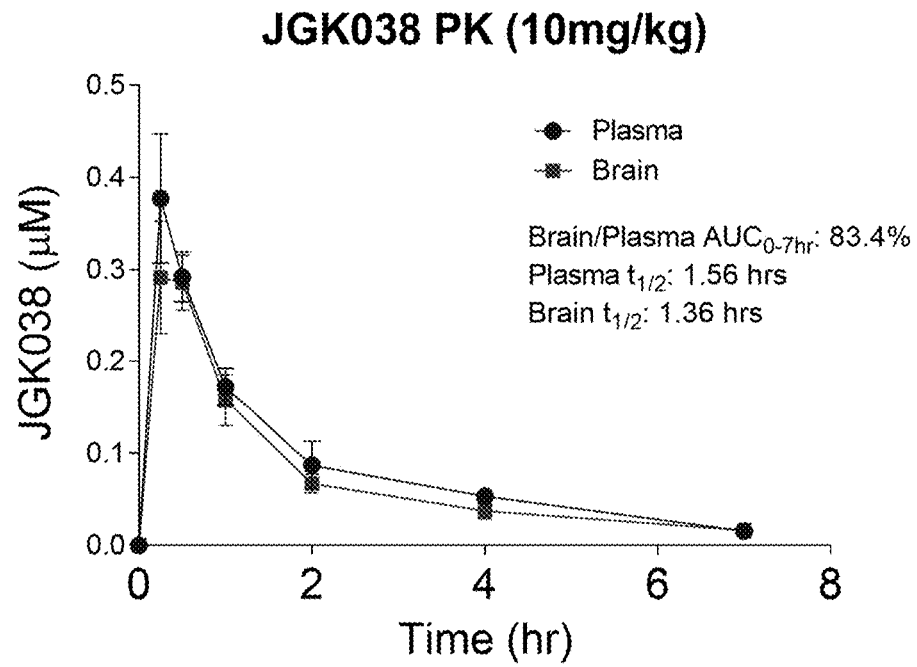
FIG. 15A depicts the pharmacokinetics of JGK038.
Figure 15B:
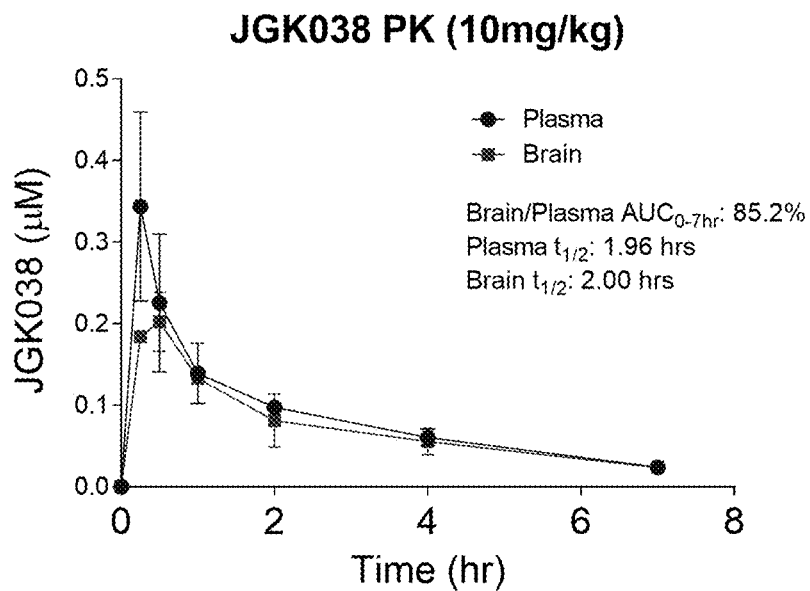
FIG. 15B depicts the pharmacokinetics of JGK038.
Figure 16A:
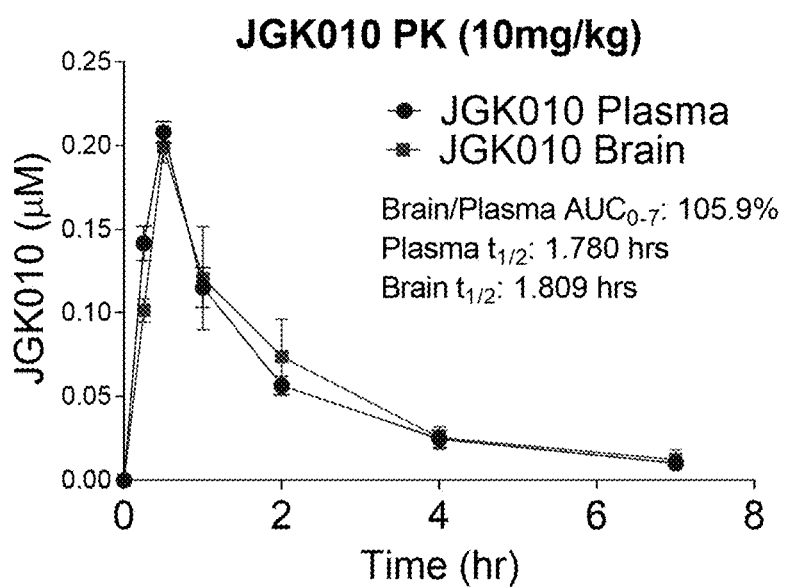
FIG. 16A depicts the pharmacokinetics of JGK010.
Figure 16B:
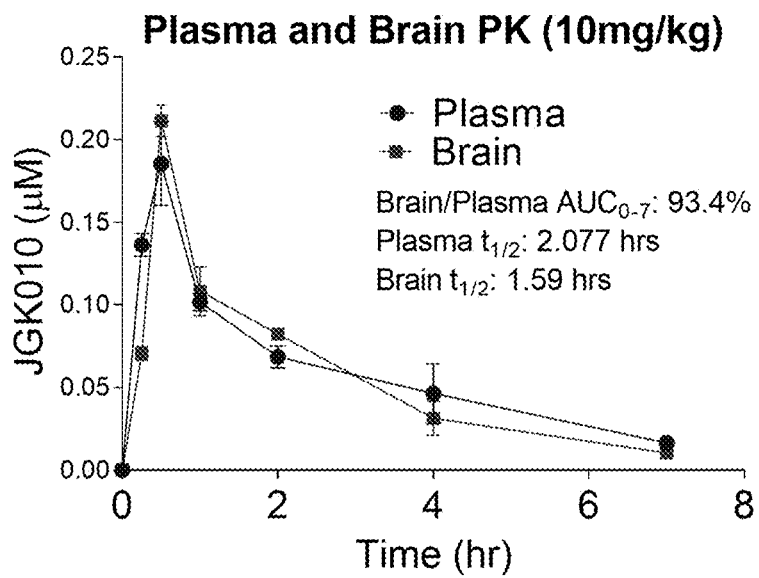
FIG. 16B depicts the pharmacokinetics of JGK010.
Figure 17A:
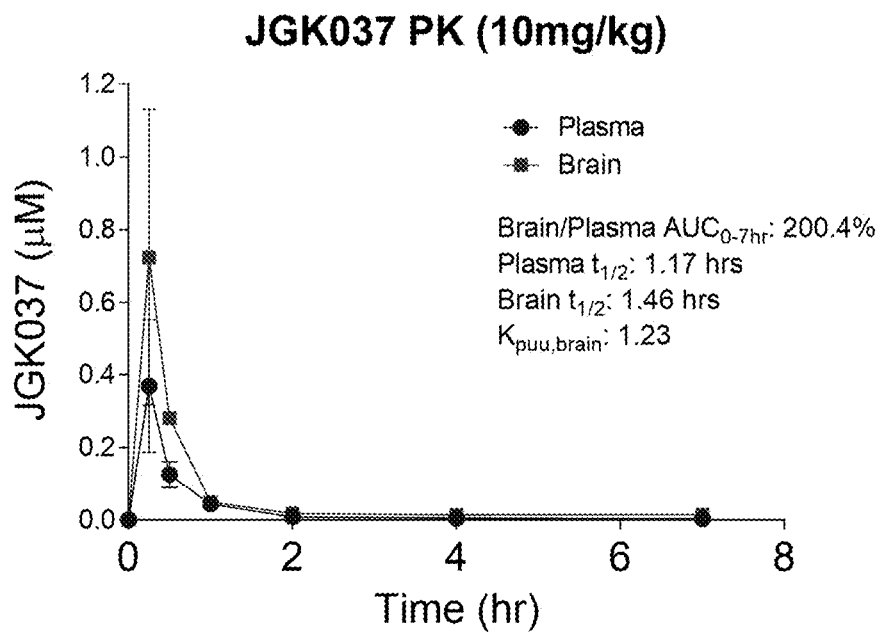
FIG. 17A depicts the pharmacokinetics of JGK037.
Figure 17B:
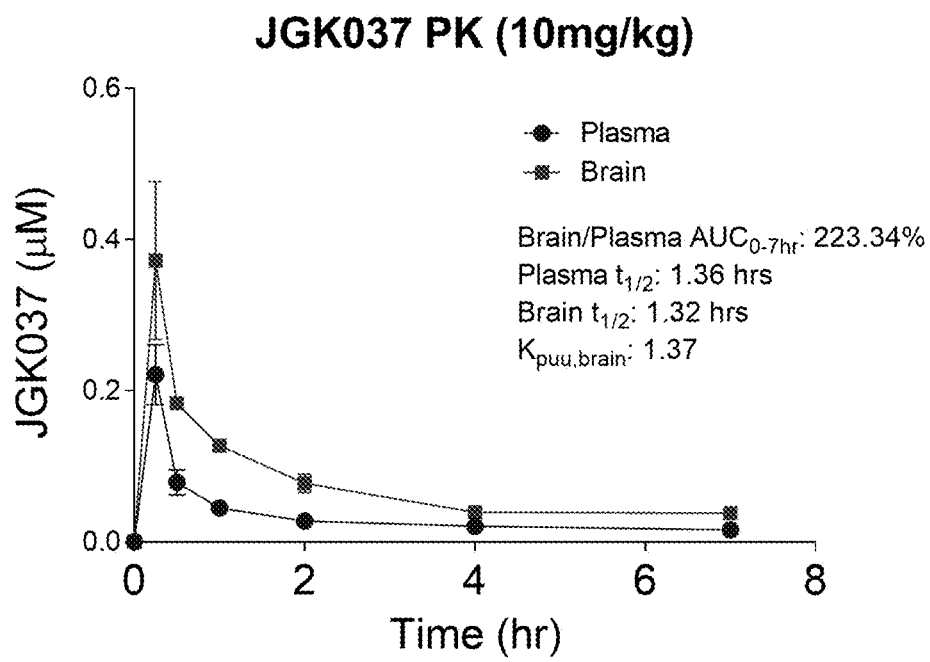
FIG. 17B depicts the pharmacokinetics of JGK037.
Figure 18A:
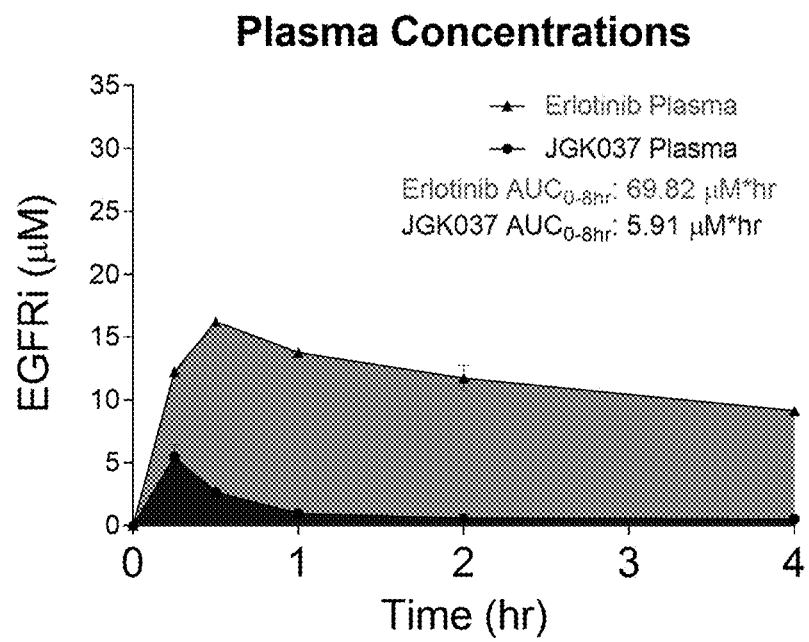
FIG. 18A depicts a comparison of mouse brain/blood pharmacokinetics between Erlotinib and JGK037.
Figure 18B:
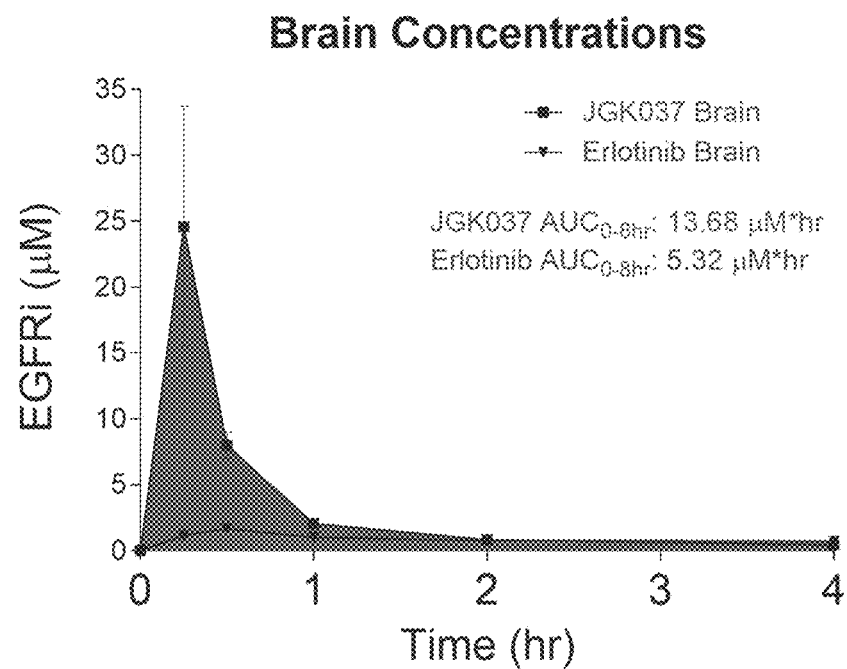
FIG. 18B depicts a comparison of mouse brain/blood pharmacokinetics between Erlotinib and JGK037.
Figure 19:
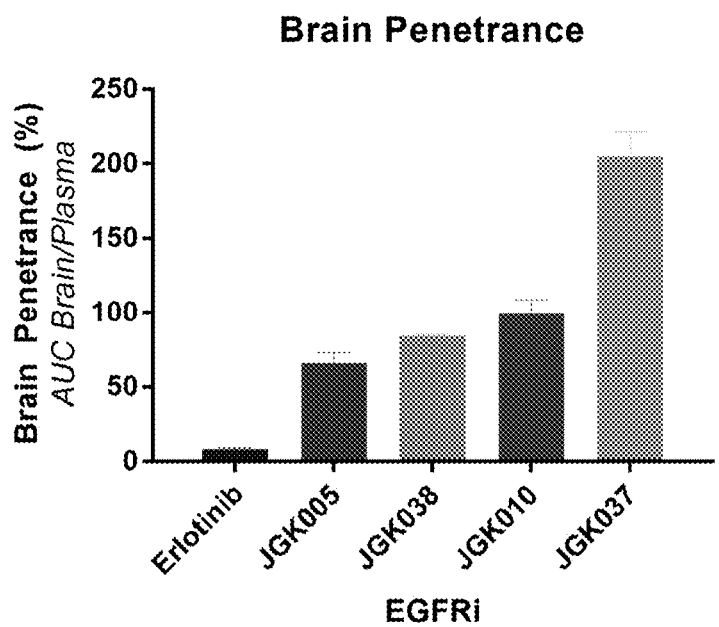
FIG. 19 depicts the brain penetration of erlotinib and exemplary compounds of the disclosure.
Figure 20:
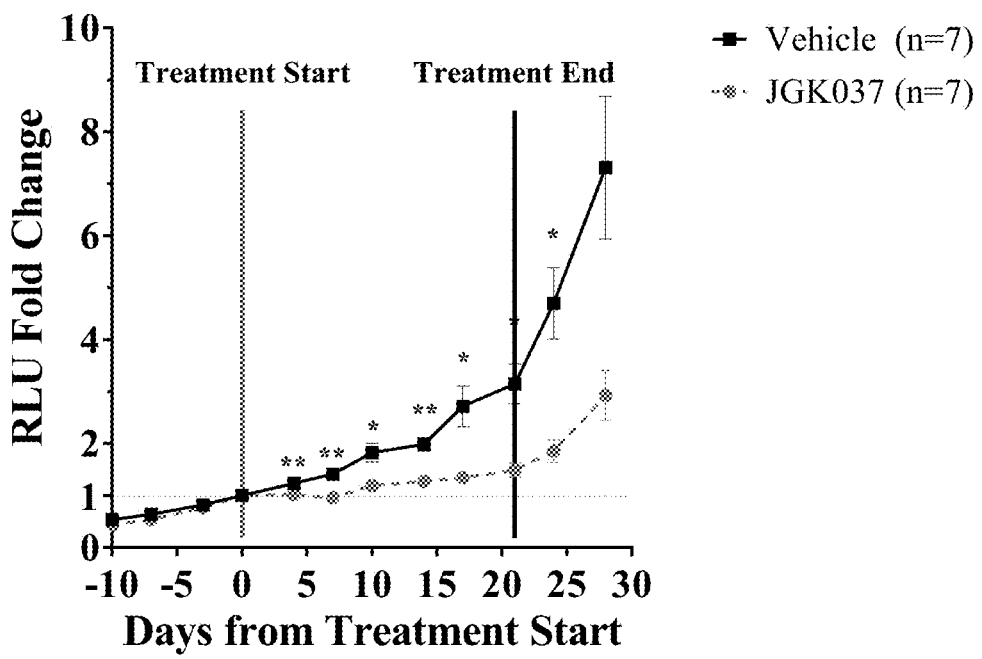
FIG. 20 depicts the effect of treatment with either a vehicle or JGK037 on RLU change.

Gliomas are the most commonly occurring form of brain tumor, with glioblastoma multiforme (GBM) being most malignant form, causing 3-4% of all cancer-related deaths (Louis et al. (2007) *Acta. Neuropathol.* 114: 97-109.). The World Health Organization defines GBM as a grade IV cancer characterized as malignant, mitotically active, and predisposed to necrosis. GBM has a very poor prognosis with a 5-year survival rate of 4-5% with the median survival rate of GBM being 12.6 months (McLendon et al. (2003) *Cancer.* 98:1745-1748.). This can attributed to unique treatment limitations such as a high average age of onset, tumor location, and poor current understandings of the tumor pathophysiology (Louis et al. (2007) *Acta. Neuropathol.* 114: 97-109). The standard current standard of care for GBM includes tumor resection with concurrent radiotherapy and chemotherapy and in recent years there have been few marked improvements that increase survival rates (Stewart, et al. (2002) *Lancet.* 359:1011-1018.).

The standard for GBM chemotherapy is temozolomide (TMZ), which is a brain-penetrant alkylating agent that methylates purines (A or G) in DNA and induces apoptosis (Stupp, et al. (2005) *N. Engl. J. Med.* 352:987-996). However, TMZ use has drawbacks in that significant risk arises from DNA damage in healthy cells and that GBM cells can rapidly develop resistance towards the drug (Carlsson, et al. (2014) *EMBO. Mol. Med.* 6: 1359-1370). As such, additional chemotherapy options are urgently required.

EGFR is a member of the HER superfamily of receptor tyrosine kinases together with ERBB2, ERBB3, and ERBB4. A common driver of GBM progression is EGFR amplification, which is found in nearly 40% of all GBM cases (Hynes et al. (2005) *Nat. Rev. Cancer.* 5: 341-354; Hatanpaa et al. (2010) *Neoplasia.* 12:675-684). Additionally, EGFR amplification is associated with the presence of EGFR protein variants: in 68% of EGFR mutants; there is a deletion in the N-terminal ligand-binding region between amino acids 6 and 273. These deletions in the ligand-binding domains of EGFR can lead to ligand-independent activation of EGFR (Yamazaki et al. (1990) *Jpn. J. Cancer Res.* 81: 773-779.).

Small molecule tyrosine kinase inhibitors (TKIs) are the most clinically advanced of the EGFR-targeted therapies, and both reversible and irreversible inhibitors are in clinical trials. Examples of the reversible inhibitors and irreversible inhibitors include erlotinib, gefitinib, lapatinib, PKI166, canertinib and pelitinib (Mischel et al. (2003) *Brain Pathol.* 13: 52-61). Mechanistically, these TKIs compete with ATP for binding to the tyrosine kinase domain of EGFR, however, these EGFR-specific tyrosine kinase inhibitors have been relatively ineffective against gliomas, with response rates only reaching as high as 25% in the case of erlotinib (Mischel et al. (2003) *Brain Pathol.* 13: 52-61; Gan et al. (2009) *J. Clin. Neurosci.* 16: 748-54). Although TKIs are well tolerated and display some antitumor activity in GBM patients, the recurrent problem of resistance to receptor inhibition limits their efficacy (Learn et al. (2004) *Clin. Cancer. Res.* 10: 3216-3224; Rich et al. (2004) *Nat. Rev. Drug Discov.* 3: 430-446). Additionally, recent studies have shown that brain plasma concentrations of gefitinib and erlotinib following therapy were only 6-11% of the starting dose, suggesting that these compounds may be failing to cross the blood-brain barrier as illustrated in table 1 (Karpel-Massler et al. (2009) *Mol. Cancer Res.* 7:1000-1012). Thus, insufficient delivery to the target may be another cause of the disappointing clinical results.

TABLE 1

Brain Penetration Rates of the Current Standard of Care Drugs

| Compound | Primary | Daily Dose | Plasma (ng/ml) | CSF (ng/ml) | Brain Penetration rate (%) |
|---|---|---|---|---|---|
| Afatinib | EGFR-mutant NSCLC | 50 | 66.7 | 0.46 | 0.7 |
| Alectinib | ALK-mutant NSCLC | 1200 | 1.5 (unbound conc.) | 1.3 | 86.7 |
| Crizotinib | ALK-mutant NSCLC | 500 | 237 | 0.616 | 0.26 |
| Erlotinib | EGFR-mutant NSCLC | 150 | 1140 ± 937 | 28.7 ± 16.8 | 2.77 ± 0.45 |
|  | EGFR-mutant NSCLC | 1500 (weekly) | 4445.9 | 51.1 | 1.2 |
| Gefitinib | EGFR-mutant NSCLC | 250 | 326 ± 116 | 3.7 ± 1.9 | 1.13 ± 0.36 |
|  | EGFR-mutant NSCLC | 750-1000 | 1345.9-5094.4 | 14.7-143.1 | 1.07-3.58 |
| Lapatinib | HER2 + breast cancer | 1250 | 1515, 3472 | 1.3, 4.5 | 0.09, 0.13 |

In light of this evidence, there remains an unmet clinical need for potent tyrosine kinase inhibitors that have the ability to cross the blood brain barrier and treat inhibit EGFR and its isoforms.

Furthermore, cross-talk among oncogenic signaling and metabolic pathways is shown by the inventors to create opportunities for novel combination therapies in GBM. More specifically, the inventors have discovered that acute inhibition of EGFR-driven glucose uptake induces minimal cell death, yet lowers the apoptotic threshold in patient-derived GBM cells and "primes" cells for apoptosis. Unexpectedly, mechanistic studies, by the inventors, revealed that Bcl-xL blocks cytoplasmic p53 from triggering intrinsic apoptosis, leading to tumor survival. Pharmacological stabilization of p53 (such as for example, with the brain-penetrant small molecule, Idasanutlin) enables p53 to engage the intrinsic apoptotic machinery, promoting synergistic lethality with targeting EGFR-driven glucose uptake in GBM xenografts. Notably, the inventors also discovered that rapid changes in $^{18}$F-fluorodeoxyglucose ($^{18}$F-FDG) uptake using, for example, non-invasive positron emission tomography could predict sensitivity to the combination in vivo.

The inventors, inter alia, identify a critical link between oncogene signaling, glucose metabolism, and cytoplasmic p53, which could be exploited for combination therapy in GBM and other malignancies Compounds of the Disclosure In one aspect, the present disclosure provides compounds of Formula I or Formula I*:

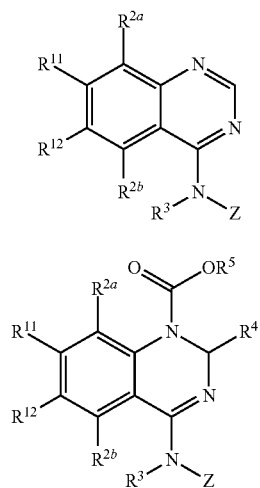

or a pharmaceutically acceptable salt thereof, wherein:

Z is aryl or heteroaryl;

$R^{2a}$ and $R^{2b}$ are each independently selected from hydrogen, alkyl, halo, CN, and $NO_2$;

$R^3$ is hydrogen, alkyl, or acyl;

$R^4$ is alkoxy;

$R^5$ is alkyl; $R^7$ and $R^8$ are, each independently, selected from hydrogen, alkyl, such as alkoxyalkyl, aralkyl, or arylacyl;

$R^{11}$ is hydrogen, alkyl, halo, CN, $NO_2$, $OR^7$, cycloalkyl, heterocyclyl, aryl or heteroaryl; and $R^{12}$ is hydrogen, alkyl, halo, CN, $NO_2$, $OR^8$, cycloalkyl, heterocyclyl, aryl or heteroaryl; or $R^{11}$ and $R^{12}$ taken together complete a carbocyclic or heterocyclic ring.

In certain preferred embodiments of Formula I or Formula I*, at least one of is $R^{2a}$ and $R^{2b}$ not H. In certain such embodiments of Formula I or Formula I*, if $R^{2a}$ is hydrogen, then $R^{2b}$ is selected from alkyl, halo, CN, and $NO_2$. In other such embodiments of Formula I or Formula I*, if $R^{2b}$ is hydrogen, then Rea is selected from alkyl, halo, CN, and $NO_2$.

In certain embodiments of Formula I or Formula I*, the compound is a compound of Formula (IVa) or Formula (IVb):

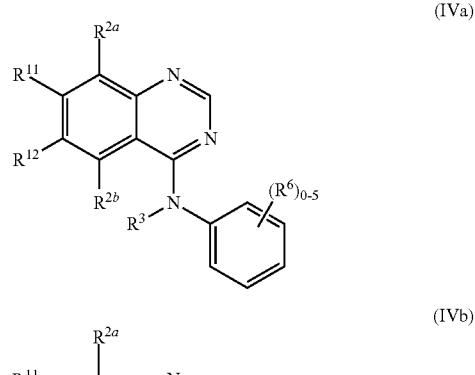

or a pharmaceutically acceptable salt thereof, wherein each instance of $R^6$ is independently selected from alkyl, alkoxy, OH, CN, $NO_2$, halo, alkenyl, alkynyl, aralkyloxy, cycloalkyl, heterocyclyl, aryl, or heteroaryl.

In certain embodiments, of Formula I, I*, Iva, and IVb, $R^{11}$ is hydrogen. In other preferred embodiments, $R^{11}$ is $OR^7$.

In certain embodiments, of Formula I, I*, Iva, and IVb, $R^7$ is hydrogen. In other embodiments, $R^7$ is alkyl. In yet other embodiments, $R^7$ is alkoxyalkyl. In yet other embodiments, $R^7$ is arylacyl.

In certain embodiments, of Formula I, I*, Iva, and IVb, $R^{12}$ is heteroaryl, such as furanyl. In certain embodiments, the heteroaryl is substituted with alkyl, alkoxy, OH, CN, $NO_2$, halo,

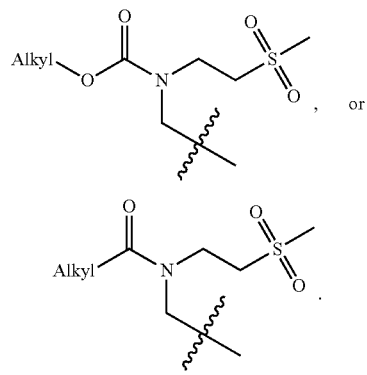

In other preferred embodiments, $R^{12}$ is $OR^8$.

In certain embodiments of Formula I, I*, Iva, and IVb, $R^8$ is hydrogen. In other embodiments, $R^8$ is alkyl. In yet other embodiments, $R^8$ is alkoxyalkyl. In certain embodiments, $R^8$ is alkyl substituted with

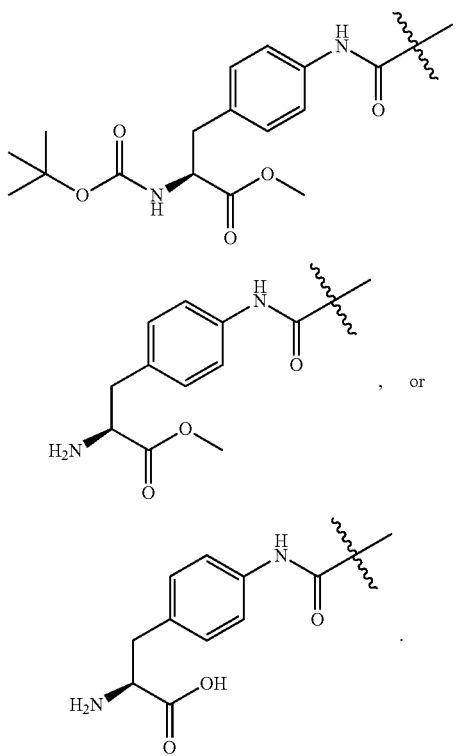

In certain preferred embodiments, of Formula I, I*, Iva, and IVb, $R^{11}$ and $R^{12}$ combine to form a carbocyclic or heterocyclic ring, such as a 5-member, 6-member, or 7-member carbocyclic or heterocyclic ring. In certain embodiments, the carbocyclic or heterocyclic ring is substituted with hydroxyl, alkyl (e.g., methyl), or alkenyl (e.g., vinyl).

In certain embodiments, of Formula I, I*, Iva, and IVb, the compound is a compound of Formula Ia, Ib, Ic, or Id:

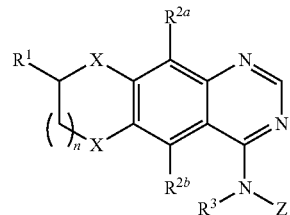

(Ic)

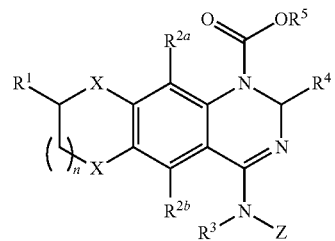

(Id)

or a pharmaceutically acceptable salt thereof, wherein:
X is O, S, or NH;
Z is aryl or heteroaryl;
$R^1$ is hydrogen or alkyl;
$R^{2a}$ and $R^{2b}$ are each independently selected from hydrogen, alkyl, halo, CN, and $NO_2$;
$R^3$ is hydrogen, alkyl, or acyl;
$R^4$ is alkoxy;
$R^5$ is alkyl; and
n is 0-3.

In certain embodiments of Formula Ia, Ib, Ic, or Id, either $R^{2a}$ or $R^{2b}$ is selected from alkyl, halo, CN, and $NO_2$. In certain preferred embodiments of Formula Ia, Ib, Ic, or Id, Z is phenyl. In certain preferred embodiments of Formula Ia, Ib, Ic, or Id, X is O. In certain preferred embodiments of Formula Ia, Ib, Ic, or Id, n is 1.

In certain embodiments of Formula Ia, Ib, Ic, or Id, the compound is a compound of Formula (IIa) or Formula (IIb):

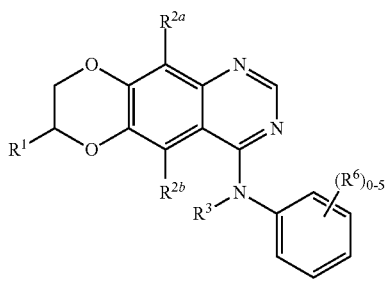

(IIa)

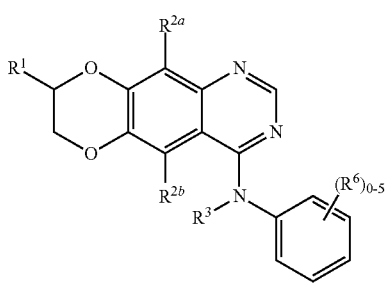

(IIb)

or a pharmaceutically acceptable salt, wherein
each instance of $R^6$ is independently selected from alkyl, alkoxy, OH, CN, $NO_2$, halo, alkenyl, alkynyl, aralkyloxy, cycloalkyl, heterocyclyl, aryl, or heteroaryl.

In certain embodiments, wherein $R^1$ is represented by Formula A:

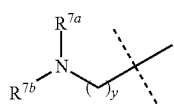

(A)

wherein,
$R^{7a}$ and $R^{7b}$ are each independently selected from alkyl, alkenyl, alkynl, cycloalkyl, heterocyclyl, aryl or heteroaryl; or $R^{7a}$ and $R^{7b}$ combine to form a heterocyclyl; and
y is 0-3

In certain embodiments of Formula IIa or IIb, $R^1$ is alkyl (e.g., methyl or ethyl). In certain embodiments, $R^1$ is substituted with heterocyclyl (e.g., morpholinyl, piperidinyl, pyrrolodinyl, or piperazinyl, such as N-methyl piperazinyl). In other embodiments, $R^1$ is substituted with amino (e.g., dimethyl amino) In other embodiments, $R^1$ is alkyl substituted with hydroxyl. In certain preferred embodiments, $R^1$ is in the S configuration. In other embodiments, $R^1$ is in the R configuration.

In certain preferred embodiments of Formula IIa or IIb, $R^3$ is hydrogen. In other embodiments, $R^3$ is acyl. In certain embodiments, $R^3$ is alkylacyl. In certain embodiments, $R^3$ is alkyloxyacyl. In certain embodiments, $R^3$ is acyloxyalkyl. In certain embodiments, $R^3$ is

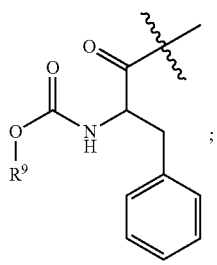

;

and $R^9$ is alkyl.

In certain embodiments of Formula IIa or IIb, Z is aryl or heteroaryl optionally substituted with one or more $R^6$; and each instance of $R^6$ is independently selected from alkyl, alkoxy, OH, CN, $NO_2$, halo, alkenyl, alkynyl, aralkyloxy, cycloalkyl, heterocyclyl, aryl, or heteroaryl. In certain preferred embodiments, Z is phenyl substituted with 1, 2, 3, 4, or 5 $R^6$. In certain embodiments, each $R^6$ is independently selected from halo, alkyl, alkynyl, or arylalkoxy. In even more preferred embodiments, Z is 2-fluoro-3-chlorophenyl, 2-fluorophenyl, 2,3-difluorophenyl, 2,4-difluorophenyl, 2,5-difluorophenyl, 2,6-difluorophenyl, 2,4,6-trifluorophenyl, pentafluorophenyl, 2-fluoro-3-bromophenyl, 2-fluoro-3-ethynylphenyl, and 2-fluoro-3-(trifluoromethyl)phenyl. In other even more preferred embodiments, Z is 3-ethynylphenyl. In yet other even more preferred embodiments, Z is 3-chloro-4-((3-fluorobenzyl)oxy)benzene. In yet other even more preferred embodiments, Z is 3-chloro-2-(trifluoromethyl)phenyl. In yet other even more preferred embodiments, Z is 3-bromophenyl. In yet other even more preferred embodiments, Z is 2-fluoro,5-bromophenyl. In yet other even more preferred embodiments, Z is 2,6-difluoro,5-bromophenyl. In certain embodiments, Z is substituted with one $R^6$ selected from

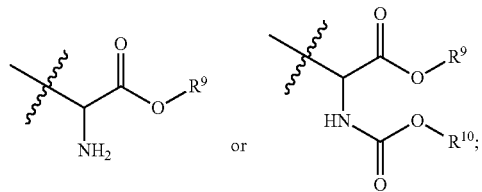

and $R^9$ and $R^{10}$ are independently selected from alkyl.

In certain embodiments of Formula IIIa or IIIb, the compound is a compound of Formula (IIIa):

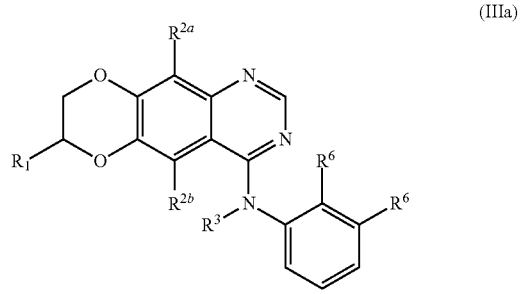

(IIIa)

and each $R^6$ is independently selected from fluoro, chloro, or bromo.

In certain embodiments of Formula IIIa or IIIb, the compound is a compound of Formula (IIIb):

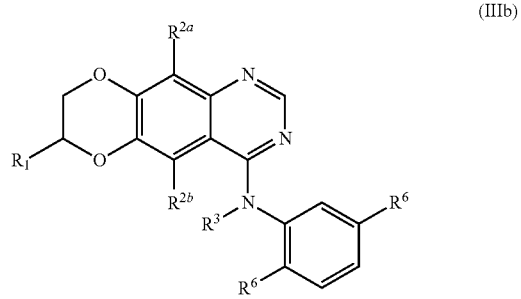

(IIIb)

and each $R^6$ is independently selected from fluoro, chloro, or bromo.

In certain embodiments of Formula IIIa or IIIb, the compound is a compound of Formula (IIIc):

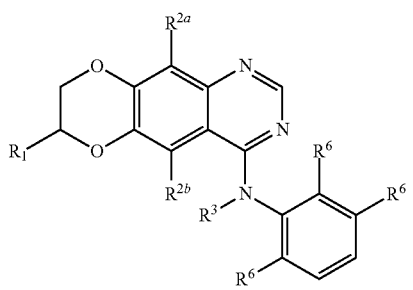

(IIIc)

and each $R^6$ is independently selected from fluoro, chloro, or bromo.

In certain embodiments of Formula Ia, Ib, Ic, Id, IIa, IIb, IIIc, IIIb, or IIIc, $R^{2a}$ is halo (e.g., fluoro). In other preferred embodiments, $R^{2a}$ is hydrogen.

In certain embodiments of Formula Ia, Ib, Ic, Id, IIa, IIb, IIIc, IIIb, or IIIc, $R^{2b}$ is halo (e.g., fluoro). In other preferred embodiments, $R^{2b}$ is hydrogen.

In certain embodiments of Formula Ia, Ib, Ic, Id, IIa, IIb, IIIa, IIIb, or IIIc, the compound is

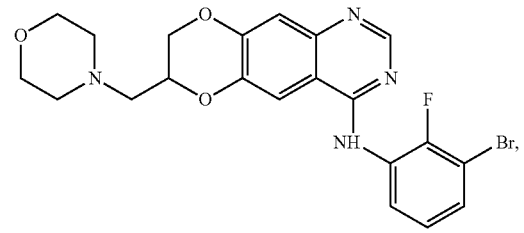

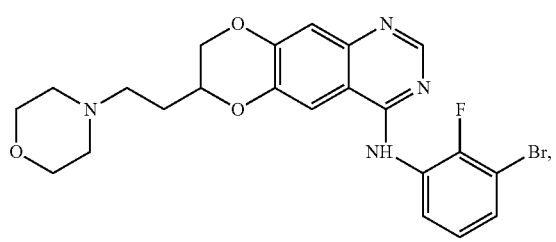

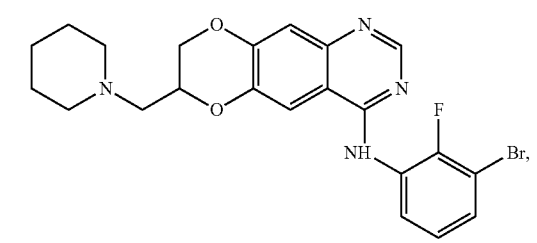

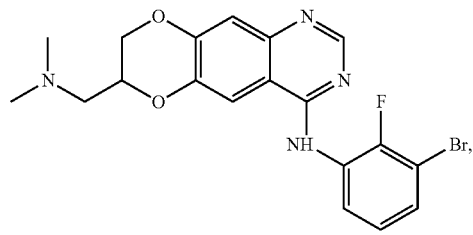

-continued

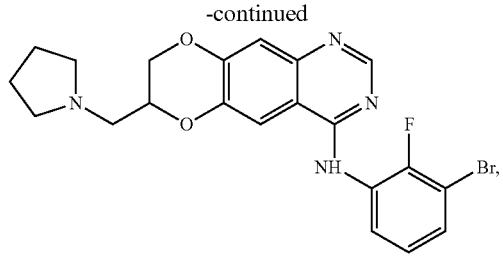

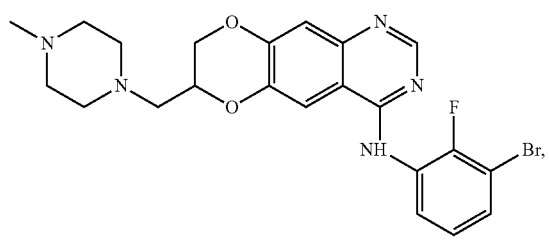

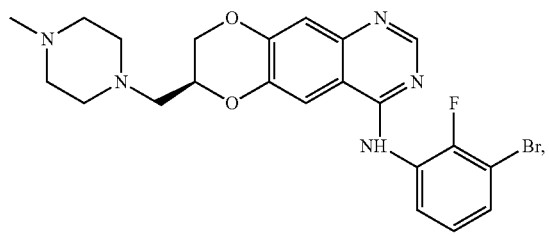

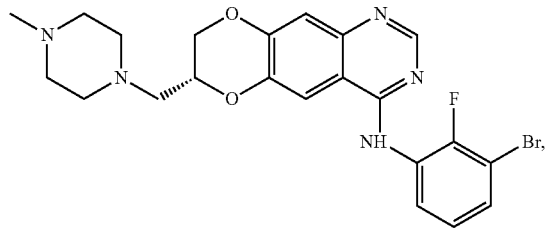

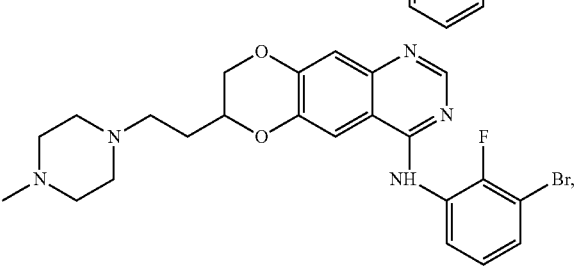

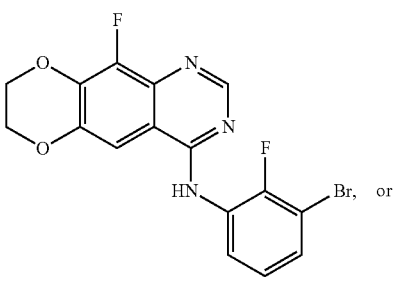 or

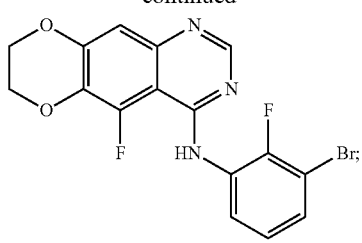
or a pharmaceutically acceptable salt thereof.
In certain embodiments of Formula Ia, Ib, Ic, Id, IIa, IIb, IIIa, IIIb, or IIIc, the compound is
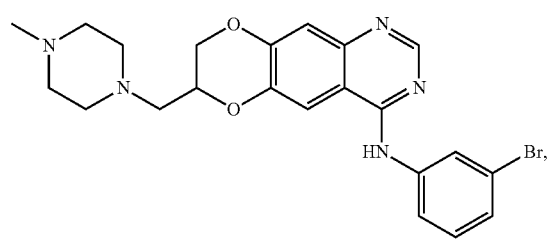
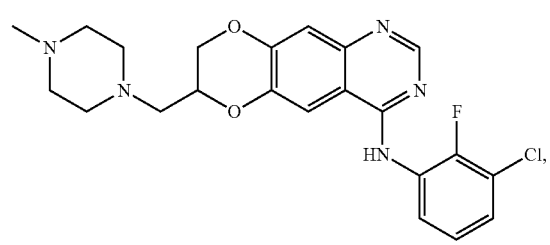
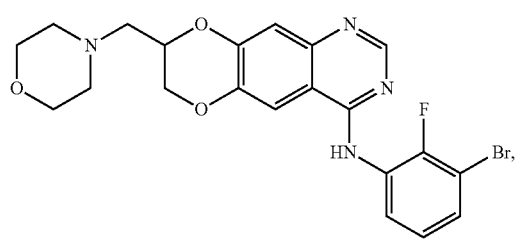
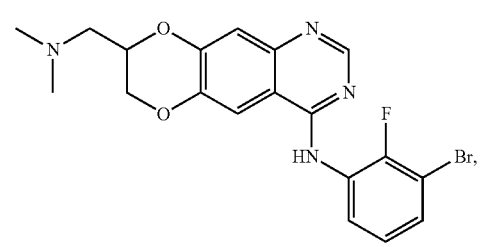
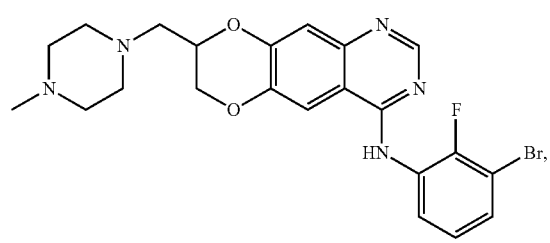
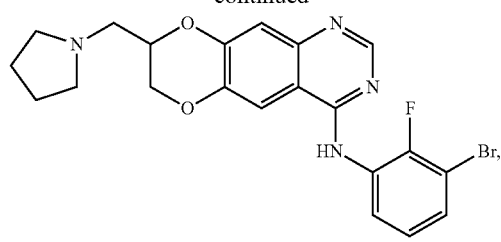
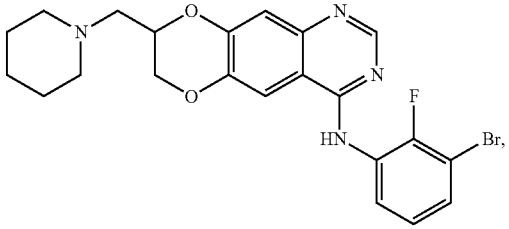
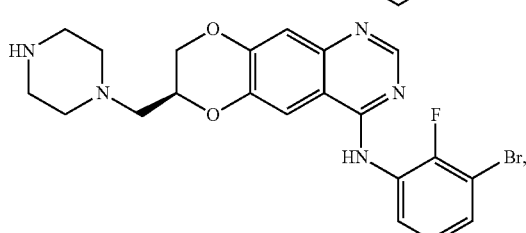
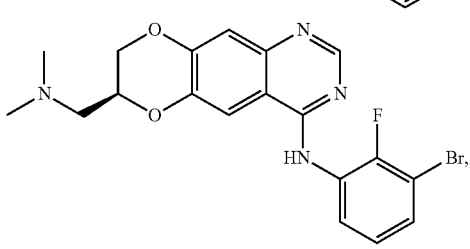
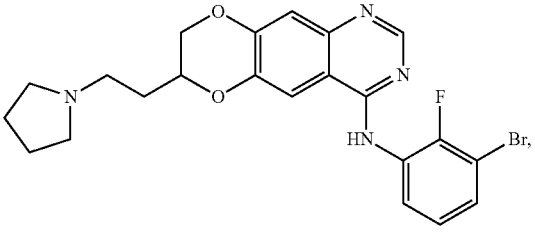
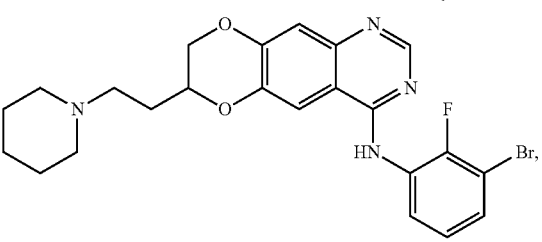

-continued

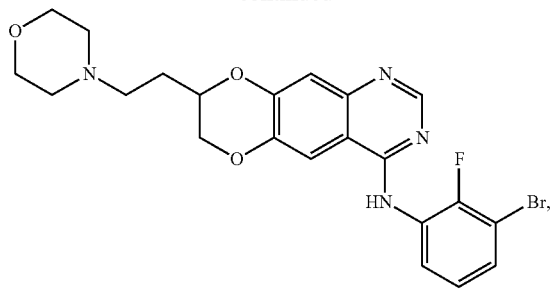

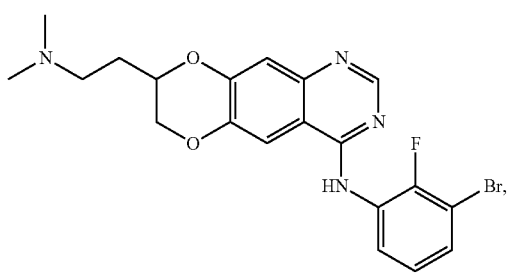

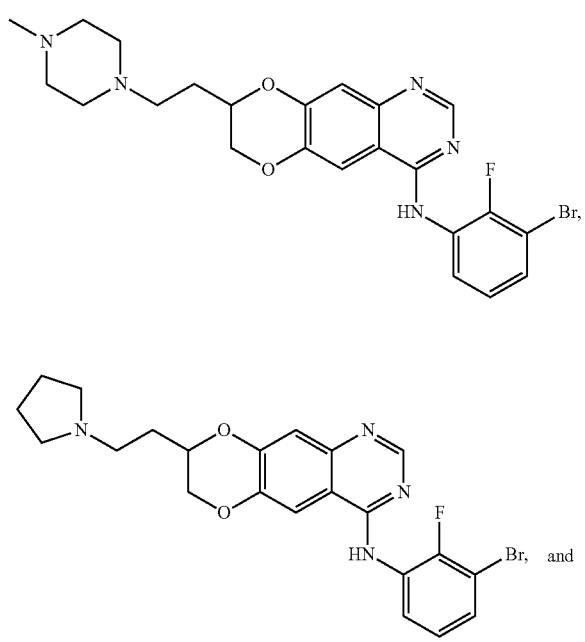

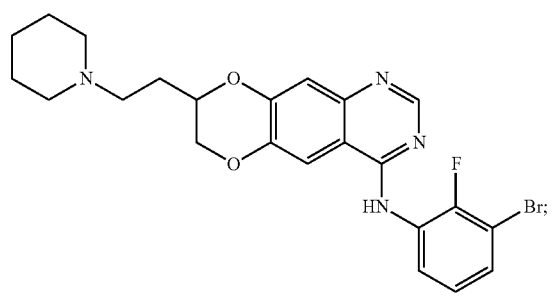

or a pharmaceutically acceptable salt thereof.

In certain embodiments of Formula I, the compound is

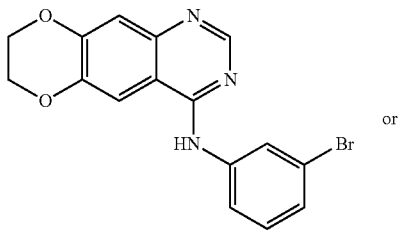

or

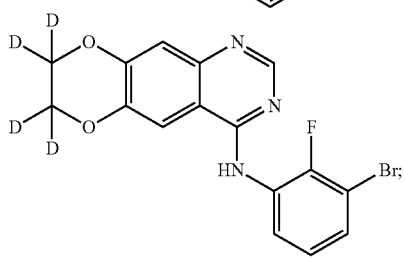

or a pharmaceutically acceptable salt thereof.

In certain embodiments of Formula Ia, Ib, Ic, Id, IIa, IIb, IIIa, IIIb, or IIIc, the compound is

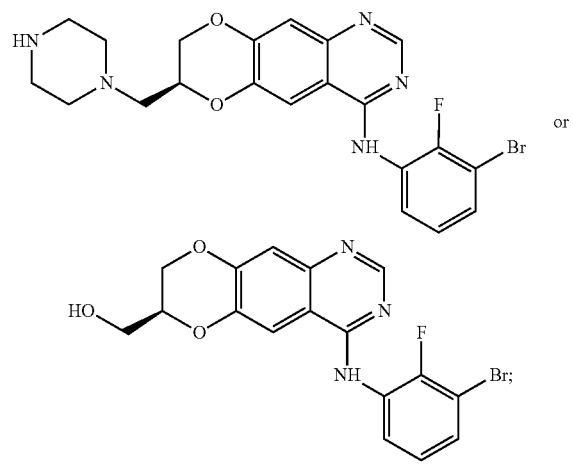

or a pharmaceutically acceptable salt thereof.

Methods of Treatment

In certain aspects, the present disclosure provides methods of inhibiting EGFR or ΔEGFR, comprising administering to a subject an amount of a compound of the disclosure.

In certain aspects, the present disclosure provides methods of treating cancer comprising of administering to a subject in need of a treatment for cancer an amount of a compound of the disclosure. In certain embodiments, the cancer is bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, or prostate cancer. In certain embodiments, the cancer is glioma, astrocytoma or glioblastoma. In certain embodiments, the cancer is glioblastoma. In certain embodiments, the cancer is glioblastoma multiforme. In certain embodiments, the method reduces cancer cell proliferation.

In certain aspects, the present disclosure provides methods of treating cancer in a subject, the method comprising administering to the subject a glucose metabolism inhibitor and an additional agent, wherein the glucose metabolism is a compound of the disclosure or a pharmaceutically acceptable salt thereof and the additional agent is a cytoplasmic p53 stabilizer. In certain embodiments, the cancer is bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, or prostate cancer. In certain embodiments, the cancer is glioma, astrocytoma or glioblastoma. In certain embodiments, the cancer is glioblastoma. In certain embodiments, the cancer is glioblastoma multiforme. In certain embodiments, the method reduces cancer cell proliferation. In certain embodiments, the cancer is relapsed or refractory. In other embodiments, the cancer is treatment naïve.

In certain embodiments, the subject has been determined to be susceptible to the glucose metabolism inhibitor by a method comprising:
a. obtaining a first blood sample from the subject;
b. placing the subject on a ketogenic diet;
c. obtaining a second blood sample from the subject after being placed on a ketogenic diet for a period of time;
d. measuring glucose level in the first and in the second blood sample;
e. comparing the glucose level in the second blood sample with the glucose level in the first blood sample; and
f. determining that the subject is susceptible if the glucose level in the second blood sample is reduced as compared to glucose levels in the first blood sample.

In certain embodiments, the reduction in the glucose level between the second blood sample and the control blood sample is about or greater than 0.15 mM. In certain embodiments, the reduction in the glucose level between the second blood sample and the control blood sample is about or greater than 0.20 mM. In certain embodiments, the reduction in the glucose level between the second blood sample and the control blood sample is in the range of 0.15 mM-2.0 mM. In certain embodiments, the reduction in the glucose level between the second blood sample and the control blood sample is in the range of 0.25 mM-1.0 mM.

In certain embodiments, the cytoplasmic p53 stabilizer is an MDM2 inhibitor. In certain embodiments, the MDM2 inhibitor is a nutlin. In certain embodiments, the MDM2 inhibitor is nutlin-3 or idasanutlin. In certain embodiments, the subject is administererd 50 mg to 1600 mg of idasanutlin. In certain embodiments, the subject is administererd 100 mg of idasanutlin. In certain embodiments, the subject is administered 150 mg of idasanutlin. In certain embodiments, the subject is administered 300 mg of idasanutlin. In certain embodiments, the subject is administered 400 mg of idasanutlin. In certain embodiments, the subject is administered 600 mg of idasanutlin. In certain embodiments, the subject is administered 1600 mg of idasanutlin. In other embodiments, the MDM2 inhibitor is RO5045337, RO5503781, RO6839921, SAR405838, DS-3032, DS-3032b, or AMG-232.

In certain embodiments, the cytoplasmic p53 stabilizer is a BCL-2 inhibitor. In certain embodiments, the BCL-2 inhibitor is antisense oligodeoxynucleotide G3139, mRNA antagonist SPC2996, venetoclax (ABT-199), GDC-0199, obatoclax, paclitaxel, navitoclax (ABT-263), ABT-737, NU-0129, S 055746, or APG-1252.

In certain embodiments, the cytoplasmic p53 stabilizer is a Bcl-xL inhibitor. In certain embodiments, the Bcl-xL inhibitor is WEHI 539, ABT-263, ABT-199, ABT-737, sabutoclax, AT101, TW-37, APG-1252, or gambogic acid.

In certain embodiments, the glucose metabolism inhibitor and the cytoplasmic p53 stabilizer are administered in the same composition. In other embodiments, the glucose metabolism inhibitor and the cytoplasmic p53 stabilizer are administered in separate compositions.

In certain embodiments, the method further comprises administration of an additional therapy.

Types and Stages of Gliomas

Primary malignant brain tumors are tumors that start in the brain or spine are known collectively as gliomas. Gliomas are not a specific type of cancer but are a term used to describe tumors that originate in glial cells. Examples of primary malignant brain tumors include astrocytomas, pilocytic astrocytomas, pleomorphic xanthoastrocytomas, diffuse astrocytomas, anaplastic astrocytomas, GBMs, gangliogliomas, oligodendrogliomas, ependymomas. According to the WHO classification of brain tumors, astrocytomas have been categorized into four grades, determined by the underlying pathology. The characteristics that are used to classify gliomas include mitoses, cellular or nuclear atypia, and vascular proliferation and necrosis with pseudopalisading features. Malignant (or high-grade) gliomas include anaplastic glioma (WHO grade III) as well as glioblastoma multiforme (GBM; WHO grade IV). These are the most aggressive brain tumors with the worst prognosis.

GBMs is the most common, complex, treatment resistant, and deadliest type of brain cancer, accounting for 45% of all brain cancers, with nearly 11,000 men, women, and children diagnosed each year. GBM (also known as grade-4 astrocytoma and glioblastoma multiforme) are the most common types of malignant (cancerous) primary brain tumors. They are extremely aggressive for a number of reasons. First, glioblastoma cells multiply quickly, as they secrete substances that stimulate a rich blood supply. They also have an ability to invade and infiltrate long distances into the normal brain by sending microscopic tendrils of tumor alongside normal cells. Two types of glioblastomas are known. Primary GBM are the most common form; they grow quickly and often cause symptoms early. Secondary glioblastomas are less common, accounting for about 10 percent of all GBMs. They progress from low-grade diffuse astrocytoma or anaplastic astrocytoma, and are more often found in younger patients. Secondary GBM are preferentially located in the frontal lobe and carry a better prognosis.

GBM is usually treated by combined multi-modal treatment plan including surgical removal of the tumor, radiation and chemotherapy. First, as much tumor as possible is removed during surgery. The tumor's location in the brain often determines how much of it can be safely removed. After surgery, radiation and chemotherapy slow the growth of remaining tumor cells. The oral chemotherapy drug, temozolomide, is most often used for six weeks, and then monthly thereafter. Another drug, bevacizumab (known as Avastin®), is also used during treatment. This drug attacks the tumor's ability to recruit blood supply, often slowing or even stopping tumor growth.

Novel investigational treatments are also used and these may involve adding treatments to the standard therapy or replacing one part of the standard therapy with a different treatment that may work better. Some of these treatments include immunotherapy such as vaccine immunotherapies, or low-dose pulses of electricity to the area of the brain where the tumor exists and nano therapies involving spherical nucleic acids (SNAs) such as NU-0129. In some embodiments, the methods of the current disclosure are used in combination with one or more of the aforementioned therapies.

Embodiments of the methods and compositions discussed herein are also contemplated to be applicable to other types of cancers, including but not limited to lung cancer, non-CNS cancers, CNS cancers, and CNS metastases such as brain metastases, leptomeningeal metastases, choroidal metastases, spinal cord metastases, and others.

Cytoplasmic p53 Stabilizers

The inventors have demonstrated that the pharmacological p53 stabilization, such as with a CNS-penetrant small molecule, for example, was synergistically lethal with the inhibition of EGFR-driven glucose uptake in patient-derived, primary GBM models. The inventors have demonstrated, for the first time, that the non-transcriptional functions of p53 can have a critical role in stimulating intrinsic apoptosis in metabolic responders. Accordingly, the methods of treatment described herein comprise the administration of cytoplasmic p53 stabilizer(s) in combination with glucose metabolism inhibitors. Cytoplasmic p53 stabilizer(s) and glucose metabolism inhibitors can be administered in the same or in different compositions, cocomitantly or sequentially. It is contemplated that in some embodiments a single p53 stabilizer is used and in other embodiments more than on p53 stabilizer is used. For example, the combination of nutlin with ABT 737 (which binds BCL-2 and BCL-XL) is reported to synergistically target the balance of pro-apoptotic and anti-apoptotic proteins at the mitochondrial level, thereby promoting cell death. (Hoe et al. 2014. Nature Reviews. Vol. 13. pp. 217) As intended herein, a cytoplasmic p53 stabilizer is any small molecule, antibody, peptide, protein, nucleic acid or derivatives thereof that can pharmacologically stabilize or activate p53 directly or indirectly. The stabilization of cytoplasmic p53 leads to priming cells, such as cancer cells, for apoptosis.

MDM2 Antagonists

Protein levels of p53 within cells are tightly controlled and kept low by its negative regulator, the E3 ubiquitin protein ligase MDM2. In embodiments of the methods or composition of the current disclosure, the cytoplasmic p53 stabilizer is an MDM2 antagonist/inhibitor. In some embodiments, the MDM2 antagonist is a nutlin. In further embodiments, the nutlin is nutlin-3 or idasanutlin. In other embodiments, the MDM2 antagonist is RO5045337 (also known as RG7112), RO5503781, RO6839921, SAR405838 (also known as MI-773), DS-3032, DS-3032b, or AMG-232 or any other MDM2 inhibitor.

Other compounds within the scope of the current methods known to bind MDM-2 include Ro-2443, MI-219, MI-713, MI-888, DS-3032b, benzodiazepinediones (for example, TDP521252), sulphonamides (for example, NSC279287), chromenotriazolopyrimidine, morpholinone and piperidinones (AM-8553), terphenyls, chalcones, pyrazoles, imidazoles, imidazole-indoles, isoindolinone, pyrrolidinone (for example, PXN822), priaxon, piperidines, naturally derived prenylated xanthones, SAH-8 (stapled peptides) sMTide-02, sMTide-02a (stapled peptides), ATSP-7041 (stapled peptide), spiroligomer (α-helix mimic). Other compounds that are known to cause protein folding of MDM2 include PRIMA-1MET (also known as APR-246) Aprea 102-105, PK083, PK5174, PK5196, PK7088, benzothiazoles, stictic acid and NSC319726.

BCL-2 Inhibitors

In further embodiments of the current methods or compositions, the cytoplasmic p53 stabilizer is a BCL-2 inhibitor. In some embodiments, the BCL-2 inhibitor is, for example, antisense oligodeoxynucleotide G3139, mRNA antagonist SPC2996, venetoclax (ABT-199), GDC-0199, obatoclax, paclitaxel, navitoclax (ABT-263), ABT-737, NU-0129, S 055746, APG-1252 or any other BCL-2 inhibitor.

Bcl-xL Inhibitors

In yet further embodiments of the current methods or compositions, the cytoplasmic p53 stabilizer is a Bcl-xL inhibitor. In some embodiments, the Bcl-xL inhibitor is, for example, WEHI 539, ABT-263, ABT-199, ABT-737, sabutoclax, AT101, TW-37, APG-1252, gambogic acid or any other Bcl-xL inhibitor.

Methods of Assessment

Glucose Uptake Tests

In embodiments of the methods and compositions of the current disclosure, the subject with GBM or cancer is classified to be either a "metabolic responder" or a "metabolic non-responder" i.e. determined to be susceptible to glucose metabolism inhibitors. In certain embodiments, the classification of the subject is prior to administering to the subject a treatment comprising a glucose metabolism inhibitor and a cytoplasmic p53 stabilizer. Accordingly, the current disclosure provides for methods for assessing a cancer, classifying a subject, determining the susceptibility of a subject to treatments involve analysis of glucose metabolism, glycolysis or glucose uptake. Methods to classify a subject as metabolic responder is described in details in Example 1. Techniques to monitor glycolysis and glucose uptake is provided by T. TeSlaa and M. A. Teitell. 2014. Methods in Enzymology, Volume 542, pp. 92-114, incorporated herein by reference.

Glycolysis is the intracellular biochemical conversion of one molecule of glucose into two molecules of pyruvate with the concurrent generation of two molecules of ATP. Pyruvate is a metabolic intermediate with several potential fates including entrance into the tricarboxylic acid (TCA) cycle within mitochondria to produce NADH and $FADH_2$. Alternatively, pyruvate can be converted into lactate in the cytosol by lactate dehydrogenase with concurrent regeneration of NAD from NADH. An increased flux through glycolysis supports the proliferation of cancer cells by providing, for example, additional energy in the form of ATP as well as glucose-derived metabolic intermediates for nucleotide, lipid, and protein biosynthesis. Warburg (Oncologia. 1956; 9(2):75-83) first observed that proliferating tumor cells augment aerobic glycolysis, the conversion of glucose to lactate in the presence of oxygen, in contrast to nonmalignant cells that mainly respire when oxygen is available. This mitochondrial bypass, called the Warburg effect, occurs in rapidly proliferating cells including cancer cells, activated lymphocytes, and pluripotent stem cells. The Warburg effect has been exploited for clinical diagnostic tests that use positron emission tomography (PET) scanning to identify increased cellular uptake of fluorinated glucose analogs such as $^{18}F$-deoxyglucose.

Thus, glycolysis represent a target for therapeutic and diagnostic methods. In the context of the current methods, the measurement of glucose uptake and lactate excretion by malignant cells may be useful to detect shifts in glucose catabolism and/or susceptibility to glucose metabolism inhibitors. Detecting such shifts is important for methods of treating GBM, methods of reducing the risk of ineffective therapy, methods for reducing the chances of tumor survival.

For the purposes of this disclosure, $^{18}$F-deoxyglucose PET serves in certain embodiments as a rapid non-invasive functional biomarker to predict sensitivity to p53 activation. This non-invasive anlaysis could be particularly valuable for malignant brain tumors where pharmacokinetic/pharmacodynamics assessment is extremely difficult and impractical. In some cases, delayed imaging protocols (41) and parametric response maps (PRMs) with MRI fusion can be useful for quantifying the changes in tumore $^{18}$F-FDG uptake (42).

In certain aspects, the methods can relate to measuring glucose uptake and lactate production. For cells in culture, glycolytic flux can be quantified by measuring glucose uptake and lactate excretion. Glucose uptake into the cell is through glucose transporters (Glut1-Glut4), whereas lactate excretion is through monocarboxylate transporters (MCT1-MCT4) at the cell membrane.

Extracellular Glucose and Lactate

Methods to detect glucose uptake and lactate excretion include, for example, extracellular glucose or lactate kit, extracellular bioanalyzer, ECAR measurement, [3H]-2-DG or [14C]-2-DG uptake $^{18}$FDG uptake or 2-NBDG uptake.

Commercially available kits and instruments are available to quantify glucose and lactate levels within cell culture media. Kit detection methods are usually colorimetric or fluorometric and are compatible with standard lab equipment such as spectrophotometers. BioProfile Analyzers (such as Nova Biomedical) or Biochemistry Analyzers (such as for example YSI Life Sciences) can measure levels of both glucose and lactate in cell culture media. GlucCell (Cesco BioProducts) can measure only glucose levels in cell culture media. While each commercial method has a different detection protocol, the collection of culture media for analysis is the same.

Extracellular Acidification Rate

Glycolysis can also be determined through measurements of the extracellular acidification rate (ECAR) of the surrounding media, which is predominately from the excretion of lactic cid per unit time after its conversion from pyruvate. The Seahorse extracellular flux (XF) analyzer (Seahorse Bioscience) is a tool for measuring glycolysis and oxidative phosphorylation (through oxygen consumption) simultaneously in the same cells.

Glucose Analog Uptake

Certain embodiments of the methods of the current disclosure include the use of glucose analogs. As would be familiar to a person skilled in the art, to determine the glucose uptake rate by cells, a labeled isoform of glucose can be added to the cell culture media and then measured within cells after a given period of time. Exemplary types of glucose analogs for these studies include but are not limited to radioactive glucose analogs, such as 2-deoxy-D-[1,2-3H]-glucose, 2-deoxy-D-[1-14C]-glucose, or 2-deoxy-2-($^{18}$F)-fluoro-D-glucose ($^{18}$FDG), or fluorescent glucose analogs, such as 2-[N-(7-nitrobenz-2-oxa-1,3-diaxol-4-yl)amino]-2-deoxyglucose (2-NBDG). Measurements of radioactive glucose analog uptake require a scintillation counter, whereas 2-NBDG uptake is usually measured by flow cytometry or fluorescent microscopy. In some embodiments, the glucose uptake is measured by the uptake of radio-labelled glucose 2-deoxy-2-[fluorine-18]fluoro-D-glucose ($^{18}$F-FDG). In further embodiments, detecting the $^{18}$F-FDG is by positron emission tomography (PET). In some embodiments, the biopsy is taken from a GBM tumor. A detailed description of an example of measuring $^{18}$F-FDG is provided in the examples below.

In certain aspects, the methods can relate to comparing glucose uptake of a biological sample such as a tumor sample with a control. Fold increases or decreases may be, be at least, or be at most 1-, 2-, 3-, 4-, 5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 100- or more, or any range derivable therein. Alternatively, differences in expression between a sample and a reference may be expressed as a percent decrease or increase, such as at least or at most 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000% difference, or any range derivable therein.

Other ways to express relative expression levels are with normalized or relative numbers such as 0.001, 0.002, 0.003, 0.004, 0.005, 0.006, 0.007, 0.008, 0.009, 0.01, 0.02, 0.03. 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or any range derivable therein. In some embodiments, the levels can be relative to a control.

Algorithms, such as the weighted voting programs, can be used to facilitate the evaluation of biomarker levels. In addition, other clinical evidence can be combined with the biomarker-based test to reduce the risk of false evaluations. Other cytogenetic evaluations may be considered in some embodiments.

Methods of Synthesis

In another aspect, the present disclosure provides methods of making compounds of Formula I, I*, or a pharmaceutically acceptable salt thereof, according to Scheme 1 or Scheme 2:

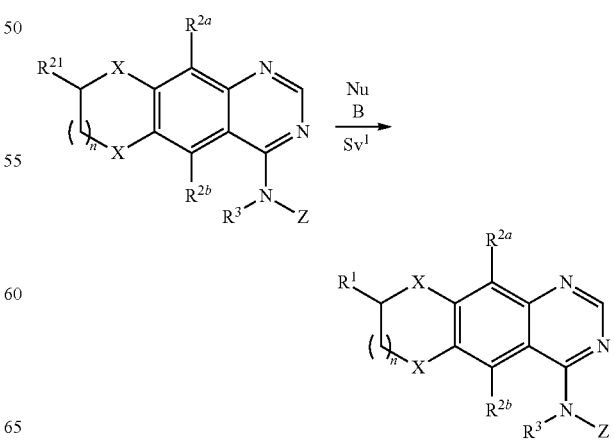

Scheme 1

Scheme 2

[Chemical structure showing reactant with R$^{2a}$, R$^{2b}$, R$^{21}$, R$^3$, X, N, Z groups and (X)$_n$, reacting with Nu, B, Sv$^1$ to give product with R$^1$ group]

wherein:

X is O, S, or NH;

Z is aryl or heteroaryl;

R$^1$ is alkyl;

R$^{2a}$ and R$^{2b}$ are each independently selected from hydrogen, alkyl, halo, CN, and NO$_2$;

R$^3$ is hydrogen, alkyl, or acyl;

R$^4$ is alkoxy;

R$^5$ is alkyl;

R$^{21}$ is an alkyl substituted with a leaving group, e.g., a haloalkyl or sulfonylalkyl;

B is a base;

Nu is a nitrogen-containing heterocycle (e.g., having at least one N—H bond), aminoalkyl, or hydroxyalkyl;

Sv$^1$ is a solvent; and n is 0-3.

In certain preferred embodiments, R$^{21}$ is sufonylalkyl (e.g., CH$_3$S(O)$_2$OCH$_2$—).

In certain embodiments, B is a nitrogenous base (e.g., triethylamine or diisopropylethylamine)

In certain embodiments, Nu is a nitrogen-containing heterocycle having at least one N—H bond (e.g., morpholine, N-methylpiperazine, piperidine, or pyrrolidine). In other embodiments, Nu is aminoalkyl (e.g., dimethylamine)

In certain embodiments, the solvent is an aprotic solvent (e.g., dimethylformamide).

In certain preferred embodiments, the method further comprises a step according to scheme 3 or 4:

Scheme 3

[Chemical structure showing reactant with R$^{22}$, R$^{2a}$, R$^{2b}$, R$^{23a}$, R$^{23b}$, X, N groups and (X)$_n$, reacting with R$^{24}$, Sv$^2$]

Scheme 4

[Chemical structures showing the scheme 4 reaction sequence with R$^{22}$, R$^{2a}$, R$^{2b}$, R$^{23a}$, R$^{23b}$, R$^{24}$, X, N groups reacting with Sv$^2$ to give products including final product with R$^3$, N, Z groups]

wherein:

R$^{22}$ is alkyl or hydroxyalkyl;

R$^{23a}$ and R$^{23b}$ are each alkyl;

R$^{24}$ is aminoaryl or aminoheteroaryl; and

Sv$^2$ is an acid.

In certain preferred embodiments, R$^{22}$ is hydroxyalkyl.

In certain embodiments, R$^{23a}$ and R$^{23b}$ are each methyl.

In certain embodiments, R$^{24}$ is aminoaryl. In other embodiments, R$^{24}$ is aminoheteroaryl.

In certain embodiments, Sv$^2$ is an alkylacid (e.g., acetic acid).

In certain preferred embodiments, the step in scheme 3 or 4 is performed at a temperature in the range 115-150° C. In certain embodiments, the step is performed at a temperature in the range 125-130° C. In certain embodiments, the step further comprises treatment with a base, such as ammonium hydroxide.

In certain embodiments, the method further comprises a purification step. In certain embodiments, the purification step comprises column chromatography, preparative thin layer chromatography, or high performance liquid chromatography.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

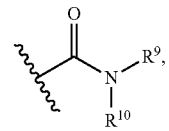

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

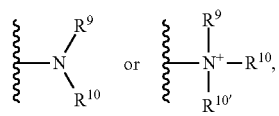

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

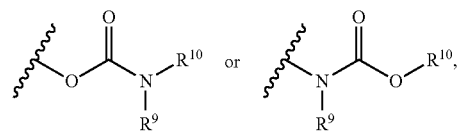

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —OCO$_2$—.

The term "carboxy", as used herein, refers to a group represented by the formula —CO$_2$H.

The term "ester", as used herein, refers to a group —C(O)OR$^9$ wherein R$^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

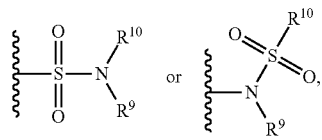

wherein R$^9$ and R$^{10}$ independently represents hydrogen or hydrocarbyl.

The term "sulfoxide" is art-recognized and refers to the group-S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

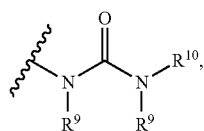

wherein R$^9$ and R$^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos.

6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

EXAMPLES

The invention now being generally described, it will be more readily understood by reference to the following examples which are included merely for purposes of illustration of certain aspects and embodiments of the present invention, and are not intended to limit the invention.

Example 1

Preparation of Exemplary Compounds of the JGK Series

General Procedures: Compounds of the JGK series may be prepared by the methods described below, or by any other suitable method. The JGK series compounds are sometimes referred to herein with a JCN prefix. All reactions were routinely carried out under an inert atmosphere of argon. Unless otherwise noted, materials were obtained from commercial suppliers and were used without purification. All solvents were purified and dried by standard techniques just before use. THF and Et$_2$O were freshly distilled from sodium and benzophenone. Methylene chloride, toluene, and benzene were purified by refluxing with CaH$_2$. Reactions were checked by thin layer chromatography (Kieselgel 60 F254, Merck). Spots were detected by viewing under a UV light, and by colorizing with charring after dipping in a p-anisaldehyde solution or phosphomolybdic acid solution. In aqueous work-up, all organic solutions were dried over anhydrous magnesium sulfate and filtered prior to rotary evaporation at water pump pressure. The crude compounds were purified by column chromatography on a silica gel (SilicaFlash P60, 230-400 mesh, SiliCycle Inc). Proton ($^1$H) and carbon ($^{13}$C) NMR spectra were obtained on a Bruker AV 400 (400/100 MHz) or Bruker AV500 (500/125 MHz) spectrometer. Chemical shifts are reported in ppm units with Me$_4$Si or CHCl$_3$ as the internal standard. Splitting patterns are designated by: s, singlet; d, doublet; t, triplet; m, multiplet; b, broad. High resolution mass spectrometry data was obtained using a Thermo Fisher Scientific Exactive Plus with IonSense ID-CUBE DART source.

Preparation of JGK001, JGK003

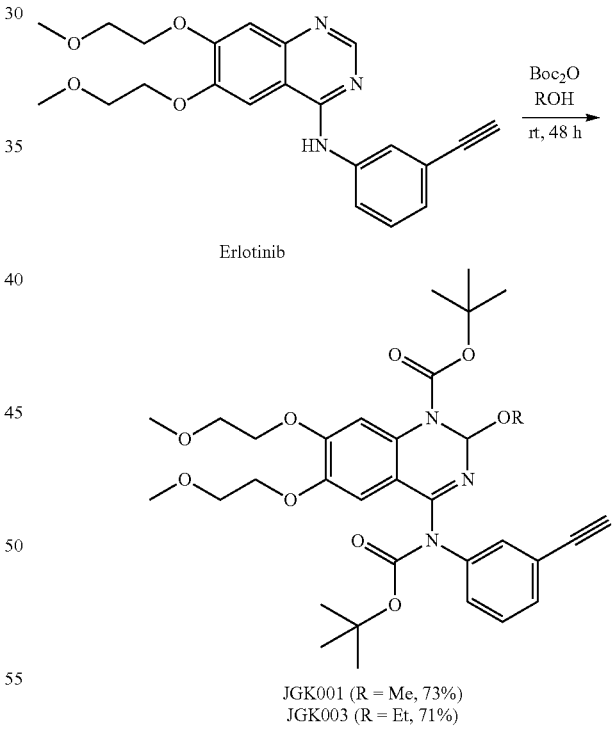

JGK001 (R = Me, 73%)
JGK003 (R = Et, 71%)

[JGK001] To a solution of Erlotinib (134 mg, 0.3406 mmol) in anhydrous methanol (5.0 mL) was added Di-tert-butyl dicarbonate (228 mg, 1.7029 mmol) in one portion at room temperature. After being stirred at the same temperature for 48 h and concentrated in vacuo. The reaction mixture was diluted with H$_2$O (30 mL) and EtOAc (30 mL). The layers were separated, and the aqueous layer was extracted with EtOAc (2×30 mL). The combined organic layers were washed successively with H$_2$O and saturated brine, dried over anhydrous MgSO$_4$, filtered, and concentrated in vacuo. The residue was purified by column chromatography (silica gel, hexanes/EtOAc, 3/1) to give JGK001 (156 mg, 73%); $^1$H NMR (400 MHz, CDCl$_3$) δ 7.86 (s, 1H), 7.43 (s, 1H), 7.20-7.23 (m, 2H), 7.16 (td, J=1.2, 7.6 Hz, 1H), 7.09 (d, J=8.0 Hz, 1H), 4.16-4.25 (m, 4H), 3.80 (t, J=5.2 Hz, 2H), 3.77 (t, J=5.2 Hz, 2H), 3.45 (s, 3H), 3.44 (s, 3H), 3.44 (s, 3H), 3.03 (s, 1H), 1.55 (s, 9H), 1.11 (s, 9H); $^{13}$C NMR (100 MHz, CDCl$_3$) δ 152.1, 151.5, 149.2, 148.8, 145.7, 142.7, 130.6, 128.9, 127.4, 125.3, 122.6, 121.5, 114.7, 111.4, 108.0, 90.7, 83.7, 83.3, 82.9, 76.8, 70.9, 70.7, 68.8, 68.7, 59.2, 59.1, 55.0, 28.2, 27.3; HRMS-ESI [M+H]$^+$ found 626.3061 [calcd for C$_{33}$H$_{43}$N$_3$O$_9$ 625.2993].

[JGK003] To a solution of Erlotinib (101 mg, 0.2567 mmol) in anhydrous ethanol (2.6 mL) was added Di-tert-butyl dicarbonate (172 mg, 1.2836 mmol) in one portion at room temperature. After being stirred at the same temperature for 48 h and concentrated in vacuo. The reaction mixture was diluted with H$_2$O (30 mL) and EtOAc (30 mL). The layers were separated, and the aqueous layer was extracted with EtOAc (2×30 mL). The combined organic layers were washed successively with H$_2$O and saturated brine, dried over anhydrous MgSO$_4$, filtered, and concentrated in vacuo. The residue was purified by column chromatography (silica gel, hexanes/EtOAc, 3/1) to give JGK003 (117 mg, 71%); $^1$H NMR (400 MHz, CDCl$_3$) δ 7.86 (s, 1H), 7.43 (s, 1H), 7.34 (s, 1H), 7.21-7.24 (m, 2H), 7.16 (d, J=7.6 Hz, 1H), 7.10 (d, J=7.6 Hz, 1H), 4.17-4.25 (m, 4H), 3.61-3.82 (m, 6H), 3.46 (s, 3H), 3.45 (s, 3H), 3.02 (s, 1H), 1.55 (s, 9H), 1.23 (t, J=6.8 Hz, 3H), 1.12 (s, 9H); $^{13}$C NMR (100 MHz, CDCl$_3$) δ 152.0, 151.4, 149.2, 148.9, 145.5, 143.0, 130.8, 128.8, 127.3, 125.3, 122.5, 121.7, 114.7, 111.3, 107.9, 89.3, 83.7, 83.2, 82.8, 76.7, 70.9, 70.7, 68.8, 68.6, 63.0, 59.2, 59.1, 28.2, 27.4, 14.6; HRMS-ESI [M+H]$^+$ found 640.3211 [calcd for C$_{34}$H$_{45}$N$_3$O$_9$ 639.3150].

Preparation of JGK002

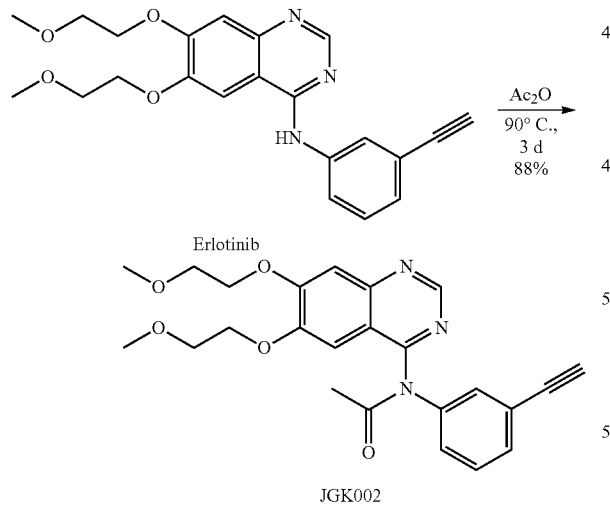

To a solid of erlotinib (165 mg, 0.4194 mmol) was added acetic anhydride (5.0 mL). After being heated at 90° C. (bath temperature) with stirring for 3 d, the reaction mixture was cooled to room temperature and neutralized with saturated aqueous NaHCO$_3$ (20 mL), and diluted with EtOAc (20 mL). The layers were separated, and the aqueous layer was extracted with EtOAc (2×30 mL). The combined organic layers were washed successively with H$_2$O and saturated brine, dried over anhydrous MgSO$_4$, filtered, and concentrated in vacuo. The residue was purified by column chromatography (silica gel, hexanes/EtOAc, 1/1 to 1/3) to give JGK002 (161 mg, 88% isolated yield); $^1$H NMR (400 MHz, CDCl$_3$) δ 9.06 (s, 1H), 7.45 (t, J=1.6 Hz, 1H,), 7.37-7.39 (m, 2H), 7.36 (s, 1H), 7.30-7.34 (m, 1H), 7.15 (s, 1H), 4.32 (t, J=4.8 Hz, 2H), 4.16 (t, J=4.8 Hz, 2H), 3.86 (t, J=4.8 Hz, 2H), 3.79 (t, J=4.8 Hz, 2H), 3.46 (s, 3H), 3.45 (s, 3H), 3.06 (s, 1H), 2.14 (s, 3H); $^{13}$C NMR (100 MHz, CDCl$_3$) δ 170.5, 158.8, 156.1, 153.5, 151.1, 150.8, 141.0, 130.9, 130.3, 129.3, 127.5, 123.4, 117.2, 107.9, 103.1, 82.4, 78.4, 70.6, 70.3, 68.9, 68.7, 59.3, 59.3, 23.7; HRMS-ESI [M+H]$^+$ found 436.1811 [calcd for C$_{24}$H$_{25}$N$_3$O$_5$ 435.1788].

Preparation of JGK010, JGK032-General Procedure for Substitution with Aniline Analogues

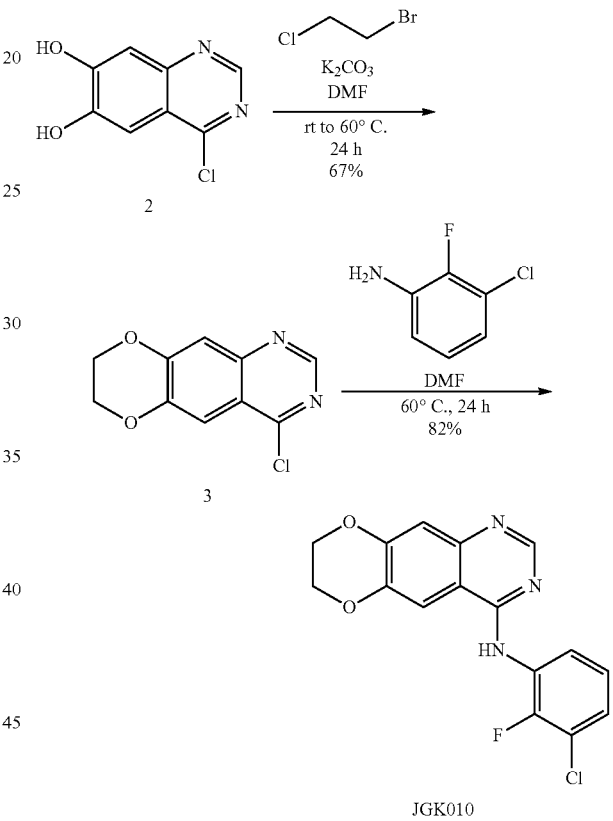

[Cyclization] To a solution of diol 2 (530 mg, 2.6959 mmol) in DMF (13.5 mL, 0.2 M) was added in one portion potassium carbonate (1490 mg), followed by successive dropwise addition of 1-bromo-2-chloroethane (1.3 mL) at room temperature under Ar. After being heated at 60° C. (bath temperature) with stirring for 24 h, the reaction mixture was cooled to room temperature, quenched with H$_2$O (50 mL). The layers were separated, and the aqueous layer was extracted with EtOAc (50 mL). The combined organic layers were washed successively with H$_2$O and saturated brine, dried over anhydrous MgSO$_4$, filtered, and concentrated in vacuo. The residue was purified by column chromatography (silica gel, hexanes/EtOAc, 6/1 to 3/1) to give fused-chloroquinazoline 3 (404 mg, 67%); $^1$H NMR (400 MHz, CDCl$_3$) δ 8.84 (s, 1H), 7.64 (s, 1H), 7.47 (s, 1H), 4.43-4.45 (m, 2H), 4.39-4.42 (m, 2H). [known compound; Chilin, A. et al. *J. Med. Chem.* 2010, 53, 1862-1866]

[JGK010] To a solution of fused-chloroquinazoline 3 (114 mg, 0.5120 mmol) in DMF (2.6 mL) was dropwise added 3-chloro-2-fluoroaniline (0.10 mL) at room temperature. After being heated at 60° C. (bath temperature) with stirring for 24 h, the reaction mixture was cooled to room temperature and diluted with Et$_2$O (30.0 mL) to give white suspension. The resulting white solid were washed successively with Et$_2$O (2×50 mL) and collected to give JGK010 (140 mg, 82%); $^1$H NMR (400 MHz, CDCl$_3$) δ 8.68 (s, 1H), 8.59 (ddd, J=3.2, 6.8, 6.8 Hz, 1H), 7.39 (s, 1H), 7.34 (s, 1H), 7.29 (s, 1H), 7.10-7.18 (m, 2H), 4.38-4.43 (m, 4H); $^1$H NMR (500 MHz, DMSO-d$_6$) δ 11.78 (s, 1H), 8.79 (s, 1H), 8.45 (s, 1H), 7.62 (t, J=7.0 Hz, 1H), 7.50 (t, J=7.0 Hz, 1H), 7.43 (s, 1H), 7.34 (t, J=8.0 Hz, 1H), 4.46-4.53 (m, 2H), 4.40-4.52 (m, 2H); $^{13}$C NMR (125 MHz, DMSO-d$_6$) δ 159.8, 154.0, 152.2, 149.9, 145.7, 135.2, 129.9, 128.1, 126.4, 125.8, 120.9, 111.3, 108.1, 105.8, 65.5, 64.6; HRMS-ESI [M+H]$^+$ found 332.0551 [calcd for C$_{16}$H$_{11}$ClFN$_3$O$_2$ 331.0518].

Preparation of JGK005

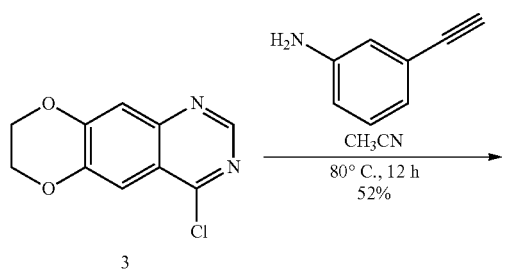

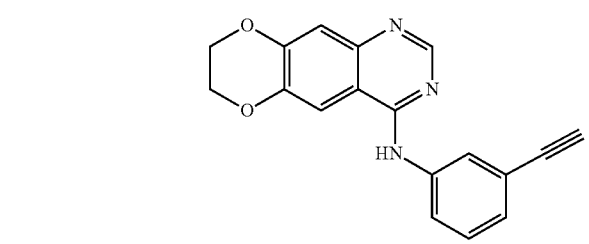

JGK005

To a solution of fused-chloroquinazoline 3 (14 mg, 0.0628 mmol) in CH$_3$CN (2.0 mL) was dropwise added 3-ethynylaniline (0.05 mL) at room temperature. After being heated at 80° C. (bath temperature) with stirring for 12 h, the reaction mixture was cooled to room temperature, and concentrated in vacuo. The residue was purified by column chromatography (silica gel, hexanes/EtOAc, 3/1) to give JGK005 (10 mg, 52%); $^1$H NMR (400 MHz, DMSO-d$_6$) δ 9.45 (s, 1H), 8.43 (s, 1H), 8.04-8.05 (m, 2H), 7.87-7.90 (m, 1H), 7.34 (t, J=7.9 Hz, 1H), 7.14-7.16 (m, 2H), 4.35-4.39 (m, 4H), 4.14 (s, 1H); $^{13}$C NMR (100 MHz, DMSO-d$_6$) δ 156.8, 153.3, 149.5, 146.5, 144.1, 140.2, 129.3, 126.7, 124.9, 122.7, 122.1, 113.0, 110.4, 108.8, 84.0, 80.9, 64.9, 64.6; HRMS-ESI [M+H]$^+$ found 304.1079 [calcd for C$_{18}$H$_{13}$N$_3$O$_2$ 303.1002].

JGK025

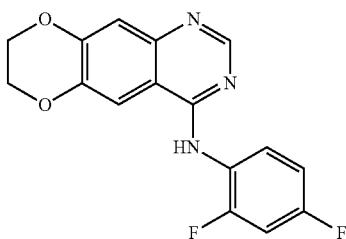

Preparation of JGK025 was followed by General Procedure; JGK025 (25%); $^1$H NMR (400 MHz, DMSO-d$_6$) δ 11.30 (s, 1H), 8.73 (s, 1H), 8.28 (s, 1H), 7.51-7.58 (m, 1H), 7.41-7.48 (m, 1H), 7.35 (s, 1H), 7.17-7.23 (m, 1H), 4.44-4.50 (m, 2H), 4.39-4.44 (m, 2H); $^{13}$C NMR (125 MHz, MeOD) δ 161.6 (J=245.9 Hz), 160.0, 157.6 (J=249.6 Hz), 152.1, 150.1, 145.6, 135.4, 130.4, 121.4, 112.4, 110.9, 108.1, 108.1, 105.4, 65.5, 64.6; HRMS-ESI [M+H]$^+$ found 316.0890 [calcd for C$_{16}$H$_{11}$F$_2$N$_3$O$_2$ 315.0813].

JGK026

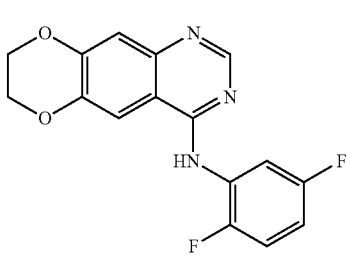

Preparation of JGK026 was followed by General Procedure; JGK026 (22%); $^1$H NMR (400 MHz, DMSO-d$_6$) δ 11.09 (s, 1H), 8.74 (s, 1H), 8.18 (s, 1H), 7.39-7.51 (m, 2H), 7.30 (s, 1H), 7.23-7.29 (m, 1H), 4.45-4.49 (m, 2H), 4.40-4.44 (m, 2H); $^{13}$C NMR (125 MHz, MeOD) δ 159.8, 158.1 (J=239.6 Hz), 153.7 (J=243.2 Hz), 152.1, 150.1, 145.7, 135.7, 126.0, 117.9, 117.8, 116.0, 110.9, 108.2, 106.2, 65.5, 64.6; HRMS-ESI [M+H]$^+$ found 316.0893 [calcd for C$_{16}$H$_{11}$F$_2$N$_3$O$_2$ 315.0813].

JGK027

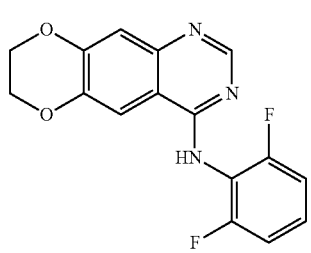

Preparation of JGK027 was followed by General Procedure; JGK027 (6%); $^1$H NMR (400 MHz, DMSO-d$_6$) δ 11.23 (bs, 1H), 8.75 (s, 1H), 8.29 (s, 1H), 7.91 (s, 1H), 7.46-7.55 (m, 1H), 7.29 (t, J=8.1 Hz, 2H), 4.46-4.50 (m, 2H), 4.40-4.46 (m, 2H); $^{13}$C NMR (125 MHz, MeOD) δ 163.6, 160.7, 160.4, 158.4, 152.5, 151.5, 146.2, 130.6, 115.6, 113.5, 113.4, 111.9, 109.3, 108.2, 66.2, 65.3; HRMS-ESI [M+H]$^+$ found 316.0889 [calcd for C$_{16}$H$_{11}$F$_2$N$_3$O$_2$ 315.0813].

JGK028

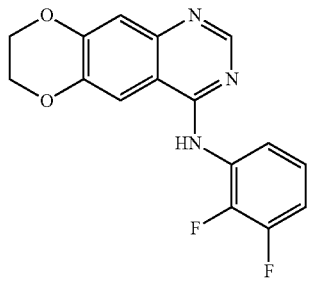

Preparation of JGK028 was followed by General Procedure; JGK028 (41%); $^1$H NMR (500 MHz, MeOD) δ 8.64 (s, 1H), 8.03 (s, 1H), 7.31-7.38 (m, 2H), 7.24-7.31 (m, 2H), 4.50-4.55 (m, 2H), 4.44-4.50 (m, 2H); $^{13}$C NMR (125 MHz, MeOD) δ 160.1, 152.8, 150.9 (J=245.6 Hz), 149.0, 146.2, 145.9 (J=249.7 Hz), 134.6, 126.0, 124.0, 123.1, 116.2, 109.8, 107.8, 105.0, 65.2, 64.2; HRMS-ESI [M+H]$^+$ found 316.0884 [calcd for $C_{16}H_{11}F_2N_3O_2$ 315.0813].

JGK029

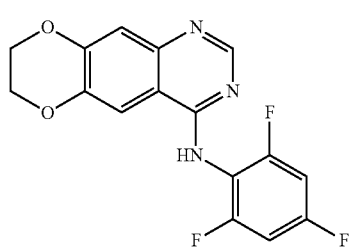

Preparation of JGK029 was followed by General Procedure; JGK029 (52%); $^1$H NMR (500 MHz, MeOD) δ 8.60 (s, 1H), 7.98 (s, 1H), 7.29 (s, 1H), 7.07-7.13 (m, 2H), 4.50-4.53 (m, 2H), 4.44-4.48 (m, 2H); $^{13}$C NMR (125 MHz, DMSO-d$_6$) δ 161.7, 160.3, 158.6, 158.1, 153.2, 150.3, 144.4, 143.7, 117.2, 113.8, 113.0, 112.3, 109.5, 101.5, 65.3, 64.5; HRMS-ESI [M+H]$^+$ found 334.0794 [calcd for $C_{16}H_{10}F_3N_3O_2$ 333.0719].

JGK017

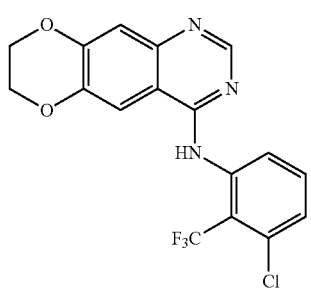

Preparation of JGK017 was followed by General Procedure; JGK017 (5%); $^1$H NMR (500 MHz, CDCl$_3$) δ 8.59 (s, 1H), 8.15 (d, J=8.3 Hz, 1H), 7.49 (t, J=8.1 Hz, 1H), 7.38 (s, 1H), 7.34 (d, J=7.9 Hz, 1H), 7.21 (s, 1H), 4.41-4.42 (m, 2H), 4.38-4.40 (m, 2H); $^{13}$C NMR (125 MHz, CDCl$_3$) δ 156.4, 153.2, 149.7, 146.7, 144.5, 138.4, 133.5, 132.2, 128.2, 125.4, 119.9, 119.7, 114.3, 110.4, 105.7, 64.5, 64.3.

Preparation of JGK004

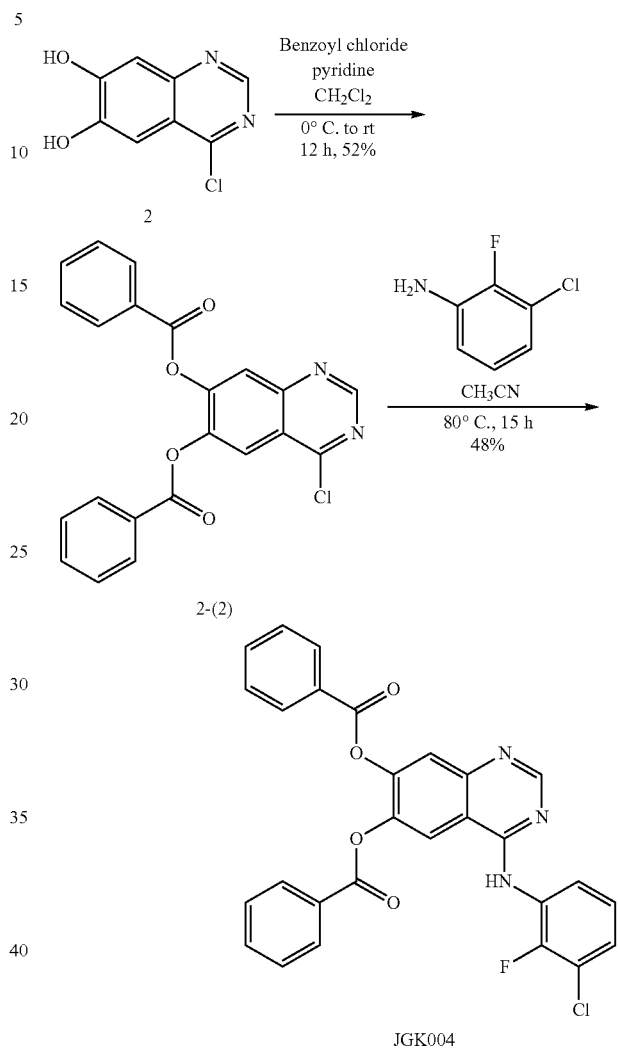

[Benzoylation] To a cooled (0° C.) solution of diol 2 (205 mg, 1.0428 mmol) in anhydrous CH$_2$Cl$_2$ (5.2 mL, 0.2 M) was dropwise added successively pyridine (0.5 mL) and benzoyl chloride (0.7 mL) under Ar. After being stirred at the room temperature for 12 h, the reaction mixture was quenched with saturated aqueous NH$_4$Cl (20 mL), and diluted with CH$_2$Cl$_2$ (20 mL). The layers were separated, and the aqueous layer was extracted with CH$_2$Cl$_2$ (2×50 mL). The combined organic layers were washed successively with H$_2$O and saturated brine, dried over anhydrous MgSO$_4$, filtered, and concentrated in vacuo. The residue was purified by column chromatography (silica gel, hexanes/EtOAc, 10/1) to give benzoyl chloroquinazoline 2-(2) (220 mg, 52%); $^1$H NMR (400 MHz, CDCl$_3$) δ 9.07 (s, 1H), 8.31 (s, 1H), 8.16 (s, 1H), 8.04-8.07 (m, 4H), 7.53-7.58 (m, 2H), 7.34-7.39 (m, 4H).

[JGK004] To a solution of benzoyl chloroquinazoline 2-(2) (180 mg, 0.444 mmol) in CH$_3$CN (3.0 mL) was dropwise added 3-chloro-2-fluoroaniline (0.06 mL, 0.533 mmol) at room temperature. After being heated at 80° C. (bath temperature) with stirring for 15 h, the reaction mixture was cooled to room temperature, and concentrated in vacuo. The residue was purified by column chromatography (silica gel, hexanes/EtOAc, 3/1) to give JGK004 (109 mg, 48%); $^1$H NMR (400 MHz, CDCl$_3$) δ 8.85 (s, 1H), 8.48-8.53 (m, 1H), 8.08 (t, J=7.2 Hz, 4H), 7.99 (d, J=3.2 Hz, 2H), 7.51-7.59 (m, 3H), 7.39 (dd, J=8.4, 16.0 Hz, 4H), 7.16-7.21 (m, 2H); $^{13}$C NMR (125 MHz, CDCl$_3$) δ 164.2, 163.7, 156.6, 155.1, 150.6, 149.1, 148.6, 147.5, 142.1, 134.1, 134.1, 130.3, 130.2, 128.6, 128.6, 128.1, 128.0, 127.9, 127.8, 125.3, 124.6, 124.5, 122.9, 121.6, 121.0, 120.9, 114.4, 113.3; HRMS-ESI [M+H]$^+$ found 514.0963 [calcd for C$_{28}$H$_{17}$ClFN$_3$O$_4$ 513.0886].

Preparation of JGK006

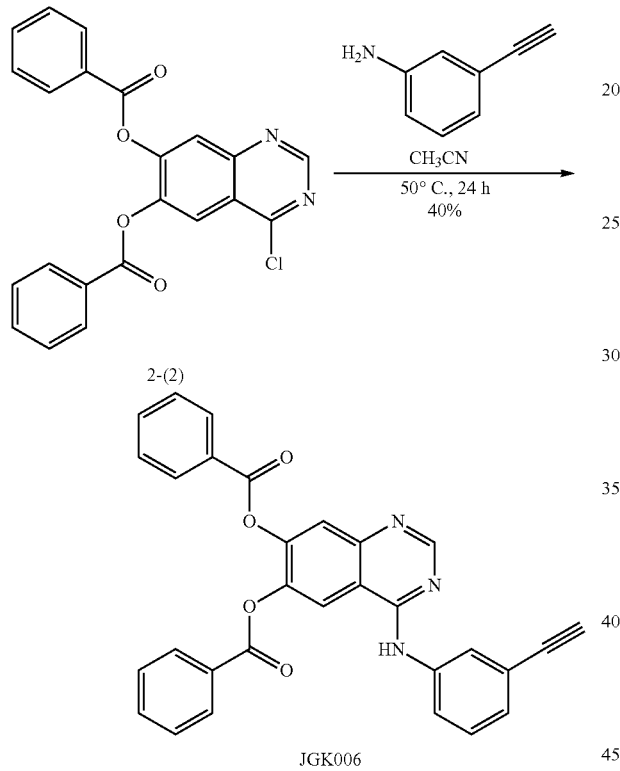

To a solution of benzoyl chloroquinazoline 2-(2) (100 mg, 0.247 mmol) in CH$_3$CN (3.0 mL) was dropwise added 3-ethynylaniline (0.05 mL, 0.430 mmol) at room temperature. After being heated at 50° C. (bath temperature) with stirring for 24 h, the reaction mixture was cooled to room temperature and concentrated in vacuo. The residue was purified by column chromatography (silica gel, hexanes/EtOAc, 4/1) to give JGK006 (48 mg, 40%); $^1$H NMR (400 MHz, CDCl$_3$) δ 8.71 (s, 1H), 8.03 (d, J=8.0 Hz, 2H), 7.96 (s, 1H), 7.90-7.95 (m, 2H), 7.79 (s, 1H), 7.62-7.75 (m, 3H), 7.55 (t, J=7.3 Hz, 1H), 7.48 (t, J=7.5 Hz, 1H), 7.37 (t, J=7.4 Hz, 2H), 7.22-7.31 (m, 4H), 3.04 (s, 1H); $^{13}$C NMR (100 MHz, CDCl$_3$) δ 164.8, 163.9, 156.7, 155.3, 148.9, 146.9, 141.3, 138.1, 134.1, 134.0, 130.3, 130.1, 128.9, 128.6, 128.5, 128.1, 128.0, 127.9, 124.8, 122.7, 122.4, 122.1, 115.1, 113.1, 83.3; HRMS-ESI [M+H]$^+$ found 486.1443 [calcd for C$_{30}$H$_{19}$N$_3$O$_4$ 485.1370]

Preparation of JGK032

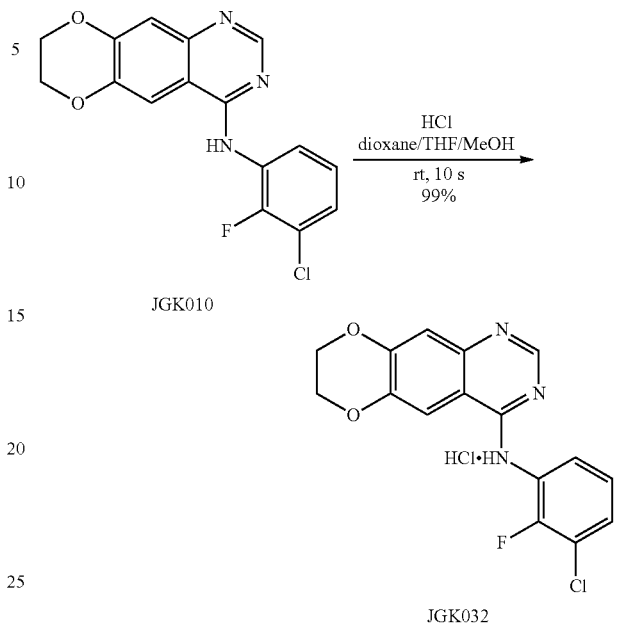

1.0 M hydrogen chloride solution was generated by addition of hydrogen chloride solution (0.1 mL, 4.0 M in dioxane, 0.4 mmol) to THF (0.3 mL) at room temperature. To a solution of JGK010 (6.1 mg, 0.01839 mmol) in MeOH was dropwise added the above-generated hydrogen chloride solution (0.030 mL, 0.030 mmol) at room temperature. After being stirred at the same temperature for 10 seconds, the reaction mixture was concentrated in vacuo to give JGK032 (6.7 mg, 99%); $^1$H NMR (500 MHz, DMSO-d$_6$) δ 11.63 (s, 1H), 8.81 (s, 1H), 8.36 (s, 1H), 7.63 (ddd, J=1.6, 6.9, 8.3 Hz, 1H), 7.39 (s, 1H), 7.35 (ddd, J=1.1, 8.1, 16.2 Hz, 1H), 4.49-4.51 (m, 2H), 4.43-4.45 (m, 2H).

Preparation of JGK012

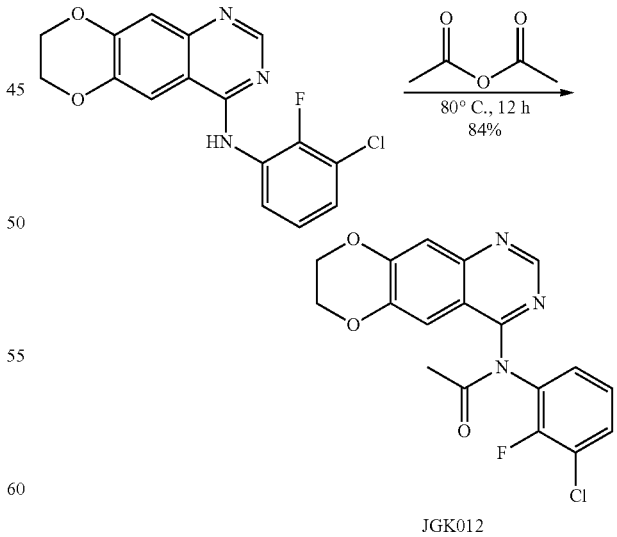

To a solid of JGK010 (39 mg, 0.1176 mmol) was added acetic anhydride (5.0 mL). After being heated at 80° C. (bath temperature) with stirring for 12 h, the reaction mixture was cooled to room temperature and neutralized with saturated aqueous NaHCO$_3$ (20 mL), and diluted with EtOAc (20 mL). The layers were separated, and the aqueous layer was extracted with EtOAc (2×30 mL). The combined organic layers were washed successively with H$_2$O and saturated brine, dried over anhydrous MgSO$_4$, filtered, and concentrated in vacuo. The residue was purified by column chromatography (silica gel, hexanes/EtOAc, 2/1 to 1/1) to give JGK012 (37 mg, 84% isolated yield); $^1$H NMR (400 MHz, CDCl$_3$) δ 9.01 (s, 1H), 7.49 (s, 1H), 7.44 (s, 1H), 7.31-7.41 (m, 2H), 7.09 (t, J=8.0 Hz, 1H), 4.41-4.43 (m, 2H), 4.37-4.40 (m, 2H), 2.15 (s, 3H); $^{13}$C NMR (125 MHz, CDCl$_3$) δ 170.2, 159.2, 153.3, 151.3, 149.7, 145.8, 130.6, 129.8, 129.7, 124.7, 122.5, 122.4, 117.7, 113.6, 109.2, 64.5, 64.2, 22.9; HRMS-ESI [M+H]$^+$ found 374.0701 [calcd for C$_{18}$H$_{13}$ClFN$_3$O$_3$ 373.0623].

Preparation of JGK015

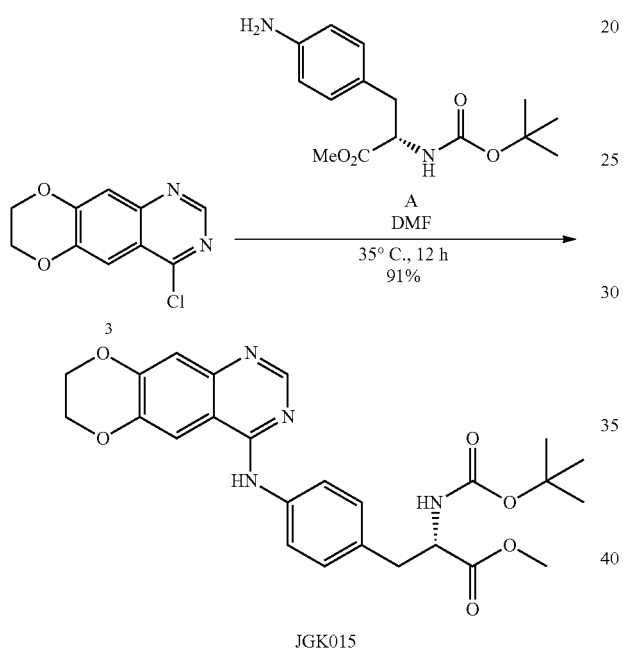

To a solution of L-amino acid analogue A (227 mg, 0.7712 mmol) in DMF (3.0 mL) was added in one portion fused-chloroquinazoline 3 (117 mg, 0.5932 mmol) at room temperature. After being heated at 35° C. (bath temperature) with stirring for 12 h, the reaction mixture was cooled to room temperature and diluted with saturated brine (30.0 mL) and EtOAc (30.0 mL) to give yellow suspension. The layers were separated, and the aqueous layer was extracted with EtOAc (2×50 mL). The combined organic layers were concentrated in vacuo. The residue was purified by column chromatography (silica gel, CH$_2$Cl$_2$/MeOH, 40/1 to 10/1) to give JGK015 (261 mg, 92%); $^1$H NMR (500 MHz, CDCl$_3$) δ 8.57 (s, 1H), 7.64 (s, 1H), 7.61 (d, J=8.0 Hz, 2H), 7.37 (s, 1H), 7.27 (s, 1H), 7.08 (d, J=8.5 Hz, 2H), 5.09 (d, J=7.5 Hz, 1H), 4.54 (dd, J=6.0, 13.5 Hz, 1H), 4.31-4.33 (m, 2H), 4.27-4.29 (m, 2H), 3.68 (s, 3H), 3.06 (dd, J=5.6, 14.0 Hz, 1H), 3.00 (dd, J=6.1, 13.8 Hz, 1H), 1.39 (s, 9H); $^{13}$C NMR (125 MHz, CDCl$_3$) δ 172.4, 156.5, 155.2, 153.6, 149.1, 146.3, 143.8, 137.6, 131.6, 129.7, 121.7, 113.8, 110.3, 106.6, 80.0, 64.4, 64.2, 54.4, 52.2, 37.6, 28.3; HRMS-ESI [M+H]$^+$ found 481.2082 [calcd for C$_{25}$H$_{28}$N$_4$O$_6$ 480.2003].

Preparation of JGK016, JGK023

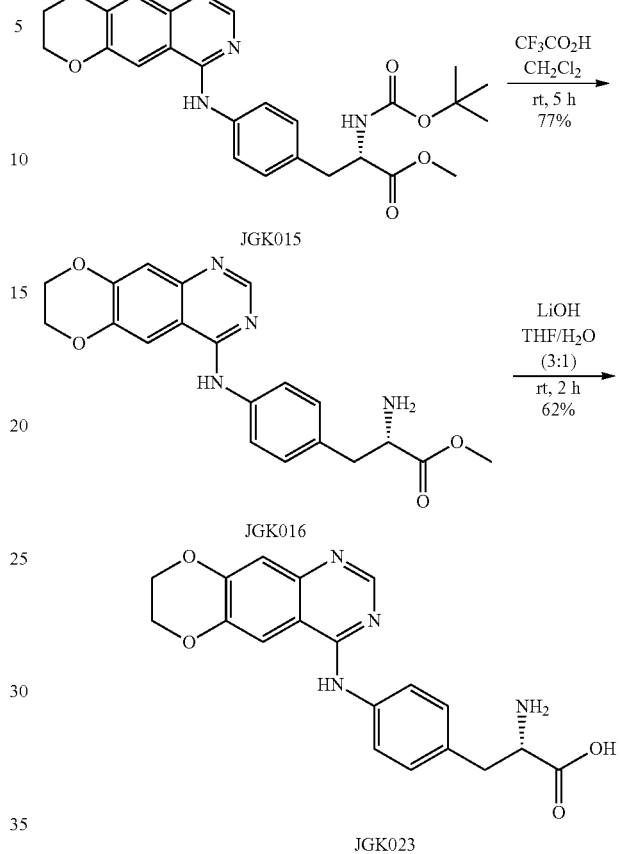

[JGK016 (Boc deprotection)] To a solution of JGK015 (121 mg, 0.251 mmol) in anhydrous CH$_2$Cl$_2$ (5 mL, 0.05 M) was dropwise added trifluoroacetic acid (1.0 mL) at room temperature. After being stirred at the same temperature for 5 h, the reaction mixture was quenched with saturated aqueous NaHCO$_3$ (20 mL), and diluted with CH$_2$Cl$_2$ (20 mL). The layers were separated, and the aqueous layer was extracted with CH$_2$Cl$_2$ (2×30 mL). The combined organic layers were washed successively with H$_2$O and saturated brine, dried over anhydrous MgSO$_4$, filtered, and concentrated in vacuo. The residue was purified by column chromatography (silica gel, CH$_2$Cl$_2$/MeOH, 20/1) to give JGK016 (74 mg, 77%); $^1$H NMR (400 MHz, DMSO-d$_6$) δ 10.5 (s, 1H), 8.68 (s, 1H), 8.43 (s, 2H), 8.20 (s, 1H), 7.68 (d, J=8.4 Hz, 2H), 7.26 (d, J=8.4 Hz, 2H), 7.23 (s, 1H), 4.44-4.46 (m, 2H), 4.39-4.41 (m, 2H), 3.68 (s, 3H), 3.03-3.13 (m, 2H); $^1$H NMR (400 MHz, CD$_3$OD) δ 8.26 (s, 1H), 7.73 (s, 1H), 7.60 (d, J=8.4 Hz, 2H), 7.17 (d, J=8.4 Hz, 2H), 7.08 (s, 1H), 4.31-4.35 (m, 4H), 3.72 (t, J=6.6 Hz, 1H), 3.68 (s, 3H), 3.27-3.29 (m, 1H), 3.01 (dd, J=5.9, 13.6 Hz, 1H), 2.89 (dd, J=7.0, 13.5 Hz, 1H); $^{13}$C NMR (100 MHz, CD$_3$OD) δ 174.4, 157.4, 152.6, 149.7, 145.0, 144.2, 137.5, 132.8, 129.2, 122.8, 122.3, 111.5, 110.1, 107.9, 64.5, 64.1, 55.2, 51.0, 39.5; HRMS-ESI [M+H]$^+$ found 381.1553 [calcd for C$_{20}$H$_{20}$N$_4$O$_4$ 380.1479].

[JGK023 (Hydrolysis)] To a cooled (0° C.) solution of JGK016 (42 mg, 0.1104 mmol) in THF/H$_2$O (3:1, total 4.0 mL) was added in one portion lithium hydroxide (14 mg). After being stirred at the room temperature for 2 h, the reaction mixture was neutralized with 1N HCl and diluted with EtOAc (20 mL). The layers were separated, and the aqueous layer was extracted with EtOAc (100 mL). The combined organic layers were washed successively with H₂O and saturated brine, dried over anhydrous MgSO₄, filtered, and concentrated in vacuo. The residue was purified by column chromatography (silica gel, CH₂Cl₂/MeOH, 30/1 to 15/1) to give JGK023 (25 mg, 62%); ¹H NMR (400 MHz, CDCl₃) δ 8.62 (s, 1H), 8.12 (s, 1H), 7.71 (d, J=8.4 Hz, 2H), 7.40 (d, J=8.4 Hz, 2H), 7.24 (s, 1H), 4.48-4.50 (m, 2H), 4.42-4.44 (m, 2H), 4.28 (t, J=6.8 Hz, 1H), 3.32-3.37 (m, 1H), 3.20 (dd, J=7.6, 14.8 Hz, 1H); ¹³C NMR (125 MHz, CDCl₃) δ 169.7, 159.1, 152.4, 148.8, 146.0, 136.1, 134.1, 133.1, 129.7, 129.7, 124.8, 124.8, 110.0, 108.1, 104.9, 65.2, 64.2, 53.6, 35.4; HRMS-ESI [M+H]⁺ found 367.1334 [calcd for $C_{19}H_{18}N_4O_4$ 366.1322].

Preparation of JGK020

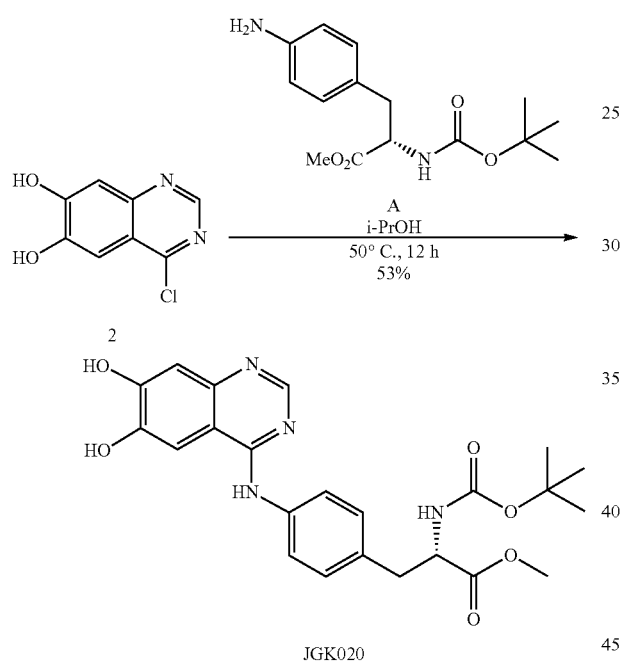

To a solution of chloroquinazoline 2 (104 mg, 0.5294 mmol) in isopropyl alcohol (5.3 mL) was dropwise added amino acid (187 mg) at room temperature. After being heated at 50° C. (bath temperature) with stirring for 12 h, the reaction mixture was cooled to room temperature and concentrated in vacuo. The residue was purified by column chromatography (silica gel, hexanes/EtOAc, 5/1 to 3/1) to give JGK020 (128 mg, 53%); ¹H NMR (400 MHz, DMSO-d₆) δ 10.68 (s, 1H), 10.22 (br, 1H), 8.64 (s, 1H), 7.91 (s, 1H), 7.53 (d, J=8.4 Hz, 2H), 7.26-7.31 (m, 4H), 4.12-4.18 (m, 1H), 3.59 (s, 3H), 2.98 (dd, J=5.2, 14.0 Hz, 1H), 2.84 (dd, J=10.0, 13.2 Hz, 1H), 1.30 (s, 9H); ¹³C NMR (125 MHz, DMSO-d₆) δ 173.0, 158.2, 155.9, 155.6, 148.7, 148.4, 136.1, 135.8, 129.7, 124.7, 107.6, 107.3, 103.3, 78.8, 55.7, 52.3, 36.3, 28.6; HRMS-ESI [M+H]⁺ found 455.1920 [calcd for $C_{23}H_{26}N_4O_6$ 454.1846].

JGK014

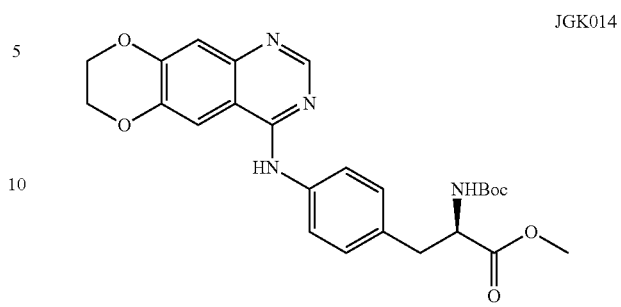

JGK014 (26%); ¹H NMR (400 MHz, CDCl₃) δ 8.62 (s, 1H), 7.66 (d, J=8.4 Hz, 2H), 7.35 (s, 1H), 7.16 (d, J=8.4 Hz, 2H), 4.99 (d, J=7.6 Hz, 1H), 4.56-4.62 (m, 1H), 4.36-4.42 (m, 4H), 3.73 (s, 3H), 3.03-3.15 (m, 2H), 1.43 (s, 9H); ¹³C NMR (125 MHz, CDCl₃) δ 172.4, 156.5, 155.2, 153.6, 149.1, 146.3, 143.8, 137.6, 131.6, 129.7, 121.7, 113.8, 110.3, 106.6, 80.0, 64.4, 64.2, 54.4, 52.2, 37.6, 28.3; HRMS-ESI [M+H]⁺ found 481.2080 [calcd for $C_{25}H_{28}N_4O_6$ 480.2003].

JGK021

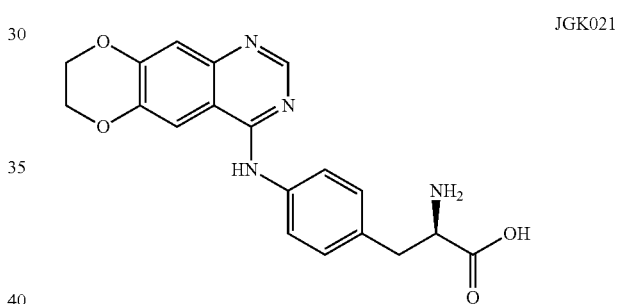

Preparation of JGK021 was followed by synthetic procedure of JGK023; ¹H NMR (400 MHz, CDCl₃) δ 8.62 (s, 1H), 8.12 (s, 1H), 7.71 (d, J=8.4 Hz, 2H), 7.40 (d, J=8.4 Hz, 2H), 7.24 (s, 1H), 4.48-4.50 (m, 2H), 4.42-4.44 (m, 2H), 4.28 (t, J=6.8 Hz, 1H), 3.32-3.37 (m, 1H), 3.20 (dd, J=7.6, 14.8 Hz, 1H); ¹³C NMR (125 MHz, CDCl₃) δ 169.7, 159.1, 152.4, 148.8, 146.0, 136.1, 134.1, 133.1, 129.7, 129.7, 124.8, 124.8, 110.0, 108.1, 104.9, 65.2, 64.2, 53.6, 35.4; HRMS-ESI [M+H]⁺ found 367.1347 [calcd for $C_{19}H_{18}N_4O_4$ 366.1322].

Preparation of JGK022

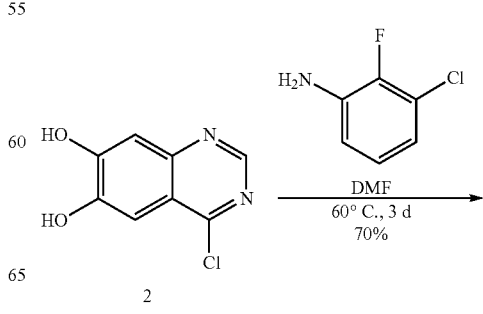

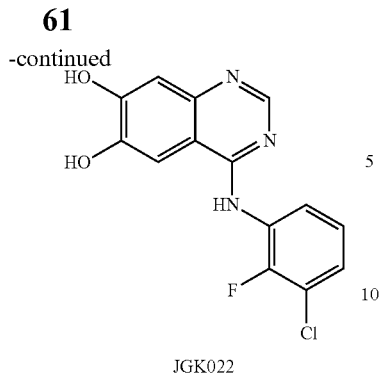

JGK022

To a solution of diol X (121 mg, 0.6155 mmol) in DMF (3.0 mL) was dropwise added 3-chloro-2-fluoroaniline (0.14 mL) at room temperature. After being heated at 60° C. (bath temperature) with stirring for 3 d, the reaction mixture was cooled to room temperature and diluted with Et$_2$O (30.0 mL) to give white suspension. The resulting white solid were washed successively with Et$_2$O (3×50 mL) and CH$_2$Cl$_2$ (2×30 mL) and collected to give JGK022 (132 mg, 70%); $^1$H NMR (400 MHz, DMSO-d$_6$) δ 11.16 (br, 1H), 10.43 (br, 1H), 8.68 (s, 1H), 7.91 (s, 1H), 7.58 (t, J=7.1 Hz, 1H), 7.48 (t, J=6.8 Hz, 1H), 7.40 (s, 1H), 7.30 (t, J=8.1 Hz, 1H); $^{13}$C NMR (125 MHz, DMSO-d$_6$) δ 159.1, 156.4, 154.1, 152.1, 149.1, 148.3, 135.1, 129.7, 128.1, 126.8, 125.7, 120.8, 107.4, 106.9, 102.9; HRMS-ESI [M+H]$^+$ found 306.0437 [calcd for C$_{14}$H$_9$ClFN$_3$O$_2$ 305.0361].

Preparation of JGK018

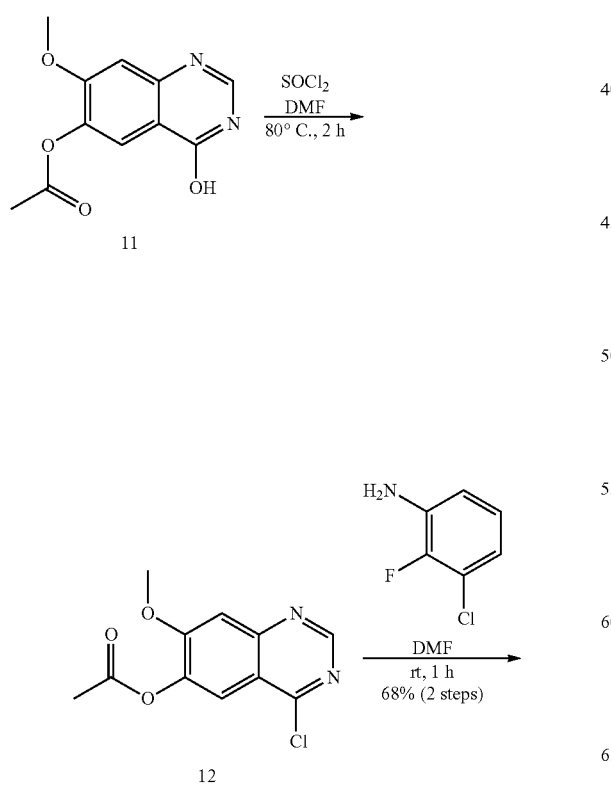

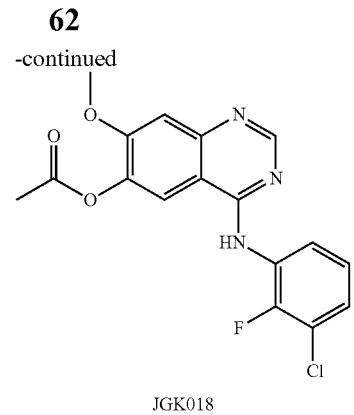

JGK018

[Chlorination] To a solution of 11 (500 mg, 2.134 mmol) in thionyl chloride (7.5 mL, 0.28 M) was dropwise added dimethylformamide (0.15 mL). After being heated at 80° C. (bath temperature) with stirring for 2 h, the reaction mixture was cooled to room temperature and concentrated in vacuo. The residue was washed successively with Et$_2$O (200 mL), and immediately used to the next step.

[Substitution] To a solution of above generated chloroquinazoline 12 in anhydrous DMF (11 mL, 0.2 M) was dropwise added 3-chloro-2-fluoroaniline (0.50 mL, 4.548 mmol) at room temperature under Ar. After being stirred at the same temperature for 1 h, the reaction mixture was diluted with Et$_2$O (100.0 mL) to give white suspension. The resulting white solid were washed successively with Et$_2$O (2×50 mL) and collected to give JGK018 (525 mg, 68%); The spectroscopic data was matched with Zhang, X. et al *J. Med. Chem.* 2015, 58, 8200-8215.

Preparation of 13

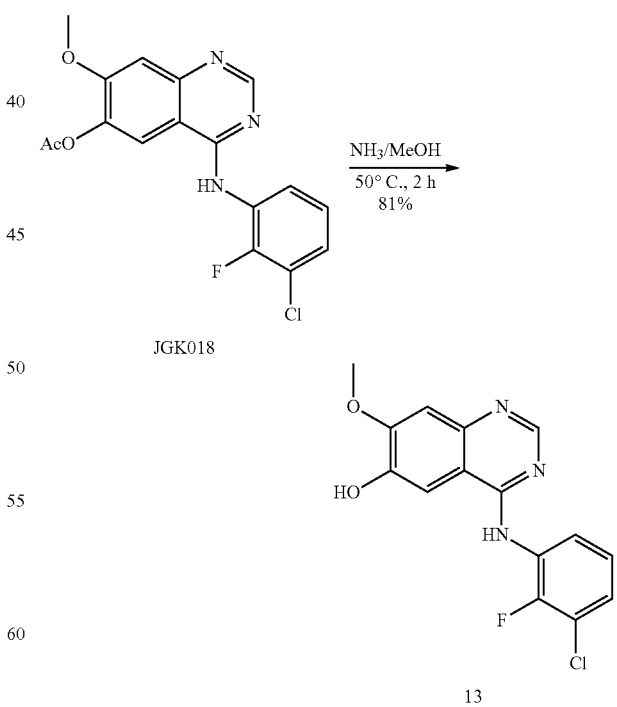

[Acetyl Deprotection] To JGK018 (550 mg, 1.520 mmol) was dropwise added ammonia solution (8.0 mL, 7 N in methanol). After being heated at 50° C. (bath temperature)

in sealed tube with stirring for 2 h, the reaction mixture was cooled to room temperature and concentrated in vacuo. The resulting white solid were washed successively with Et₂O (2×50 mL) and collected to give 13 (394 mg, 81%); The resulting spectroscopic data was matched with that of Zhang, X. et al *J. Med. Chem.* 2015, 58, 8200-8215.

Preparation of 14

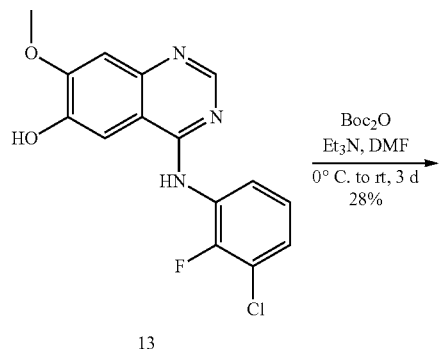

To a cooled (0° C.) solution of 13 (113 mg, 0.353 mmol) in anhydrous DMF (2 mL) was dropwise added triethylamine (0.25 mL, 1.767 mmol) followed by dropwise addition of Di-tert-butyl dicarbonate (62 mg, 0.459 mmol) in anhydrous DMF (2 mL) under Ar. After being stirred at room temperature for 3 d, the reaction mixture was quenched with saturated aqueous H₂O (10 mL), and diluted with EtOAc (10 mL). The layers were separated, and the aqueous layer was extracted with EtOAc (2×50 mL). The combined organic layers were washed successively with H₂O and saturated brine, dried over anhydrous MgSO₄, filtered, and concentrated in vacuo. The residue was purified by column chromatography (silica gel, hexanes/EtOAc, 5/1 to 3/1) to give 14 (42 mg, 28% isolated yield); ¹H NMR (400 MHz, CDCl₃) δ 8.69 (s, 1H), 8.39-8.45 (m, 1H), 7.64 (s, 1H), 7.44 (s, 1H), 7.11-7.16 (m, 2H), 3.90 (s, 3H), 1.59 (s, 9H); ¹³C NMR (125 MHz, CDCl₃) δ 156.2 (J=39.5 Hz), 154.9, 151.3, 150.3, 149.5 (J=224.1 Hz), 140.4, 128.1 (J=9.6 Hz), 124.8, 124.4 (J=4.8 Hz), 121.5, 120.8 (J=51.2 Hz), 113.5, 109.0, 108.8, 84.6, 56.2, 27.6;

Preparation of C

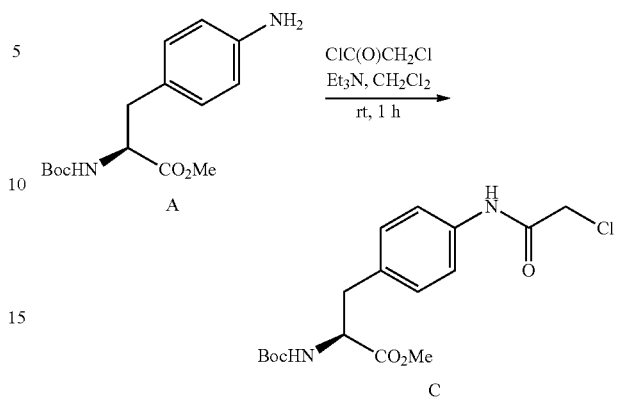

To a solution of A¹ (56 mg, 0.1904 mmol) in anhydrous CH₂Cl₂ (2 mL) was dropwise added triethylamine (0.08 mL, 0.5712 mmol) followed by addition of chloroacetyl chloride (0.05 mL, 0.6286 mmol) at room temperature under Ar. After being stirred at the same temperature for 1 h, the reaction mixture was quenched with saturated aqueous NH₄Cl (20 mL), and diluted with CH₂Cl₂ (20 mL). The layers were separated, and the aqueous layer was extracted with CH₂Cl₂ (2×30 mL). The combined organic layers were washed successively with H₂O and saturated brine, dried over anhydrous MgSO₄, filtered, and concentrated in vacuo. The crude product was used for the next step without further purification.

Preparation of JGK031

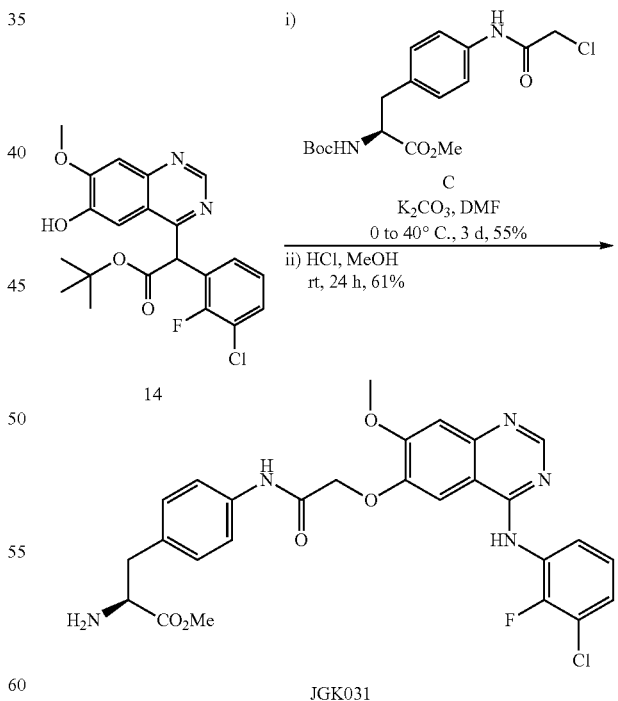

[Alkylation] To a cooled (0° C.) solution of 14 (44 mg, 0.1058 mmol) in DMF (2.0 mL) was added in one portion potassium carbonate (73 mg, 0.528 mmol) followed by dropwise addition of above generated C (0.1904 mmol) in DMF (2.0 mL) at room temperature. After being heated at 40° C. (bath temperature) with stirring for 3 d, the reaction mixture was quenched with H$_2$O (10 mL), and diluted with EtOAc (10 mL). The layers were separated, and the aqueous layer was extracted with EtOAc (2×50 mL). The combined organic layers were washed successively with H$_2$O and saturated brine, dried over anhydrous MgSO$_4$, filtered, and concentrated in vacuo. The residue was purified by column chromatography (silica gel, hexanes/EtOAc, 100/1 to 30/1) to give alkylated product 14-(2) (43 mg, 55% isolated yield); $^1$H NMR (400 MHz, CDCl$_3$) δ 8.16 (s, 1H), 7.48 (d, J=8.4 Hz, 2H), 7.44 (s, 1H), 6.98-7.13 (m, 5H), 6.34 (m, 1H), 4.95 (d, J=7.4 Hz, 1H), 4.54 (d, J=6.5 Hz, 1H), 4.48 (s, 2H), 3.69 (s, 6H), 2.95-3.13 (m, 2H), 1.53 (s, 9H), 1.40 (s, 9H).

[Deprotection] To a solution of alkylated product 14-(2) (26 mg, 0.0348 mmol) in anhydrous MeOH (5.0 mL) was dropwise added 0.5 N hydrochloride solution (0.5 mL). After being stirred at the same temperature for 24 h, the reaction mixture was concentrated in vacuo. The residue was purified by column chromatography (reverse phase silica gel, MeOH or MeOH/H$_2$O, 10/1) to give JGK031 (12 mg, 61%); $^1$H NMR (400 MHz, MeOD) δ 8.20 (s, 1H), 7.67 (s, 1H), 7.49 (t, J=7.9 Hz, 2H), 7.24-7.30 (m, 1H), 7.11-7.21 (m, 4H), 3.94 (s, 3H), 3.59 (s, 3H), 2.83-3.01 (m, 2H); HRMS-ESI [M+H]$^+$ found 554.1631 [calcd for C$_{27}$H$_{25}$ClFN$_5$O$_5$ 553.1522].

Preparation of JGK033

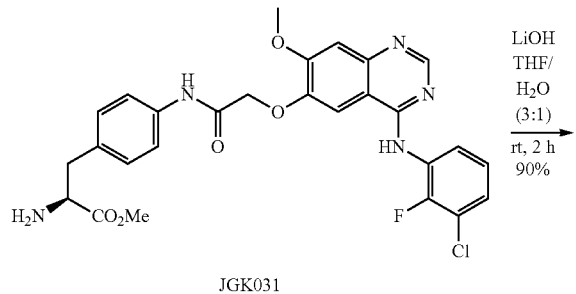

JGK031

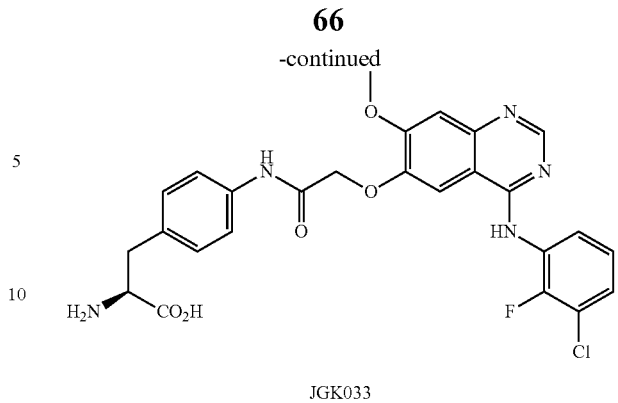

JGK033

To a solution of JGK031 (5 mg, 0.009026 mmol) in anhydrous THF (6 mL) and H$_2$O (2 mL) was added lithium hydroxide.H$_2$O (3 mg) in one portion. After being stirred at room temperature for 2 h, the reaction mixture was neutralized with 1N hydrochloride solution and concentrated in vacuo. The residue was purified by reverse column chromatography (reverse phase silica gel, MeOH/H$_2$O, 5/1) to give JGK033 (4.4 mg, 90%); $^1$H NMR (400 MHz, MeOD) δ 7.16 (s, 1H), 6.32 (s, 1H), 6.03 (d, J=8.2 Hz, 2H), 5.89-5.98 (m, 2H), 5.59-5.79 (m, 4H), 4.00 (s, 2H), 2.51 (s, 3H), 2.46 (t, J=5.6 Hz, 1H); $^{13}$C NMR (125 MHz, MeOD) δ 163.9, 159.4, 157.2, 154.3, 152.1, 149.5, 137.1, 135.4, 129.7, 126.9, 124.6, 121.5, 120.3, 108.0, 106.9, 97.8, 56.6, 53.5, 35.6; HRMS-ESI [M+H]$^+$ found 540.1435 [calcd for C$_{26}$H$_{23}$ClFN$_5$O$_5$ 539.1366].

Preparation of JGK008

Lapatinib

JGK008

To a solution of lapatinib (326 mg, 0.561 mmol) in anhydrous MeOH (5.6 mL) and CH$_2$Cl$_2$ (5.6 mL) was dropwise Di-tert-butyl dicarbonate (378 mg, 2.819 mmol) in one portion under Ar. After being stirred at room temperature for 2 d, the reaction mixture was quenched with saturated aqueous H$_2$O (10 mL), and diluted with CH$_2$Cl$_2$ (10 mL). The layers were separated, and the aqueous layer was extracted with CH$_2$Cl$_2$ (5×50 mL). The combined organic layers were washed successively with H$_2$O and saturated brine, dried over anhydrous MgSO$_4$, filtered, and concentrated in vacuo. The residue was purified by column chromatography (silica gel, hexanes/EtOAc, 3/1 to 1/1) to give JGK008 (119 mg, 31% isolated yield); $^1$H NMR (500 MHz, CDCl$_3$) δ 8.71 (bs, 1H), 8.64 (s, 1H), 8.44 (s, 1H), 7.85-7.95 (m, 3H), 7.68 (d, J=7.8 Hz, 1H), 7.32-7.37 (m, 1H), 7.21 (dd, J=8.4, 10.8 Hz, 2H), 6.98-7.03 (m, 1H), 6.96 (d, J=8.9 Hz, 1H), 6.39 (d, J=47.1 Hz, 1H), 5.13 (s, 2H), 4.53 (d, J=32.2 Hz, 2H), 3.99 (t, J=7.3 Hz, 2H), 3.39 (d, J=66.1 Hz, 2H), 2.89 (s, 3H), 1.49 (s, 9H); $^{13}$C NMR (125 MHz, CDCl$_3$) δ 163.9, 162.0, 158.0, 154.2, 152.7, 151.7, 151.0, 139.1 (d, J=7.3 Hz), 132.4, 130.1 (d, J=8.1 Hz), 129.1, 128.6, 128.2, 125.1, 123.1, 122.4, 122.3, 115.4, 114.9 (d, J=21.0 Hz), 114.1 (d, J=13.9 Hz), 113.9, 111.5, 110.9, 107.7, 81.3, 70.9, 45.0, 43.6, 42.3, 41.4, 41.2, 28.4; HRMS-ESI [M+H]$^+$ found 681.1946 [calcd for C$_{34}$H$_{34}$ClFN$_4$O$_6$S 680.1866].

Preparation of JGK011

NMR (125 MHz, CDCl$_3$) δ 171.4, 171.2, 163.9, 162.2, 162.0, 154.0, 153.7, 152.5, 151.0, 138.5 (J=7.3 Hz), 134.2, 130.8, 130.3, 130.2, 129.9, 129.1, 127.4, 123.9, 122.4 (J=2.9 Hz), 121.8, 118.0, 115.1, 115.0, 114.0 (J=5.2 Hz), 113.8, 111.1, 108.9, 70.1 (J=1.7 Hz), 52.3, 47.0, 41.4, 40.7, 23.7, 21.8; HRMS-ESI [M+H]$^+$ found 665.1628 [calcd for C$_{33}$H$_{30}$ClFN$_4$O$_6$S 664.1553].

Example 2

Preparation of Further Exemplary Compounds of the JGK Series

General Chemistry Information

All chemicals, reagents, and solvents were purchased from commercial sources when available and were used as received. When necessary, reagents and solvents were purified and dried by standard methods. Air- and moisture-sensitive reactions were carried out under an inert atmosphere of argon in oven-dried glassware. Microwave-irradiated reactions were carried out in a single mode reactor CEM Discover microwave synthesizer. Room temperature reactions were carried out at ambient temperature (approximately 23° C.). All reactions were monitored by thin layer chromatography (TLC) on precoated Merck 60 F$_{254}$ silica gel plates with spots visualized by UV light (λ=254, 365 nm) or by using an alkaline KMnO$_4$ solution. Flash column chromatography (FC) was carried out on SiO$_2$ 60 (particle size 0.040-0.063 mm, 230-400 mesh). Concentration under reduced pressure (in vacuo) was performed by rotary evaporation at 25-50° C. Purified compounds were further dried under high vacuum or in a desiccator. Yields correspond to purified compounds, and were not further optimized. Proton nuclear magnetic resonance ($^1$H NMR) spectra were recorded on Bruker spectrometers (operating at 300, 400, or 500 MHz). Carbon NMR ($^{13}$C NMR) spectra were recorded on Bruker spectrometers (either at 400 or 500 MHz). NMR chemical shifts (δ ppm) were referenced to the residual

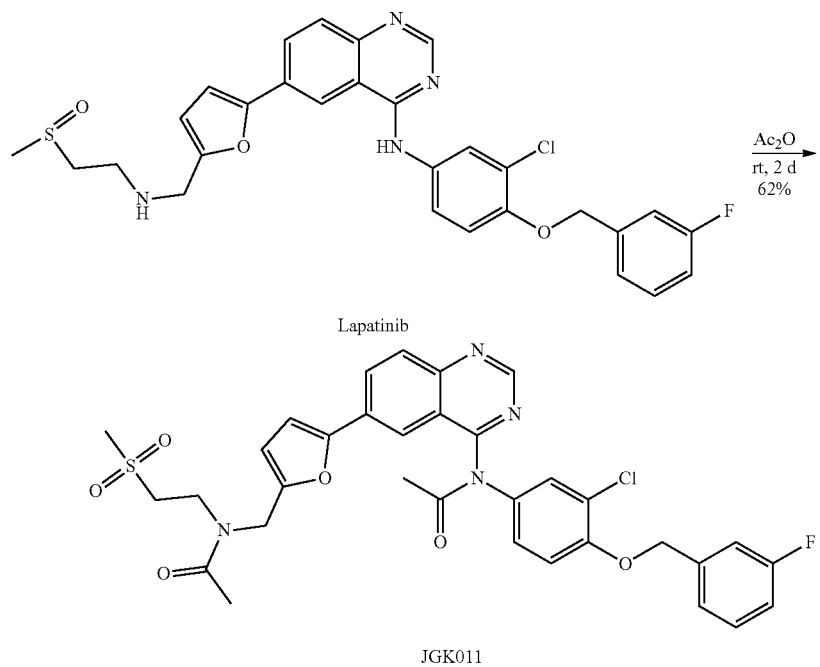

To a solid of lapatinib (68 mg, 0.353 mmol) was added acetic anhydride (5.0 mL) under Ar. After being stirred at room temperature for 2 d, the reaction mixture was concentrated in vacuo. The residue was purified by column chromatography (silica gel, hexanes/EtOAc, 3/1 to 1/3) to give JGK002 (48 mg, 62% isolated yield); $^1$H NMR (500 MHz, CDCl$_3$) δ 9.18 (s, 1H), 8.10-8.17 (m, 3H), 7.50 (d, J=2.5 Hz, 1H), 7.27-7.36 (m, 2H), 7.18 (dd, J=7.6, 13.8 Hz, 2H), 6.97-7.03 (m, 2H), 6.79 (d, J=3.3 Hz, 1H), 6.44 (d, J=3.3 Hz, 1H), 5.14 (s, 2H), 4.66 (s, 2H), 3.86 (t, J=6.6 Hz, 2H), 3.30 (t, J=6.6 Hz, 2H), 2.95 (s, 3H), 2.33 (s, 3H), 2.23 (s, 3H); $^{13}$C solvent signals. $^1$H NMR data are reported as follows: chemical shift in ppm; multiplicity (s=singlet, d=doublet, t=triplet, q=quartet, quint=quintet, m=multiplet/complex pattern, td=triplet of doublets, ddd=doublet of doublet of doublets, br=broad signal); coupling constants (J) in Hz, integration. Data for $^{13}$C NMR spectra are reported in terms of chemical shift, and if applicable coupling constants. High resolution mass (HRMS) spectra were recorded on a Thermo Fisher Scientific Exactive Plus with IonSense ID-CUBE DART source mass spectrometer. Compounds 4-chloro-7,8-dihydro[1,4]dioxino[2,3-g]quinazoline (1), 4-chloroquinazoline-6,7-diol (2), and JGK010 were prepared as previously reported.

General Procedure A for the Synthesis of 4-Anilinoquinazoline Compounds JGK035-JGK041, and JKG043.

A mixture of the 4-chloroquinazoline (1 equiv) in iPrOH (0.1-0.3 M) was treated with the aniline (1 equiv), and the mixture was heated at 80° C. under microwave irradiation (60 W) for 15-20 min. The mixture was cooled to 23° C., treated with additional aniline (1 equiv), and again subjected to microwave irradiation (80° C., 60 W, 15-20 min). The mixture was either concentrated under reduced pressure, or the precipitated 4-anilinoquinazoline hydrochloride salt was isolated by filtration (washings with cold iPrOH). The residue was suspended in sat. aq. NaHCO$_3$, and extracted with CH$_2$Cl$_2$ (3×). The combined organic extracts were washed with water, brine, dried (Na$_2$SO$_4$), filtered, and concentrated. Purification by FC (elution with a gradient of CH$_2$Cl$_2$/EtOAc or hexanes/EtOAc) afforded the desired products typically as white to off-white, or pale-yellow solids.

N-(2-Fluorophenyl)-7,8-dihydro[1,4]dioxino[2,3-g]quinazolin-4-amine (JGK035)

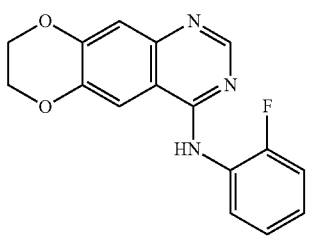 [SMILES: Fc1ccccc1Nc1ncnc2cc3c(cc12)OCCO3]

Following general procedure A, compound JGK035 was prepared from 4-chloroquinazoline 1 (51 mg, 0.23 mmol) and 2-fluoroaniline (40 μL, 0.48 mmol) in iPrOH (1.5 mL). FC (CH$_2$Cl$_2$/EtOAc 10:1→10:4) gave JGK035 (56 mg, 82%) as a white solid. $^1$H NMR (500 MHz, CDCl$_3$): δ 8.68 (s, 1H), 8.64 (td, J=8.2, 1.7 Hz, 1H), 7.38 (s, 1H), 7.36 (br, 1H), 7.31 (s, 1H), 7.22 (t, J=7.5 Hz, 1H), 7.17 (ddd, J=11.2, 8.3, 1.5 Hz, 1H), 7.10-7.05 (m, 1H), 4.44-4.37 ppm (m, 4H). $^{13}$C NMR (126 MHz, CDCl$_3$): δ 156.08, 153.60, 153.50 (d, J=242.7 Hz), 149.52, 146.65, 144.34, 127.31 (d, J=9.5 Hz), 124.66 (d, J=3.7 Hz), 123.97 (d, J=7.8 Hz), 122.89, 115.06 (d, J=19.3 Hz), 114.46, 110.62, 106.10, 64.69, 64.51 ppm. HRMS (DART): m/z [M−H]$^-$ calcd for C$_{16}$H$_{11}$FN$_3$O$_2$$^-$, 296.0841; found, 296.0841.

4-Chloro(7,7,8,8-$^2$H$_4$)-7,8-dihydro[1,4]dioxino[2,3-g]quinazoline (3)

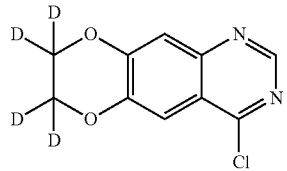 [SMILES: [2H]C1([2H])Oc2cc3ncnc(Cl)c3cc2OC1([2H])[2H]]

A solution of compound 2 (193 mg, 0.98 mmol) in dry DMF (4.8 mL) was treated with Cs$_2$CO$_3$ (788 mg, 2.42 mmol), stirred for 5 min, and treated dropwise with 1-bromo-2-chloro($^2$H$_4$)ethane (270 μL, 3.16 mmol). The mixture was stirred at 23° C. for 1 h, and then at 70° C. for 18 h. After the mixture was cooled to 23° C., all volatiles were removed in vacuo. The residue was dissolved in CH$_2$Cl$_2$ (40 mL), washed with water (2×13 mL), brine (13 mL), dried (Na$_2$SO$_4$), filtered, and evaporated. Purification by FC (CH$_2$Cl$_2$/EtOAc 1:0→10:1.5) afforded the title compound 3 (109 mg, 49%) as a white fluffy solid. $^1$H NMR (400 MHz, CDCl$_3$): δ 8.84 (s, 1H), 7.64 (s, 1H), 7.47 ppm (s, 1H). $^{13}$C NMR (101 MHz, CDCl$_3$): δ 160.19, 152.52, 151.54, 147.93, 146.06, 120.10, 113.72, 110.83 ppm (two upfield carbons not observed). HRMS (DART): m/z [M+H]$^+$ calcd for C$_{10}$H$_4$D$_4$ClN$_2$O$_2$$^+$, 227.0520; found, 227.0516.

N-(3-Chloro-2-fluorophenyl)(7,7,8,8-$^2$H$_4$)-7,8-dihydro[1,4]dioxino[2,3-g]quinazolin-4-amine (JGK036)

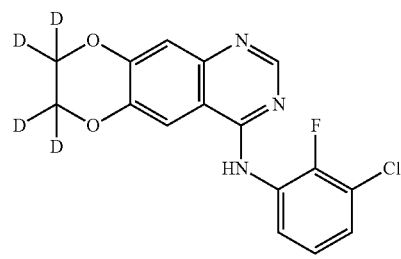 [SMILES: [2H]C1([2H])Oc2cc3ncnc(Nc4cccc(Cl)c4F)c3cc2OC1([2H])[2H]]

Following general procedure A, compound JGK036 was prepared from 4-chloroquinazoline 3 (55 mg, 0.24 mmol) and 3-chloro-2-fluoroaniline (52 μL, 0.47 mmol) in iPrOH (1.2 mL). JGK036.HCl was isolated by filtration from the crude reaction mixture, and after basification and extraction gave pure JGK036 (67 mg, 82%) as a pale-yellow solid. $^1$H NMR (500 MHz, DMSO-d$_6$): δ 9.62 (s, 1H), 8.34 (s, 1H), 7.93 (s, 1H), 7.53-7.43 (m, 2H), 7.27 (td, J=8.1, 1.3 Hz, 1H), 7.19 ppm (s, 1H). $^{13}$C NMR (126 MHz, DMSO-d$_6$): δ 157.17, 153.10, 152.45 (d, J=249.2 Hz), 149.28, 146.04, 143.68, 128.21 (d, J=12.0 Hz), 127.27, 127.03, 124.87 (d, J=4.7 Hz), 120.11 (d, J=16.7 Hz), 112.48, 109.64, 108.35, 63.50 (m, 2C's). HRMS (DART): m/z [M+H]$^+$ calcd for C$_{16}$H$_8$D$_4$ClFN$_3$O$_2$$^+$, 336.0848; found, 336.0841.

N-(3-Bromo-2-fluorophenyl)-7,8-dihydro[1,4]di-oxino[2,3-g]quinazolin-4-amine (JGK037)

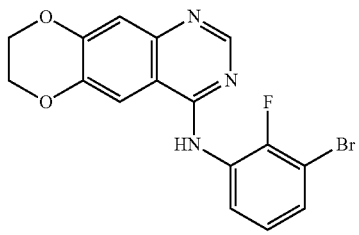 [SMILES: Fc1c(Br)cccc1Nc1ncnc2cc3c(cc12)OCCO3]

Following general procedure A, compound JGK037 was prepared from 4-chloroquinazoline 1 (100 mg, 0.45 mmol) and 3-bromo-2-fluoroaniline (100 μL, 0.89 mmol) in iPrOH (1.5 mL). FC (CH$_2$Cl$_2$/EtOAc 10:0→10:3) gave JGK037 (150 mg, 89%) as a pale-yellow solid. $^1$H NMR (500 MHz, CDCl$_3$): δ 8.68 (s, 1H), 8.65 (ddd, J=8.3, 7.4, 1.5 Hz, 1H), 7.39 (s, 1H), 7.35 (br, 1H), 7.29 (s, 1H), 7.29-7.24 (m, 1H), 7.11 (td, J=8.2, 1.6 Hz, 1H), 4.44-4.38 ppm (m, 4H). $^{13}$C NMR (126 MHz, CDCl$_3$): δ 155.89, 153.37, 150.15 (d, J=242.2 Hz), 149.70, 146.75, 144.53, 128.65 (d, J=10.5 Hz), 127.24, 125.31 (d, J=4.7 Hz), 121.79, 114.53, 110.59, 108.59 (d, J=19.4 Hz), 105.93, 64.70, 64.51 ppm. HRMS (DART): m/z [M−H]$^−$ calcd for C$_{16}$H$_{10}$BrFN$_3$O$_2^−$, 373.9946; found, 373.9946.

N-{2-Fluoro-3-[(triethylsilyl)ethynyl]phenyl}-7,8-dihydro[1,4]dioxino[2,3-g]quinazolin-4-amine (4)

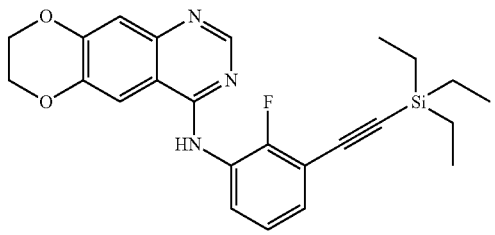 [SMILES: CC[Si](C#Cc1cccc(Nc2ncnc3cc4c(cc23)OCCO4)c1F)(CC)CC]

A 1 dram vial was charged with JGK010 (75 mg, 0.23 mmol), XPhos (19.7 mg, 0.041 mmol), Cs$_2$CO$_3$ (195 mg, 0.60 mmol), [PdCl$_2$.(MeCN)$_2$] (3.6 mg, 0.014 mmol). The vial was evacuated and backfilled with argon (repeated at least twice). Dry acetonitrile (1 mL) was added, and the orange suspension was stirred at 23° C. for 25 min, then ethynyltriethylsilane (150 μL, 0.84 mmol) was injected. The tube was sealed, and the reaction mixture stirred at 95° C. in a preheated oil bath for 3.5 h. The suspension was allowed to reach 23° C., diluted with EtOAc, filtered through a plug of SiO$_2$ (washings with EtOAc), and evaporated. Purification by FC (SiO$_2$; hexanes/EtOAc 8:2→4:6) afforded the title compound 4 (48 mg, 49%) as a yellow foamy solid. $^1$H NMR (500 MHz, CDCl$_3$): δ 8.681 (td, J=8.1, 1.9 Hz, 1H), 8.678 (s, 1H), 7.382 (s, 1H), 7.376 (br, 1H), 7.28 (s, 1H), 7.21-7.12 (m, 2H), 4.44-4.38 (m, 4H), 1.07 (t, J=7.9 Hz, 9H), 0.71 ppm (q, J=7.9 Hz, 6H). $^{13}$C NMR (126 MHz, CDCl$_3$): δ 155.95, 153.81 (d, J=248.0 Hz), 153.44, 149.62, 146.66, 144.47, 127.68, 127.60, 124.15 (d, J=4.5 Hz), 122.79, 114.49, 111.77 (d, J=14.6 Hz), 110.61, 105.97, 98.65, 98.49 (d, J=3.7 Hz), 64.70, 64.51, 7.63, 4.50 ppm. HRMS (DART): m/z [M+H]$^+$ calcd for C$_{24}$H$_{27}$N$_3$O$_2$Si$^+$, 436.1851; found, 436.1831.

N-(3-Ethynyl-2-fluorophenyl)-7,8-dihydro[1,4]di-oxino[2,3-g]quinazolin-4-amine (JGK038)

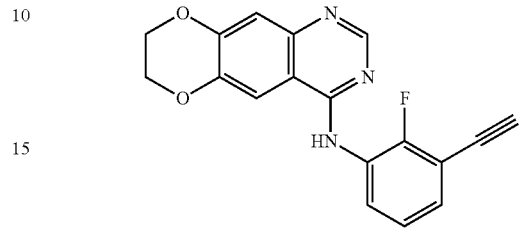

A mixture of compound 4 (40 mg, 0.09 mmol) in wet THF (0.9 mL) was treated dropwise with a 1 M solution of TBAF in THF (450 μL, 0.45 mmol), and the mixture was stirred at 23° C. for 18 h. Water (10 mL) was added, and the mixture was extracted with EtOAc (3×15 mL). The combined organics were washed with brine (20 mL), dried (Na$_2$SO$_4$), filtered, and evaporated. Purification by FC (SiO$_2$; hexanes/EtOAc 7:3→3:7), followed by a second FC (SiO$_2$; CH$_2$Cl$_2$/EtOAc 1:0→6:4) afforded JGK038 (19 mg, 64%) as an off-white solid. $^1$H NMR (500 MHz, CDCl$_3$): δ 8.69 (td, J=8.0, 1.8 Hz, 1H), 8.67 (s, 1H), 7.38 (s, 1H), 7.36 (br, 1H), 7.29 (s, 1H), 7.24-7.15 (m, 2H), 4.43-4.38 (m, 4H), 3.34 ppm (s, 1H). $^{13}$C NMR (126 MHz, CDCl$_3$): δ 155.94, 154.04 (d, J=248.8 Hz), 153.39, 149.65, 146.70, 144.47, 127.81, 127.68 (d, J=9.1 Hz), 124.30 (d, J=4.7 Hz), 123.47, 114.49, 110.58, 110.50 (d, J=14.3 Hz), 105.99, 82.95 (d, J=3.5 Hz), 76.70 (d, J=1.6 Hz), 64.69, 64.50 ppm. HRMS (DART): m/z [M+H]$^+$ calcd for C$_{18}$H$_{13}$FN$_3$O$_2^+$, 322.0986; found, 322.0981.

N-[2-Fluoro-3-(trifluoromethyl)phenyl]-7,8-dihydro[1,4]dioxino[2,3-g]quinazolin-4-amine (JGK039)

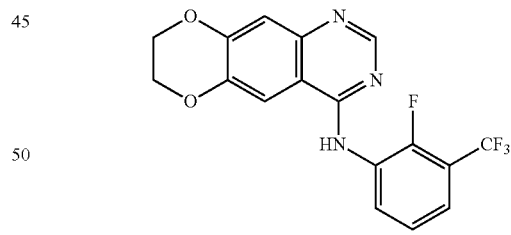

Following general procedure A, compound JGK039 was prepared from 4-chloroquinazoline 1 (37 mg, 0.17 mmol) and 2-fluoro-3-(trifluoromethyl)aniline (42 μL, 0.33 mmol) in iPrOH (1.5 mL). FC (CH$_2$Cl$_2$/EtOAc 1:0→10:3) gave JGK039 (35 mg, 58%) as an off-white solid. $^1$H NMR (500 MHz, CDCl$_3$): δ 9.00-8.92 (m, 1H), 8.70 (s, 1H), 7.42 (br, 1H), 7.40 (s, 1H), 7.35-7.28 (m, 2H), 7.30 (s, 1H), 4.46-4.38 ppm (m, 4H). $^{13}$C NMR (126 MHz, CDCl$_3$): δ 155.77, 153.24, 150.27 (d, J=252.0 Hz), 149.81, 146.80, 144.66, 128.62 (d, J=8.5 Hz), 126.34, 124.44, 124.40, 122.66 (q, J=272.4 Hz), 120.41 (q, J=4.6 Hz), 114.58, 110.55, 105.86, 64.70, 64.51 ppm. HRMS (DART): m/z [M−H]$^−$ calcd for C$_{17}$H$_{10}$F$_4$N$_3$O$_2^−$, 364.0715; found, 364.0712.

4-Chloro-8,9-dihydro-7H-[1,4]dioxepino[2,3-g]quinazoline (5)

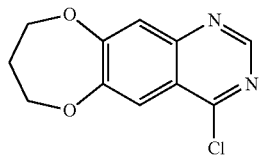 [SMILES: Clc1ncnc2cc3c(cc12)OCCCO3]

A solution of compound 2 (100 mg, 0.51 mmol) in dry DMF (10 mL) was treated with $Cs_2CO_3$ (460 mg, 1.41 mmol), stirred for 15 min, and treated dropwise with 1,3-dibromopropane (135 μL, 1.33 mmol). The mixture was stirred at 23° C. for 1 h, and then at 65° C. for 18 h. After cooling to 23° C., all volatiles were removed in vacuo. The residue was suspended in $CH_2Cl_2$ (20 mL), and washed with water (2×5 mL), dried ($Na_2SO_4$), filtered, and evaporated. Purification by FC (hexanes/$CH_2Cl_2$ 1:10→0:1→$CH_2Cl_2$/EtOAc 10:1.5), followed by a second FC (hexanes/EtOAc 10:1→10:3) gave the title compound 5 (41 mg, 34%) as a white solid. $^1$H NMR (500 MHz, $CDCl_3$): δ 8.87 (s, 1H), 7.75 (s, 1H), 7.55 (s, 1H), 4.46 (t, J=5.8 Hz, 2H), 4.40 (t, J=6.0 Hz, 2H), 2.34 ppm (quint, J=5.9 Hz, 2H). $^{13}$C NMR (126 MHz, $CDCl_3$): δ 160.57, 158.86, 153.10, 153.03, 148.88, 120.83, 118.19, 115.64, 70.51, 70.33, 30.51 ppm. HRMS (DART): m/z [M+H]$^+$ calcd for $C_{11}H_{10}ClN_2O_2^+$, 237.0425; found, 237.0416.

N-(3-Chloro-2-fluorophenyl)-8,9-dihydro-7H-[1,4]dioxepino[2,3-g]quinazolin-4-amine (JGK040)

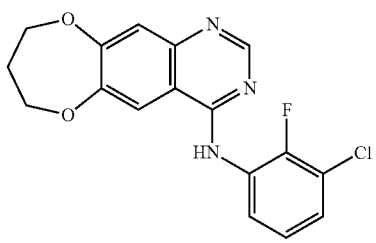 [SMILES: Fc1c(Cl)cccc1Nc1ncnc2cc3c(cc12)OCCCO3]

Following general procedure A, compound JGK040 was prepared from 4-chloroquinazoline 5 (33 mg, 0.14 mmol) and 3-chloro-2-fluoroaniline (32 μL, 0.29 mmol) in iPrOH (1.5 mL). FC ($CH_2Cl_2$/EtOAc 1:0→10:3.5) gave JGK040 (34 mg, 70%) as a white solid. $^1$H NMR (500 MHz, DMSO-$d_6$): δ 9.72 (s, 1H), 8.39 (s, 1H), 8.08 (s, 1H), 7.53-7.45 (m, 2H), 7.29 (s, 1H), 7.27 (td, J=8.1, 1.3 Hz, 1H), 4.32 (t, J=5.5 Hz, 2H), 4.29 (t, J=5.6 Hz, 2H), 2.22 ppm (quint, J=5.6 Hz, 2H). $^{13}$C NMR (126 MHz, DMSO-$d_6$): δ 157.43, 156.67, 153.85, 152.48 (d, J=249.3 Hz), 150.74, 147.29, 128.05 (d, J=12.0 Hz), 127.41, 127.04, 124.91 (d, J=4.7 Hz), 120.13 (d, J=16.5 Hz), 117.52, 113.81, 110.77, 70.75, 70.62, 30.80 ppm. HRMS (DART): m/z [M+H]$^+$ calcd for $C_{17}H_{14}ClFN_3O_2^+$, 346.0753; found, 346.0740.

8-Chloro-2H-[1,3]dioxolo[4,5-g]quinazoline (6)

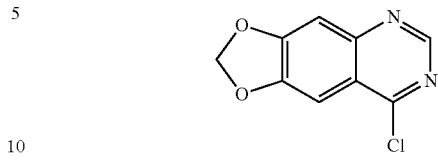

A solution of compound 2 (100 mg, 0.51 mmol) in dry DMF (3.4 mL) was treated with $Cs_2CO_3$ (335 mg, 1.03 mmol), and stirred at 23° C. for 15 min. The mixture was treated dropwise with chloroiodomethane (130 μL, 1.79 mmol), stirred for 1 h, and then at 70° C. for 17 h. After the mixture was cooled to 23° C., all volatiles were removed in vacuo. The residue was suspended in $CH_2Cl_2$ (30 mL), washed with water (2×7 mL), dried ($Na_2SO_4$), filtered, and evaporated. Purification by FC (hexanes/$CH_2Cl_2$ 3:10→0:1→$CH_2Cl_2$/EtOAc 10:2) gave the title compound 6 (38 mg, 36%) as a white, fluffy solid. $^1$H NMR (400 MHz, $CDCl_3$): δ 8.85 (s, 1H), 7.49 (s, 1H), 7.32 (s, 1H), 6.21 ppm (s, 2H). $^{13}$C NMR (126 MHz, $CDCl_3$): δ 159.82, 154.89, 152.79, 150.94, 149.78, 121.23, 105.23, 102.89, 101.12 ppm. HRMS (DART): m/z [M+H]$^+$ calcd for $C_9H_6ClN_2O_2^+$, 209.0112; found, 209.0104.

N-(3-Chloro-2-fluorophenyl)-2H-[1,3]dioxolo[4,5-g]quinazolin-8-amine (JGK041)

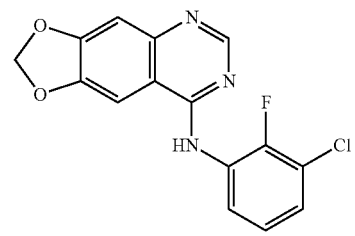 [SMILES: Fc1c(Cl)cccc1Nc1ncnc2cc3c(cc12)OCO3]

Following general procedure A, compound JGK041 was prepared from 4-chloroquinazoline 6 (35 mg, 0.17 mmol) and 3-chloro-2-fluoroaniline (38 μL, 0.35 mmol) in iPrOH (1.5 mL). FC ($CH_2Cl_2$/EtOAc 1:0→1:1) gave JGK041 (35 mg, 66%) as a pale-yellow solid. $^1$H NMR (500 MHz, DMSO-$d_6$): δ 9.53 (s, 1H), 8.37 (s, 1H), 7.84 (s, 1H), 7.53-7.44 (m, 2H), 7.27 (td, J=8.1, 1.3 Hz, 1H), 7.20 (s, 1H), 6.25 ppm (s, 2H). $^{13}$C NMR (126 MHz, DMSO-$d_6$): δ 157.37, 153.10, 152.60, 152.43 (d, J=248.9 Hz), 148.56, 147.28, 128.30 (d, J=11.9 Hz), 127.17, 126.90, 124.88 (d, J=4.8 Hz), 120.12 (d, J=16.4 Hz), 109.82, 104.59, 102.38, 98.77 ppm. HRMS (DART): m/z [M+H]$^+$ calcd for $C_{15}H_{10}ClFN_3O_2^+$, 318.0440; found, 318.0435.

[(3-Chloro-2-fluorophenyl)(7,8-dihydro[1,4]dioxino[2,3-g]quinazolin-4-yl)amino]methyl acetate (JGK043)

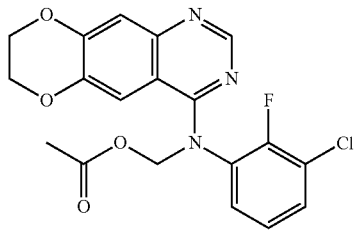 [SMILES: CC(=O)OCN(c1cccc(Cl)c1F)c1ncnc2cc3c(cc12)OCCO3]

A mixture of JGK010 (50 mg, 0.15 mmol) in dry THF (0.5 mL) was treated dropwise with a 1 M solution of LiHMDS in THF (150 μL, 0.15 mmol) at 0° C. After stirring for 15 min at that temperature, the mixture was added dropwise to a solution of chloromethyl acetate (55 μL, 0.57 mmol) in dry THF (0.5 mL). The flask which initially contained the solution of JGK010 was rinsed with 0.5 mL of dry THF and added to the reaction mixture. After stirring at 0° C. for 2 h, stirring was continued at 23° C. for 22 h. Sat. aq. NaHCO$_3$ (10 mL) were added, and the mixture was extracted with EtOAc (3×10 mL). The combined organics were dried (Na$_2$SO$_4$), filtered, and evaporated in vacuo. Purification by FC (CH$_2$Cl$_2$/EtOAc 1:0→1:1) afforded the title compound JGK043 (30 mg, 49%) as a pale-yellow solid. $^1$H NMR (500 MHz, CDCl$_3$): δ 7.93 (s, 1H), 7.88 (s, 1H), 7.08-6.97 (m, 2H), 6.94 (td, J=7.2, 2.1 Hz, 1H), 6.82 (s, 1H), 5.73 (s, 2H), 4.40-4.29 (m, 4H), 2.12 ppm (s, 3H). $^{13}$C NMR (126 MHz, CDCl$_3$): δ 170.33, 152.96, 150.10 (d, J=245.6 Hz), 149.37, 148.05, 143.24, 140.17 (d, J=13.1 Hz), 131.89, 124.17, 124.12 (d, J=4.8 Hz), 122.59 (d, J=2.4 Hz), 121.33 (d, J=17.1 Hz), 115.41, 114.31, 102.24, 71.19, 65.07, 64.23, 20.85 ppm. HRMS (DART): m/z [M+H]$^+$ calcd for C$_{19}$H$_{16}$ClFN$_3$O$_4$$^+$, 404.0808; found, 404.0792.

Example 3

Preparation of Further Exemplary Compounds of the JGK Series

General Procedures: All chemicals, reagents, and solvents were purchased from commercial sources when available and were used as received. When necessary, reagents and solvents were purified and dried by standard methods. Air- and moisture-sensitive reactions were carried out under an inert atmosphere of argon in oven-dried glassware. Microwave-irradiated reactions were carried out in a single mode reactor CEM Discover microwave synthesizer. Room temperature (RT) reactions were carried out at ambient temperature (approximately 23° C.). All reactions were monitored by thin layer chromatography (TLC) on precoated Merck 60 F$_{254}$ silica gel plates with spots visualized by UV light (λ=254, 365 nm) or by using an alkaline KMnO$_4$ solution. Flash column chromatography (FC) was carried out on SiO$_2$ 60 (particle size 0.040-0.063 mm, 230-400 mesh). Concentration under reduced pressure (in vacuo) was performed by rotary evaporation at 25-50° C. Purified compounds were further dried under high vacuum or in a desiccator. Yields correspond to purified compounds, and were not further optimized. Proton nuclear magnetic resonance ($^1$H) NMR spectra were recorded on Bruker spectrometers (operating at 300, 400, or 500 MHz). Carbon NMR ($^{13}$C NMR) spectra were recorded on Bruker spectrometers (either at 400 or 500 MHz). NMR chemical shifts (δ ppm) were referenced to the residual solvent signals. $^1$H NMR data are reported as follows: chemical shift in ppm; multiplicity (s=singlet, d=doublet, t=triplet, q=quartet, quint=quintet, m=multiplet/complex pattern, td=triplet of doublets, ddd=doublet of doublet of doublets, br=broad signal); coupling constants (J) in Hz, integration. Data for $^{13}$C NMR spectra are reported in terms of chemical shift, and if applicable coupling constants. High resolution mass (HRMS) spectra were recorded on a Thermo Fisher Scientific Exactive Plus with IonSense ID-CUBE DART source mass spectrometer, or on a Waters LCT Premier mass spectrometer with ACQUITY UPLC with autosampler.

3-[(7,8-Dihydro[1,4]dioxino[2,3-g]quinazolin-4-yl)amino]-2-fluorobenzonitrile (JGK044)

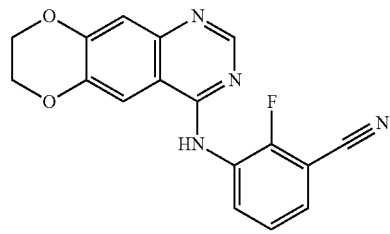 [SMILES: N#Cc1cccc(Nc2ncnc3cc4c(cc23)OCCO4)c1F]

$^1$H NMR (500 MHz, CDCl$_3$): δ=9.06-8.98 (m, 1H), 8.69 (s, 1H), 7.41 (s, 1H), 7.39 (br, 1H), 7.35-7.31 (m, 2H), 7.30 (s, 1H), 4.45-4.37 ppm (m, 4H). $^{13}$C NMR (126 MHz, CDCl$_3$): δ=155.63, 153.63 (d, J=254.6 Hz), 153.04, 149.94, 146.80, 144.76, 128.60 (d, J=7.8 Hz), 127.48, 126.58, 125.31 (d, J=4.5 Hz), 114.56, 113.80, 110.45, 105.83, 101.30 (d, J=13.9 Hz), 64.70, 64.51 ppm. HRMS (ESI): m/z [M+H]$^+$ calcd for C$_{17}$H$_{12}$FN$_4$O$_2$$^+$, 323.0939; found, 323.0927.

3-[(7,8-Dihydro[1,4]dioxino[2,3-g]quinazolin-4-yl)amino]benzonitrile (JGK045)

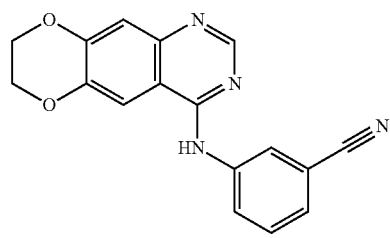 [SMILES: N#Cc1cccc(Nc2ncnc3cc4c(cc23)OCCO4)c1]

$^1$H NMR (500 MHz, DMSO-d$_6$): δ=9.68 (s, 1H), 8.52 (s, 1H), 8.46 (t, J=1.9 Hz, 1H), 8.18 (ddd, J=8.2, 2.3, 1.2 Hz, 1H), 8.08 (s, 1H), 7.58 (t, J=7.9 Hz, 1H), 7.53 (dt, J=7.6, 1.4 Hz, 1H), 7.22 (s, 1H), 4.49-4.36 ppm (m, 4H). $^{13}$C NMR (126 MHz, DMSO-d$_6$): δ=156.24, 152.69, 149.31, 146.15, 143.80, 140.52, 129.87, 126.35, 125.96, 124.15, 118.93, 112.66, 111.23, 109.96, 108.30, 64.52, 64.19 ppm. HRMS (DART): m/z [M+H]$^+$ calcd for C$_{17}$H$_{13}$N$_4$O$_2$$^+$, 305.1033; found, 305.1018.

Ethyl (3-chloro-2-fluorophenyl)7,8-dihydro[1,4]dioxino[2,3-g]quinazolin-4-ylcarbamate (JGK047)

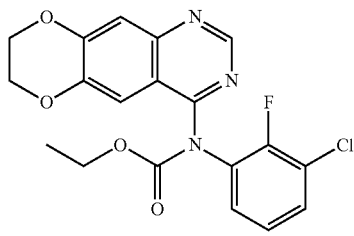 [SMILES: CCOC(=O)N(c1cccc(Cl)c1F)c1ncnc2cc3c(cc12)OCCO3]

¹H NMR (500 MHz, CDCl₃): δ=8.96 (s, 1H), 7.483 (s, 1H), 7.477 (s, 1H), 7.37 (dd, J=8.1, 6.7 Hz, 2H), 7.08 (td, J=8.1, 1.5 Hz, 1H), 4.45-4.38 (m, 4H), 4.27 (q, J=7.1 Hz, 2H), 1.22 ppm (t, J=7.1 Hz, 3H). ¹³C NMR (126 MHz, CDCl₃): 158.98, 154.43 (d, J=250.7 Hz), 153.90, 153.41, 151.17, 149.68, 145.61, 130.12, 129.85 (d, J=12.4 Hz), 128.20, 124.50 (d, J=5.1 Hz), 122.22 (d, J=16.8 Hz), 117.96, 113.51, 109.68 (d, J=2.0 Hz), 64.73, 64.36, 63.44, 14.43. ppm. HRMS (ESI): m/z [M+H]⁺ calcd for $C_{19}H_{16}ClFN_3O_4^+$, 404.0808; found, 404.0800.

(±)-4-(3-Bromo-2-fluoroanilino)-7,8-dihydro[1,4]dioxino[2,3-g]quinazolin-7-ol ((±)-JGK050)

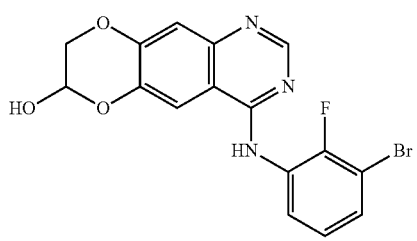 [SMILES: OC1COc2cc3ncnc(Nc4cccc(Br)c4F)c3cc2O1]

¹H NMR (500 MHz, DMSO-d₆): δ=9.61 (s, 1H), 8.34 (s, 1H), 7.91 (s, 1H), 7.72 (d, J=5.4 Hz, 1H), 7.60 (t, J=7.1 Hz, 1H), 7.55 (t, J=7.5 Hz, 1H), 7.21 (t, J=8.2 Hz, 1H), 7.19 (s, 1H), 5.70-5.59 (m, 1H), 4.27 (d, J=11.0 Hz, 1H), 4.17 ppm (d, J=10.6 Hz, 1H). ¹³C NMR (126 MHz, DMSO-d₆): δ=157.18, 153.38 (d, J=247.4 Hz), 153.13, 148.78, 146.14, 141.92, 130.12, 128.05 (d, J=13.8 Hz), 127.78, 125.45 (d, J=4.4 Hz), 111.95, 109.87, 108.71, 108.55 (d, J=20.3 Hz), 88.63, 67.23 ppm. HRMS (DART): m/z [M+H]⁺ calcd for $C_{16}H_{12}BrFN_3O_3^+$, 392.0041; found, 392.0030.

Diastereoisomeric Mixture of (±)-cis- and (±)-trans-N-(3-Bromo-2-fluorophenyl)-7,8-dimethyl-7,8-dihydro[1,4]dioxino[2,3-g]quinazolin-4-amine ((±)-cis/trans-JGK051)

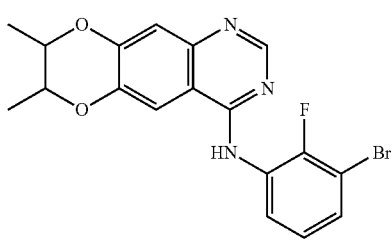 [SMILES: CC1Oc2cc3ncnc(Nc4cccc(Br)c4F)c3cc2OC1C]

¹H NMR (500 MHz, CDCl₃; (±)-cis/trans 2:1): δ=8.68 (s, 1H), 8.68-8.63 (m, 1H), 7.37 (s, 1H), 7.35 (br, 1H), 7.28 (s, 1H), 7.28-7.24 (m, 1H), 7.10 (td, J=8.2, 1.6 Hz, 1H), 4.52-4.39 (m, 1.3H), 4.09-3.98 (m, 0.7H), 1.453 (d, J=6.1 Hz, 1.1H), 1.451 (d, J=6.1 Hz, 1.1H), 1.369 (d, J=6.6 Hz, 1.9H), 1.368 ppm (d, J=6.6 Hz, 1.9H). ¹³C NMR (126 MHz, CDCl₃; (±)-cis/trans 2:1): δ=155.87, 155.84, 153.19, 150.12 (d, J=242.5 Hz), 150.09 (d, J=242.2 Hz), 149.87, 148.89, 146.77, 144.64, 143.63, 128.73 (d, J=10.0 Hz), 127.15, 127.12, 125.31 (d, J=4.7 Hz), 121.71, 121.70, 114.30, 113.93, 110.54, 110.47, 108.57 (d, J=19.4 Hz), 105.66, 105.28 ppm. HRMS (DART): m/z [M+H]⁺ calcd for $C_{18}H_{16}BrFN_3O_2^+$, 404.0404; found, 404.0393.

(±)-cis-N-(3-Bromo-2-fluorophenyl)-7,8-dimethyl-7,8-dihydro[1,4]dioxino[2,3-g]quinazolin-4-amine ((±)-JGK052)

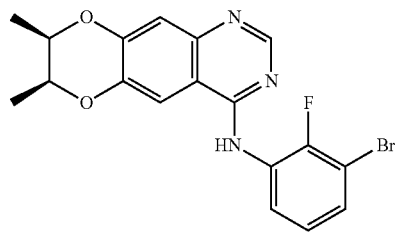 [SMILES: C[C@@H]1Oc2cc3c(Nc4cccc(Br)c4F)ncnc3cc2O[C@@H]1C]

¹H NMR (500 MHz, CDCl₃): δ=8.68 (s, 1H), 8.66 (ddd, J=8.6, 7.4, 1.6 Hz, 1H), 7.38 (s, 1H), 7.35 (br, 1H), 7.28 (s, 1H), 7.30-7.23 (m, 1H), 7.10 (td, J=8.2, 1.5 Hz, 1H), 4.50-4.41 (m, 2H), 1.369 (d, J=6.6 Hz, 3H), 1.368 ppm (d, J=6.5 Hz, 3H). ¹³C NMR (126 MHz, CDCl₃): δ=155.85, 153.19, 150.11 (d, J=242.1 Hz), 148.89, 146.77, 143.63, 128.73 (d, J=10.2 Hz), 127.14, 125.31 (d, J=4.7 Hz), 121.71, 114.30, 110.54, 108.57 (d, J=19.5 Hz), 105.65, 72.85, 72.58, 14.71, 14.55 ppm. HRMS (ESI): m/z [M+H]⁺ calcd for $C_{18}H_{16}BrFN_3O_2^+$, 404.0404; found, 404.0416.

N-(3-Bromo-4-chloro-2-fluorophenyl)-7,8-dihydro[1,4]dioxino[2,3-g]quinazolin-4-amine (JGK053)

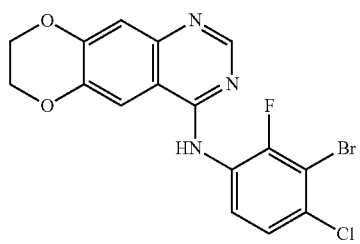

¹H NMR (500 MHz, DMSO-d₆): δ=9.70 (s, 1H), 8.35 (s, 1H), 7.94 (s, 1H), 7.61 (dd, J=8.8, 7.7 Hz, 1H), 7.55 (dd, J=8.7, 1.5 Hz, 1H), 7.20 (s, 1H), 4.47-4.35 ppm (m, 4H). ¹³C NMR (126 MHz, DMSO-d₆): δ=157.03, 154.14 (d, J=249.5 Hz), 153.01, 149.36, 146.08, 143.74, 130.75, 127.77 (d, J=2.9 Hz), 126.80 (d, J=13.4 Hz), 125.37 (d, J=3.8 Hz), 112.50, 110.15 (d, J=22.5 Hz), 109.66, 108.39, 64.51, 64.14 ppm. HRMS (DART): m/z [M+H]⁺ calcd for $C_{16}H_{11}BrClFN_3O_2^+$, 409.9702; found, 409.9697.

N-(3,4-Dibromo-2-fluorophenyl)-7,8-dihydro[1,4]dioxino[2,3-g]quinazolin-4-amine (JGK054)

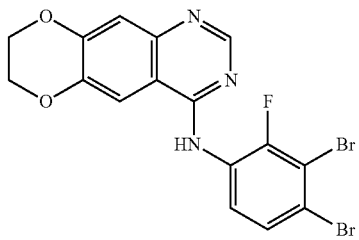 [SMILES: Fc1c(Nc2ncnc3cc4c(cc23)OCCO4)ccc(Cl)c1Br]

$^1$H NMR (500 MHz, DMSO-d$_6$): δ=9.65 (s, 1H), 8.34 (s, 1H), 7.92 (s, 1H), 7.67 (d, J=8.7 Hz, 1H), 7.55 (t, J=8.2 Hz, 1H), 7.20 (s, 1H), 4.45-4.35 ppm (m, 4H). $^{13}$C NMR (126 MHz, DMSO-d$_6$): δ=156.95, 153.98 (d, J=249.1 Hz), 152.99, 149.35, 146.09, 143.74, 128.50 (d, J=3.7 Hz), 128.14, 127.21 (d, J=13.7 Hz), 120.96, 112.51, 112.33, 109.68, 108.36, 64.51, 64.14 ppm. HRMS (DART): m/z [M+H]$^+$ calcd for C$_{16}$H$_{11}$Br$_2$FN$_3$O$_2$$^+$, 453.9197; found, 453.9191.

N-(5-Bromo-2-fluorophenyl)-7,8-dihydro[1,4]dioxino[2,3-g]quinazolin-4-amine (JGK055)

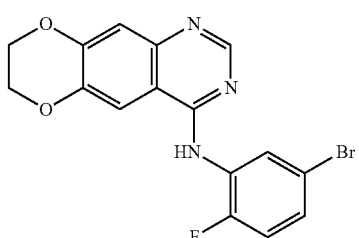

$^1$H NMR (500 MHz, CDCl$_3$): δ=8.99 (dd, J=7.3, 2.5 Hz, 1H), 8.72 (s, 1H), 7.38 (s, 1H), 7.36 (br, 1H), 7.27 (s, 1H), 7.16 (ddd, J=8.7, 4.6, 2.5 Hz, 1H), 7.04 (dd, J=10.9, 8.7 Hz, 1H), 4.44-4.36 ppm (m, 4H). $^{13}$C NMR (126 MHz, CDCl$_3$): δ=155.59, 153.35, 152.16 (d, J=243.1 Hz), 149.69, 146.67, 144.52, 128.75 (d, J=10.5 Hz), 126.16 (d, J=7.6 Hz), 125.06, 117.19 (d, J=3.4 Hz), 116.20 (d, J=20.9 Hz), 114.52, 110.48, 105.85, 64.68, 64.50 ppm. HRMS (DART): m/z [M+H]$^+$ calcd for C$_{16}$H$_{12}$BrFN$_3$O$_2$$^+$, 376.0091; found, 376.0077.

N-(3-Bromo-2,6-difluorophenyl)-7,8-dihydro[1,4]dioxino[2,3-g]quinazolin-4-amine (JGK056)

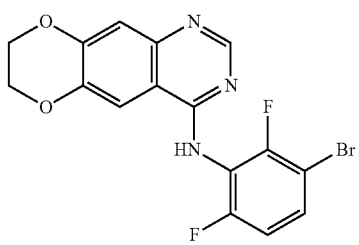 [SMILES: Fc1ccc(Br)c(F)c1Nc1ncnc2cc3c(cc12)OCCO3]

$^1$H NMR (500 MHz, DMSO-d$_6$): δ=9.60 (s, 1H), 8.32 (s, 1H), 7.94 (s, 1H), 7.74 (td, J=8.1, 5.5 Hz, 1H), 7.28 (t, J=9.3 Hz, 1H), 7.21 (s, 1H), 4.44-4.38 ppm (m, 4H). $^{13}$C NMR (126 MHz, DMSO-d$_6$): δ=157.78 (dd, J=248.8, 3.3 Hz), 157.37, 155.01 (dd, J=247.9, 4.9 Hz), 153.08, 149.47, 146.04, 143.86, 130.76 (d, J=9.3 Hz), 117.30 (t, J=17.5 Hz), 113.30 (dd, J=21.8, 3.0 Hz), 112.56, 109.45, 108.28, 103.55 (dd, J=20.4, 3.6 Hz), 64.52, 64.14 ppm. HRMS (ESI): m/z [M+H]$^+$ calcd for C$_{16}$H$_{11}$BrF$_2$N$_3$O$_2$$^+$, 393.9997; found, 394.0008.

N-(3-Bromo-2,4-difluorophenyl)-7,8-dihydro[1,4]dioxino[2,3-g]quinazolin-4-amine (JGK057)

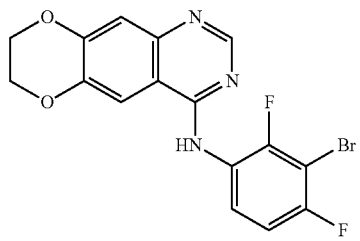 [SMILES: Fc1ccc(Nc2ncnc3cc4c(cc23)OCCO4)c(F)c1Br]

$^1$H NMR (500 MHz, CDCl$_3$): δ=8.64 (s, 1H), 8.51 (td, J=9.0, 5.6 Hz, 1H), 7.38 (s, 1H), 7.29 (s, 1H), 7.23 (br, 1H), 7.04 (ddd, J=9.2, 7.8, 2.1 Hz, 1H), 4.45-4.37 ppm (m, 4H). $^{13}$C NMR (126 MHz, CDCl$_3$): δ=156.10, 155.80 (dd, J=246.6, 3.5 Hz), 153.28, 151.25 (dd, J=245.1, 4.0 Hz), 149.74, 146.56, 144.53, 124.39 (dd, J=10.8, 3.4 Hz), 122.72 (dd, J=8.3, 1.8 Hz), 114.42, 111.49 (dd, J=22.5, 3.9 Hz), 110.34, 105.98, 97.86 (dd, J=25.7, 22.9 Hz), 64.69, 64.50 ppm. HRMS (ESI): m/z [M+H]$^+$ calcd for C$_{16}$H$_{11}$BrF$_2$N$_3$O$_2$$^+$, 393.9997; found, 394.0013.

N-(3-Bromo-5-chloro-2-fluorophenyl)-7,8-dihydro[1,4]dioxino[2,3-g]quinazolin-4-amine (JGK058)

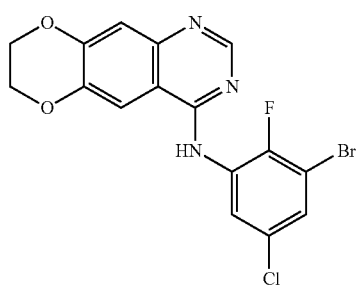 [SMILES: Fc1c(Br)cc(Cl)cc1Nc1ncnc2cc3c(cc12)OCCO3]

$^1$H NMR (500 MHz, CDCl$_3$): δ=8.88 (dd, J=6.6, 2.6 Hz, 1H), 8.73 (s, 1H), 7.41 (s, 1H), 7.37 (br, 1H), 7.26 (s, 1H), 7.28-7.23 (m, 1H), 4.44-4.39 ppm (m, 4H). $^{13}$C NMR (126 MHz, CDCl$_3$): δ=155.45, 153.13, 149.88, 148.60 (d, J=241.7 Hz), 146.76, 144.72, 130.30 (d, J=4.4 Hz), 129.26 (d, J=10.8 Hz), 126.08, 121.21, 114.60, 110.49, 108.68 (d, J=20.9 Hz), 105.71, 64.70, 64.52 ppm. HRMS (ESI): m/z [M+H]$^+$ calcd for C$_{16}$H$_{11}$BrClFN$_3$O$_2$$^+$, 409.9702; found, 409.9713.

(±)-trans-N-(3-Bromo-2-fluorophenyl)-7,8-dimethyl-7,8-dihydro[1,4]dioxino[2,3-g]quinazolin-4-amine ((±)-JGK059)

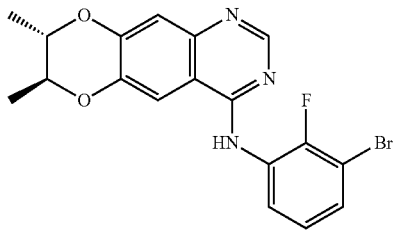 [SMILES: C[C@@H]1Oc2cc3ncnc(Nc4cccc(Br)c4F)c3cc2O[C@H]1C]

$^1$H NMR (500 MHz, CDCl$_3$): δ=8.68 (s, 1H), 8.66 (ddd, J=8.6, 7.3, 1.6 Hz, 1H), 7.376 (s, 1H), 7.375 (br, 1H), 7.28 (s, 1H), 7.28-7.24 (m, 1H), 7.10 (td, J=8.2, 1.6 Hz, 1H), 4.08-3.98 (m, 2H), 1.451 (d, J=6.1 Hz, 3H), 1.448 ppm (d, J=6.1 Hz, 3H). $^{13}$C NMR (126 MHz, CDCl$_3$): δ=155.90, 153.12, 150.12 (d, J=242.5 Hz), 149.90, 146.59, 144.65, 128.70 (d, J=10.2 Hz), 127.18, 125.30 (d, J=4.5 Hz), 121.74, 113.84, 110.43, 108.57 (d, J=19.2 Hz), 105.31, 75.31, 75.05, 17.23, 17.20 ppm. HRMS (ESI): m/z [M+H]$^+$ calcd for C$_{18}$H$_{16}$BrFN$_3$O$_2^+$, 404.0404; found, 404.0405.

N-(3,4-Dichloro-2-fluorophenyl)-7,8-dihydro[1,4]dioxino[2,3-g]quinazolin-4-amine (JGK060)

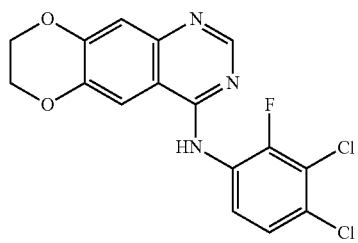 [SMILES: Fc1c(Nc2ncnc3cc4c(cc23)OCCO4)ccc(Cl)c1Cl]

$^1$H NMR (500 MHz, CDCl$_3$): δ=8.67 (s, 1H), 8.59 (t, J=8.6 Hz, 1H), 7.40 (s, 1H), 7.38 (br, 1H), 7.33 (dd, J=9.1, 2.1 Hz, 1H), 7.31 (s, 1H), 4.45-4.38 ppm (m, 4H). $^{13}$C NMR (126 MHz, CDCl$_3$): δ=155.84, 153.08, 149.98 (d, J=246.3 Hz), 149.88, 146.42, 144.67, 127.55, 127.19 (d, J=10.0 Hz), 125.30 (d, J=4.1 Hz), 121.05, 120.47 (d, J=18.2 Hz), 114.36, 110.43, 105.97, 64.71, 64.51 ppm. HRMS (ESI): m/z [M+H]$^+$ calcd for C$_{16}$H$_{11}$Cl$_2$FN$_3$O$_2^+$, 366.0207; found, 366.0207.

N-(3-Bromo-2,5-difluorophenyl)-7,8-dihydro[1,4]dioxino[2,3-g]quinazolin-4-amine (JGK061)

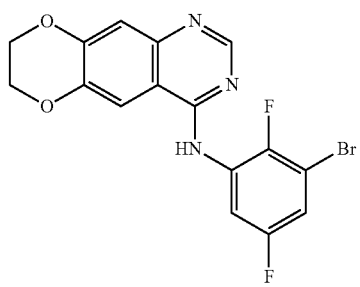 [SMILES: Fc1cc(Br)c(F)c(Nc2ncnc3cc4c(cc23)OCCO4)c1]

$^1$H NMR (500 MHz, DMSO-d$_6$): δ=9.65 (s, 1H), 8.40 (s, 1H), 7.93 (s, 1H), 7.63-7.54 (m, 2H), 7.21 (s, 1H), 4.45-4.37 ppm (m, 4H). $^{13}$C NMR (126 MHz, DMSO-d$_6$): δ=157.29 (d, J=243.5 Hz), 156.84, 152.93, 149.97 (d, J=242.9 Hz), 149.43, 146.16, 143.81, 129.22-128.44 (m), 116.30 (d, J=26.7 Hz), 113.99 (d, J=25.7 Hz), 112.53, 109.73, 108.76 (dd, J=22.5, 12.5 Hz), 108.33, 64.52, 64.15 ppm. HRMS (DART): m/z [M+H]$^+$ calcd for C$_{16}$H$_{11}$BrF$_2$N$_3$O$_2^+$, 393.9997; found, 393.9988.

(±)-N-(3-Bromo-2-fluorophenyl)-7-ethenyl-7,8-dihydro[1,4]dioxino[2,3-g]quinazolin-4-amine ((±)-JGK062)

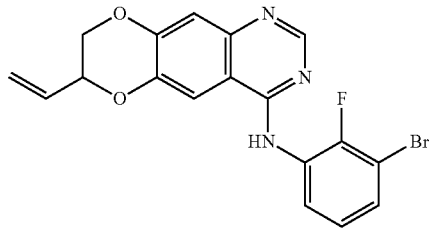 [SMILES: C=CC1COc2cc3ncnc(Nc4cccc(Br)c4F)c3cc2O1]

$^1$H NMR (500 MHz, CDCl$_3$): δ=8.68 (s, 1H), 8.65 (ddd, J=8.2, 7.3, 1.5 Hz, 1H), 7.40 (s, 1H), 7.37 (br, 1H), 7.35 (s, 1H), 7.27 (ddd, J=8.0, 6.4, 1.5 Hz, 1H), 7.10 (td, J=8.2, 1.6 Hz, 1H), 5.95 (ddd, J=17.3, 10.7, 5.8 Hz, 1H), 5.60 (dt, J=17.3, 1.2 Hz, 1H), 5.48 (dt, J=10.7, 1.1 Hz, 1H), 4.82-4.74 (m, 1H), 4.42 (dd, J=11.5, 2.5 Hz, 1H), 4.09 ppm (dd, J=11.6, 8.1 Hz, 1H). $^{13}$C NMR (126 MHz, CDCl$_3$): δ=155.90, 153.38, 150.14 (d, J=242.4 Hz), 149.12, 146.70, 144.12, 131.48, 128.64 (d, J=10.3 Hz), 127.24, 125.30 (d, J=4.7 Hz), 121.76, 120.43, 114.29, 110.69, 108.58 (d, J=19.3 Hz), 106.06, 74.03, 67.84 ppm. HRMS (DART): m/z [M+H]$^+$ calcd for C$_{18}$H$_{14}$BrFN$_3$O$_2^+$, 402.0248; found, 402.0233.

Example 4

Bioactivity and Assay Protocol of Exemplary Compounds

The Cell Free EGFR Kinase Assay was performed using the EGFR Kinase System (Promega #V3831). 13 concentrations at 2-fold dilutions from 250 nM to 0.03052 nM, a no drug control, and a no enzyme control were used in duplicates on 25 ng of EGFR enzyme per reaction. The ADP-Glo Kinase Assay (Promega #V6930) was used to measure EGFR activity in the presence of inhibitors.

The GI50 Assays were performed using patient-derived glioblastoma cells. 13 concentrations at 2-fold dilutions from 40,000 nM to 9.77 nM (for GBM lines) or from 4,000 nM to 0.977 nM (for Lung Cancer lines (HK031)) were plated on 384-well plates in quadruplicates with 1500 cells per well. Cells were incubated for 3 days and then proliferation was assessed by Cell Titer Glo (Promega #G7570). As a reference, Erlotinib exhibited an GI$_{50}$ of 642 nM (HK301) and 2788 nM (GBM39).

Pharmacokinetic studies were performed on male CD-1 mice aged 8-10 weeks. Mice were dosed as indicated in duplicates. At the time points, whole blood was obtained by retro-orbital bleeding and brain tissue was harvested. Blood samples were centrifuged to obtain plasma and brain tissue was washed and homogenized. Samples were extracted with acetonitrile and supernatant was dried using a speed-vac. Dried samples were solubilized in 50:50:0.1 acetonitrile:water:formic acid and quantified on an Agilent 6400 series Triple Quadrupole LC/MS.
TABLE 3
Activity of Exemplary Compounds
| Number | Structure | HK301 GI$_{50}$ (nM) | GBM39 GI$_{50}$ (nM) |
|---|---|---|---|
| JGK001 | 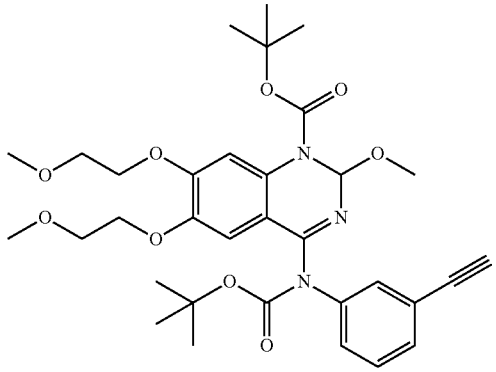 [SMILES: C#Cc1cccc(N(C(=O)OC(C)(C)C)C2=NC(OC)N(C(=O)OC(C)(C)C)c3cc(OCCOC)c(OCCOC)cc32)c1] | 2214 | 19670 |
| JGK002 | 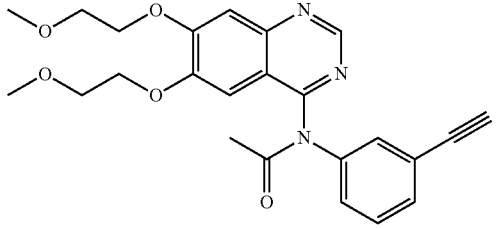 [SMILES: C#Cc1cccc(N(C(C)=O)c2ncnc3cc(OCCOC)c(OCCOC)cc23)c1] | 5448 | 19820 |
| JGK003 | 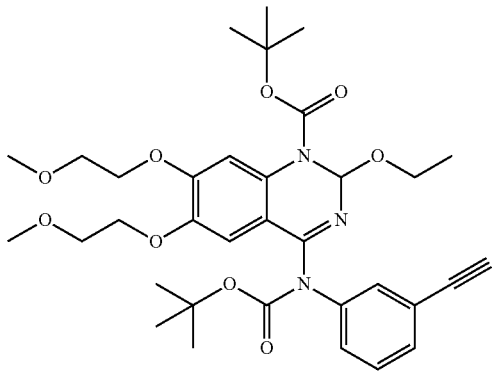 [SMILES: C#Cc1cccc(N(C(=O)OC(C)(C)C)C2=NC(OCC)N(C(=O)OC(C)(C)C)c3cc(OCCOC)c(OCCOC)cc32)c1] | 1127 | 23110 |
| JGK004 | 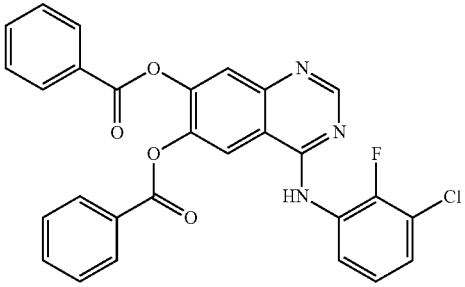 [SMILES: O=C(Oc1cc2ncnc(Nc3cccc(Cl)c3F)c2cc1OC(=O)c1ccccc1)c1ccccc1] | 23383 | 102690 |

TABLE 3-continued
Activity of Exemplary Compounds
| Number | Structure | HK301 GI$_{50}$ (nM) | GBM39 GI$_{50}$ (nM) |
|---|---|---|---|
| JGK005 | 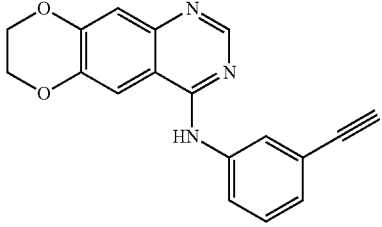 [SMILES: C#Cc1cccc(Nc2ncnc3cc4c(cc23)OCCO4)c1] | 8824 | 20536 |
| JGK006 | 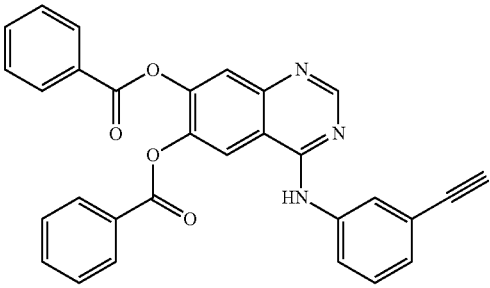 [SMILES: C#Cc1cccc(Nc2ncnc3cc(OC(=O)c4ccccc4)c(OC(=O)c4ccccc4)cc23)c1] | 11012 | 51380 |
| JGK007 | 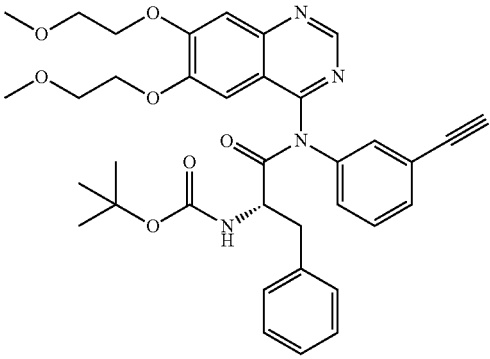 [SMILES: C#Cc1cccc(N(C(=O)[C@H](Cc2ccccc2)NC(=O)OC(C)(C)C)c2ncnc3cc(OCCOC)c(OCCOC)cc23)c1] | 92147 | — |
| JGK008 | 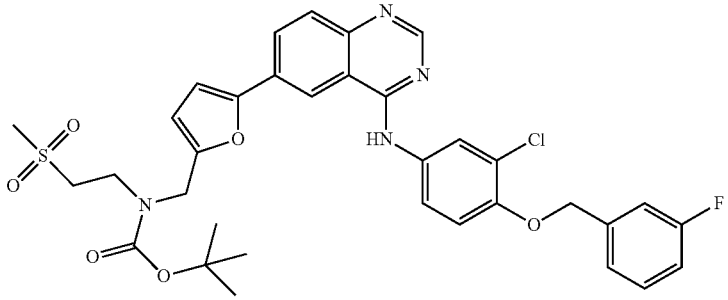 [SMILES: CC(C)(C)OC(=O)N(CCS(C)(=O)=O)Cc1ccc(-c2ccc3ncnc(Nc4ccc(OCc5cccc(F)c5)c(Cl)c4)c3c2)o1] | 81269 | — |

TABLE 3-continued

Activity of Exemplary Compounds

| Number | Structure | HK301 GI$_{50}$ (nM) | GBM39 GI$_{50}$ (nM) |
|---|---|---|---|
| JGK009 | 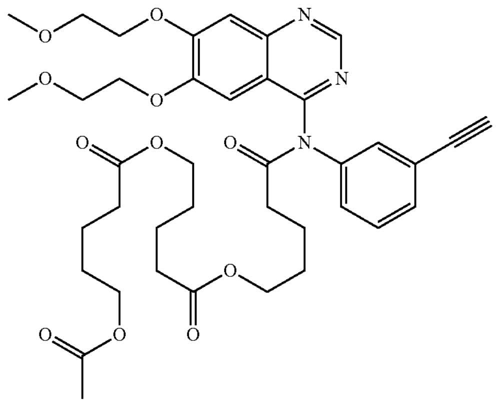 [SMILES: C#Cc1cccc(N(C(=O)CCCCOC(=O)CCCCOC(=O)CCCCOC(C)=O)c2ncnc3cc(OCCOC)c(OCCOC)cc23)c1] | 6096 | 14640 |
| JGK010 | 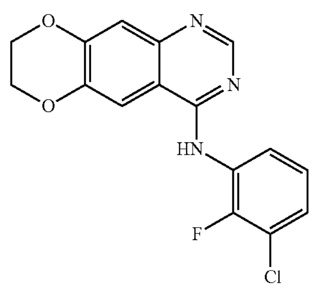 [SMILES: Fc1c(Cl)cccc1Nc1ncnc2cc3c(cc12)OCCO3] | 780.5 | 2594 |
| JGK011 | 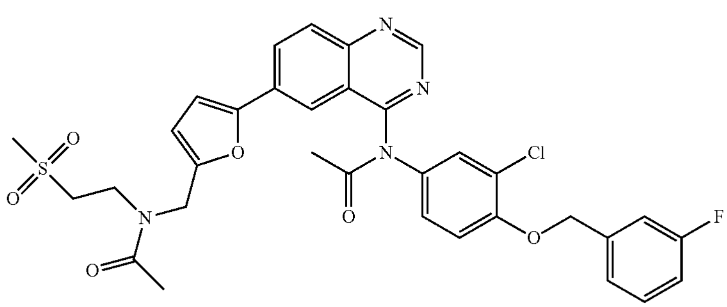 [SMILES: CC(=O)N(CCS(C)(=O)=O)Cc1ccc(-c2ccc3ncnc(N(C(C)=O)c4ccc(OCc5cccc(F)c5)c(Cl)c4)c3c2)o1] | 9206 | 3252 |
| JGK0012 | 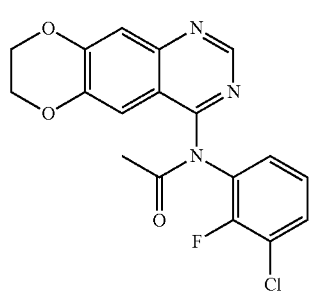 [SMILES: CC(=O)N(c1cccc(Cl)c1F)c1ncnc2cc3c(cc12)OCCO3] | 5477 | 10820 |

TABLE 3-continued

Activity of Exemplary Compounds

| Number | Structure | HK301 GI$_{50}$ (nM) | GBM39 GI$_{50}$ (nM) |
|---|---|---|---|
| JGK013 | 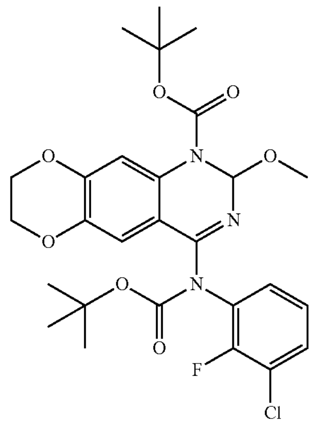 [SMILES: COC1N=C(N(C(=O)OC(C)(C)C)c2cccc(Cl)c2F)c2cc3c(cc2N1C(=O)OC(C)(C)C)OCCO3] | 1551 | 219870 |
| JGK014 | 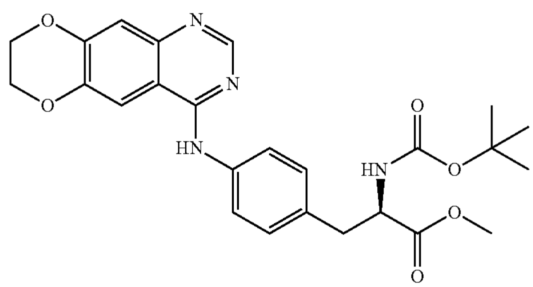 | 11816 | 27914 |
| JGK015 | 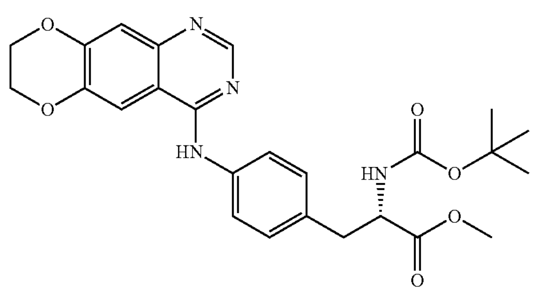 [SMILES: COC(=O)[C@H](Cc1ccc(Nc2ncnc3cc4c(cc23)OCCO4)cc1)NC(=O)OC(C)(C)C] | 2154 | 11540 |
| JGK016 | 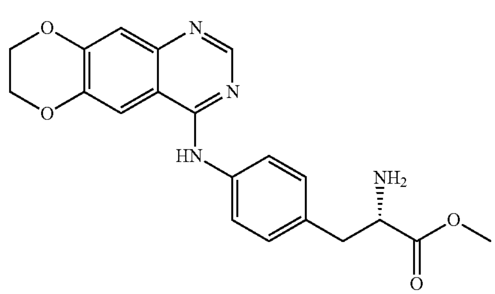 [SMILES: COC(=O)[C@@H](N)Cc1ccc(Nc2ncnc3cc4c(cc23)OCCO4)cc1] | 4052 | 61593 |

TABLE 3-continued

Activity of Exemplary Compounds

| Number | Structure | HK301 GI$_{50}$ (nM) | GBM39 GI$_{50}$ (nM) |
|---|---|---|---|
| JGK017 | 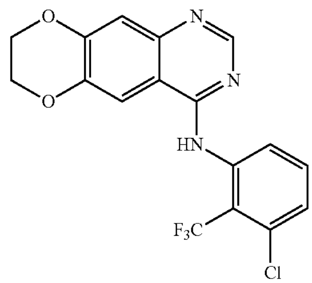 [SMILES: FC(F)(F)c1c(Cl)cccc1Nc1ncnc2cc3c(cc12)OCCO3] | 64235 | 97624 |
| JGK018 | 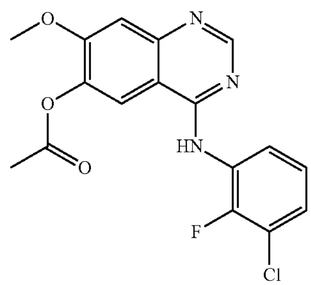 [SMILES: COc1cc2ncnc(Nc3cccc(Cl)c3F)c2cc1OC(C)=O] | 1071 | 4543 |
| JGK019 | 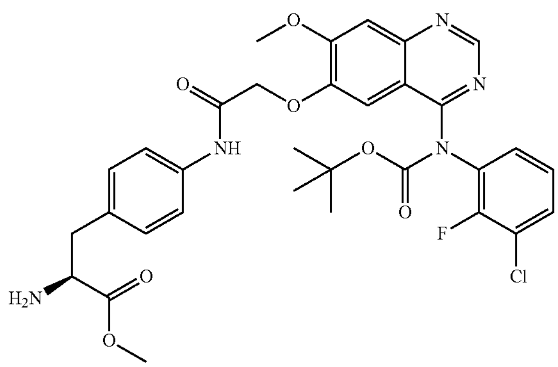 [SMILES: COC(=O)[C@@H](N)Cc1ccc(NC(=O)COc2cc3c(N(C(=O)OC(C)(C)C)c4cccc(Cl)c4F)ncnc3cc2OC)cc1] | — | — |
| JGK020 | 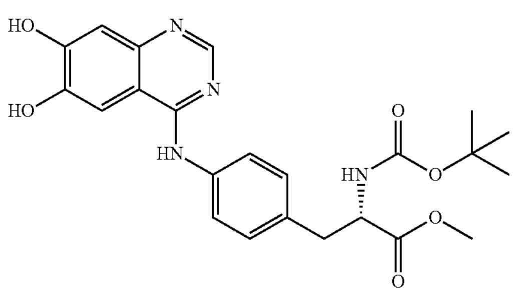 [SMILES: COC(=O)[C@H](Cc1ccc(Nc2ncnc3cc(O)c(O)cc23)cc1)NC(=O)OC(C)(C)C] | 29236 | 36179 |
| JGK021 | 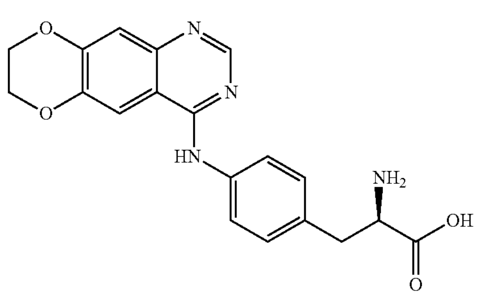 [SMILES: N[C@H](Cc1ccc(Nc2ncnc3cc4c(cc23)OCCO4)cc1)C(=O)O] | 480850 | 555780 |

TABLE 3-continued

Activity of Exemplary Compounds

| Number | Structure | HK301 GI$_{50}$ (nM) | GBM39 GI$_{50}$ (nM) |
|---|---|---|---|
| JGK022 | 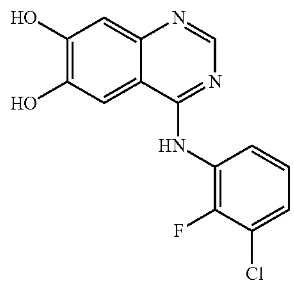 [SMILES: Oc1cc2ncnc(Nc3cccc(Cl)c3F)c2cc1O] | 31116 | 150164 |
| JGK023 | 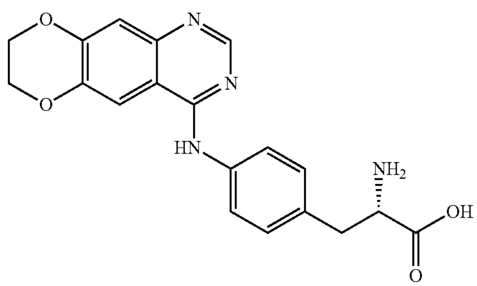 [SMILES: N[C@@H](Cc1ccc(Nc2ncnc3cc4c(cc23)OCCO4)cc1)C(=O)O] | 86230 | 96260 |
| JGK024 | 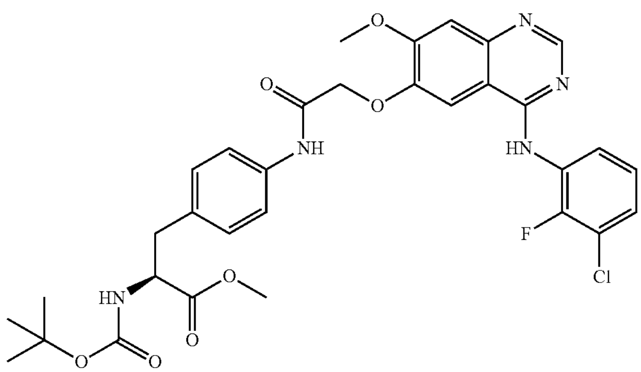 [SMILES: COC(=O)[C@H](Cc1ccc(NC(=O)COc2cc3c(Nc4cccc(Cl)c4F)ncnc3cc2OC)cc1)NC(=O)OC(C)(C)C] | 156370 | 124940 |
| JGK025 | 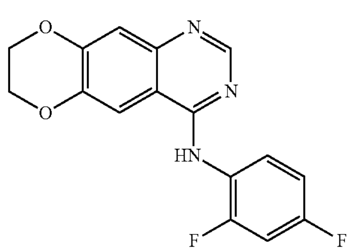 [SMILES: Fc1ccc(Nc2ncnc3cc4c(cc23)OCCO4)c(F)c1] | 10659 | 27706 |
| JGK026 | 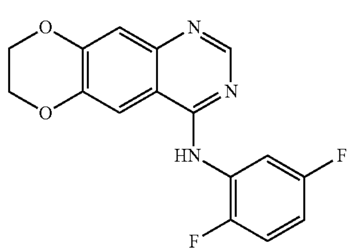 [SMILES: Fc1ccc(F)c(Nc2ncnc3cc4c(cc23)OCCO4)c1] | 6124 | 16525 |

TABLE 3-continued

Activity of Exemplary Compounds

| Number | Structure | HK301 GI$_{50}$ (nM) | GBM39 GI$_{50}$ (nM) |
|---|---|---|---|
| JGK027 | 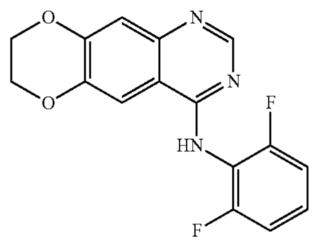 [SMILES: Fc1cccc(F)c1Nc1ncnc2cc3c(cc12)OCCO3] | 5807 | 11837 |
| JGK028 | 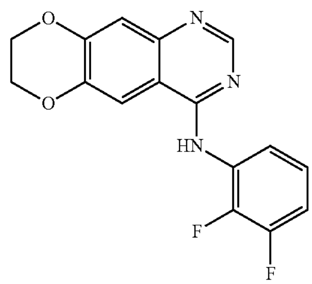 [SMILES: Fc1cccc(Nc2ncnc3cc4c(cc23)OCCO4)c1F] | 1688 | 5572 |
| JGK029 | 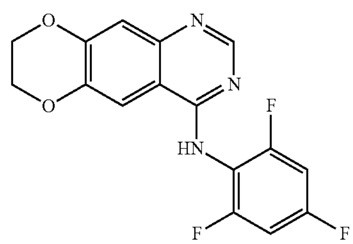 [SMILES: Fc1cc(F)c(Nc2ncnc3cc4c(cc23)OCCO4)c(F)c1] | 24395 | 33970 |
| JGK030 | 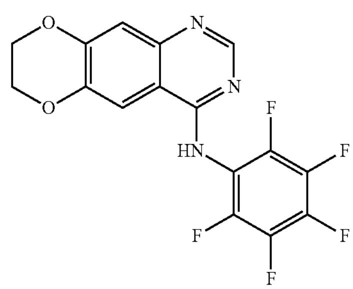 [SMILES: Fc1c(F)c(F)c(Nc2ncnc3cc4c(cc23)OCCO4)c(F)c1F] | 558742 | 961204 |
| JGK031 | 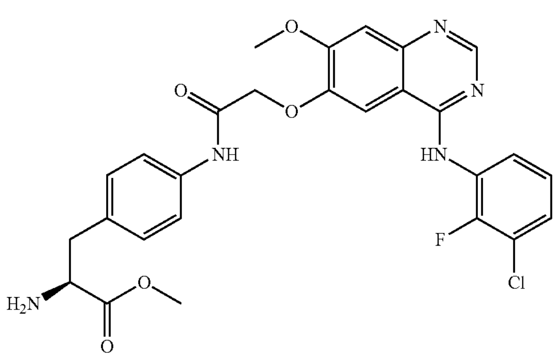 [SMILES: COC(=O)[C@@H](N)Cc1ccc(NC(=O)COc2cc3c(Nc4cccc(Cl)c4F)ncnc3cc2OC)cc1] | — | — |

TABLE 3-continued

Activity of Exemplary Compounds

| Number | Structure | HK301 GI$_{50}$ (nM) | GBM39 GI$_{50}$ (nM) |
|---|---|---|---|
| JGK032 | 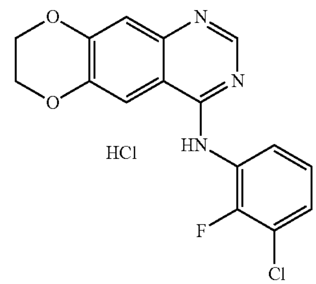 [SMILES: Fc1c(Cl)cccc1Nc1ncnc2cc3c(cc12)OCCO3 ; Cl] | 780.5 | 2594 |
| JGK033 | 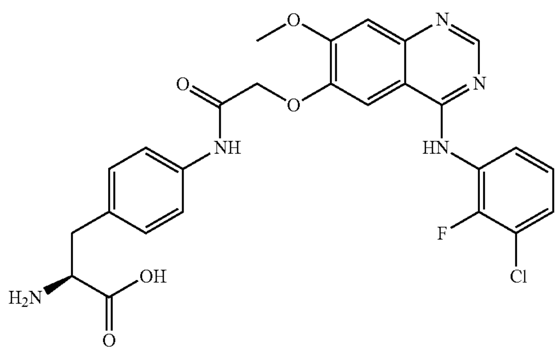 [SMILES: COc1cc2ncnc(Nc3cccc(Cl)c3F)c2cc1OCC(=O)Nc1ccc(C[C@H](N)C(=O)O)cc1] | — | — |
| JGK035 | 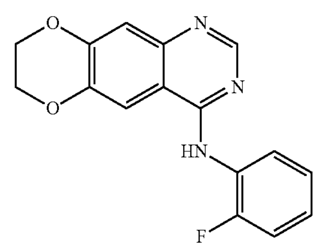 [SMILES: Fc1ccccc1Nc1ncnc2cc3c(cc12)OCCO3] | 4040 | 10721 |
| JGK036 | 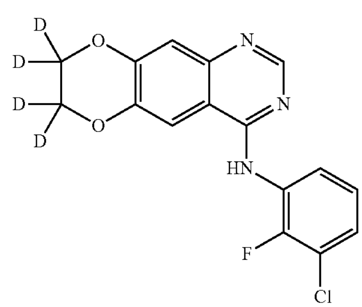 [SMILES: [2H]C1([2H])Oc2cc3ncnc(Nc4cccc(Cl)c4F)c3cc2OC1([2H])[2H]] | 1046 | 4507 |
| JGK037 | 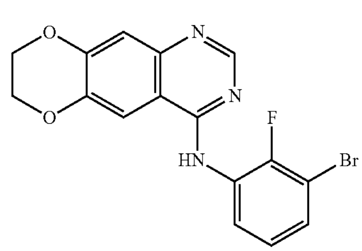 [SMILES: Fc1c(Br)cccc1Nc1ncnc2cc3c(cc12)OCCO3] | 329.3 | 1116 |

TABLE 3-continued

Activity of Exemplary Compounds

| Number | Structure | HK301 GI$_{50}$ (nM) | GBM39 GI$_{50}$ (nM) |
|---|---|---|---|
| JGK038 | 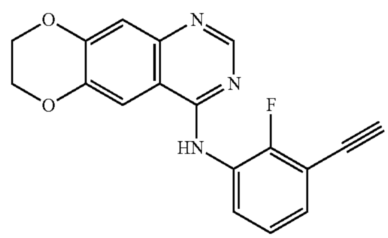 [SMILES: C#Cc1cccc(Nc2ncnc3cc4c(cc23)OCCO4)c1F] | 791.1 | 2946 |
| JGK039 | 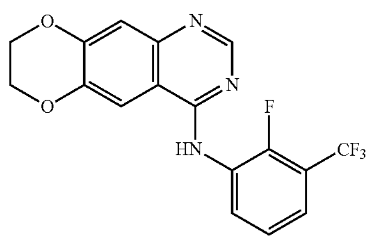 [SMILES: Fc1c(Nc2ncnc3cc4c(cc23)OCCO4)cccc1C(F)(F)F] | 3614 | 7820 |
| JGK040 | 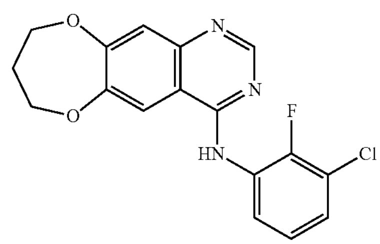 [SMILES: Fc1c(Cl)cccc1Nc1ncnc2cc3c(cc12)OCCCO3] | 1721 | 7115 |
| JGK041 | 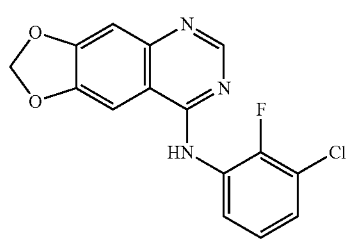 [SMILES: Fc1c(Cl)cccc1Nc1ncnc2cc3c(cc12)OCO3] | 1658 | 6042 |
| JGK042 | 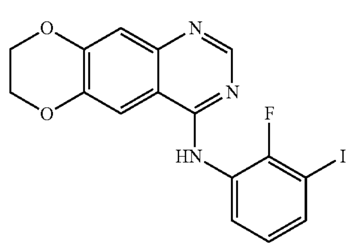 [SMILES: Fc1c(I)cccc1Nc1ncnc2cc3c(cc12)OCCO3] | 2294 | 4521 |
| JGK043 | 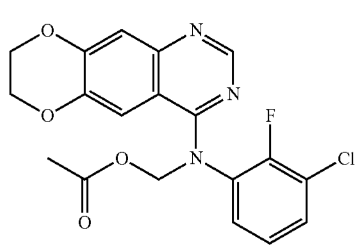 [SMILES: CC(=O)OCN(c1cccc(Cl)c1F)c1ncnc2cc3c(cc12)OCCO3] | 745 | 1778 |

TABLE 3-continued

Activity of Exemplary Compounds

| Number | Structure | HK301 GI$_{50}$ (nM) | GBM39 GI$_{50}$ (nM) |
|---|---|---|---|
| JGK044 | 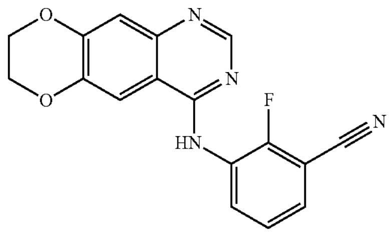 [SMILES: N#Cc1cccc(Nc2ncnc3cc4c(cc23)OCCO4)c1F] | 4522 | 5635 |
| JGK045 | 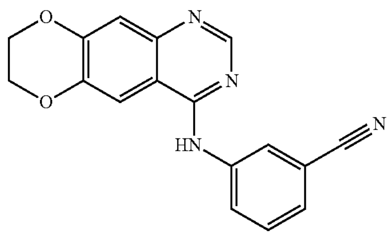 [SMILES: N#Cc1cccc(Nc2ncnc3cc4c(cc23)OCCO4)c1] | 3940 | 10939 |
| JGK047 | 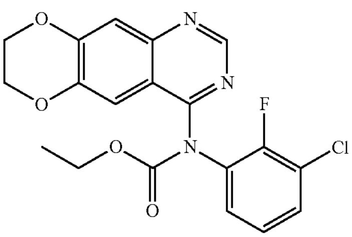 [SMILES: CCOC(=O)N(c1cccc(Cl)c1F)c1ncnc2cc3c(cc12)OCCO3] | 316000 | — |
| JGK050 | 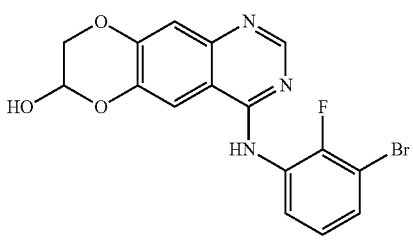 [SMILES: OC1COc2cc3ncnc(Nc4cccc(Br)c4F)c3cc2O1] | 1159 | 3568 |
| JGK051 | 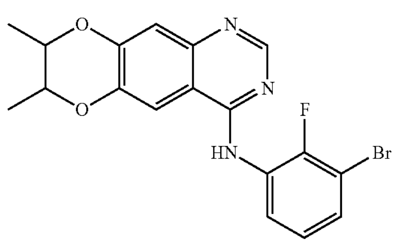 [SMILES: CC1Oc2cc3ncnc(Nc4cccc(Br)c4F)c3cc2OC1C] | 8253 | 24140 |
| JGK052 | 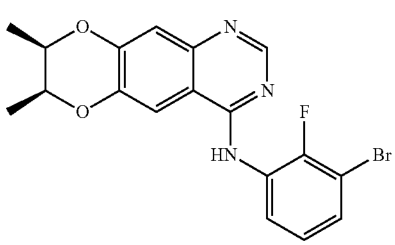 [SMILES: C[C@@H]1Oc2cc3c(Nc4cccc(Br)c4F)ncnc3cc2O[C@@H]1C] | 3866 | 9219 |

TABLE 3-continued

Activity of Exemplary Compounds

| Number | Structure | HK301 GI$_{50}$ (nM) | GBM39 GI$_{50}$ (nM) |
|---|---|---|---|
| JGK053 | 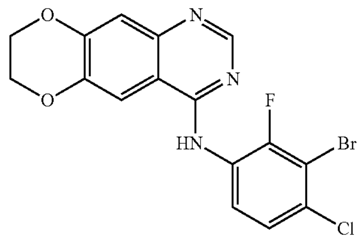 [SMILES: Fc1c(Nc2ncnc3cc4c(cc23)OCCO4)ccc(Cl)c1Br] | 2778 | 5277 |
| JGK054 | 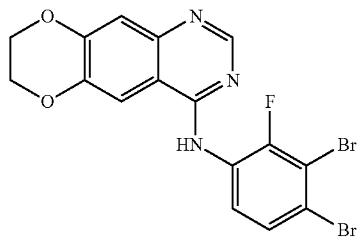 [SMILES: Fc1c(Nc2ncnc3cc4c(cc23)OCCO4)ccc(Br)c1Br] | 5723 | 7697 |
| JGK055 | 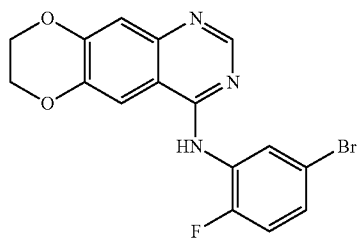 [SMILES: Fc1ccc(Br)cc1Nc1ncnc2cc3c(cc12)OCCO3] | 290.1 | 966.4 |
| JGK056 | 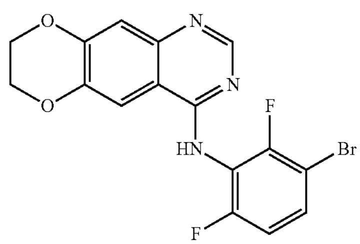 [SMILES: Fc1ccc(Br)c(F)c1Nc1ncnc2cc3c(cc12)OCCO3] | 418.7 | 1355.8 |
| JGK057 | 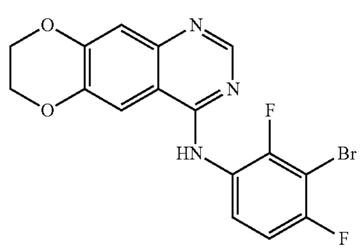 [SMILES: Fc1ccc(Nc2ncnc3cc4c(cc23)OCCO4)c(F)c1Br] | 1382.7 | 9361.5 |
| JGK058 | 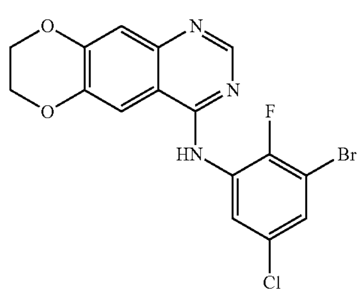 [SMILES: Fc1c(Br)cc(Cl)cc1Nc1ncnc2cc3c(cc12)OCCO3] | 1852.7 | 12974 |

TABLE 3-continued
Activity of Exemplary Compounds
| Number | Structure | HK301 GI$_{50}$ (nM) | GBM39 GI$_{50}$ (nM) |
|---|---|---|---|
| JGK059 | 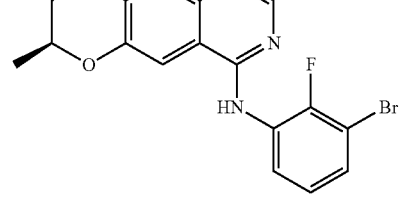 | 8110 | 11218 |
| JGK060 | 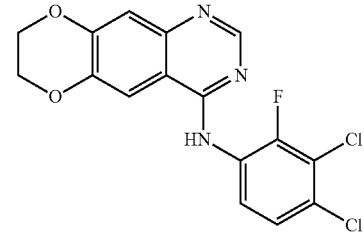 [SMILES: Fc1c(Nc2ncnc3cc4c(cc23)OCCO4)ccc(Cl)c1Cl] | 2947 | 3501 |
| JGK061 | 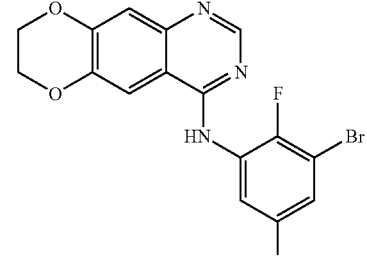 | 1131 | 1727 |
| JGK062 | 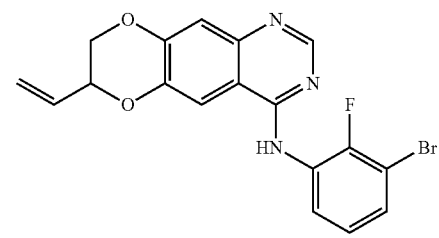 [SMILES: C=CC1COc2cc3ncnc(Nc4cccc(Br)c4F)c3cc2O1] | 3784 | 5856 |
| JGK063 | 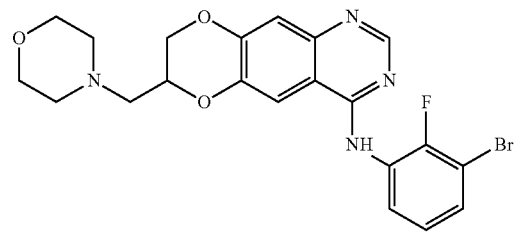 [SMILES: Fc1c(Br)cccc1Nc1ncnc2cc3c(cc12)OC(CN1CCOCC1)CO3] | 816 | 3431 |
| JGK064 | 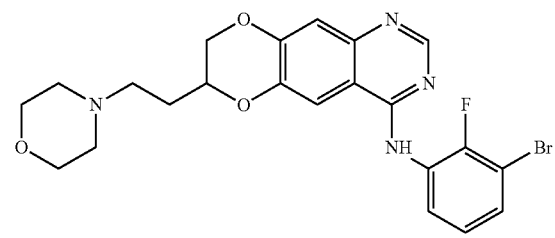 [SMILES: Fc1c(Br)cccc1Nc1ncnc2cc3c(cc12)OC(CCN1CCOCC1)CO3] | 1213 | 4005 |

TABLE 3-continued

Activity of Exemplary Compounds

| Number | Structure | HK301 GI$_{50}$ (nM) | GBM39 GI$_{50}$ (nM) |
|---|---|---|---|
| JGK065 | 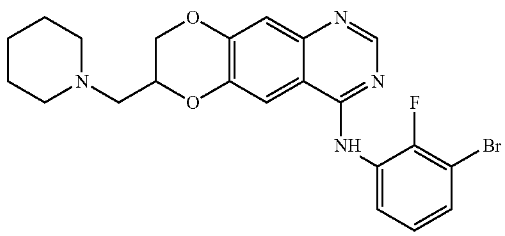 [SMILES: Fc1c(Br)cccc1Nc1ncnc2cc3c(cc12)OC(CN1CCCCC1)CO3] | 3432 | 7339 |
| JGK066 | 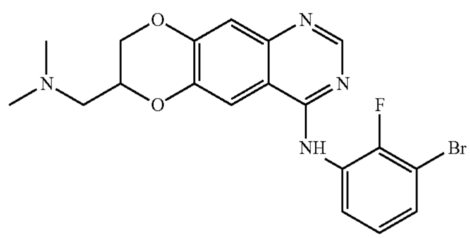 [SMILES: CN(C)CC1COc2cc3ncnc(Nc4cccc(Br)c4F)c3cc2O1] | 734 | 2395 |
| JGK067 | 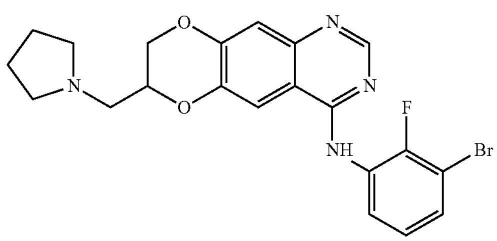 [SMILES: Fc1c(Br)cccc1Nc1ncnc2cc3c(cc12)OC(CN1CCCC1)CO3] | 898 | 2198 |
| JGK068 | 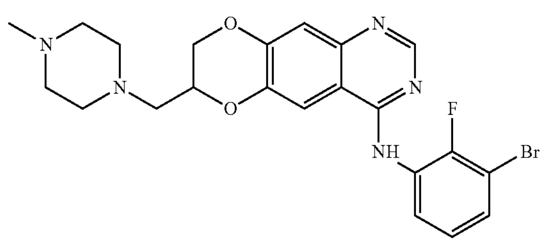 [SMILES: CN1CCN(CC2COc3cc4ncnc(Nc5cccc(Br)c5F)c4cc3O2)CC1] | 577 | 1613 |
| JGK068S | 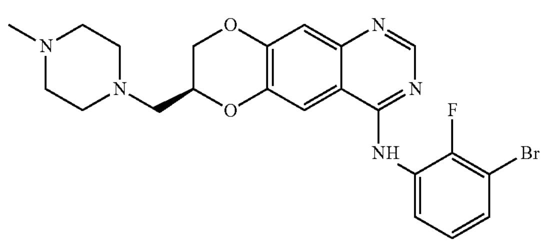 [SMILES: CN1CCN(C[C@H]2COc3cc4ncnc(Nc5cccc(Br)c5F)c4cc3O2)CC1] | 439.7 | 1212 |
| JGK068R | 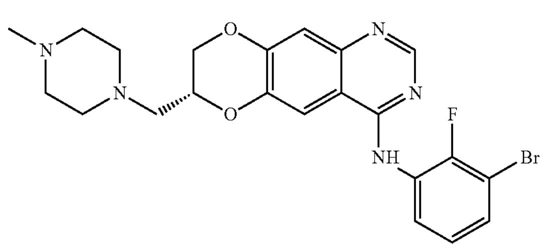 [SMILES: CN1CCN(C[C@@H]2COc3cc4ncnc(Nc5cccc(Br)c5F)c4cc3O2)CC1] | 1396 | 3384 |

TABLE 3-continued

Activity of Exemplary Compounds

| Number | Structure | HK301 GI$_{50}$ (nM) | GBM39 GI$_{50}$ (nM) |
|---|---|---|---|
| JGK069 | 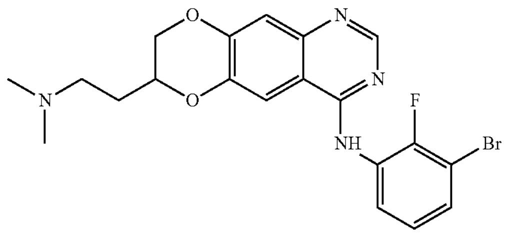 [SMILES: CN(C)CCC1COc2cc3ncnc(Nc4cccc(Br)c4F)c3cc2O1] | 659 | 2165 |
| JGK070 | 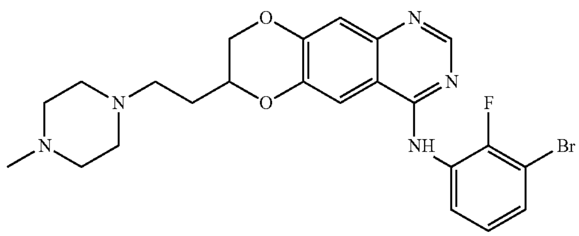 [SMILES: CN1CCN(CCC2COc3cc4ncnc(Nc5cccc(Br)c5F)c4cc3O2)CC1] | 1405 | 3333 |
| JGK071 | 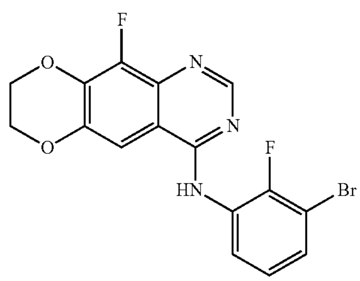 [SMILES: Fc1c(Br)cccc1Nc1ncnc2c(F)c3c(cc12)OCCO3] | 5749 | 10256 |
| JGK072 | 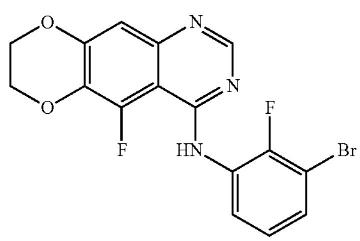 [SMILES: Fc1c(Br)cccc1Nc1ncnc2cc3c(c(F)c12)OCCO3] | 5017 | 12033 |
| JGK073 | 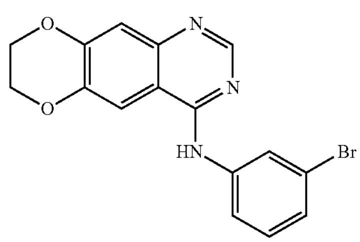 [SMILES: Brc1cccc(Nc2ncnc3cc4c(cc23)OCCO4)c1] | 2055 | 6073 |
| JGK074 | 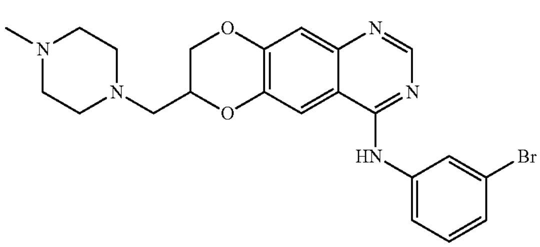 [SMILES: CN1CCN(CC2COc3cc4ncnc(Nc5cccc(Br)c5)c4cc3O2)CC1] | 2276 | 6670 |

TABLE 3-continued
Activity of Exemplary Compounds
| Number | Structure | HK301 GI$_{50}$ (nM) | GBM39 GI$_{50}$ (nM) |
|---|---|---|---|
| JGK075 | 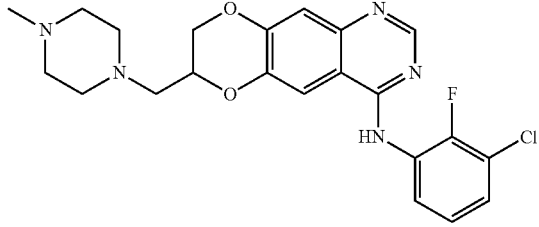 [SMILES: CN1CCN(CC2COc3cc4ncnc(Nc5cccc(Cl)c5F)c4cc3O2)CC1] | 1181 | 4005 |
| JGK076 | 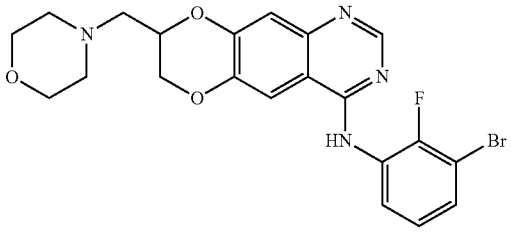 [SMILES: Fc1c(Br)cccc1Nc1ncnc2cc3c(cc12)OCC(CN1CCOCC1)O3] | 6161 | 16944 |
| JGK077 | 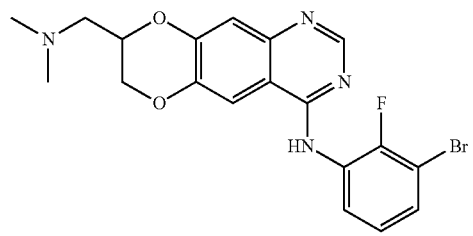 [SMILES: CN(C)CC1COc2cc3c(Nc4cccc(Br)c4F)ncnc3cc2O1] | 6844 | 16733 |
| JGK078 | 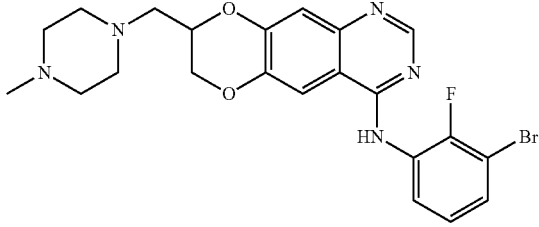 [SMILES: CN1CCN(CC2COc3cc4c(Nc5cccc(Br)c5F)ncnc4cc3O2)CC1] | 2034 | 5758 |
| JGK079 | 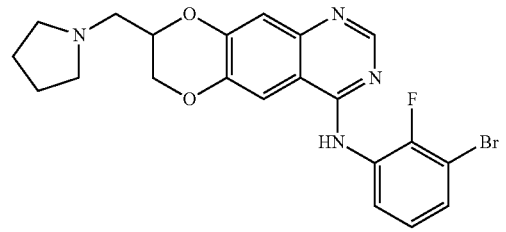 [SMILES: Fc1c(Br)cccc1Nc1ncnc2cc3c(cc12)OCC(CN1CCCC1)O3] | 7214 | 15709 |
| JGK080 | 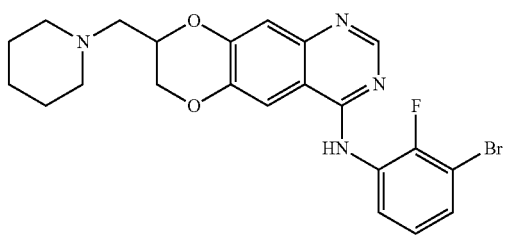 [SMILES: Fc1c(Br)cccc1Nc1ncnc2cc3c(cc12)OCC(CN1CCCCC1)O3] | 7374 | 14528 |

TABLE 3-continued

Activity of Exemplary Compounds

| Number | Structure | HK301 GI$_{50}$ (nM) | GBM39 GI$_{50}$ (nM) |
| --- | --- | --- | --- |
| JGK081 | 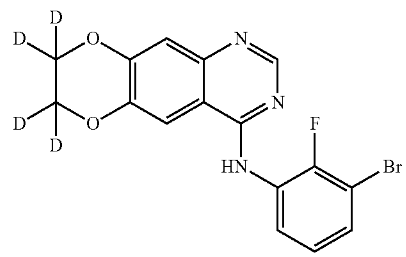 [SMILES: [2H]C1([2H])Oc2cc3ncnc(Nc4cccc(Br)c4F)c3cc2OC1([2H])[2H]] | — | — |
| JGK082S | 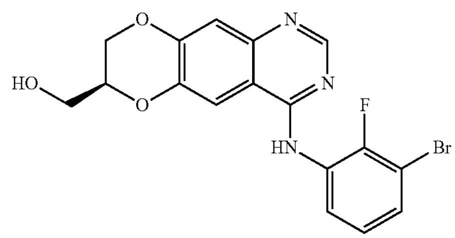 [SMILES: OC[C@H]1COc2cc3ncnc(Nc4cccc(Br)c4F)c3cc2O1] | 1668 | 1892 |
| JGK083S | 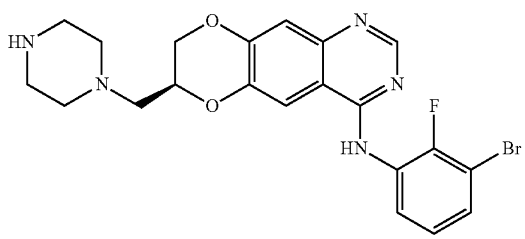 [SMILES: Fc1c(Br)cccc1Nc1ncnc2cc3c(cc12)O[C@@H](CN1CCNCC1)CO3] | 529 | 841 |
| JGK066S | 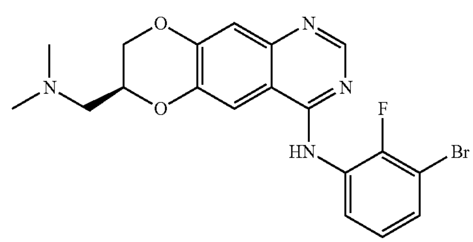 [SMILES: CN(C)C[C@H]1COc2cc3ncnc(Nc4cccc(Br)c4F)c3cc2O1] | 301 | 2633 |
| JGK084 | 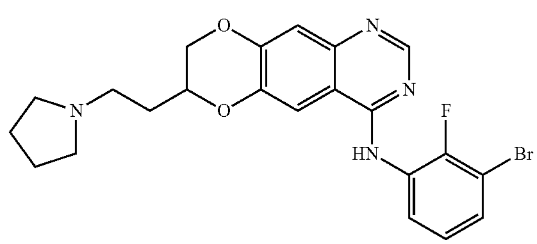 [SMILES: Fc1c(Br)cccc1Nc1ncnc2cc3c(cc12)OC(CCN1CCCC1)CO3] | 1835 | 5638 |
| JGK085 | 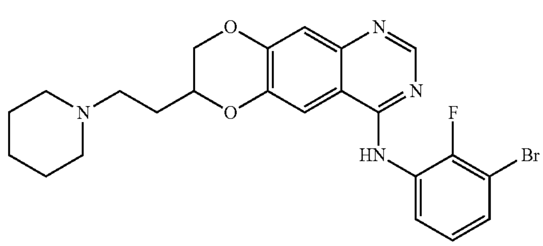 [SMILES: Fc1c(Br)cccc1Nc1ncnc2cc3c(cc12)OC(CCN1CCCCC1)CO3] | 1015 | 2617 |

TABLE 3-continued

Activity of Exemplary Compounds

| Number | Structure | HK301 GI$_{50}$ (nM) | GBM39 GI$_{50}$ (nM) |
|---|---|---|---|
| JGK086 | 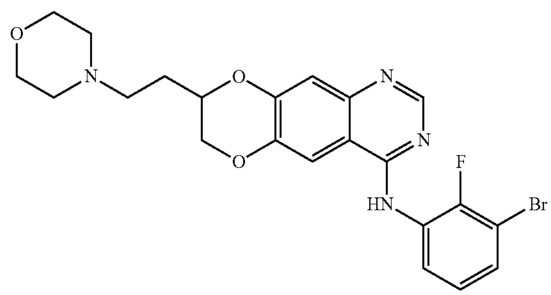 [SMILES: Fc1c(Br)cccc1Nc1ncnc2cc3c(cc12)OCC(CCN1CCOCC1)O3] | 2559 | 4453 |
| JGK087 | 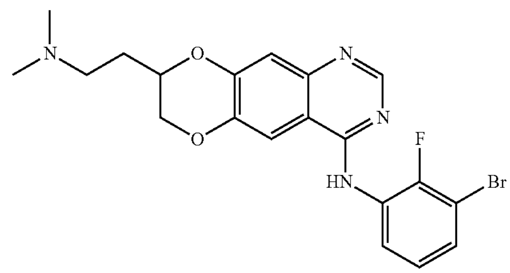 [SMILES: CN(C)CCC1COc2cc3c(Nc4cccc(Br)c4F)ncnc3cc2O1] | 3741 | 5257 |
| JGK088 | 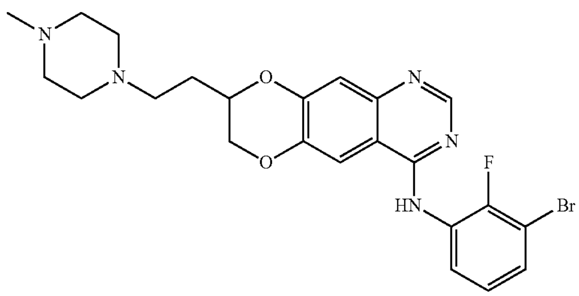 [SMILES: CN1CCN(CCC2COc3cc4c(Nc5cccc(Br)c5F)ncnc4cc3O2)CC1] | 2132 | 4061 |
| JGK089 | 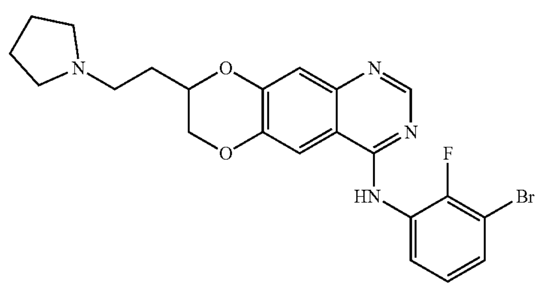 [SMILES: Fc1c(Br)cccc1Nc1ncnc2cc3c(cc12)OCC(CCN1CCCC1)O3] | 3162 | 5090 |
| JGK090 | 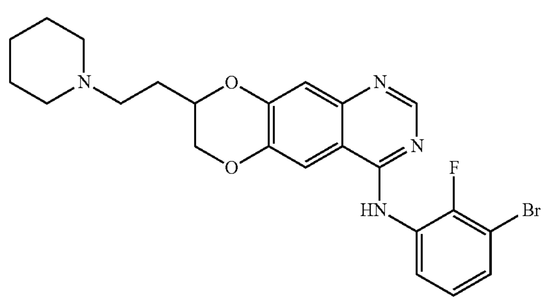 [SMILES: Fc1c(Br)cccc1Nc1ncnc2cc3c(cc12)OCC(CCN1CCCCC1)O3] | 2394 | 4330 |

Example 5

Protein Binding of Erlotinib and Exemplary Compounds of the Disclosure

Illustrated below in Table 4 is the protein binding of erlotinib and several exemplary compounds of the disclosure. Fu refers to "fraction unbound". Kpuu refers to the "unbound partition coefficient of the brain and plasma, at equilibrium".

TABLE 4

Protein Binding of Erlotinib and Exemplary Compounds of the Disclosure

| Compound | Fu (blood)/ Fu (brain) | Bound (blood)/ (brain) | Kpuu (Avg) |
|---|---|---|---|
| Erlotinib | 4.88% | 95.12% | 0.0513 |
|  | 2.93% | 97.07% |  |
| AZD3759 | 5.20% | 94.80% | 0.802 |
|  | 1.44% | 98.56% |  |
| JGK005 | 1.35% | 98.65% | 0.491 |
|  | 1.02% | 98.98% |  |
| JGK038 | 1.30% | 98.70% | 0.575 |
|  | 0.89% | 99.11% |  |
| JGK028 | 1.44% | 98.56% | 1.037 |
|  | 1.41% | 98.59% |  |
| JGK010 | 1.12% | 98.88% | 1.045 |
|  | 1.10% | 98.90% |  |
| JGK037 | 1.70% | 98.30% | 1.301 |
|  | 1.04% | 98.96% |  |
| JGK042 | 1.85% | 98.15% | 1.033 |
|  | 1.14% | 98.86% |  |
| JGK063 | 8.04% | 91.96% | 0.341 |
|  | 3.78% | 96.22% |  |
| JGK066 | 7.04% | 92.96% | 1.175 |
|  | 3.02% | 96.98% |  |
| JGK068 | 6.31% | 93.69% | 1.184 |
|  | 2.11% | 97.89% |  |
| JGK068S | 5.96% | 94.04% | 1.181 |
|  | 1.86% | 98.14% |  |
| JGK068R | 5.33% | 94.67% | 1.046 |
|  | 1.57% | 98.43% |  |
| JGK083S | 7.02% | 92.98% | 0.798 |
|  | 2.42% | 97.58% |  |

Example 6

Classification of EGFRi Metabolic Responders and Non-Responders

Figure 27A:
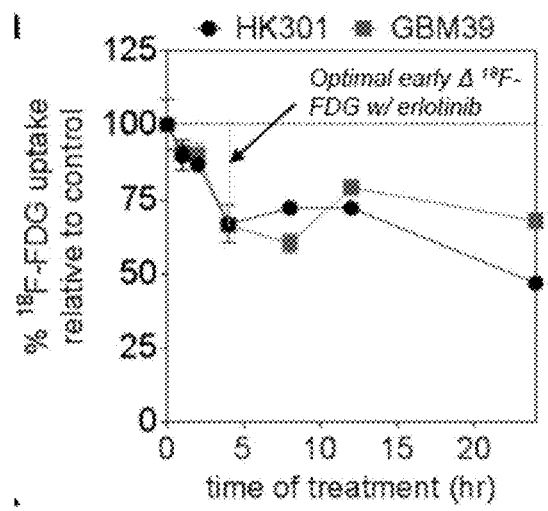
FIGS. 27A-27G depict the characterization of GBM cell lines following EGFR inhibition.
Figure 27B:
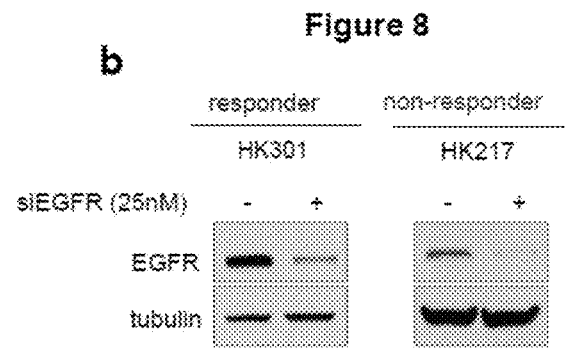
Figure 27C:
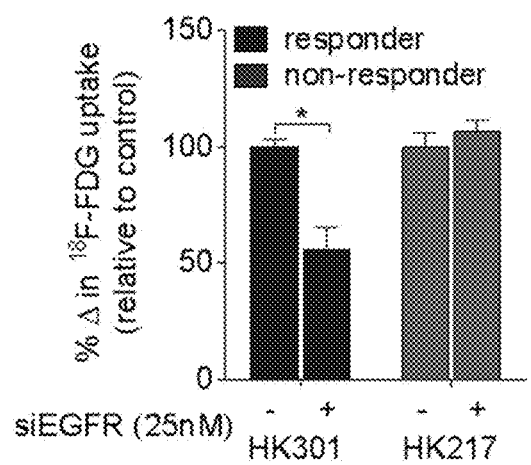
Figure 27D:
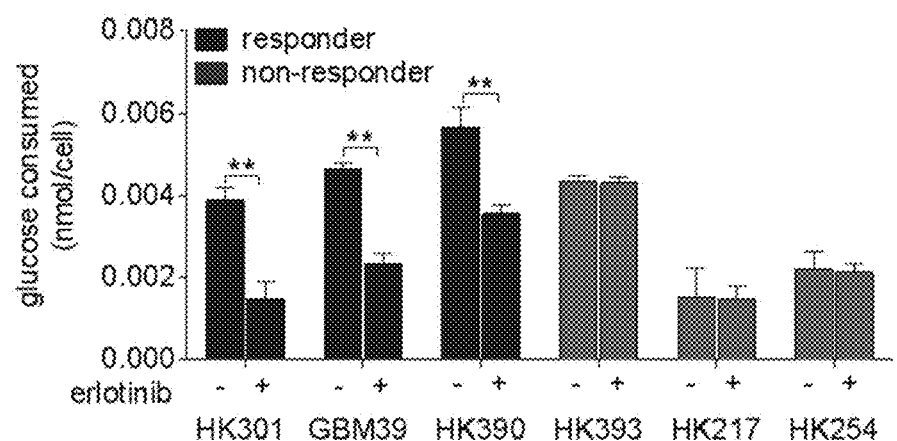
Figure 27E:
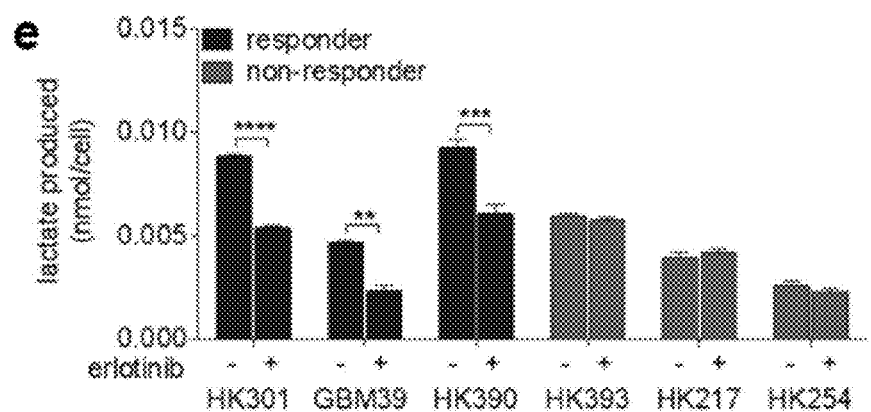
Figure 27F:
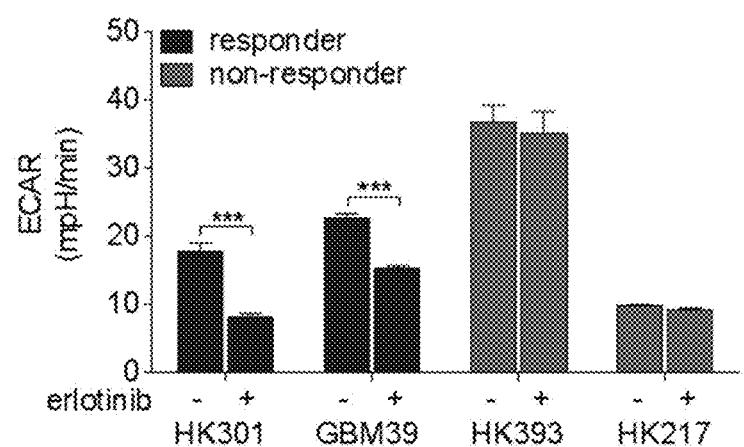
Figure 27G:
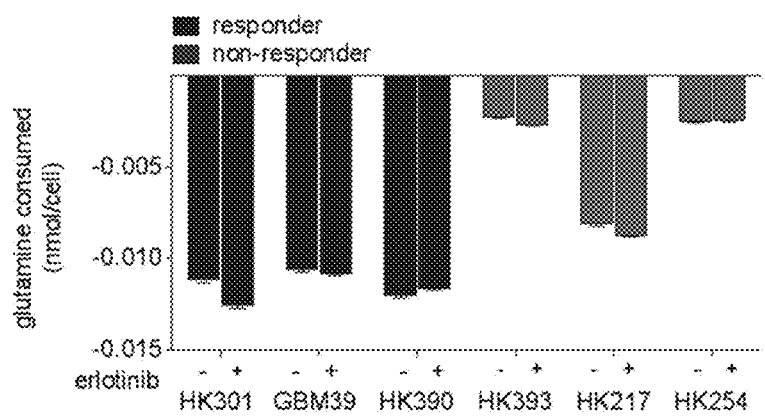
Figure 28A:
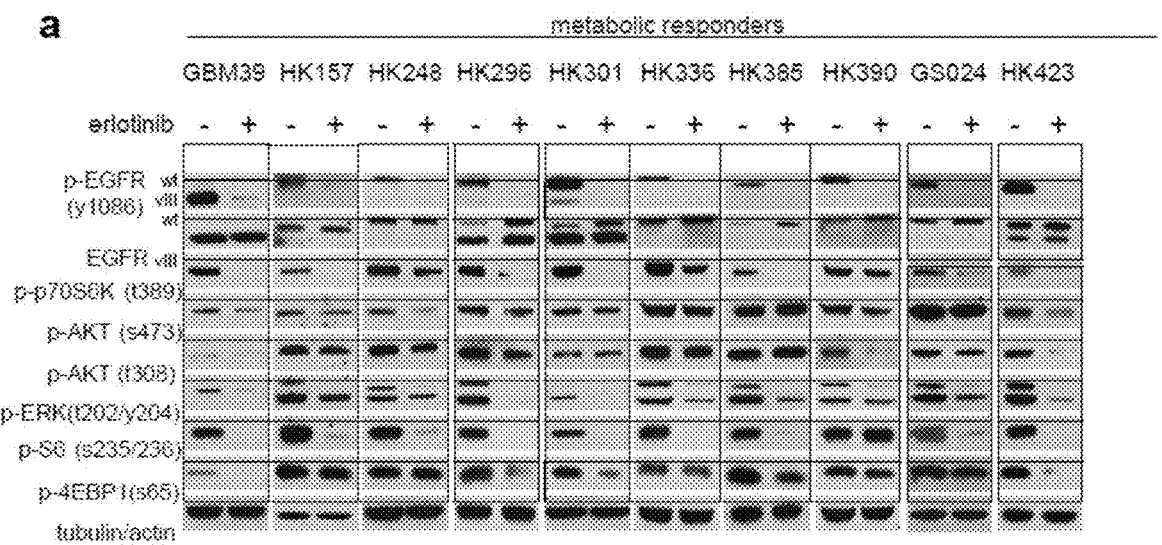
FIGS. 28A-28B depict alterations in downstream signaling following EGFR inhibition correlate with metabolic response.

Changes in glucose consumption with acute EGFR inhibition across 19 patient-derived GBM cell lines was characterized. The cells were cultured in supplemented serum-free medium as gliomaspheres which, in contrast to serum-based culture conditions, preserve many of the molecular features of patient tumors. Treatment with the EGFR tyrosine kinase inhibitor (EGFRi) erlotinib identified a subset of GBMs whose radio-labeled glucose uptake ($^{18}$F-FDG) was significantly attenuated with EGFR inhibition; hereafter termed "metabolic responders" (FIG. 21A and FIG. 27A). Silencing of EGFR using siRNA confirmed that the reduction in glucose uptake was not due to off target effects of erlotinib (FIG. 27B, 27C). Reduced $^{18}$F-FDG uptake in EGFRi treated cells was associated with decreased lactate production, glucose consumption, and extracellular acidification rate (ECAR), yet glutamine levels remained unchanged (FIG. 21B and FIG. 27D-G). Finally, decreased glucose utilization correlated with perturbations in RAS-MAPK and PI3K-AKT-mTOR signaling—each of which can regulate glucose metabolism in GBM and other cancers (FIG. 28A).

Figure 28B:
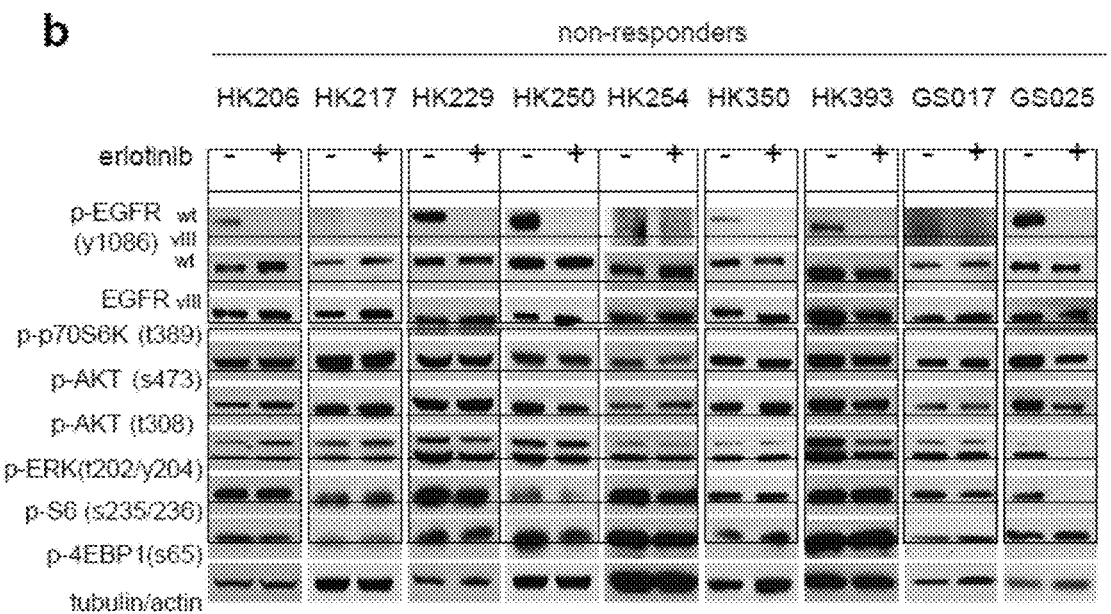
Figure 29A:
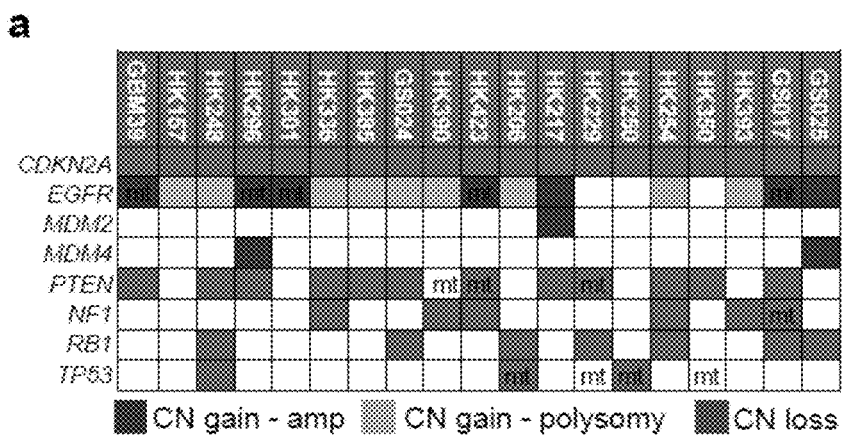
FIGS. 29A-29B depicts the genetic characterization of patient-derived GBM cell lines.
Figure 29B:
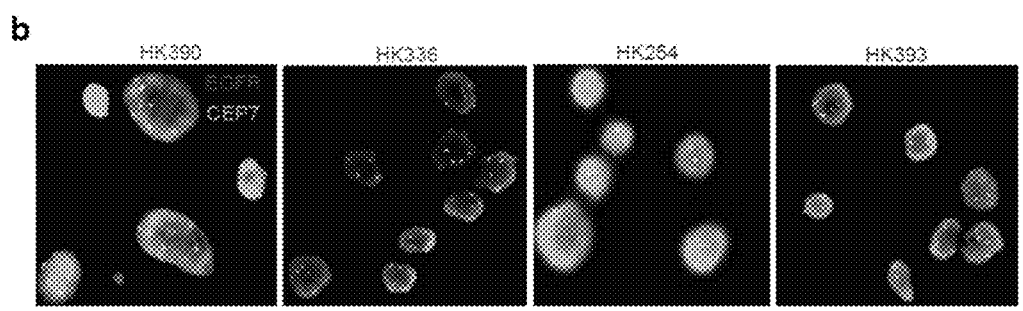

In contrast, in all "non-responders" GBMs (i.e. no change in $^{18}$F-FDG uptake with EGFRi or siRNA) (FIG. 21A and FIG. 27B, 27C), no changes in glucose consumption, lactate production, and ECAR were observed despite robust inhibition of EGFR (FIG. 21B, FIG. 27D-G, and FIG. 28B). Moreover, RAS-MAPK and PI3K-AKT-mTOR signaling were largely unaffected in these cells (FIG. 28B). Notably, while all metabolic responders had alterations in EGFR (copy number gain, mutation), 6 GBM lines without a metabolic response also contained EGFR mutations and/or copy number gains (FIG. 29A, 29B). Taken together, these data illustrate two key points. First, acute inhibition of EGFR rapidly attenuates glucose utilization in a subset of primary GBM cells, and second, genetic alterations in EGFR could not alone predict which GBMs have a metabolic response to EGFRi.

Example 7

EGFRi Metabolic Responders are Primed for Apoptosis

Figure 21C:
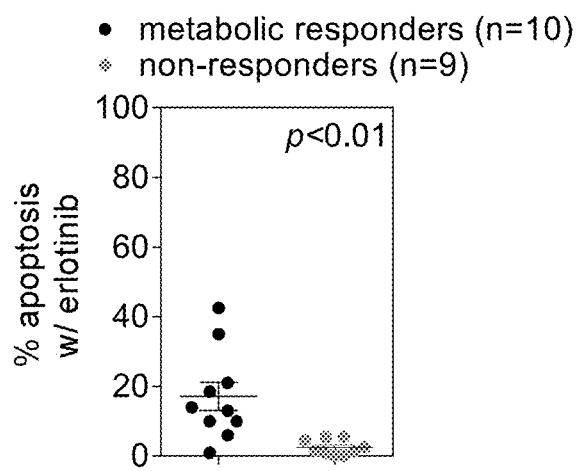
Figure 30A:
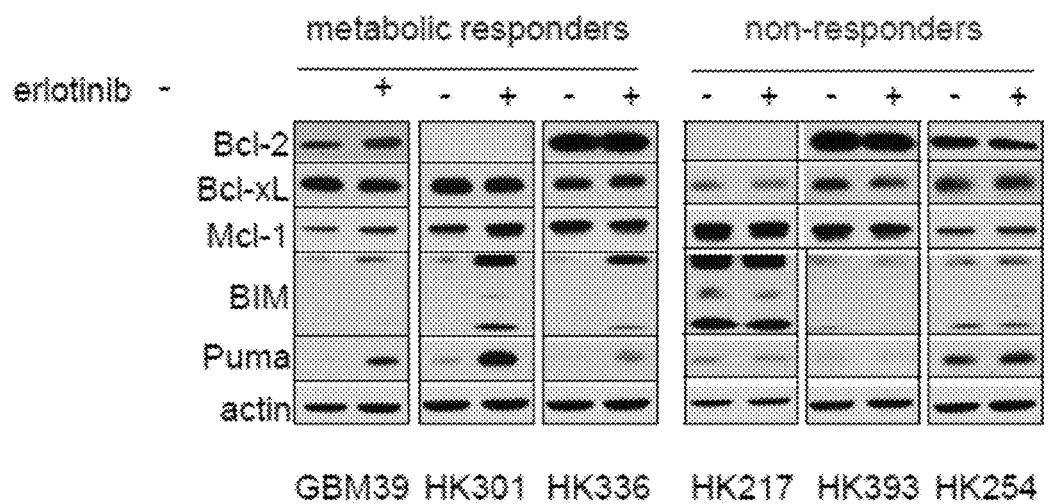
FIGS. 30A-30B depict EGFR inhibition shifts the apoptotic balance in metabolic responders.

Perturbations in glucose metabolism can induce the expression of pro-apoptotic factors and stimulate intrinsic apoptosis, suggesting that reduced glucose uptake in response to EGFRi would stimulate the intrinsic apoptotic pathway. Indeed, acute erlotinib treatment promoted the expression of the pro-apoptotic BH3-only proteins, BIM and PUMA, only in the metabolic responder cultures (FIG. 30A). However, annexin V staining revealed that the metabolic responders had only modest (~17%), albeit significantly higher, apoptosis compared with non-responders (~3%), following 72 hours of erlotinib exposure (FIG. 21C).

Figure 21D:
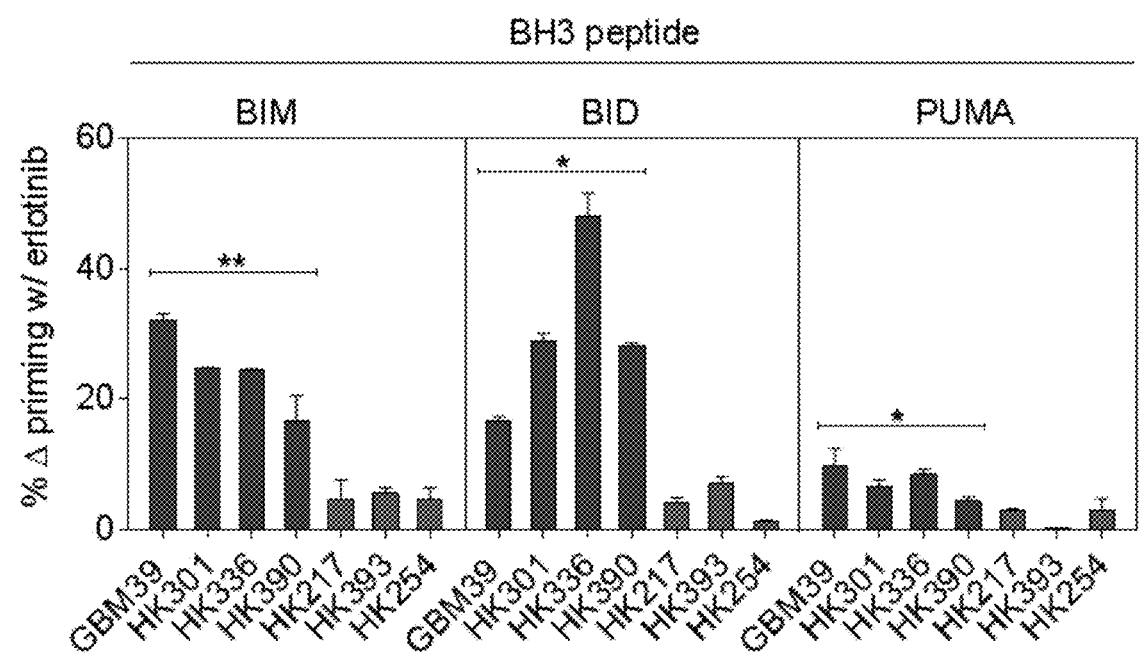
Figure 21E:
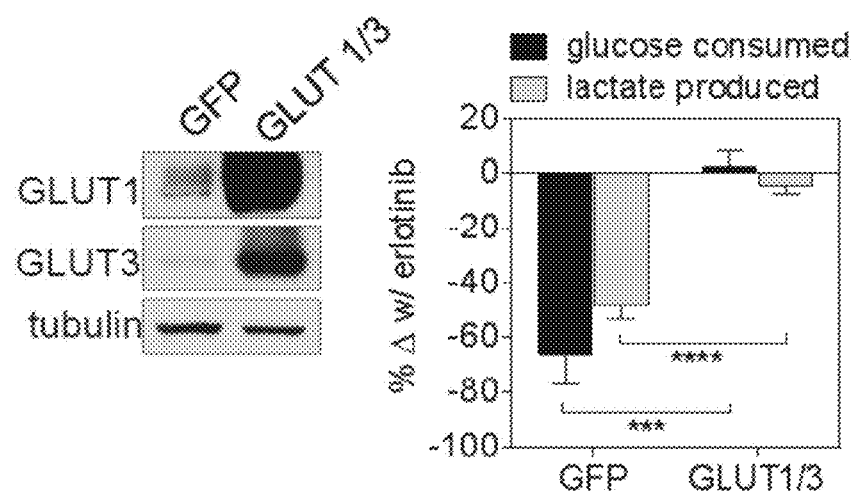
Figure 30B:
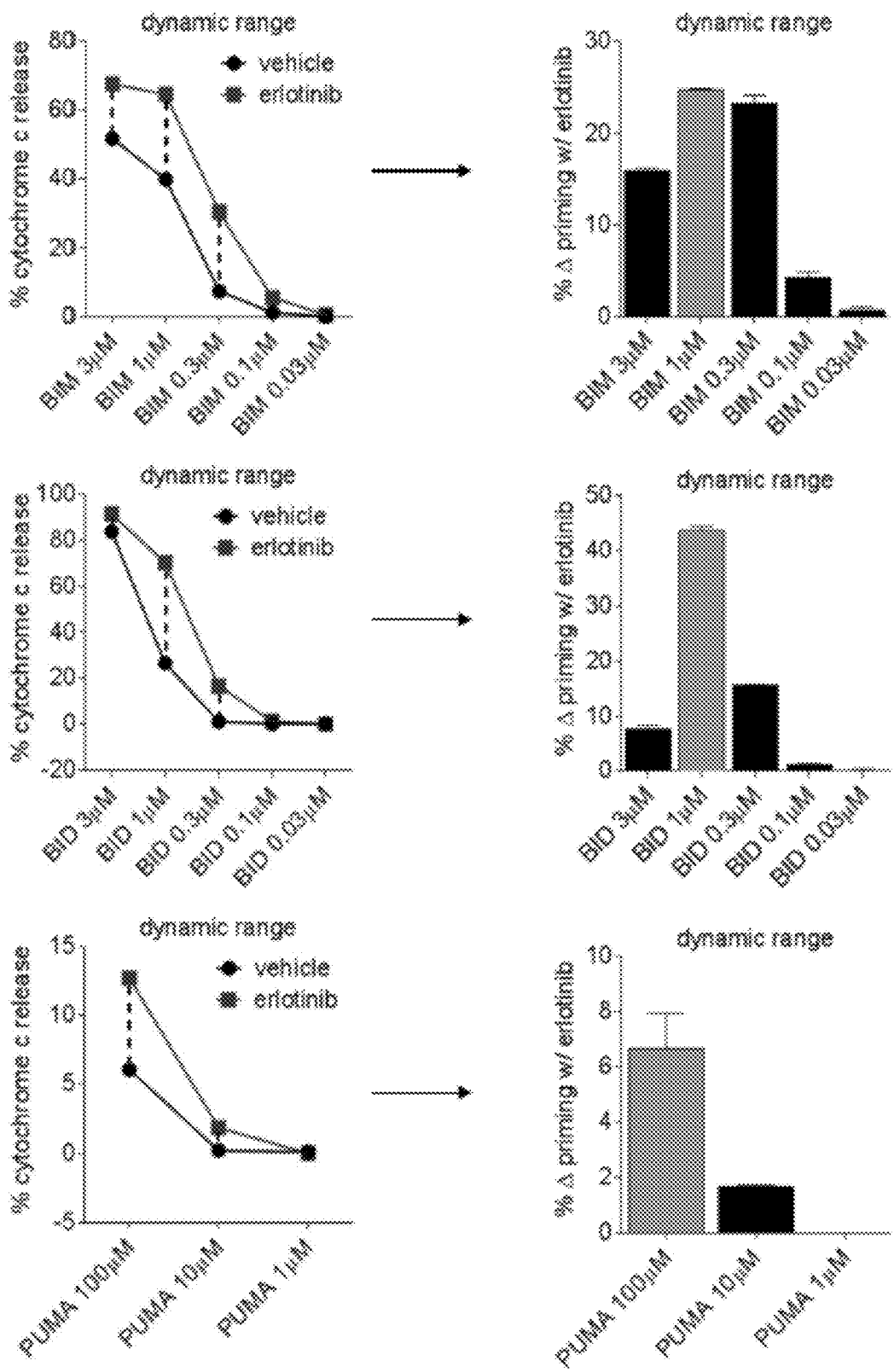
Figure 31A:
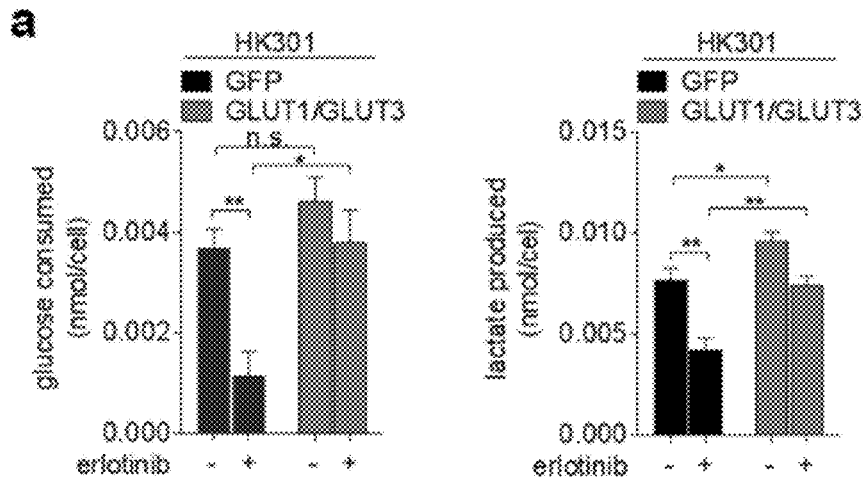
FIGS. 31A-31C depict GLUT1/3 overexpression rescues attenuated glucose metabolism caused by EGFR inhibition.
Figure 31B:
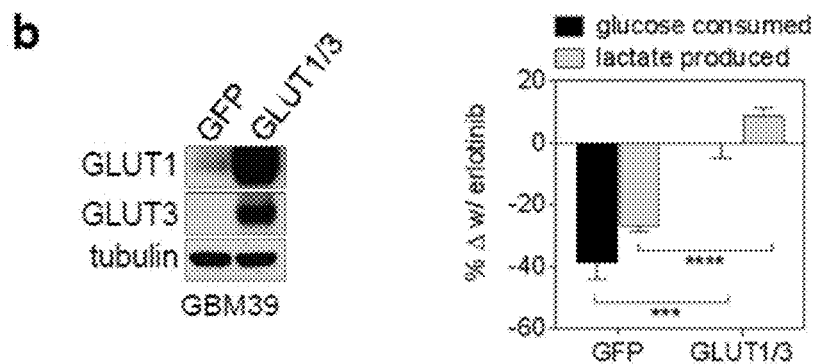
Figure 31C:
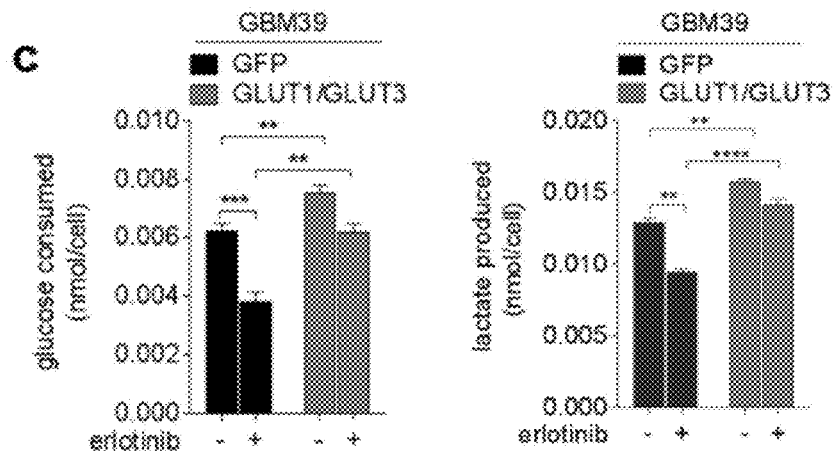

The low level of apoptosis, despite pronounced induction of pro-apoptotic factors, led the inventors to ask if perturbing glucose uptake with EGFRi "primes" GBM cells for apoptosis; thus increasing the propensity for apoptosis without inducing significant cell death. To test this, the inventors treated both metabolic responders and non-responders with erlotinib for 24 hours and performed dynamic BH3 profiling to quantify the changes in apoptotic priming (FIG. 30B). Using multiple BH3 peptides (e.g., BIM, BID, and PUMA), we observed a significant increase in apoptotic priming—as determined by the change in cytochrome c release relative to vehicle—in the metabolic responders with erlotinib treatment (FIG. 21D—dark gray bars). Importantly, priming in the metabolic responders was significantly higher than priming in the non-responders (FIG. 21D—light gray bars), supporting the premise that attenuated glucose uptake with EGFRi triggers apoptotic priming in GBM.

Figure 21F:
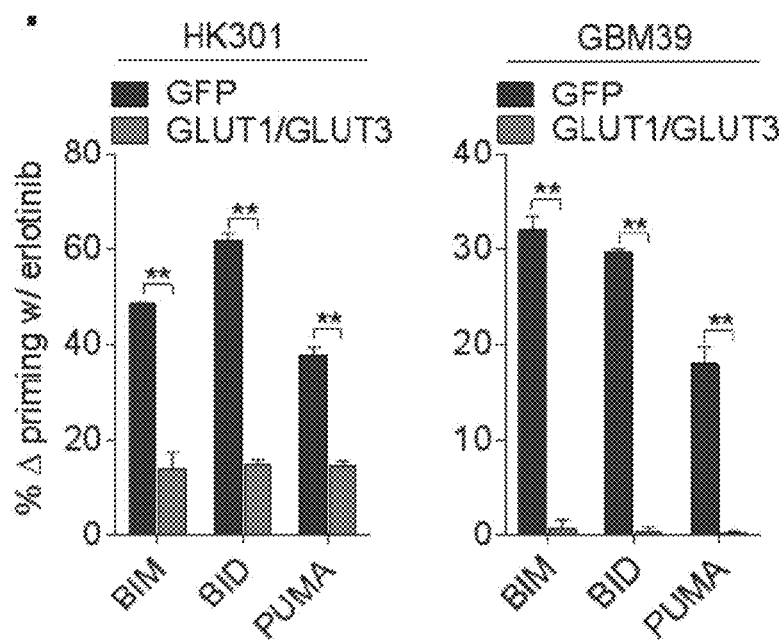

The inventors tested if reduced glucose uptake is required for apoptotic priming with EGFRi, by checking whether rescuing glucose consumption should mitigate these effects. To test this, glucose transporters 1 (GLUT1) and 3 (GLUT3) were ectopically expressed in two metabolic responders (HK301 and GBM39). Enforced expression of GLUT1 and GLUT3 (GLUT1/3) rescued EGFRi-mediated attenuation of glucose uptake and lactate production in both cell lines (FIG. 21E and FIG. 31A-C) and, importantly, markedly suppressed apoptotic priming in response to EGFRi (FIG. 21F). Collectively, these data demonstrate that EGFRi-mediated inhibition of glucose consumption, although insufficient to induce significant cell death, lowers the apoptotic threshold potentially rendering GBM cells vulnerable to agents that exploit this primed state.

Example 8

Cytoplasmic p53 is Required for Apoptotic Priming with EGFRi

The mechanism by which GBMs become primed for apoptosis with EGFRi was investigated. The inhibition of oncogene-driven glucose metabolism renders GBM cells synergistically susceptible to cytoplasmic p53 dependent apoptosis. Attenuated glucose metabolic flux in GBM, via targeting oncogenic signaling (e.g., EGFRi), results in cytoplasmic p53 engaging the intrinsic apoptotic pathway ("priming"). However, Bcl-xL blocks cytoplasmic p53-mediated cell death. Pharmacological p53 stabilization overcomes this apoptotic block, leading to synergistic lethality with combined targeting of oncogene-driven glucose metabolism in GBM.

Figure 22A:
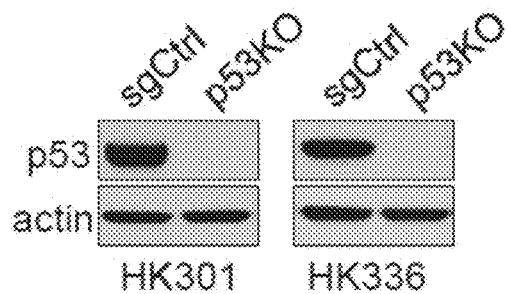
FIGS. 22A-22H depict Cytoplasmic p53 links EGFR to intrinsic apoptosis.
Figure 22B:
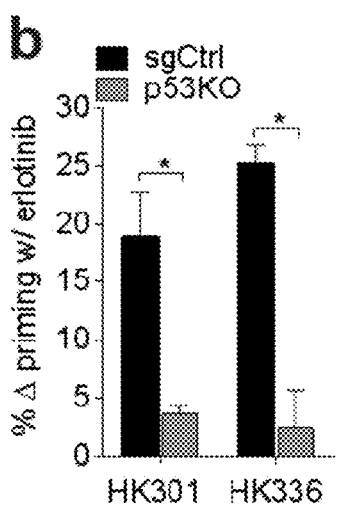
Figure 22C:
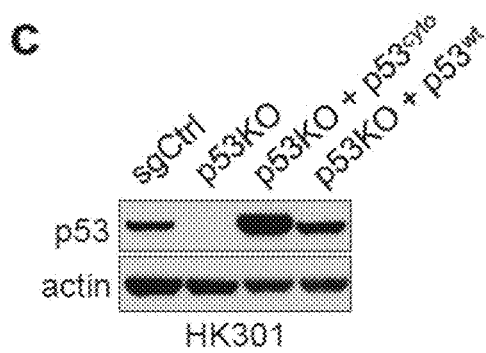
Figure 22D:
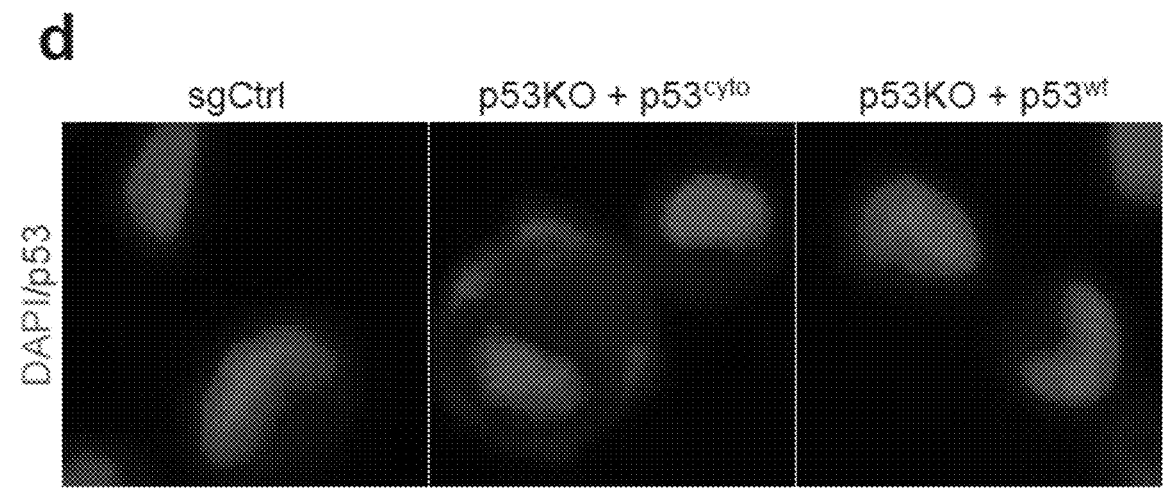
Figure 32A:
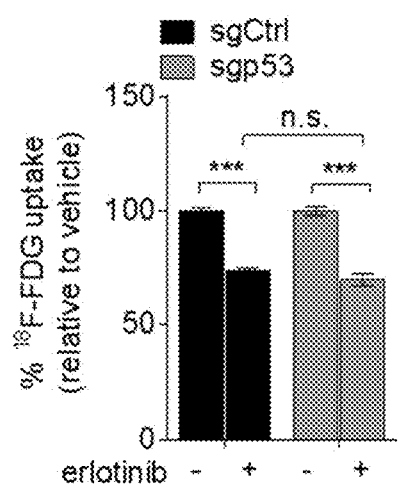
FIGS. 32A-32I depict cytoplasmic p53 is required for EGFRi-mediated apoptopic priming

In cells that are in a primed state, the anti-apoptotic Bcl-2 family proteins (e.g. Bcl-2, Bcl-xL, Mcl-1) are largely loaded with pro-apoptotic BH3 proteins (e.g., BIM, BID, PUMA, BAD, NOXA, HRK); consequently, cells are dependent on these interactions for survival. The tumor suppressor protein, p53, is known to upregulate pro-apoptotic proteins that subsequently need to be bound by anti-apoptotic Bcl-2 proteins to prevent cell death. To examine whether p53 is required for EGFRi-induced priming, we silenced p53 with CRISPR/CAS-9 (hereafter referred to as p53KO) in two metabolic responders (HK301 and HK336, FIG. 22A). While the change in glucose consumption with EGFRi was unaffected in p53KO cells (FIG. 32A), BH3 profiling revealed p53KO nearly abolished erlotinib-induced apoptotic priming in both HK301 and HK336 cells (FIG. 22B).

Figure 32B:
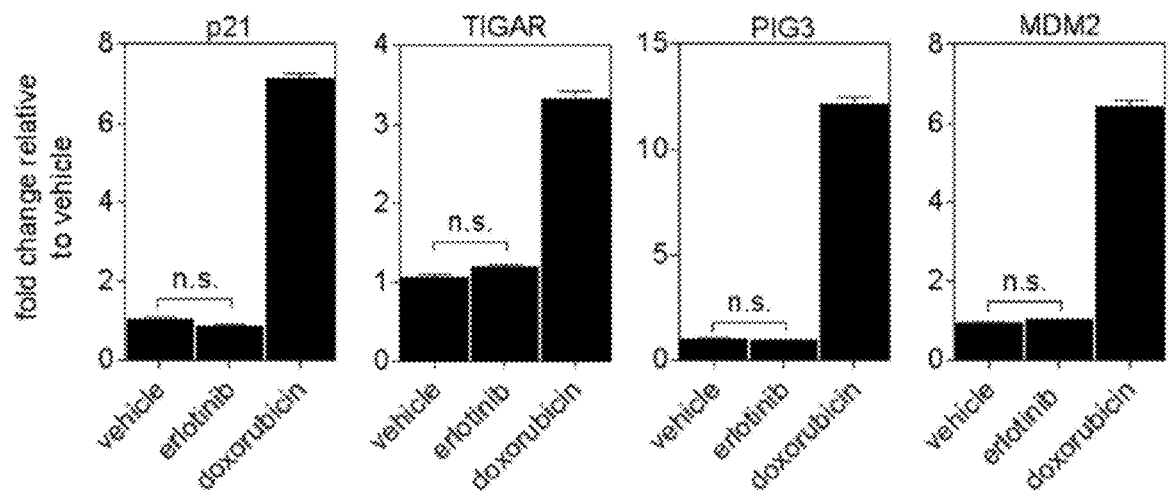
Figure 32C:
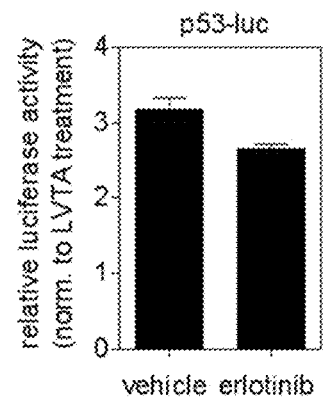

As p53 transcriptional activity has been shown to be enhanced under glucose limitation, it we investigated to determine whether p53-mediated transcription was induced by EGFRi. However, erlotinib did not increase the expression of p53-regulated genes (e.g., p21, MDM2, PIG3, TIGAR) (FIG. 32B), nor induce p53-luciferase reporter activity in HK301 metabolic responder cells (FIG. 32C). These data indicate that while p53 is required for priming with EGFRi, its transcriptional activity may not be necessary.

Figure 22E:
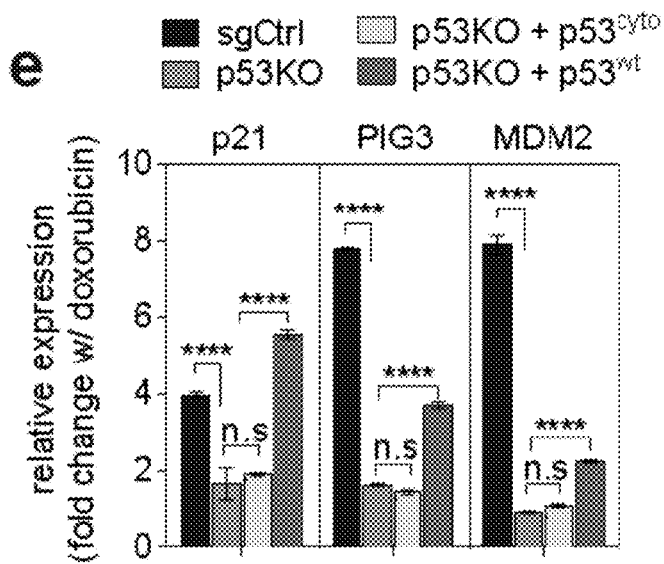
Figure 22F:
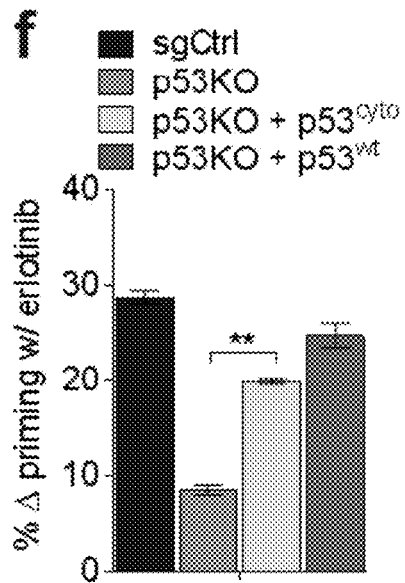
Figure 22G:
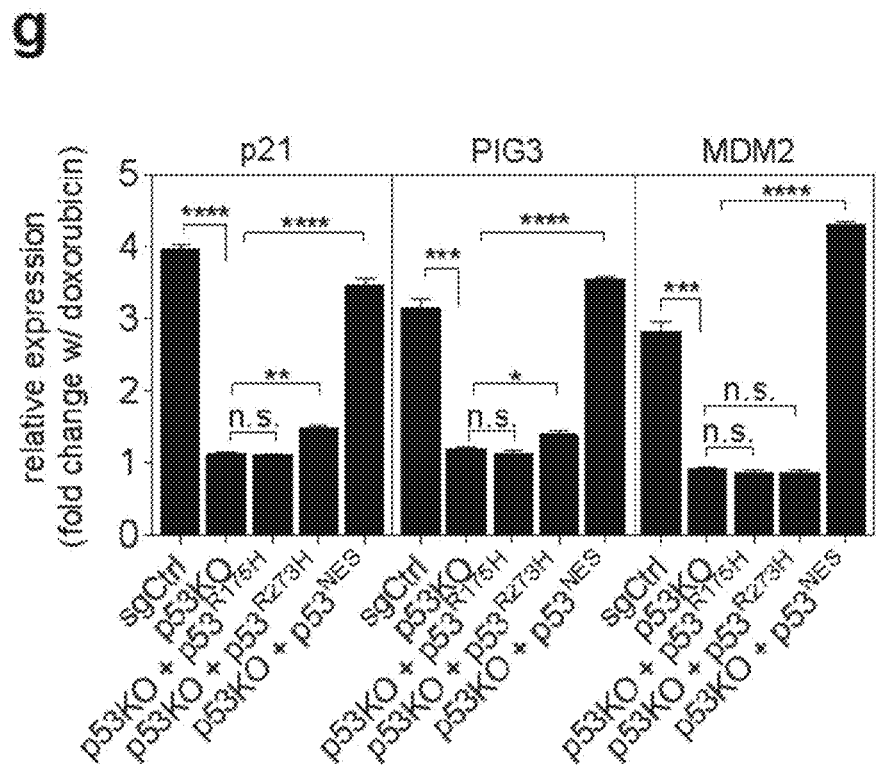
Figure 22H:
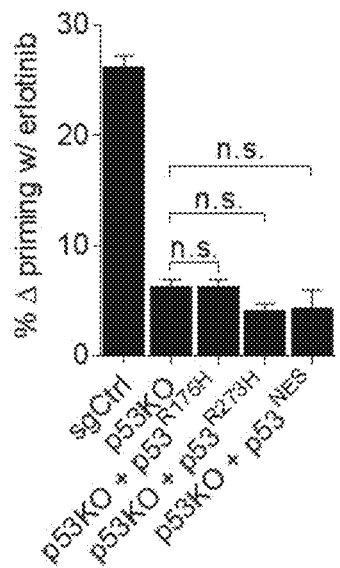
Figure 32D:
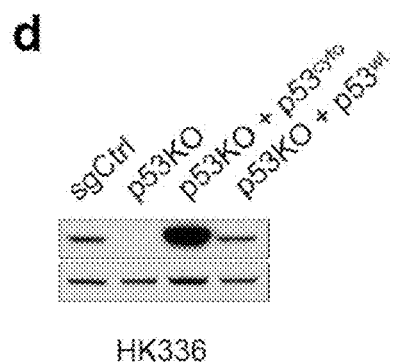
Figure 32E:
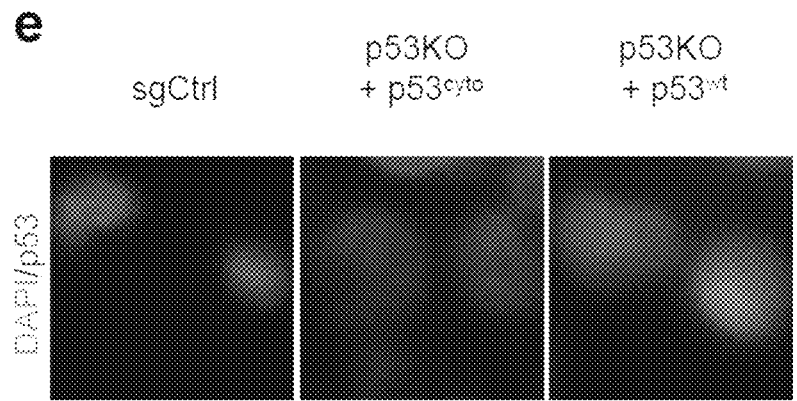
Figure 32F:
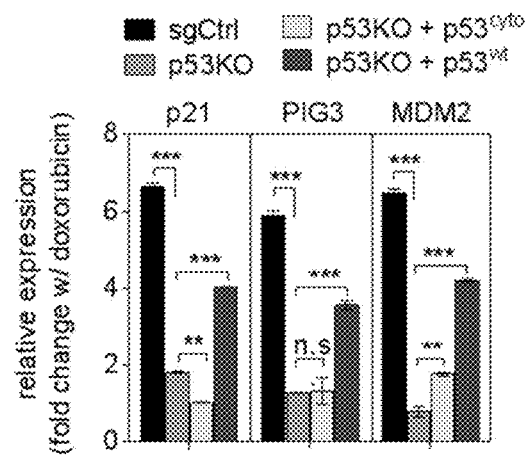

In addition to p53's well-described nuclear functions, p53 can localize in the cytoplasm where it can directly engage the intrinsic apoptotic pathway. To evaluate whether cytoplasmic p53 is important for apoptotic priming with EGFRi, we stably introduced a p53 mutant with a defective nuclear localization signal (p53$^{cyto}$) into HK301 and HK336 p53KO gliomaspheres. As expected, p53$^{cyto}$ was expressed (FIG. 22C and FIG. 32D), restricted to the cytoplasm (FIG. 22D and FIG. 32E) and had no transcriptional activity (FIG. 22E and FIG. 32F). Conversely, reconstitution of wild-type p53 (p53$^{wt}$) in HK301 and HK336 p53KO cells displayed similar localization as parental cells and rescued transcription of p53-regulated genes (FIG. 22C-E and FIG. 32E-G). Remarkably, stable introduction of p53$^{cyto}$ significantly restored priming with erlotinib in both HK301 and HK336 p53KO cells to levels comparable to p53$^{wt}$ (FIG. 22F and FIG. 32G), indicating that the cytoplasmic function of p53 is required for EGFRi-mediated priming. In support of this, introduction of a transcriptionally active (FIG. 2622G), yet nuclear-confined p53 mutant (p53$^{NES}$) into HK301 p53KO cells failed to induce EGFRi-mediated apoptotic priming (FIG. 22G, 22H and FIG. 32H). Finally, pharmacological inhibition of cytoplasmic p53 activity with pifithrin-μ (PFTμ) markedly reduced priming with erlotinib (FIG. 32I). Collectively, these results show that cytoplasmic p53 engages the intrinsic apoptotic machinery following EGFRi in GBM.

Prior work demonstrated that human tumor-derived p53 mutants—specifically those in the DNA binding domain—have diminished cytoplasmic functions in addition to transactivation deficiencies. Thus, the inventors tested whether stable expression of two of these "hotspot" p53 mutants, R175H or R273H, in HK301 p53KO would have reduced EGFRi-mediated priming (FIG. 32H). As expected, both mutants lacked transcriptional capabilities (FIG. 22G) and, consistent with reduced cytoplasmic activity, were incapable of apoptotic priming with EGFRi (FIG. 22H). Therefore, in line with previous findings, oncogenic mutations in the DNA binding domain of p53 result in "dual hits", whereby both transactivation and cytoplasmic functions are abrogated—the latter having implications for apoptotic priming with EGFRi.

Example 9

Figure 23A:
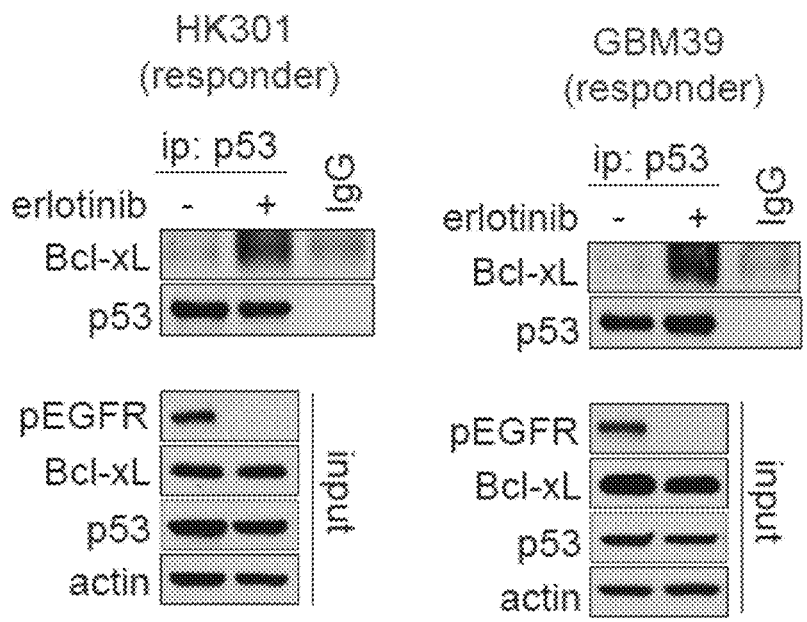
FIGS. 23A-23F depict Bcl-xL prevents GBM cell death by binding to and sequestering cytoplasmic p53 in EGFRi-metabolic responders.
Figure 23B:
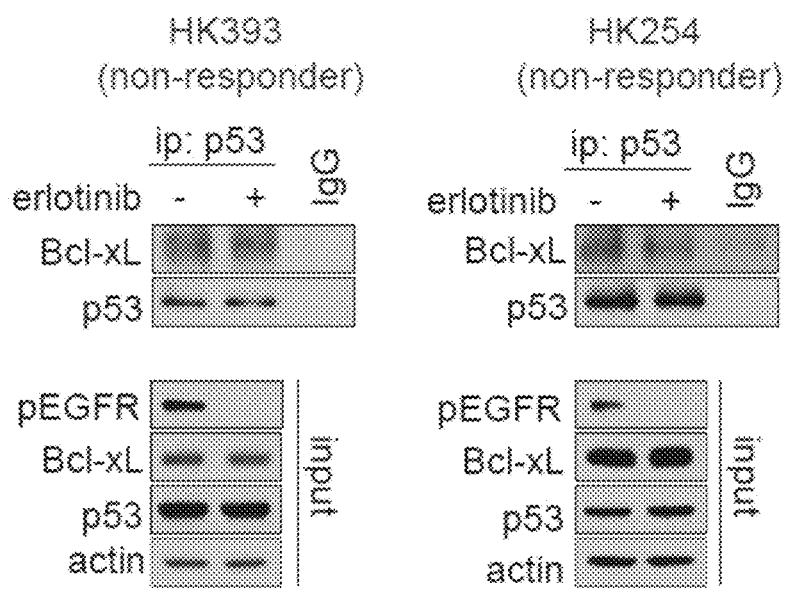
Figure 23C:
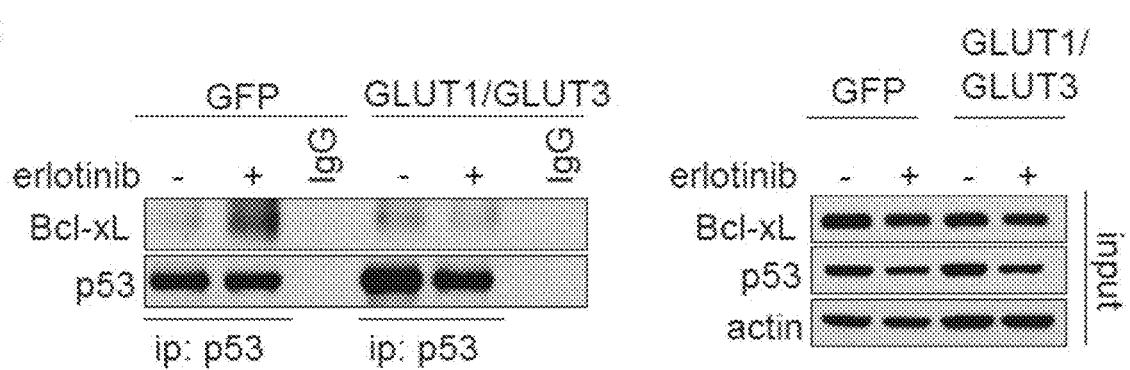
Figure 33A:
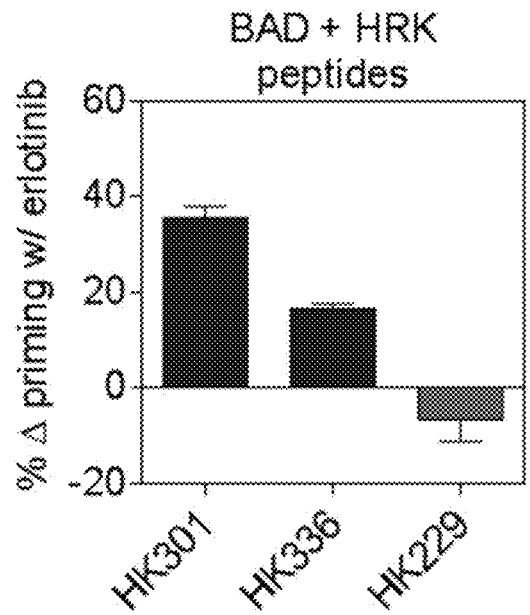
FIGS. 33A-33D depict the inhibition of EGFR-driven glucose metabolism induces a Bcl-xL dependency through cytoplasmic p53 functions.
Figure 33B:
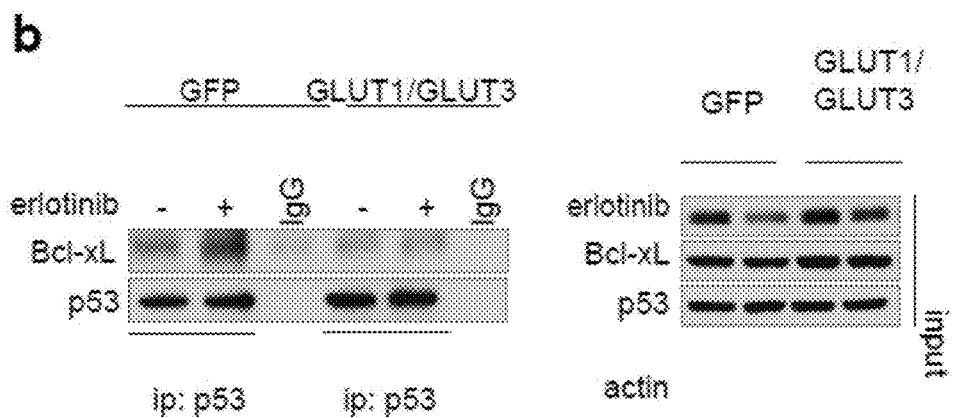

Inhibition of EGFR-Driven Glucose Uptake Creates an Exploitable Bcl-xL Dependency Bcl-xL can sequester cytoplasmic p53 and prevent p53-mediated apoptosis; thus creating a primed apoptotic state and a dependency on Bcl-xL for survival. Indeed, BH3 profiling revealed a dependence on Bcl-xL for cell survival in EGFRi metabolic responders (FIG. 33A). Therefore, we hypothesized that attenuated glucose consumption with EGFRi may result in sequestration of cytoplasmic p53 by Bcl-xL. To investigate this, we performed co-immunoprecipitations to examine the dynamics of p53-Bcl-xL interactions in response to EGFRi in both responders (n=2) and non-responders (n=2). Importantly, we observed markedly heightened Bcl-xL and p53 interactions following erlotinib treatment in metabolic responders (FIG. 23A) but not in non-responders (FIG. 23B). This suggests that inhibition of EGFR-dependent glucose consumption results in sequestration of p53 by Bcl-xL. Consistent with this interpretation, ectopic expression of GLUT1/3, which rescues the EGFRi-mediated reduction in glucose uptake and apoptotic priming, prevented the association of p53 with Bcl-xL (FIG. 23C and FIG. 33B). These findings strongly indicate that EGFRi-mediated inhibition of glucose uptake primes GBM cells for apoptosis by promoting an interaction between cytoplasmic p53 and Bcl-xL.

Figure 23D:
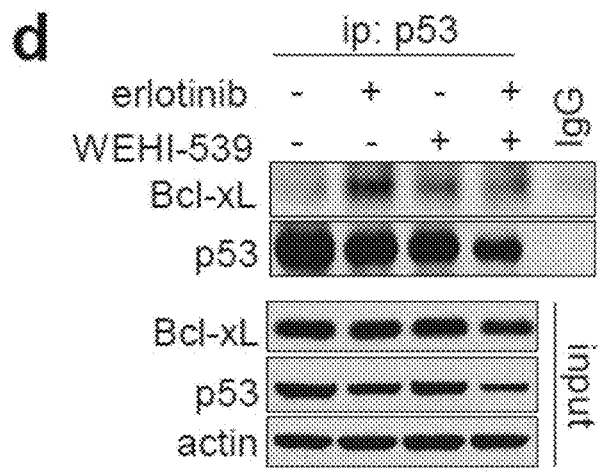
Figure 23E:
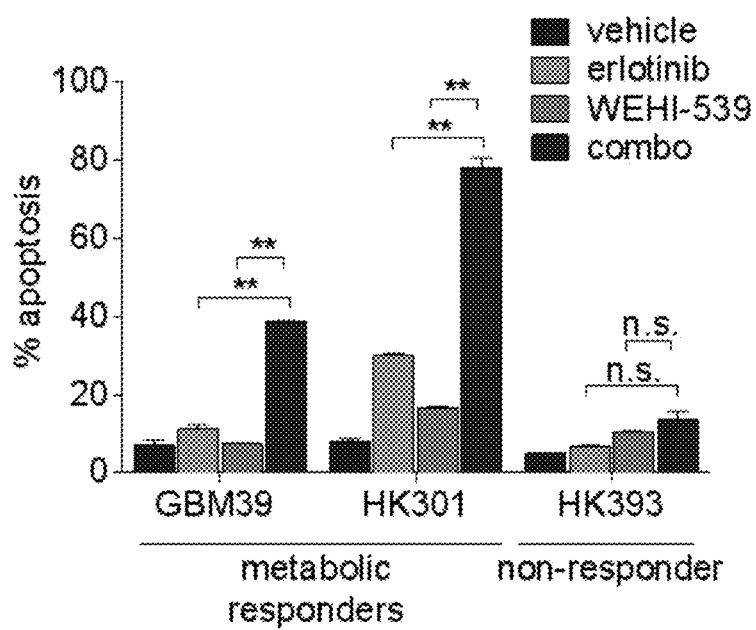
Figure 23F:
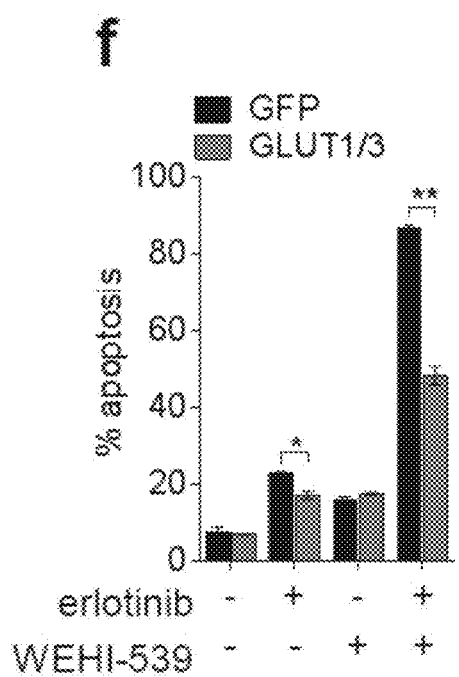
Figure 33C:
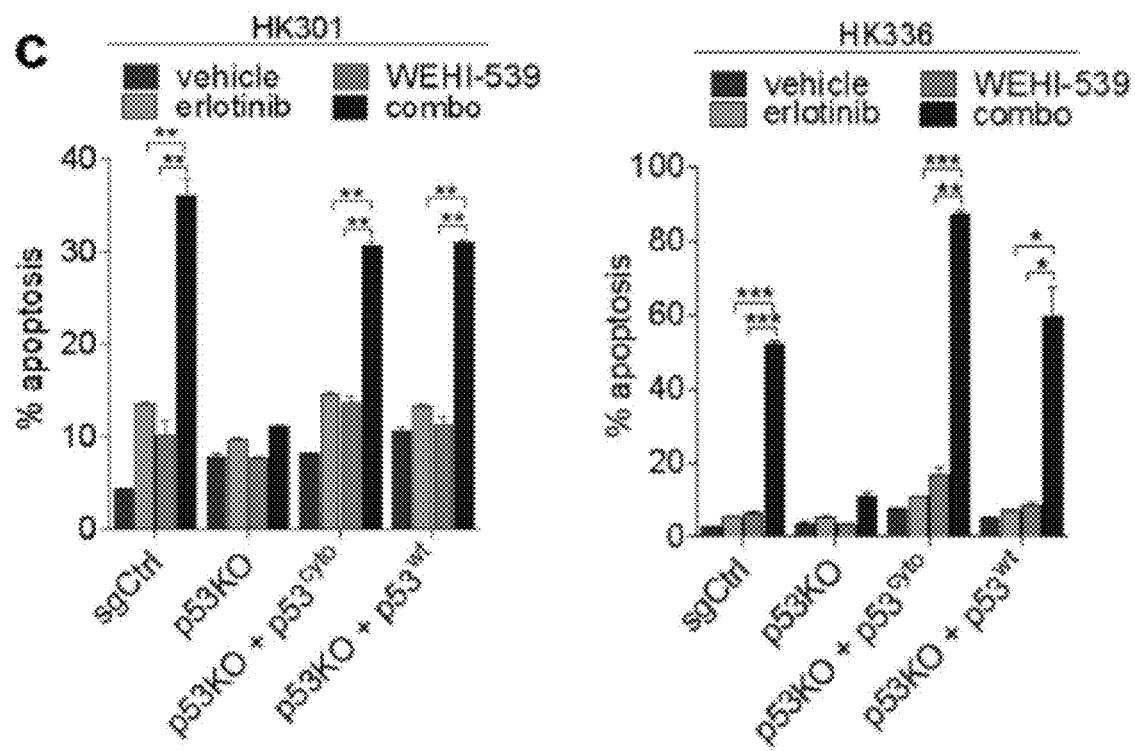
Figure 33D:
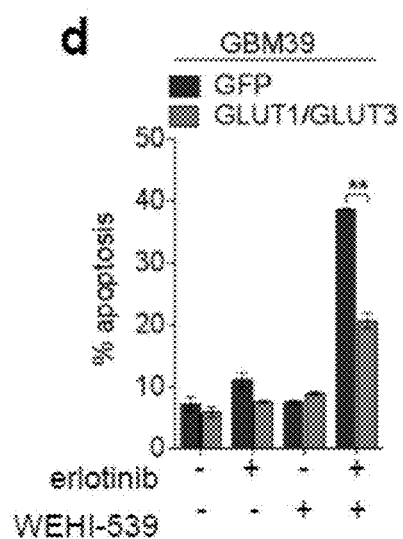

The liberation of p53 from Bcl-xL enables p53 to directly activate BAX, resulting in cytochrome c release and cell death. Once we recognized increased binding between Bcl-xL and p53 in metabolic responders in response to EGFRi, we asked whether displacement of p53 from Bcl-xL elicits apoptosis. To test this, we treated a metabolic responder (HK301) with erlotinib and the specific Bcl-xL inhibitor, WEHI-539. The addition of WEHI-539 disrupted the association of Bcl-xL with p53 under erlotinib treatment (FIG. 23D), leading to synergistic lethality in HK301 and GBM39 cells (metabolic responders) (FIG. 23E). Notably, cytoplasmic p53 was sufficient for the combinatorial effects in EGFRi metabolic responder cells (FIG. 33C). However, WEHI-539 did not enhance apoptosis in a non-responder (HK393) treated with erlotinib, suggesting that attenuation of glucose uptake with EGFRi, and subsequent association between p53 and Bcl-xL, is necessary to generate a dependence on Bcl-xL for survival (FIG. 33E). In support of this, enforced expression of GLUT1/3 significantly mitigated cell death with the drug combination (FIG. 23F and FIG. 33D).

Figure 32G:
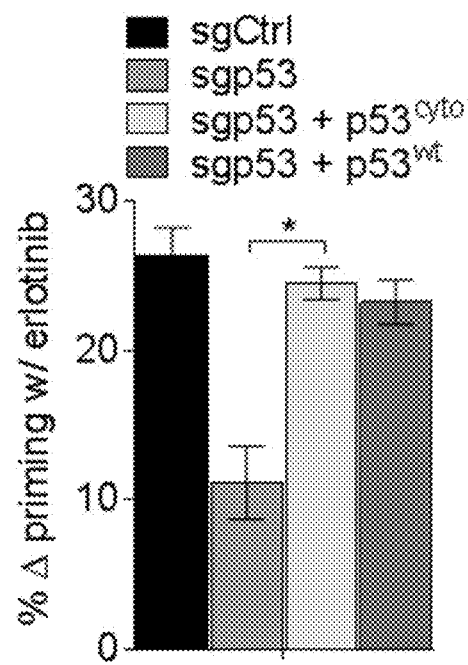
Figure 32H:
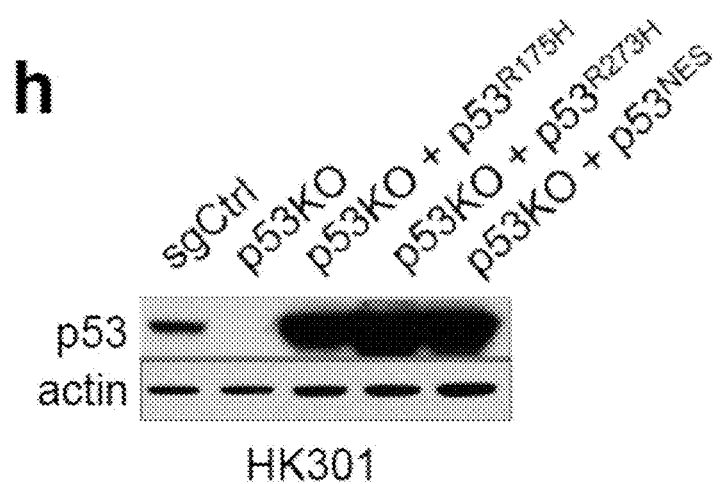
Figure 32I:
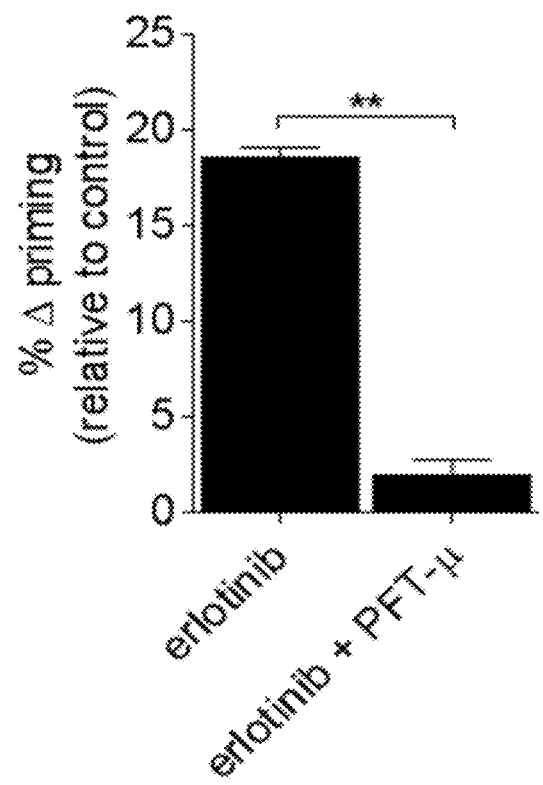

Together, these observations indicate that Bcl-xL attenuates GBM cell death in response to EGFRi-mediated inhibition of glucose uptake by sequestering cytoplasmic p53 (FIG. 32G).

Example 10

Combined Targeting of EGFR and p53 is Synergistic in EGFRi Metabolic Responders

Figure 24A:
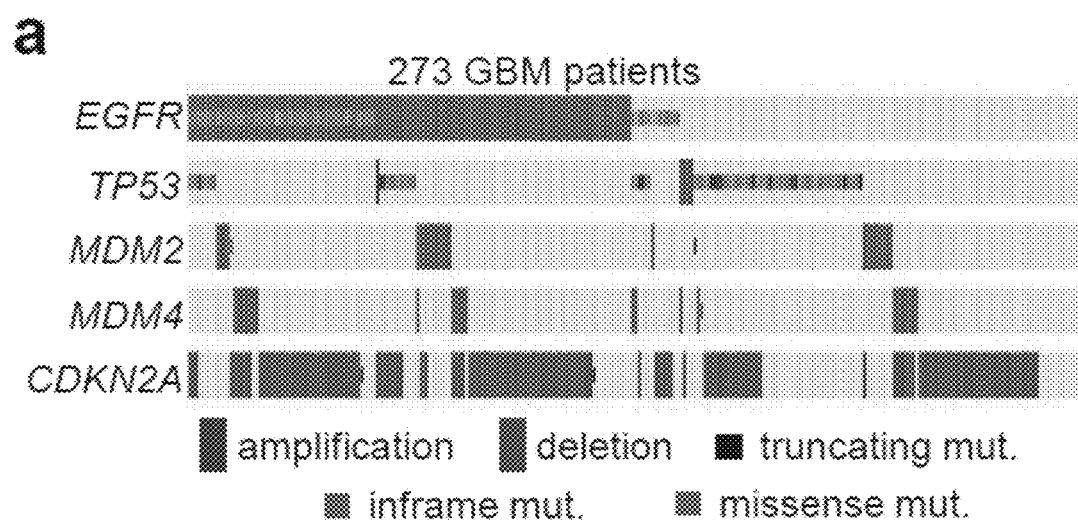
FIGS. 24A-24G depict the synergistic lethality of combined targeting of EGFR and p53.
Figures 24B, 24C:
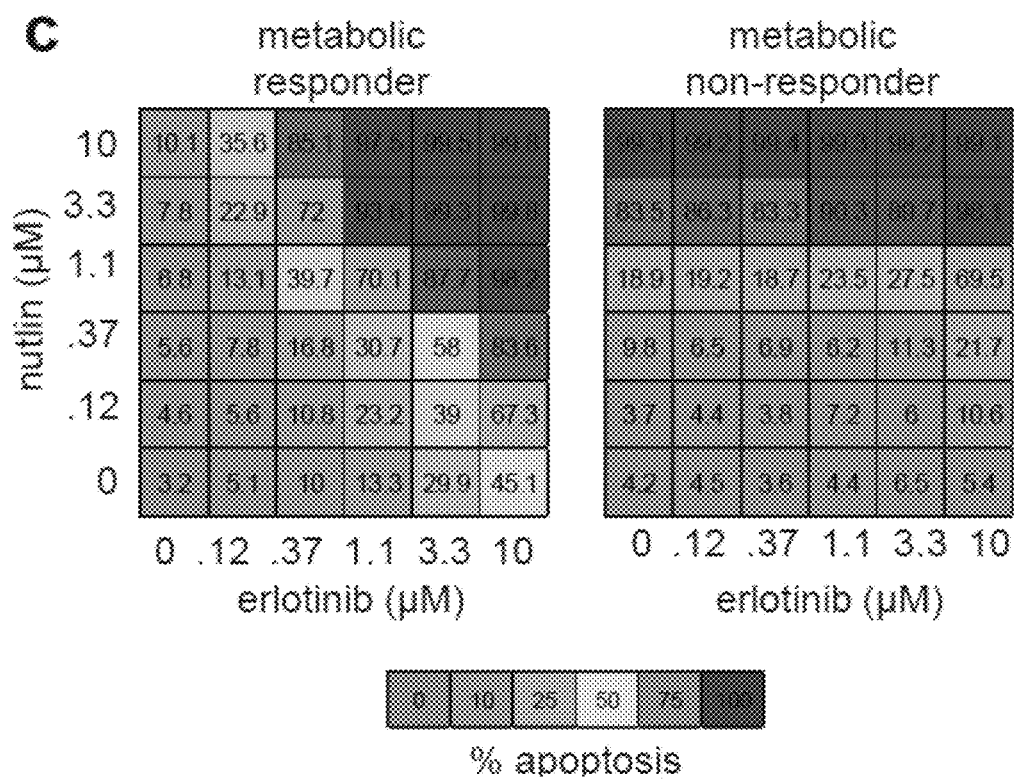
Figure 24D:
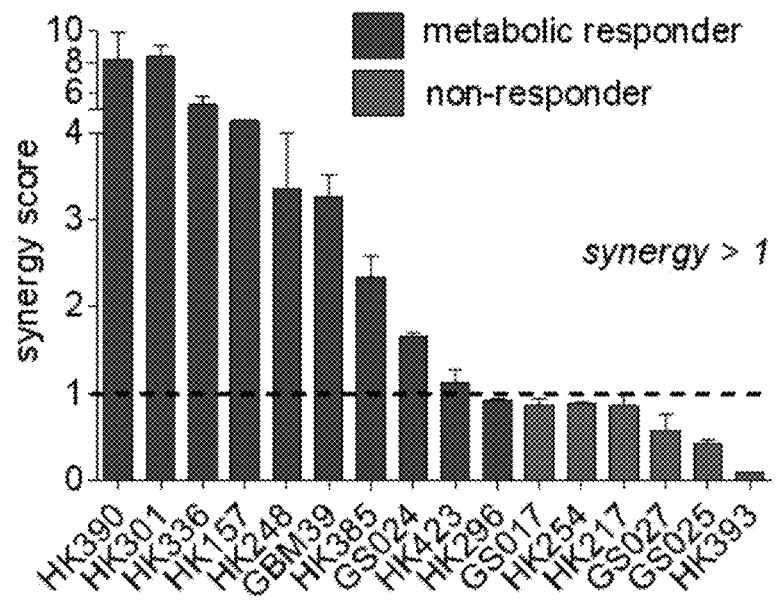
Figure 24E:
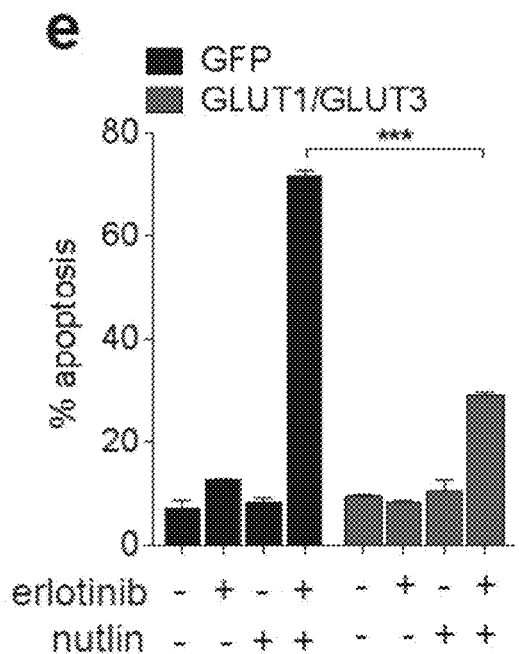
Figure 34A:
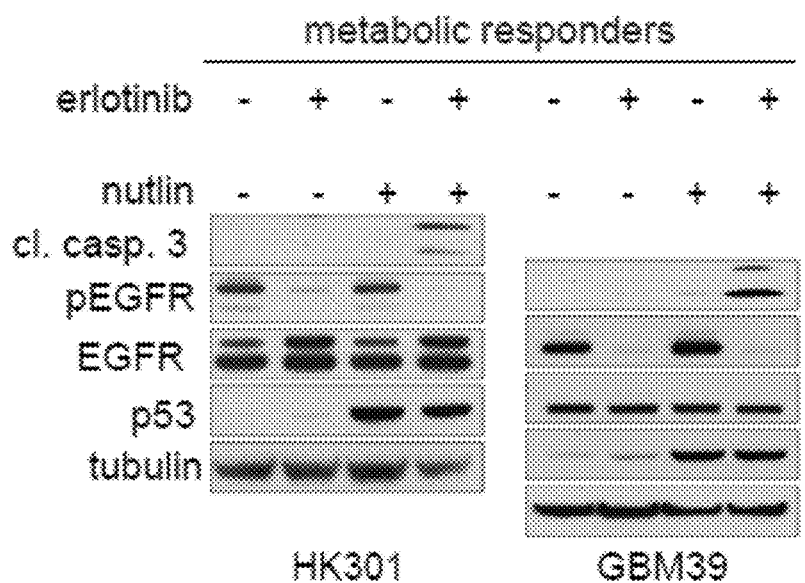
FIGS. 34A-34H depict the inhibition of EGFR-regulated glucose metabolism and p53 activation promote intrinsic apoptosis in GBM.
Figure 34B:
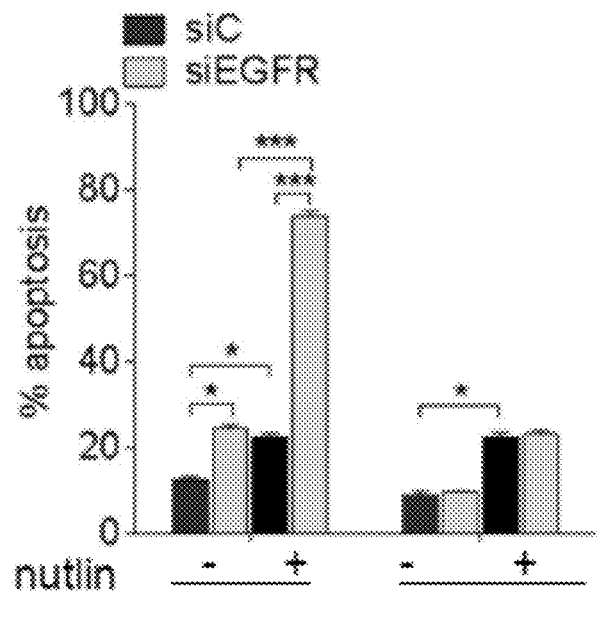
Figure 34C:
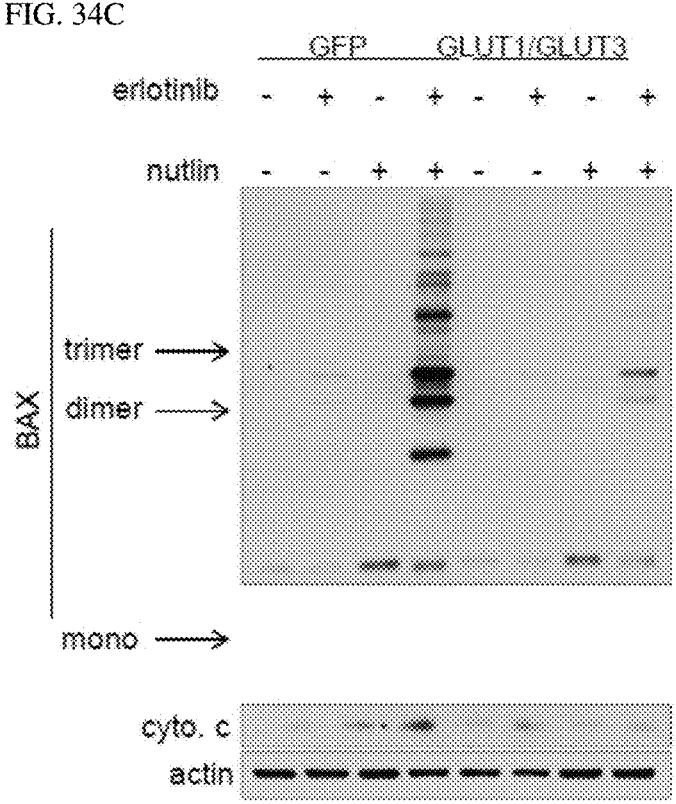

The mechanistic studies revealed a potential therapeutic opportunity in EGFR-driven GBMs that will be dependent on functional p53. While the p53 signaling axis is one of the three core pathways altered in GBM, analysis of the TCGA GBM dataset demonstrated that p53 mutations are mutually exclusive with alterations in EGFR (FIGS. 28A and 28B). Conversely, in patients with EGFR mutations or gains, the p53 pathway can be suppressed through amplification of MDM2 and/or deletions in the negative regulator of MDM2, p14 ARF, at the CDKN2A locus. Given these relationships, and the requirement of p53 for priming under EGFRi-attenuated glucose uptake, we hypothesized that stabilization of p53 via MDM2 inhibition may have similar therapeutic effects to Bcl-xL antagonism. Using nutlin—an extensively characterized inhibitor of MDM2—we found striking synergistic lethality when paired with erlotinib in a metabolic responder gliomasphere. Greater than 90% of HK301 cells underwent apoptosis with combined erlotinib and nutlin (FIG. 24C). Notably, we observed no synergy between these drugs in a metabolic non-responder (GS017, FIG. 24C). We then tested this combination across our panel of primary GBM cells (all p53 wild-type) and found synergistic lethality only in GBMs with a metabolic response to EGFRi (FIG. 24D and FIG. 34A). Genetic knockdown of EGFR confirmed synergy only in the metabolic responders (FIG. 34B). Importantly, enforced expression of GLUT1/3 significantly reduced BAX oligermization, cytochrome c release and apoptosis with combined erlotinib and nutlin (FIG. 24E and FIG. 34C), supporting the concept that inhibition of glucose metabolism with EGFRi is required for the synergistic effects of the erlotinib and nutlin combination.

Figure 24F:
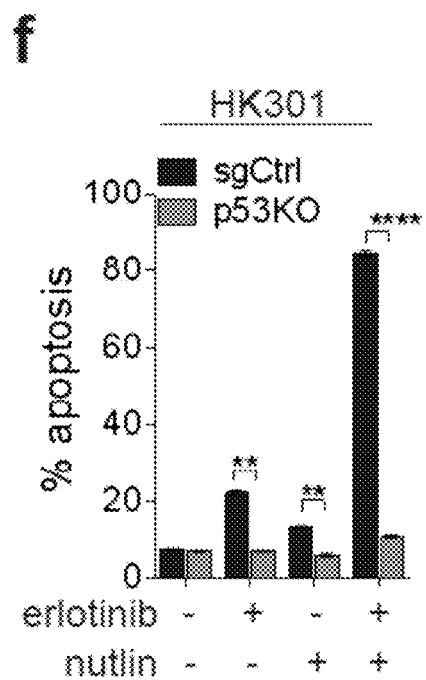
Figure 24G:
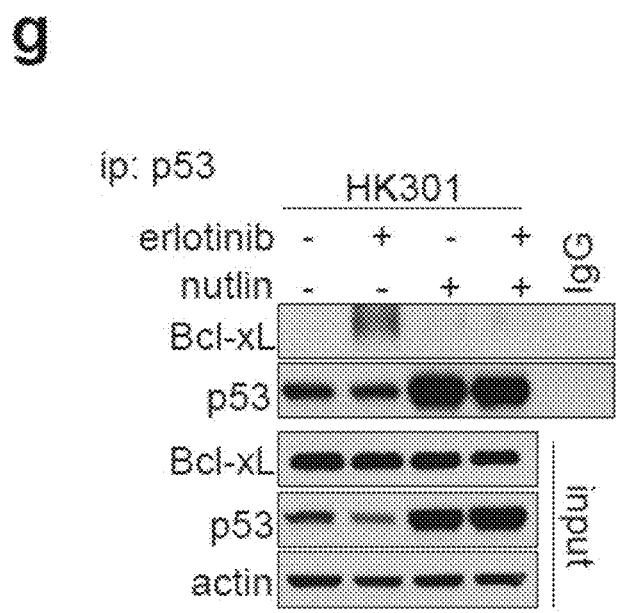
Figure 34D:
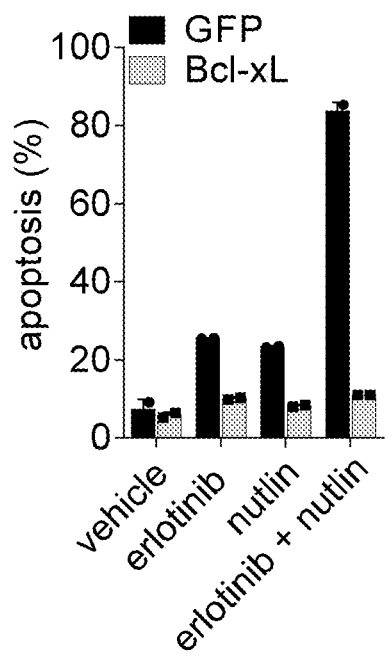
Figure 34E:
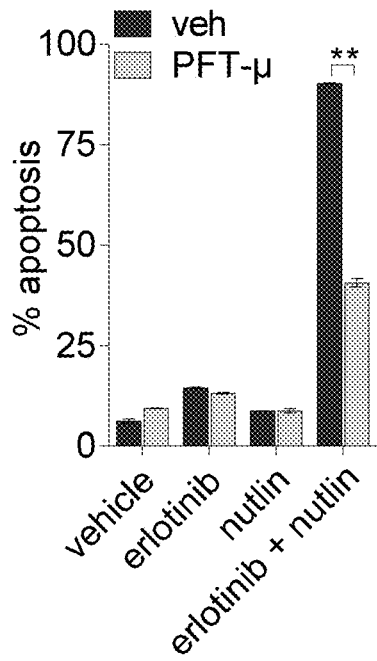
Figure 34F:
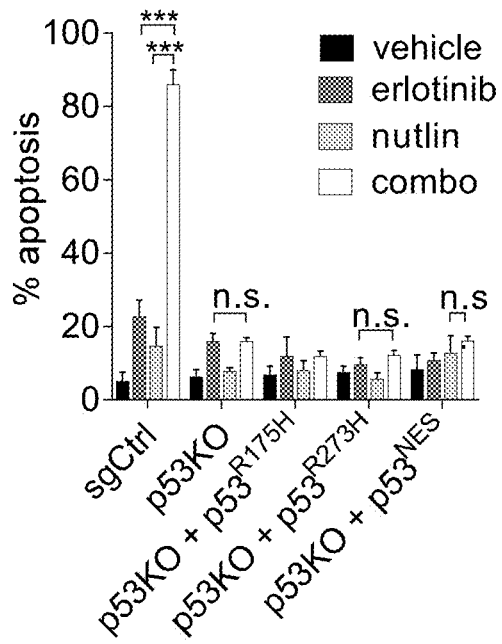
Figure 34G:
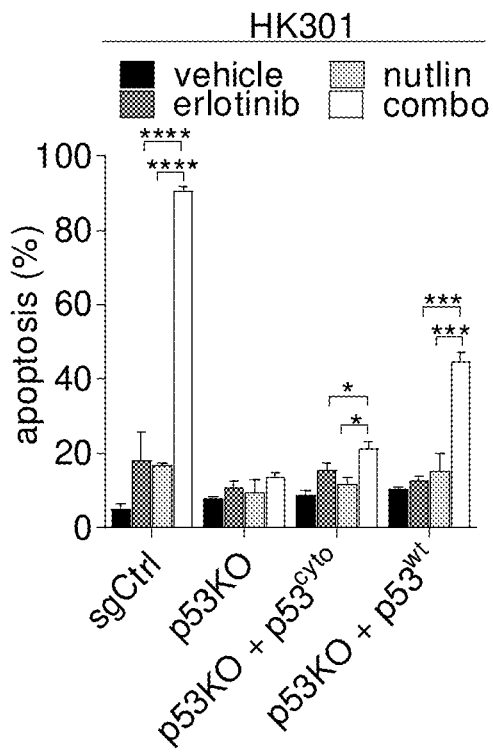
Figure 34H:
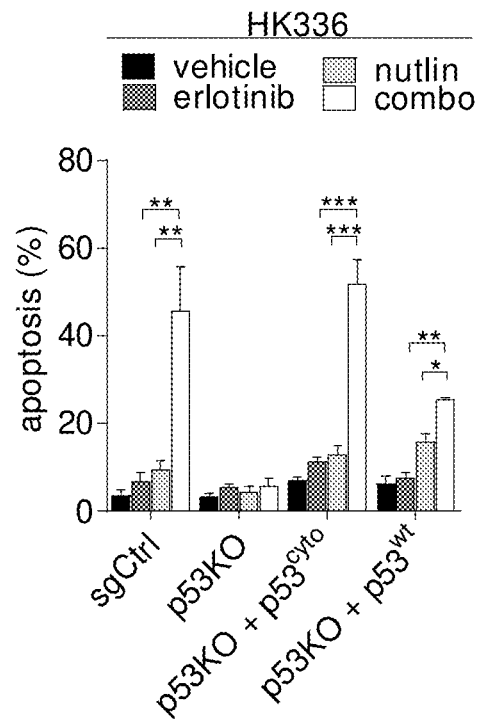

The role of p53 in eliciting cell death to combined erlotinib and nutlin was then investigated. As expected, CRISPR/CAS-9 targeting of p53 in two EGFRi metabolic responders (HK301 and HK336) completely mitigated sensitivity to the drug combination (FIG. 24F). Likewise, ectopic expression of Bcl-xL markedly suppressed cell death with combined treatment, consistent with a critical function for Bcl-xL in antagonizing p53-mediated apoptosis (FIG. 34D). Moreover, similar to the results with Bcl-xL inhibition (e.g., WEHI-539), the addition of nutlin liberated p53 from Bcl-xL under erlotinib treatment (FIG. 24G). These data are in agreement with prior observations that p53 stabilization can stimulate cytoplasmic p53-mediated apoptosis. In support of the suggestion that cytoplasmic p53 activity is required for EGFRi and nutlin induced apoptosis in metabolic responders, blocking cytoplasmic p53 activity with PFTµ significantly reduced the synergistic effects of the combination (FIG. 34E), while, HK301 cells containing the nuclear-confined p53 mutant, p53$^{NES}$, were incapable of enhanced apoptosis with erlotinib and nutlin (FIG. 34F). Finally, the cancer "hotspot" mutants, R175H and R273H, which have both transactivation and cytoplasmic deficiencies, were completely insensitive to the drug combination (FIG. 34F).

While cytoplasmic p53 is desired to promote cell death with the drug combination, we observed in some instances that both the transcription-dependent and independent functions of p53 are needed for optimal execution of synergistic apoptosis with nutlin (FIG. 34F). These results are consistent with reports that the transcription-independent functions of p53 can alone execute intrinsic apoptosis, whereas, in other contexts, may require its transcription-dependent functions to stimulate cytoplasmic p53 mediated cell kill. Collectively, the results described herein show that combined targeting of EGFR-driven glucose metabolism and p53 can induce marked synergistic cell death in primary GBM; which is dependent on the cytoplasmic functions of p53.

Example 11

Modulation of Glucose Metabolism Primes EGFRi Non-Responders for p53-Mediated Cell Death The aforementioned data led the inventors to propose a model where EGFRi-mediated attenuation of glucose metabolism primes the apoptotic machinery, resulting in synergy with pro-apoptotic stimuli such as p53 activation. The synergy lies between induction of cellular stress by EGFR inhibitors, reduction of glucose uptake and the priming of the cell for apoptosis and the stabilization of p53 by antagonists of BCL-2. EGFR inhibition can rapidly attenuate glycolysis in cellular stress. This creates a tumor-specific vulnerability in which intrinsic apoptosis can be significantly enhanced by: 1) activation of p53 (such as, for example, through nutlin, analogues or others described herein) and 2) inhibition of BCL-2 (by any of several agents as described herein such as for example, ABT-263 (Navitoclax).

Figure 35A:
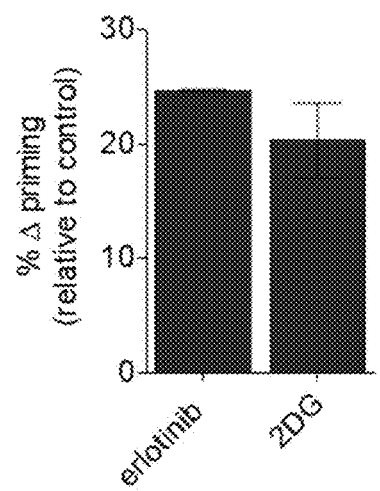
FIGS. 35A-35F depict the inhibition of glucose metabolism in metabolic responders and non-responders promotes intrinsic apoptosis.
Figure 35B:
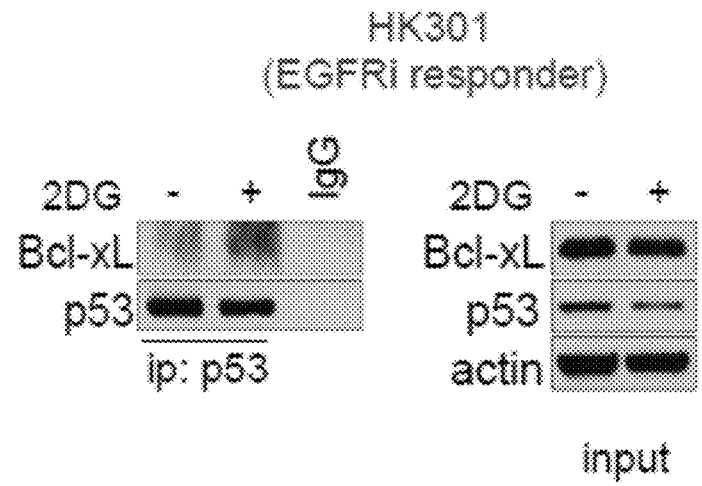
Figure 35C:
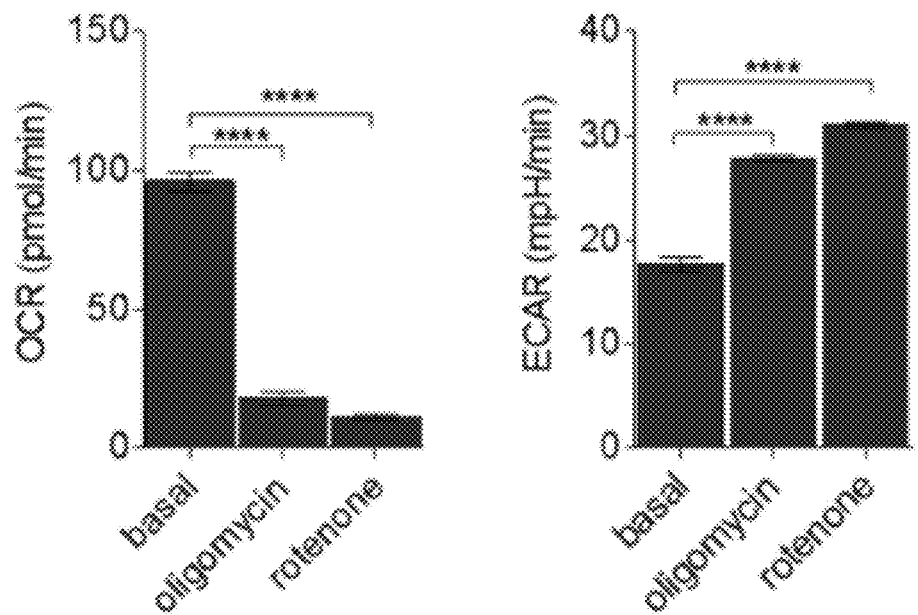
Figure 35D:
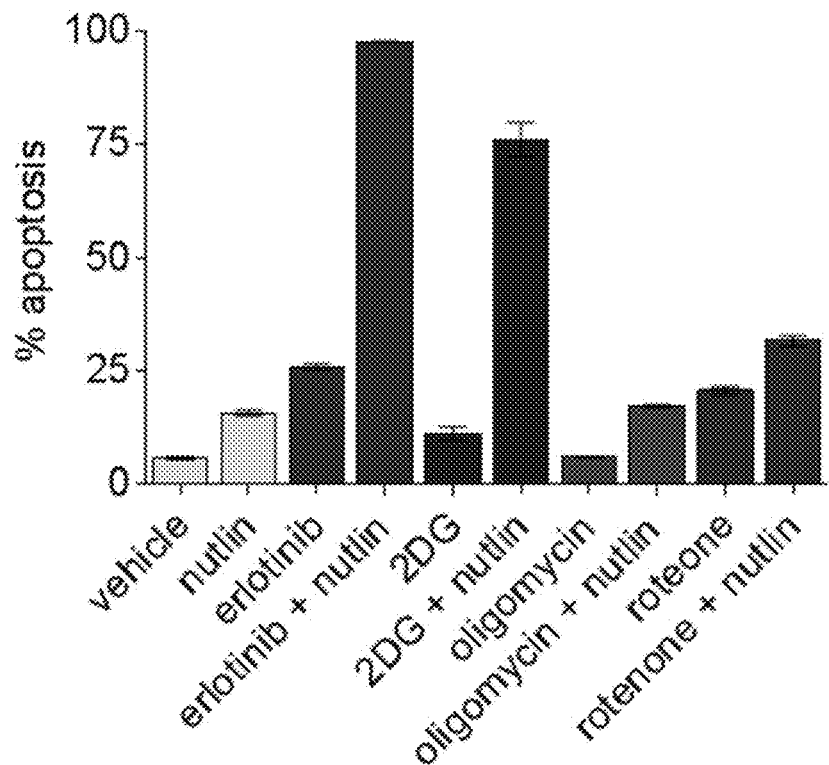
Figure 40:
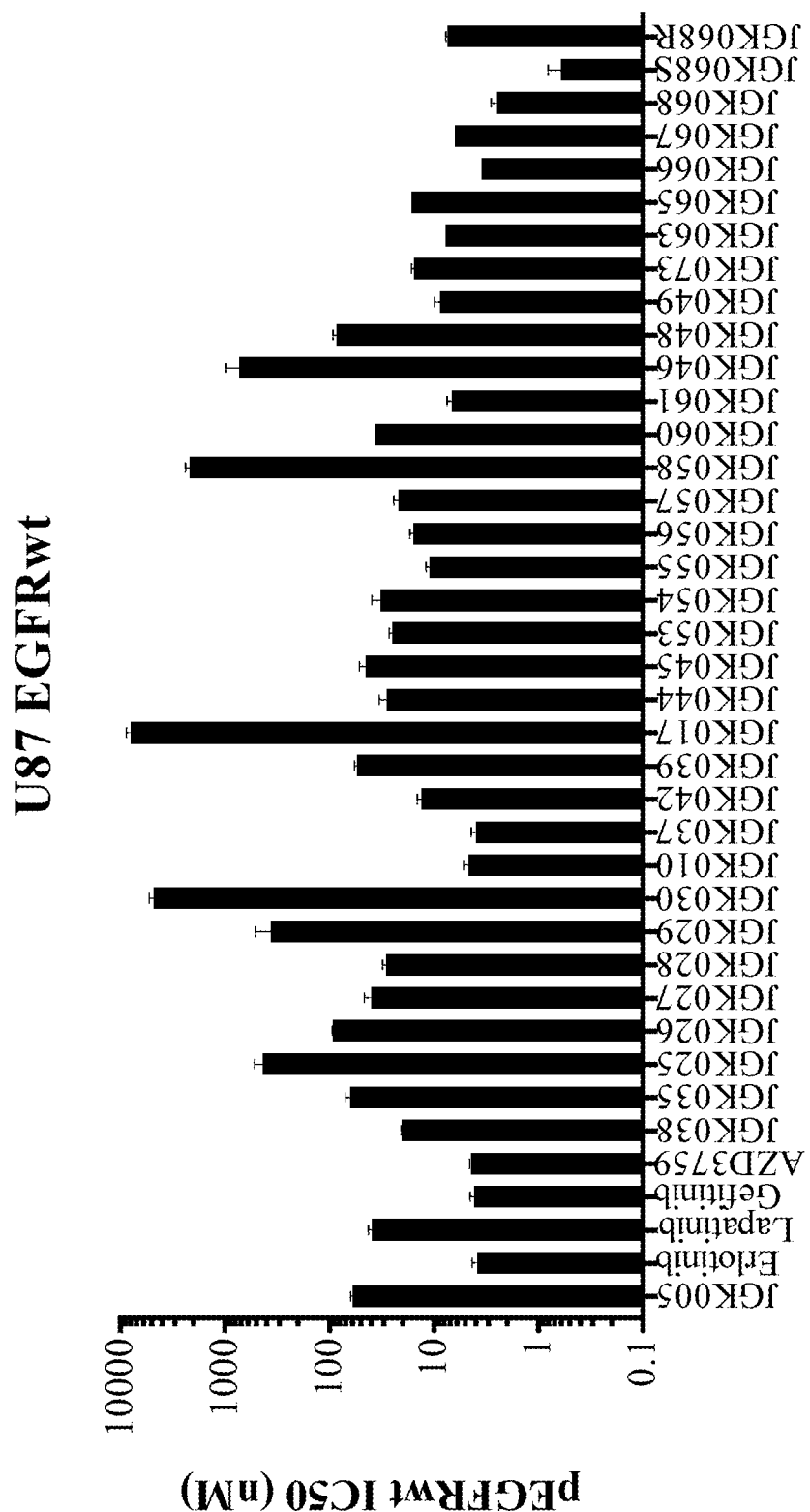
FIG. 40 depicts the activities of erlotinib, lapatinib, gefitinib, and exemplary compounds of the disclosure against U87 EGFRwt.

A logical prediction of this model is that direct inhibition of glucose metabolism should phenocopy the effects of EGFRi. Consistent with this, addition of the glucose metabolic inhibitor 2-deoxyglucose (2DG) stimulated apoptotic priming, binding of p53 to Bcl-xL, and synergy with nutlin in HK301 cells (an EGFRi metabolic responder) (FIGS. 40A, 40B, and 40D). Interestingly, inhibition of oxidative phosphorylation with oligomycin (complex V/ATP synthase) or rotenone (complex I) did not synergize with nutlin treatment in HK301 gliomaspheres (FIGS. 35C and 35D). Thus, reduced glucose metabolic flux alone, but not oxidative metabolism, appears to be sufficient for synergistic sensitivity to p53 activation.

Figure 25A:
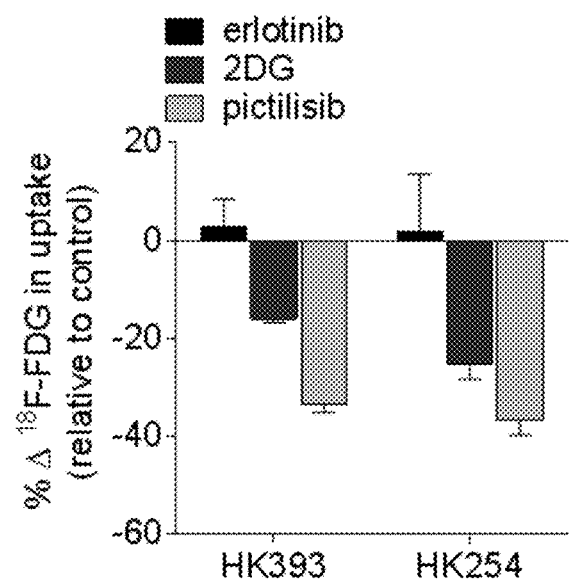
FIGS. 25A-25F depict the modulation of glucose metabolism primes EGFRi non-responders for p53-mediated cell death.
Figure 25B:
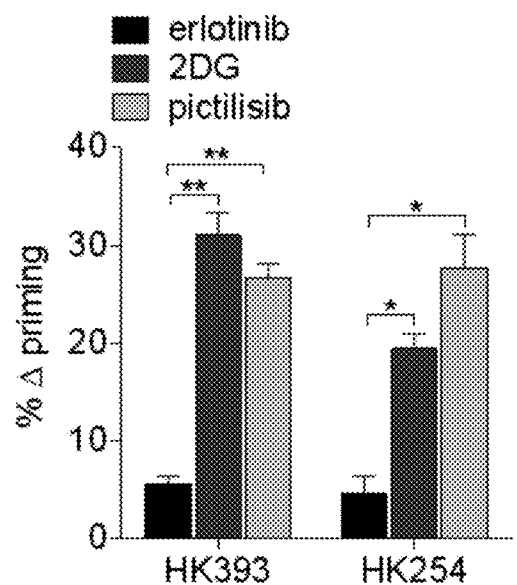
Figure 25C:
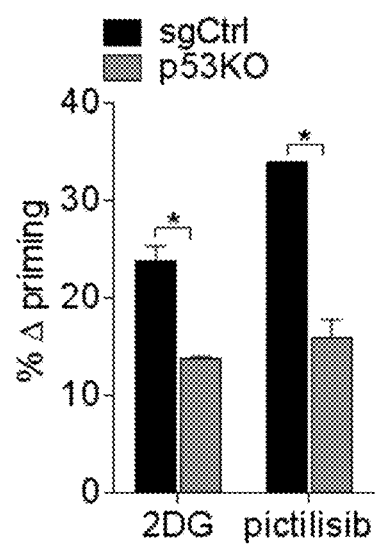
Figure 25D:
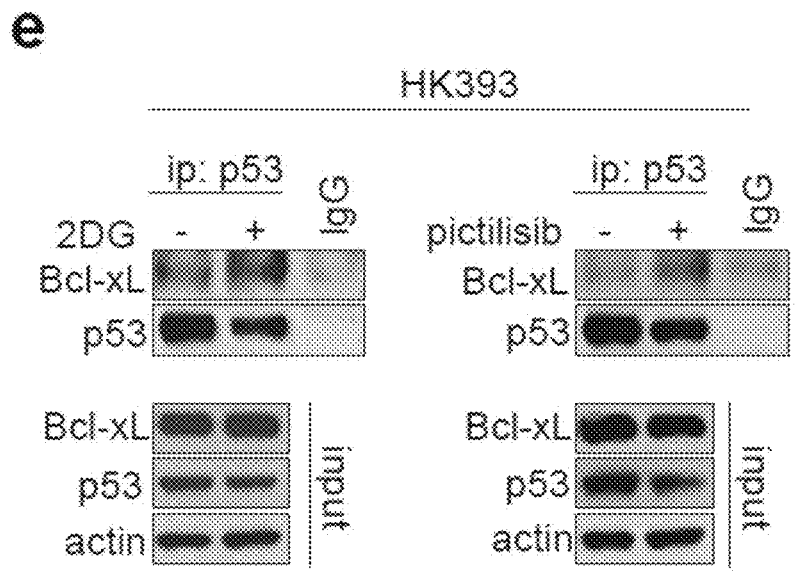
Figure 25E:
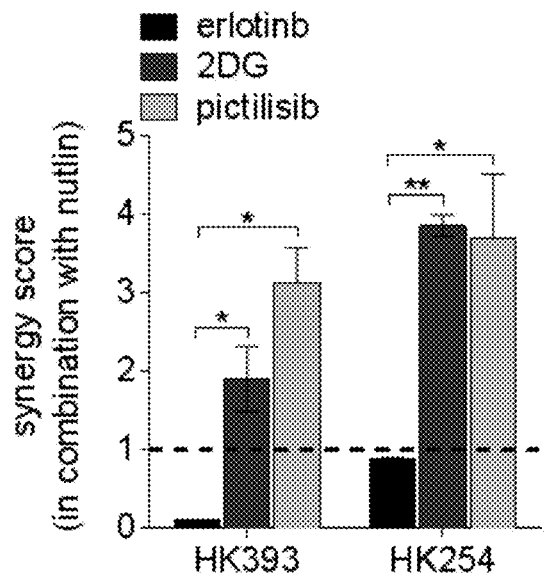
Figure 25F:
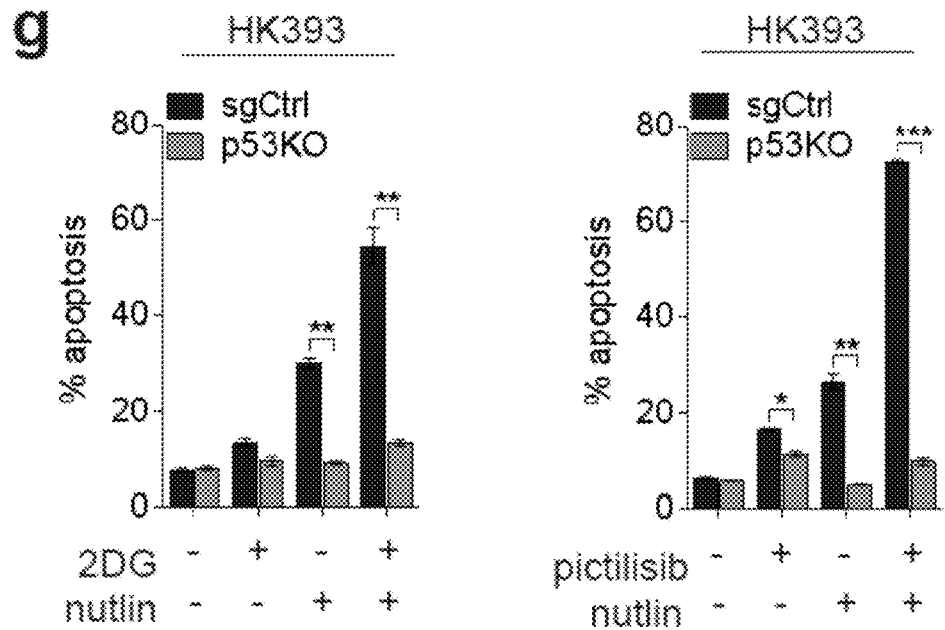
Figure 35E:
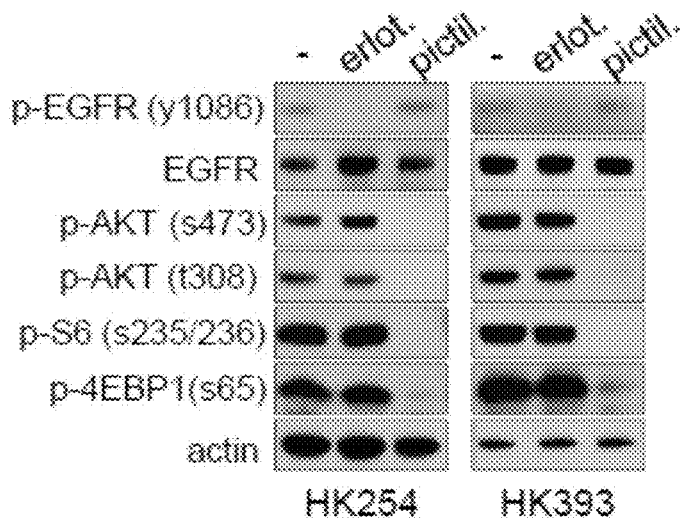
Figure 35F:
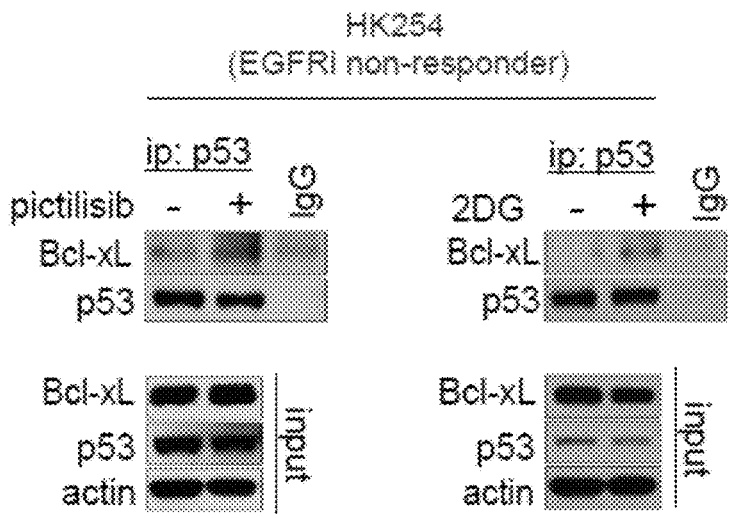

This prompted the inventors to consider whether modulating glucose consumption in EGFRi non-responders results in a similar p53-dependent vulnerability. To investigate this, they tested whether direct inhibition of glucose uptake, with 2DG, or through targeting PI3K—a well characterized driver of glucose metabolism—elicits apoptotic priming in two EGFRi metabolic non-responders (FIG. 25A). In contrast to erlotinib treatment, acute inhibition of PI3K with pictilisib abrogated PI3K-AKT-mTOR signaling (FIG. 35E), and significantly reduced $^{18}$F-FDG uptake in HK393 and HK254 cells (FIG. 25B). The decrease in glucose consumption with pictilisib was associated with significantly higher apoptotic priming and, as anticipated, 2DG completely mirrored these effects (FIGS. 25B and C). Therefore, EGFRi metabolic non-responders can be primed for apoptosis following inhibition of glucose uptake. Importantly, CRISPR/CAS-9 targeting of p53 in HK393 significantly suppressed priming mediated by 2DG or pictilisib. (FIG. 25D). Moreover, p53-dependent priming was associated with heightened Bcl-xL and p53 binding, indicative of sequestration of p53 by Bcl-xL to block apoptosis (FIG. 25E and FIG. 35F). Consistent with this interpretation, combining 2DG or pictilisib with nutlin caused significant, p53-dependent synergistic lethality in EGFRi non-responder cells (FIGS. 25F & 25G). Taken together, these data demonstrate that acute inhibition of glucose metabolism, either directly or with targeted therapy, promotes p53-dependent apoptotic priming in GBM; which, creates a targetable vulnerability for enhanced cell kill.

Example 12

Figure 41:
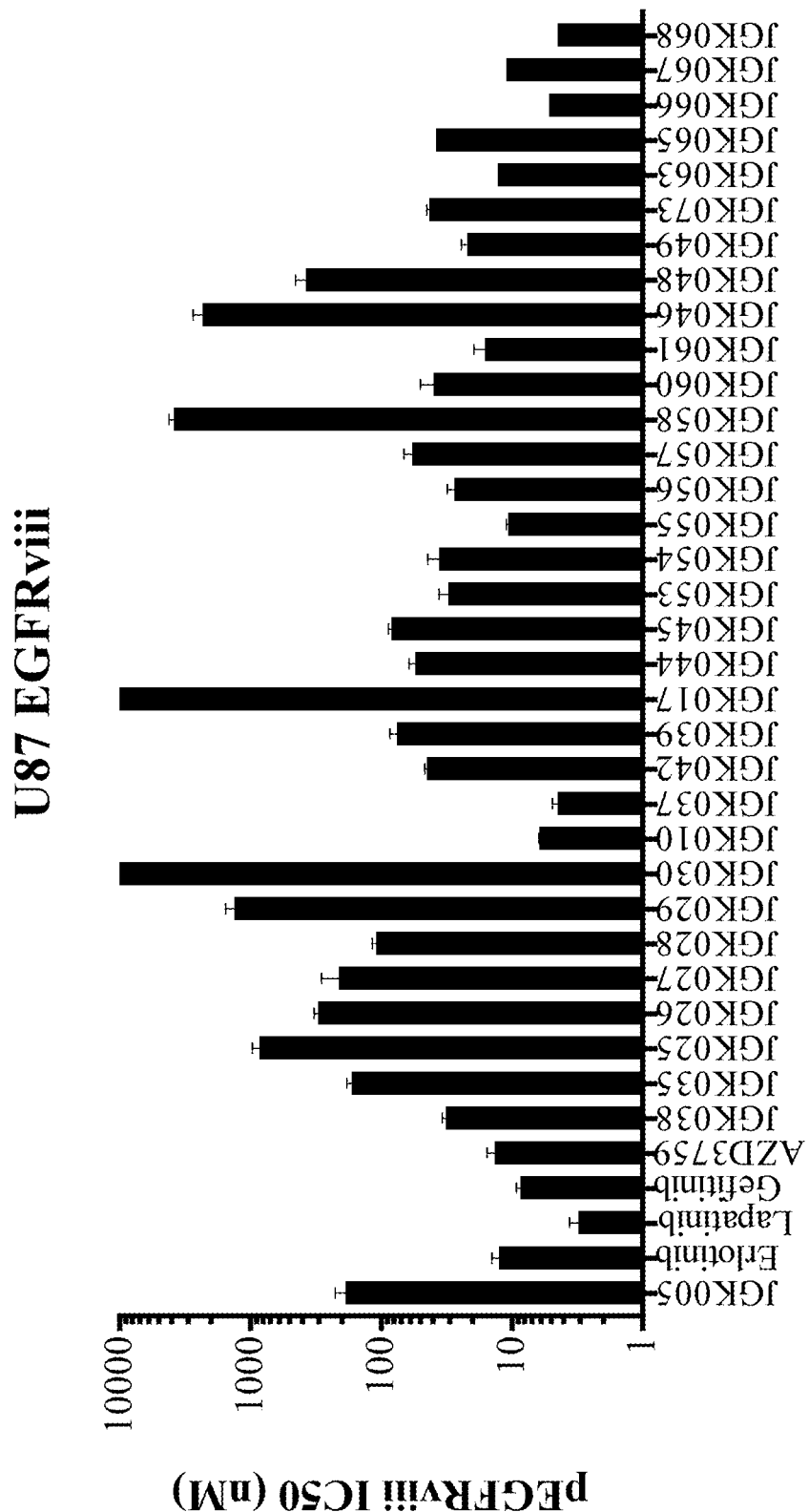
FIG. 41 depicts the activities of erlotinib, lapatinib, gefitinib, and exemplary compounds of the disclosure against U87 EGFRviii.
Figure 42:
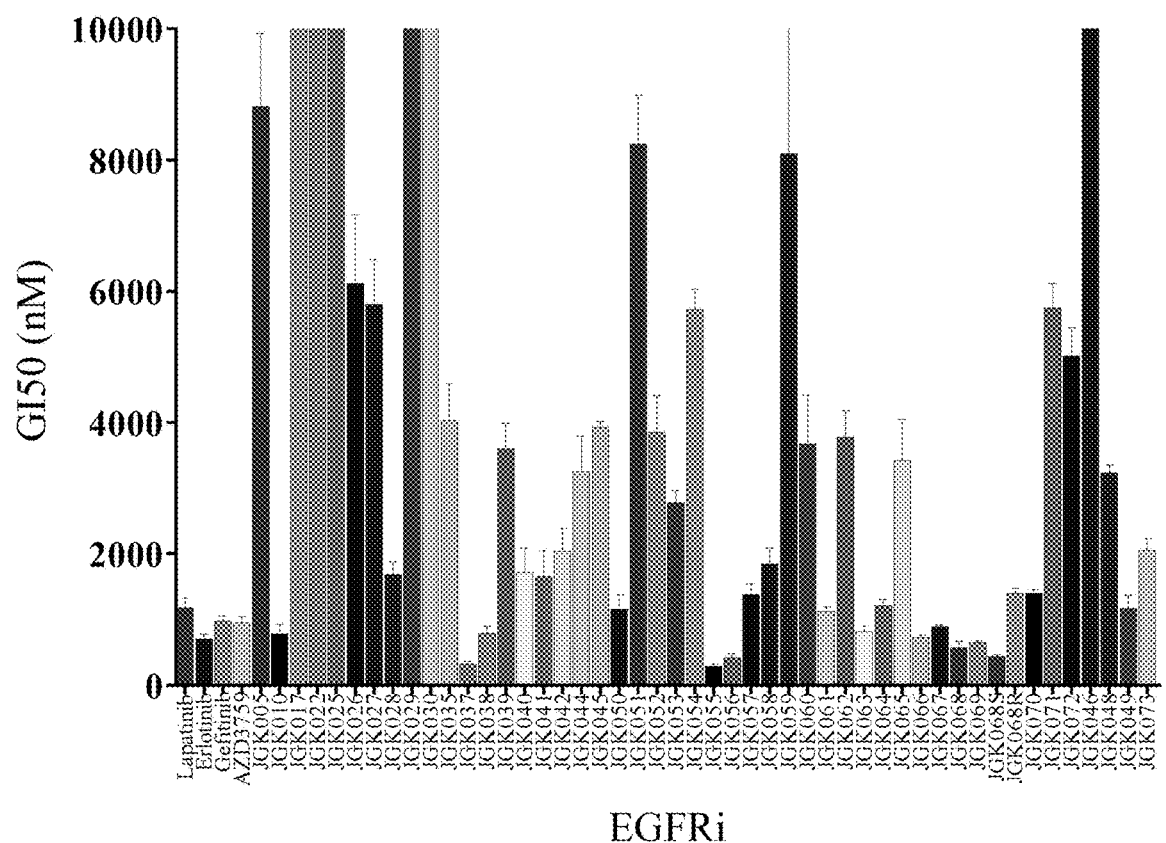
FIG. 42 depicts the activities of erlotinib, lapatinib, gefitinib, and exemplary compounds of the disclosure against HK301, a patient derived, EGFRvIII mutant GBM gliomasphere.
Figure 43:
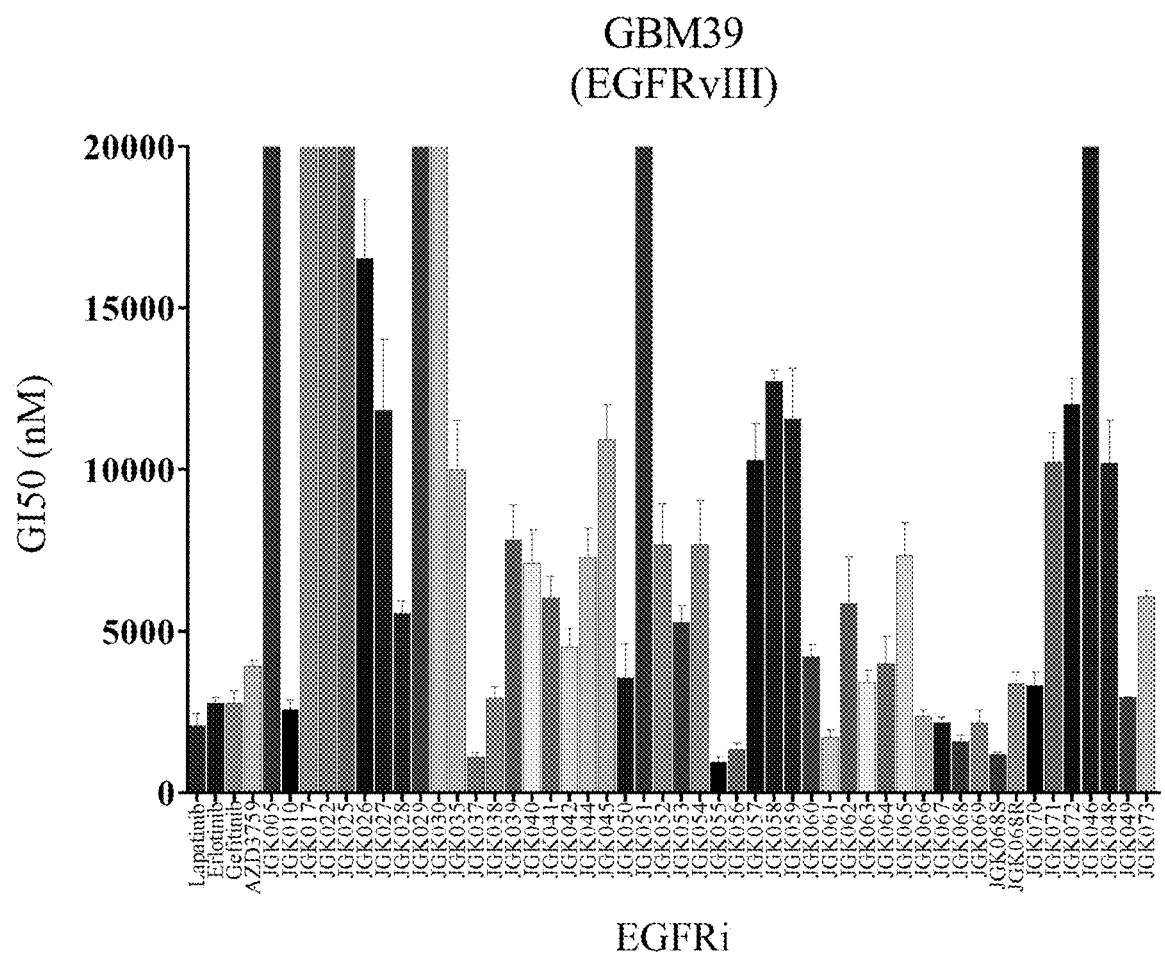
FIG. 43 depicts the activities of erlotinib, lapatinib, gefitinib, and exemplary compounds of the disclosure against GBM39, a patient derived, EGFRvIII mutant GBM gliomasphere.
Figure 44:
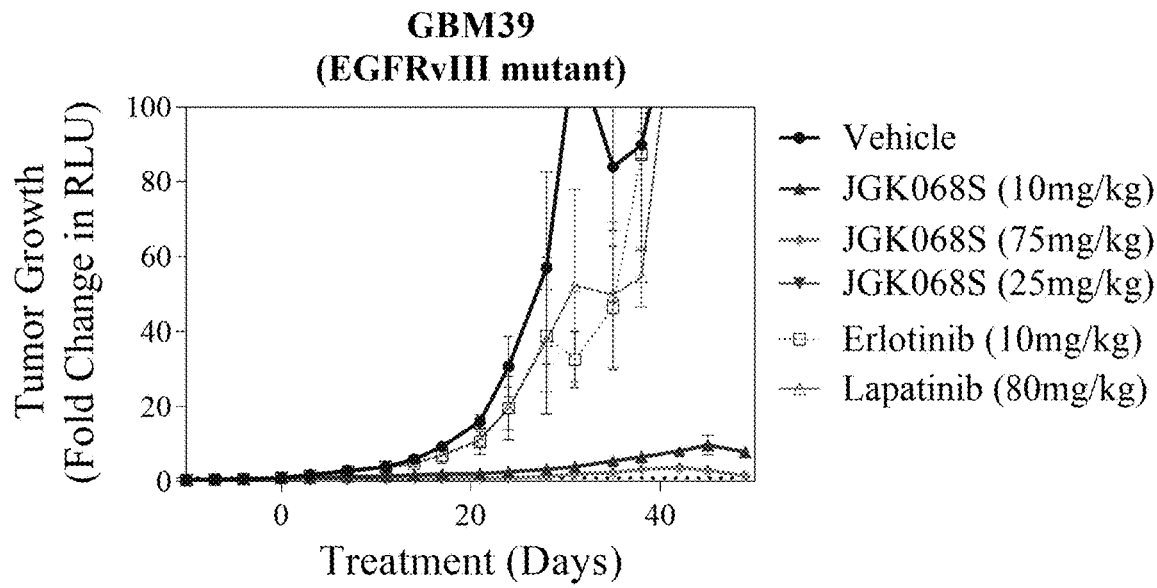
FIG. 44 depicts the activities of erlotinib, lapatinib, and exemplary compounds of the disclosure in a GBM39 EGFRvIII mutant mouse model.
Figure 45A:
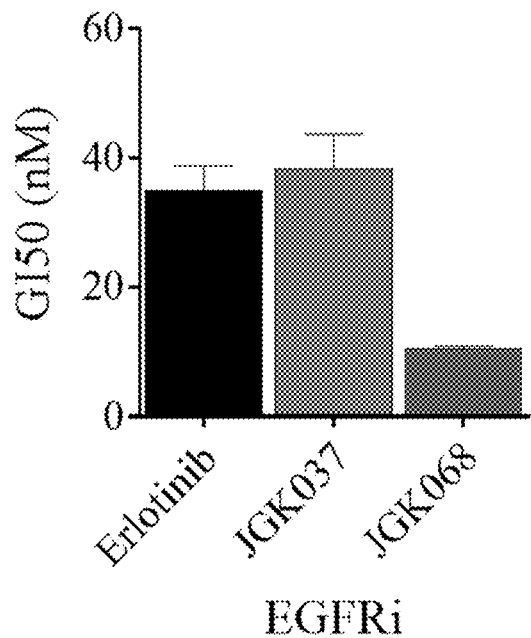
FIG. 45A depicts the activities of erlotinib and exemplary compounds of the disclosure in a HCC827 lung cancer EGFR mutant cell line.
Figure 45B:
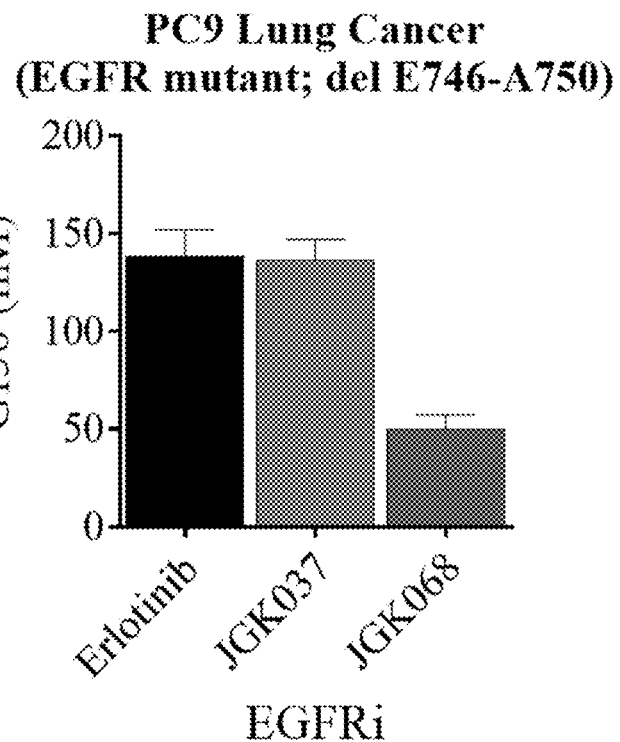
FIG. 45B depicts the activities of erlotinib and exemplary compounds of the disclosure in a PC9 lung cancer EGFR mutant cell line.
Figure 45C:
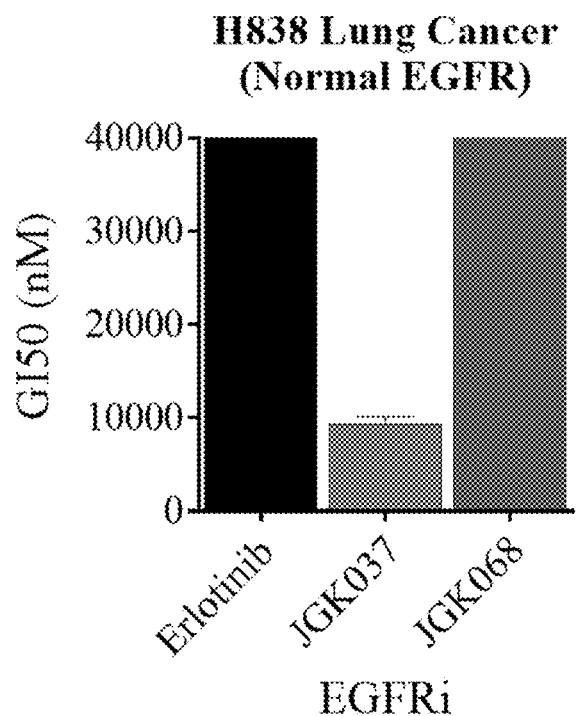
FIG. 45C depicts the activities of erlotinib and exemplary compounds of the disclosure in a H838 lung cancer mutant cell line.
Figure 46:
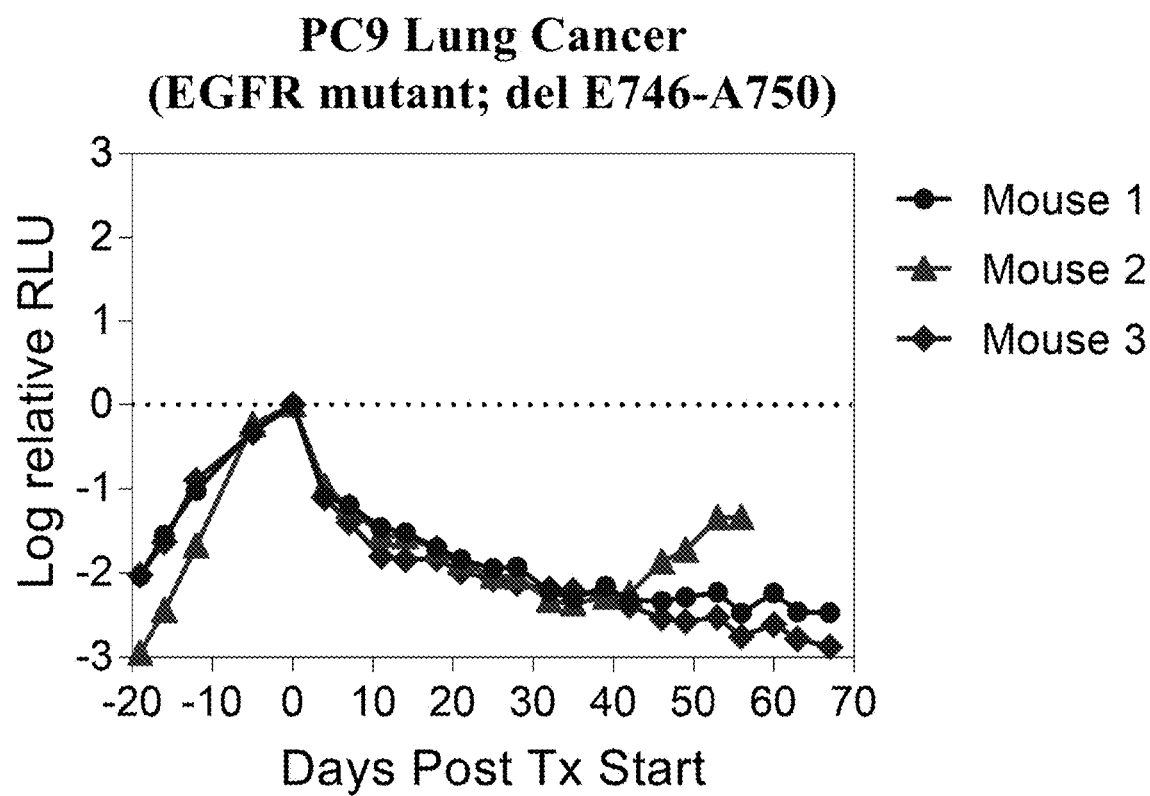
FIG. 46 depicts the activities of erlotinib and exemplary compounds of the disclosure in a PC9 lung cancer EGFR mutant mouse model.

Combinatorial Therapeutic Strategy and Non-Invasive Biomarker for Targeting GBM In Vivo The results obtained in cell culture show that combined targeting of oncogene-driven glucose metabolism and p53 has synergistic activity in primary GBM. This led the us to investigate whether this approach could be effective in orthotopic GBM xenograft models. For these studies, we employed a potent, MDM2 inhibitor, Idasanutlin, which is currently in clinical trials for many malignancies. Given the uncertainty of CNS penetration for Idasanutlin, we first demonstrated that Idasanutlin can accumulate in the brain of mice with an intact blood-brain-barrier (brain:plasma, 0.35) and stabilizes p53 in orthotopic tumor-bearing mice (FIGS. 41A & 41B).

Figure 26A:
FIGS. 26A-26H depict the combined targeting of EGFR-driven glucose uptake and p53 suppresses tumor growth in vivo.
Figure 26B:
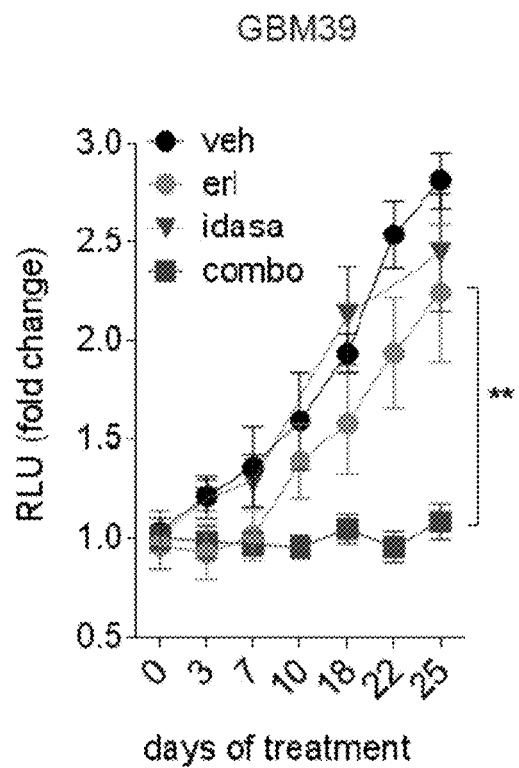
Figure 26C:
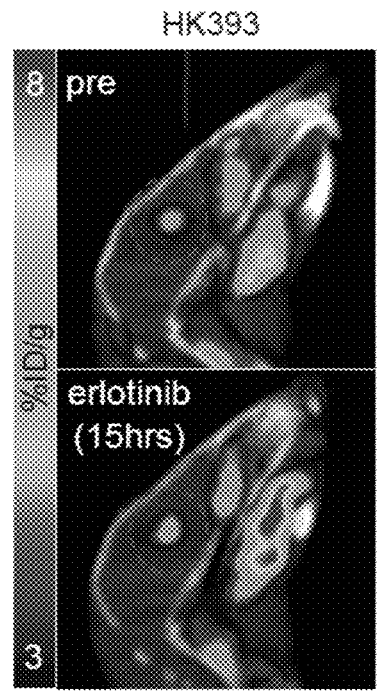
Figure 26D:
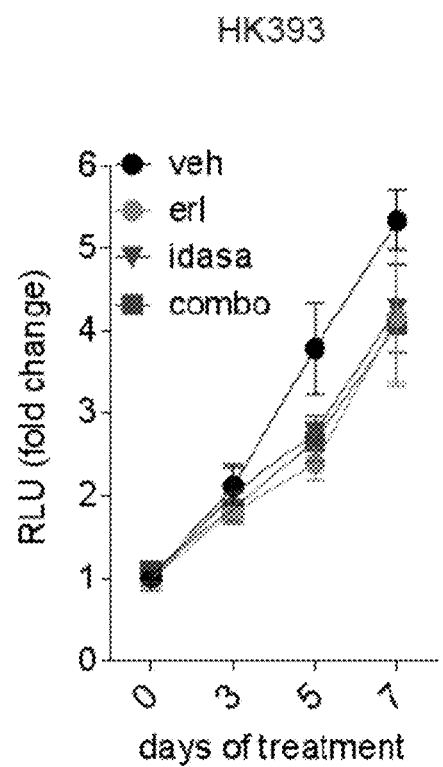
Figure 26E:
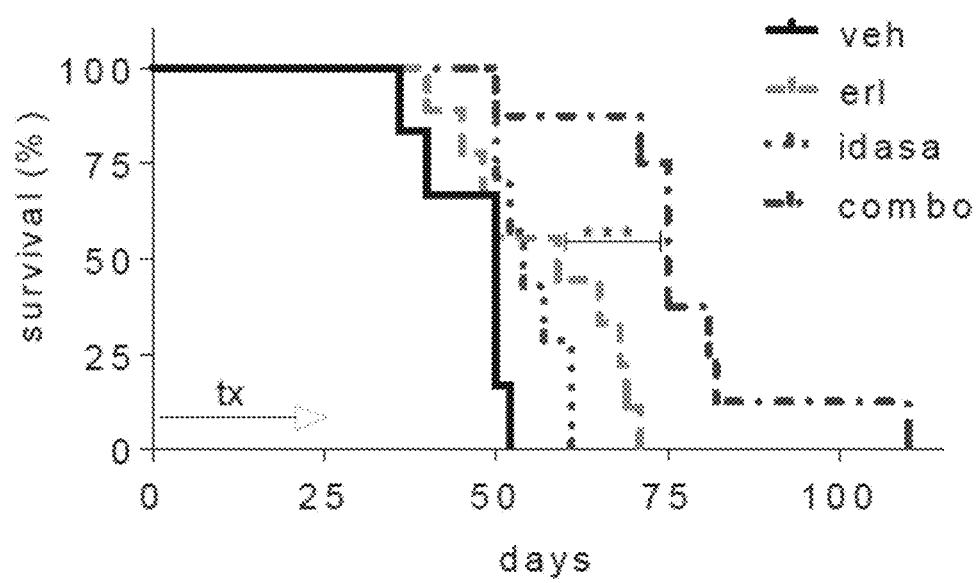
Figure 26F:
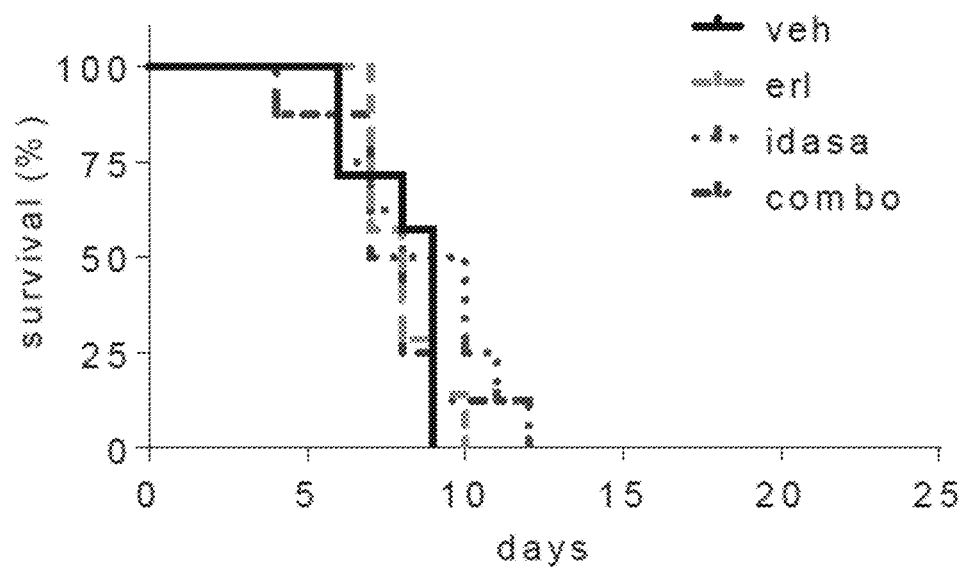
Figure 26G:
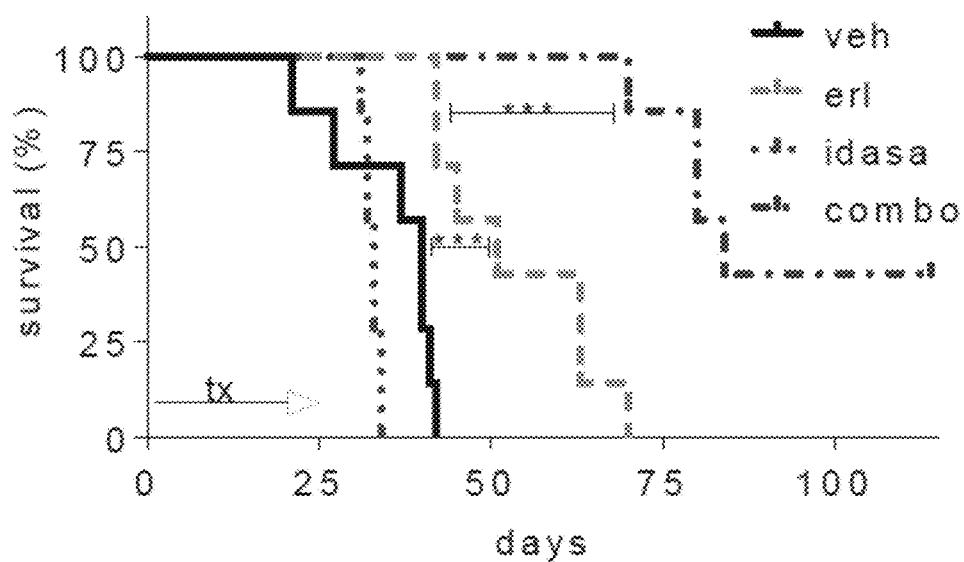
Figure 26H:
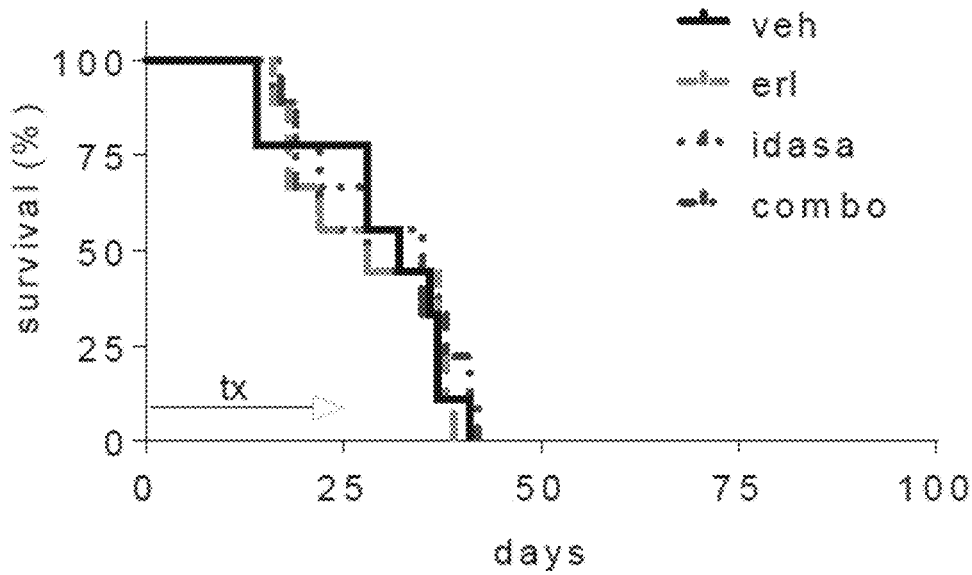
Figure 36A:
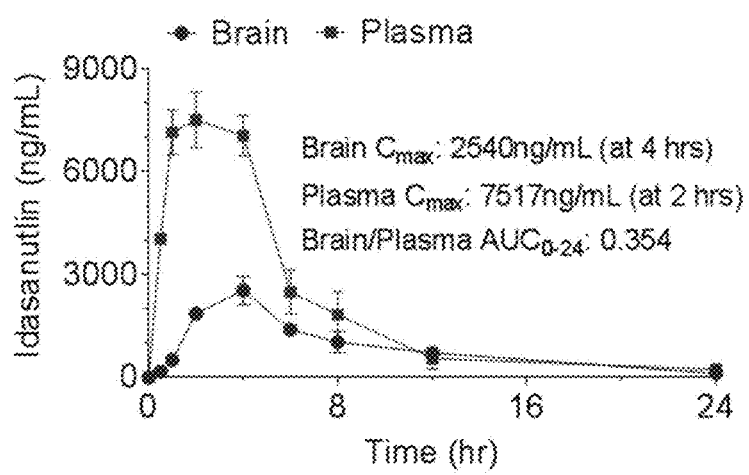
FIGS. 36A-36D depict the In vivo efficacy of EGFR inhibition and p53 activation.
Figure 36B:
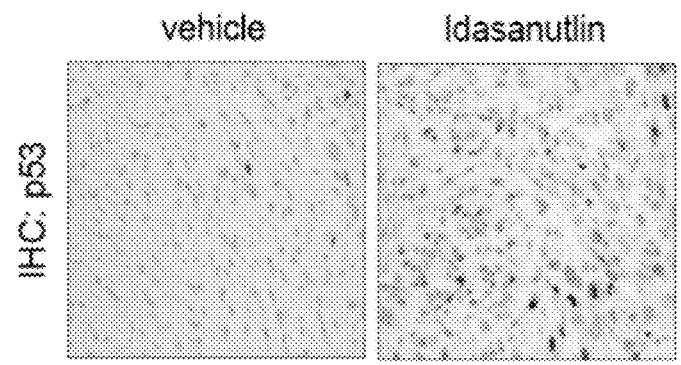
Figure 36C:
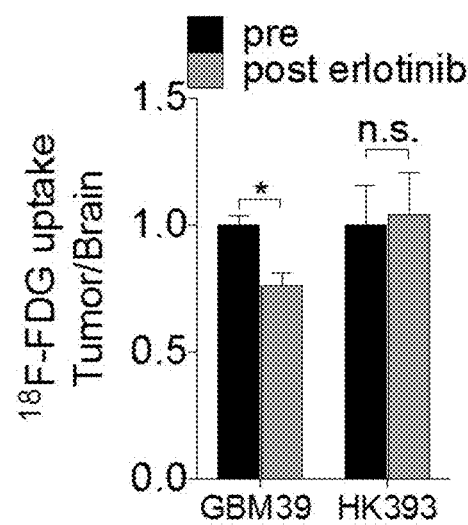
Figure 36D:
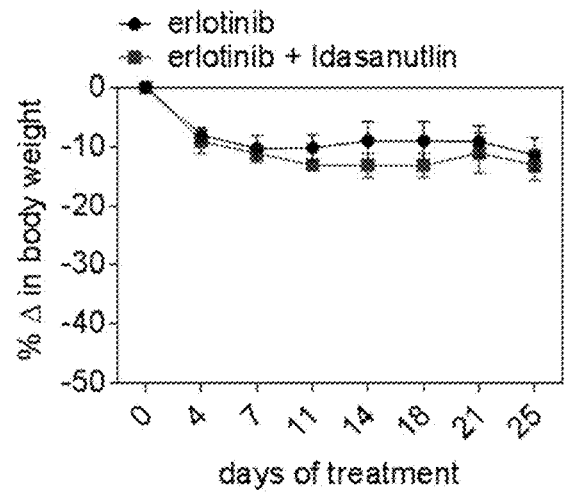

Next, as perturbations in glucose metabolism with oncogene inhibition are required for synergistic sensitivity to p53 activation, we reasoned that rapid attenuation in glucose uptake in vivo following EGFRi administration—as measured by $^{18}$F-FDG PET—could serve as a non-invasive predictive biomarker for therapeutic efficacy of combined erlotinib+Idasanutlin treatment (FIG. 26A). We observed, in orthotopic xenografts of an EGFR-metabolic responder gliomasphere (GBM39), that acute erlotinib treatment (75 mg/kg) rapidly reduced $^{18}$F-FDG uptake (15 hours post erlotinib administration) (FIG. 26B and FIG. 36C). In separate groups of mice, they tested the individual drugs and the combination of daily erlotinib (75 mg/kg) treatment and Idasanutlin (50 mg/kg). Relative to single agent controls, we observed synergistic growth inhibition—as determined by secreted gaussia luciferase—in GBM39 intracranial tumor-bearing mice, with minimal toxicity (FIG. 26B and FIG. 36D). In contrast, orthotopic xenografts of a non-metabolic responder (HK393) showed no changes in $^{18}$F-FDG uptake with acute EGFRi (FIG. 26D and FIG. 36C), nor synergistic activity with the erlotinib and Idasanutlin combination (FIG. 26E). Thus, non-invasive $^{18}$F-FDG PET, used to measure rapid changes in glucose uptake with EGFRi, was effective in predicting subsequent synergistic sensitivity to combined erlotinib and Idasanutlin.

Finally, we evaluated the effects of the drug combination on overall survival in orthotopic xenografts of either two EGFRi metabolic responders (GBM39 and HK336) or two non-responders (HK393 and GS025). All tumors were p53 wild-type (FIG. 29A). Following evidence of tumor growth (as determined by gaussia luciferase), mice were treated with vehicle, erlotinib, Idasanutlin, or the combination for up to 25 days. The drug combination led to a pronounced increase in survival only in the EGFRi metabolic responder GBM tumors (FIGS. 30F-I). Taken together, these data show that combined targeting of EGFR and p53 synergistically inhibits growth and prolongs survival in a subset of p53 wild-type GBM orthotopic xenografts. Importantly, $^{18}$F-FDG PET was valuable as a non-invasive predictive biomarker of sensitivity to this new combination therapeutic strategy.

Example 13

Direct Inhibition of Glycolysis with 2DG or Cytocahalsin B

Figure 37A:
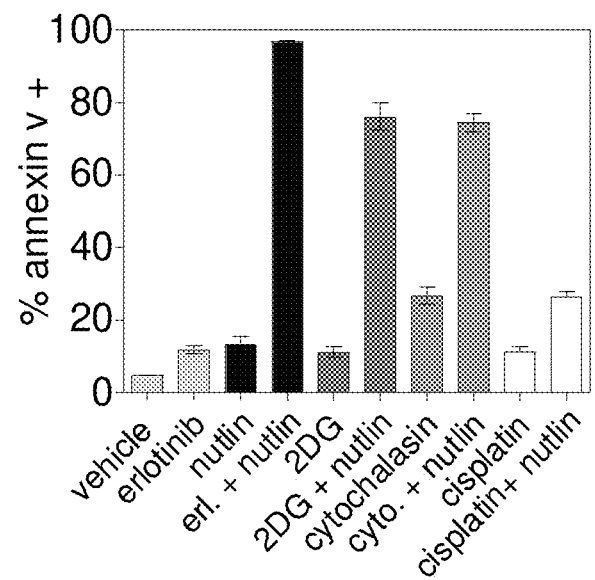
FIG. 37A depicts that direct inhibition of glycolysis with 2DG (hexokinase inhibitor) or cytochalasin B (a glucose transporter inhibitor) unexpectedly synergizes with p53 activation (with nutlin).
Figure 37B:
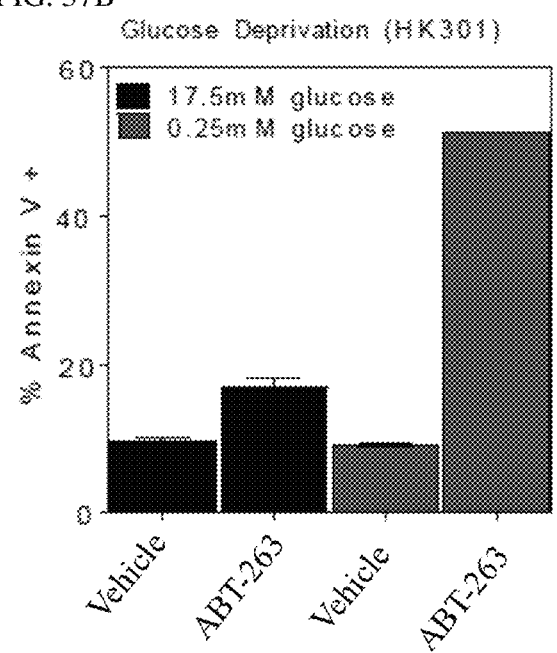
FIG. 37B depicts low glucose (0.25 mM) leads to synergistic cell kill with BCL-xL inhibition with navitoclax (ABT-263).
Figure 37C:
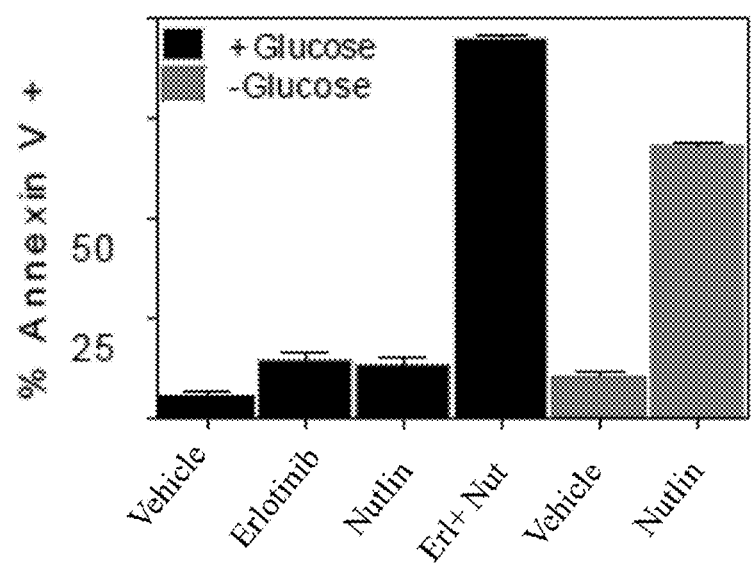
FIG. 37C depicts low glucose (0.25 mM) leads to synergistic cell kill with BCL-xL inhibition with nutlin.
Figure 38:
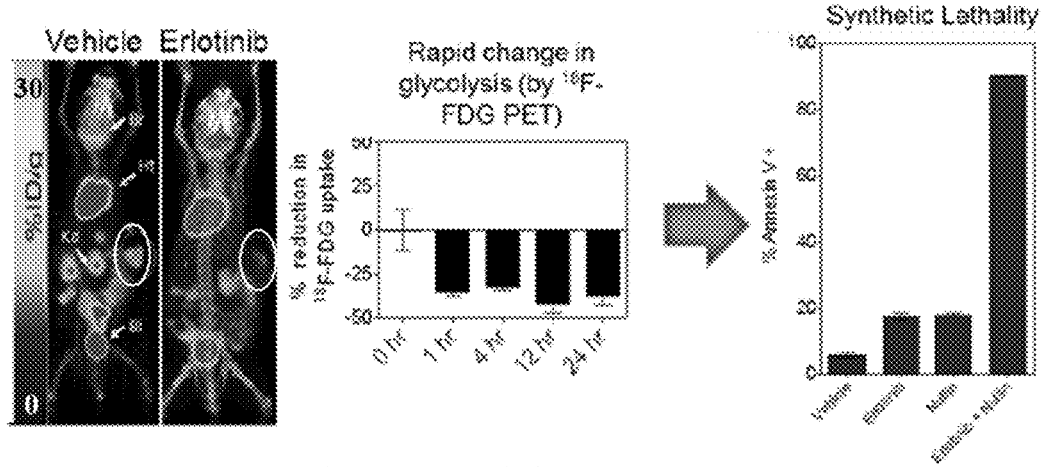
FIG. 38 depicts a comparison between metabolic responders to EGFRi inhibitor, erlotinib, and metabolic non-responders. The combination of erlotinib and nutlin leads to an unexpected synergistic synthetic lethality in metabolic responders but not in non-responders.
Figure 38:
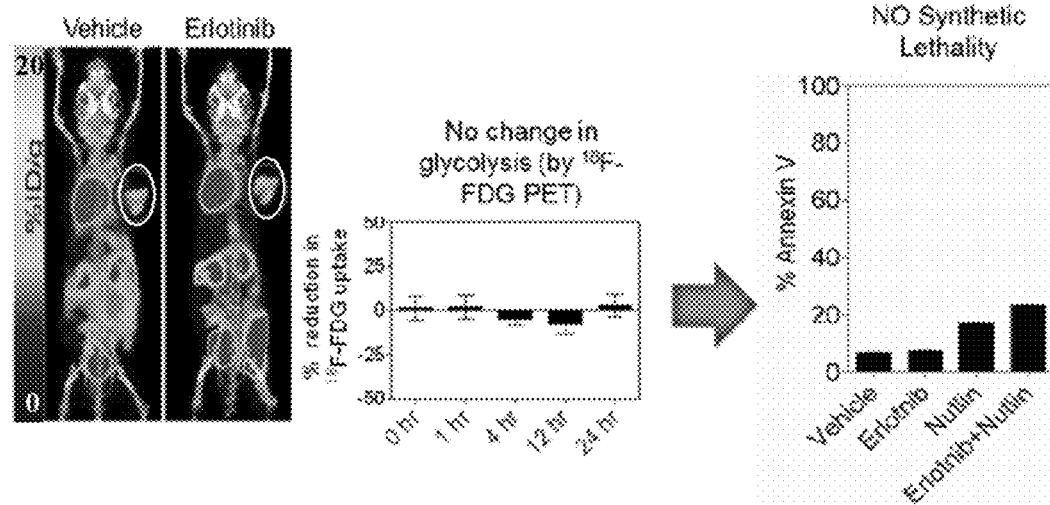
Figure 39A:
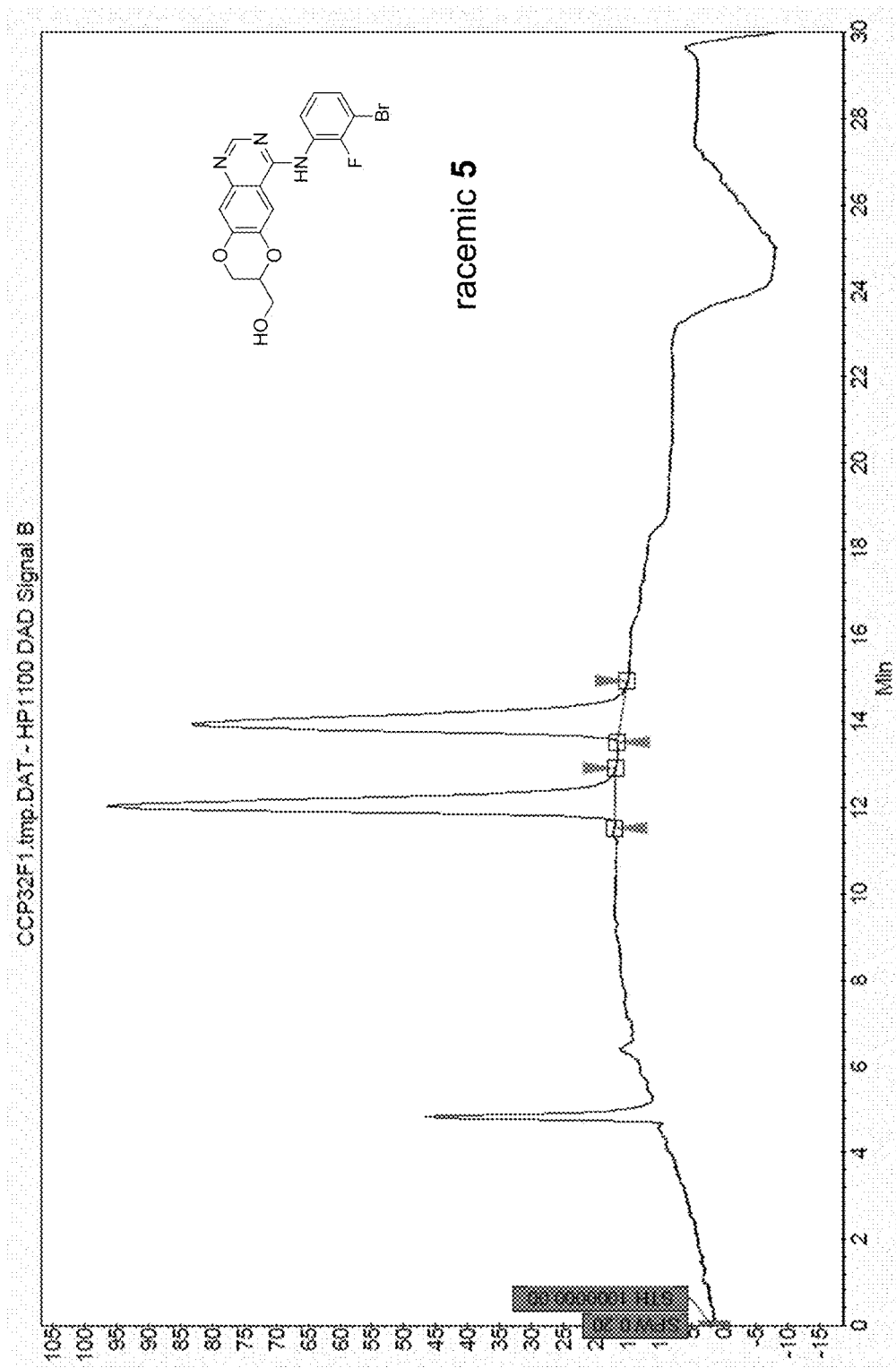
FIG. 39A shows the enantiomeric purity of synthetic intermediate 5 as determined by chiral SFC (Chiralpak AD-3 column, 40% MeOH).
Figure 39B:
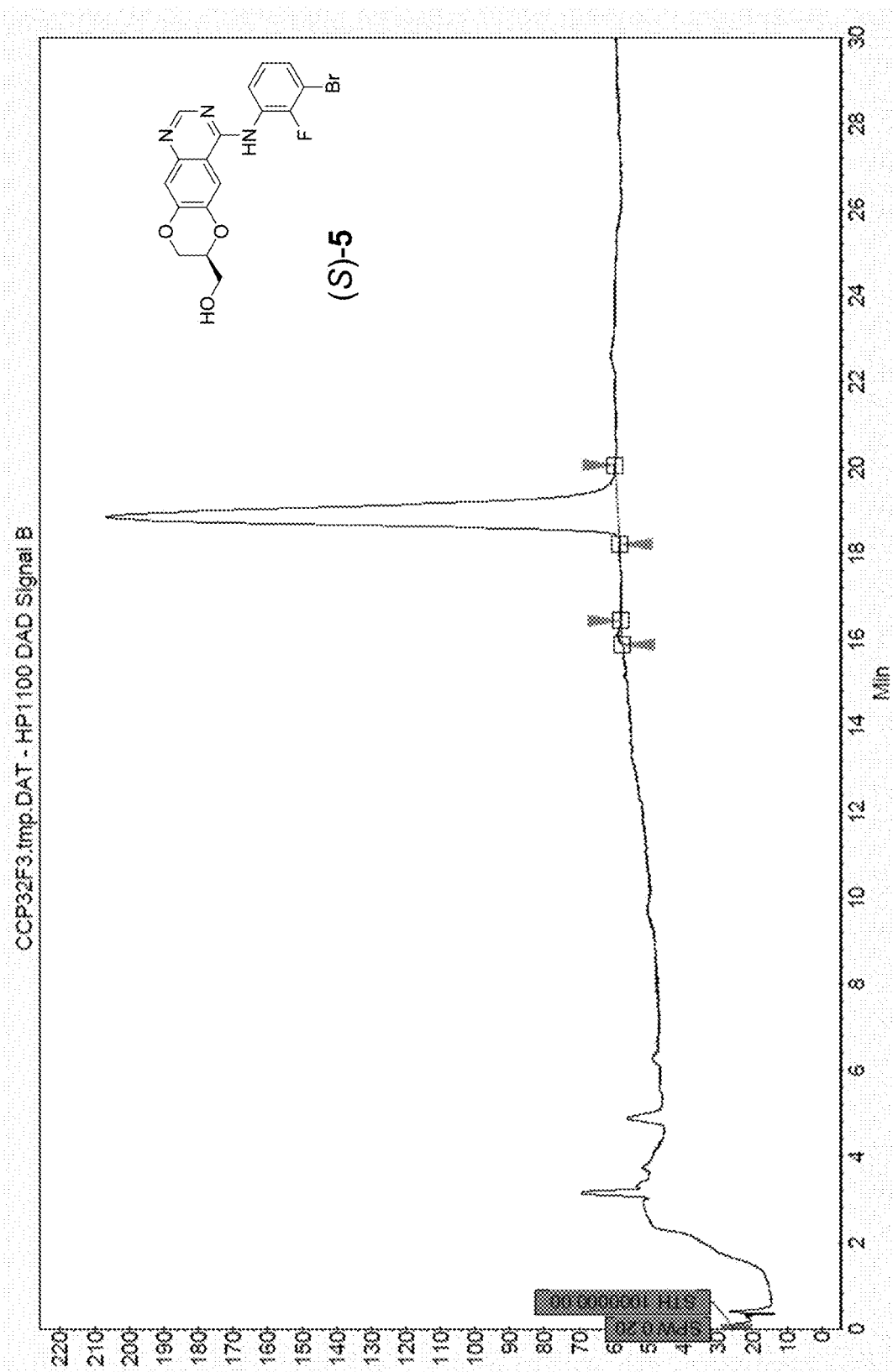
FIG. 39B shows the enantiomeric purity of synthetic intermediate (S)-5 as determined by chiral SFC (Chiralpak AD-3 column, 40% MeOH).
Figure 39C:
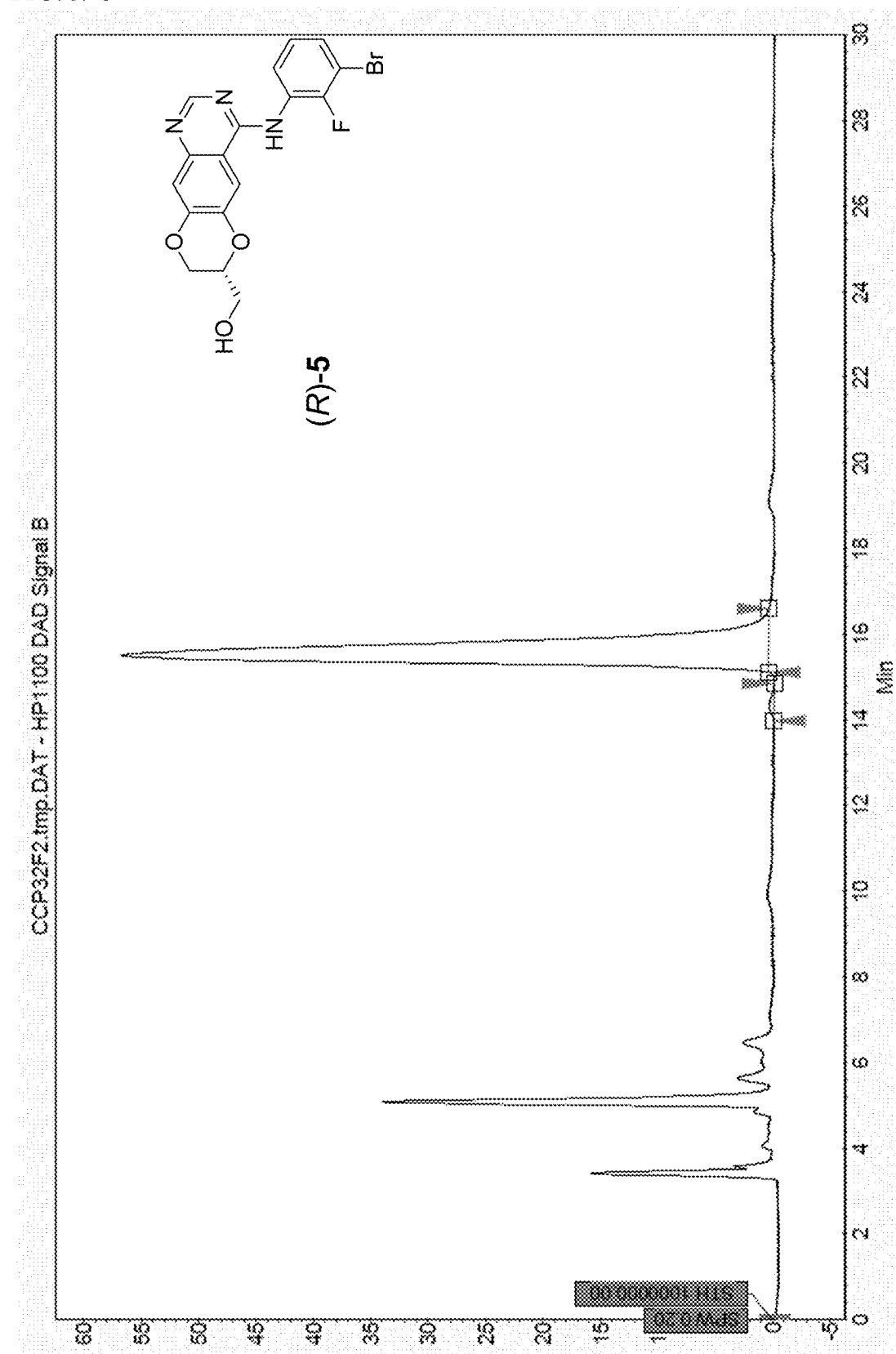
FIG. 39C show the enantiomeric purity of synthetic intermediate (R)-5 as determined by chiral SFC (Chiralpak AD-3 column, 40% MeOH).
Figure 39D:
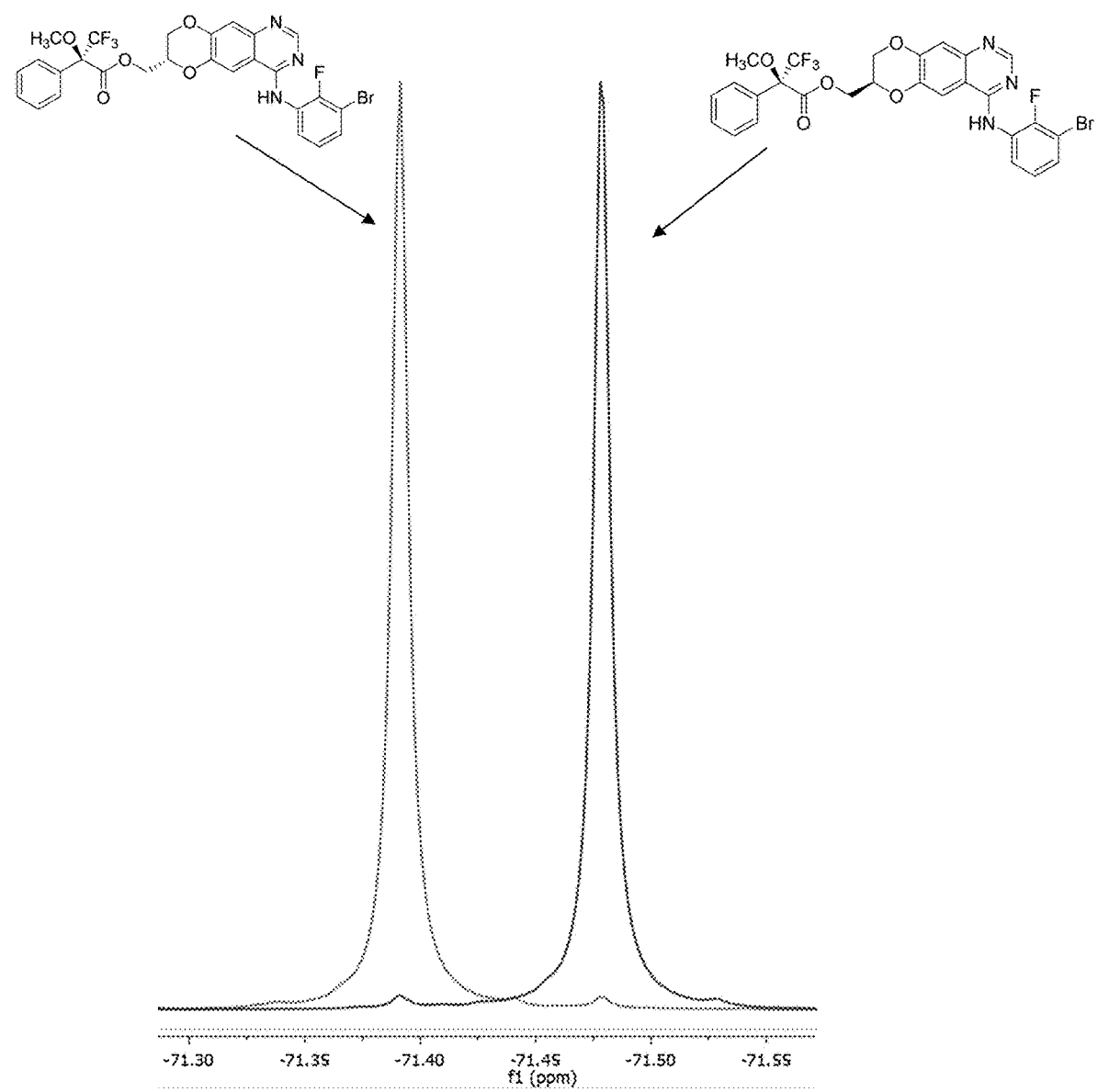
FIG. 39D show the enantiomeric purity of Mosher ester derivatives 5 as determined by chiral SFC (Chiralpak AD-3 column, 40% MeOH).

We tested how direct inhibition of glycolysis with a hexokinase inhibitor (2DG) and a glucose transporter inhibitor (cytochalasin B) affect p53 activation by nutlin. The results shown in FIG. 37 demonstrate that low glucose (0.25 mM) leads to synergistic cell kill with BCL-xL inhibition with navitoclax or nutlin. Cell death was measured using annexin V staining in gliomasphere samples treated for 72 hours with glycolytic inhibitors 2DG or cytochalasin B as single agents or in combination with p53 activator, nutlin. The same effects were recapitulated by culturing gliomaspheres in low glucose conditions (0.25 mM) and treating them with nutlin or navitoclax (ABT-263) for 72 hours.

Example 14

Experimental Procedures

Mice

Female NOD scid gamma (NSG), 6-8 weeks of age, were purchased from the University of California Los Angeles (UCLA) medical center animal breeding facility. Male CD-1 mice, 6-8 weeks of age, were purchased from Charles River. All mice were kept under defined flora pathogen-free conditions at the AAALAC-approved animal facility of the Division of Laboratory Animals (DLAM) at UCLA. All animal experiments were performed with the approval of the UCLA Office of Animal Resource Oversight (OARO).

Patient-Derived GBM Cells

All patient tissue to derive GBM cell cultures was obtained through explicit informed consent, using the UCLA Institutional Review Board (IRB) protocol: 10-00065. As previously described[12], primary GBM cells were established and maintained in gliomasphere conditions consisting of DMEM/F12 (Gibco), B27 (Invitrogen), Penicillin-Streptomycin (Invitrogen), and Glutamax (Invitrogen) supplemented with Heparin (5 µg/mL, Sigma), EGF (50 ng/mL, Sigma), and FGF (20 ng/mL, Sigma). All cells were grown at 37° C., 20% $O_2$, and 5% $CO_2$ and were routinely monitored and tested negative for the presence of mycoplasma using a commercially available kit (MycoAlert, Lonza). At the time of experiments, most HK lines used were between 20-30 passages (exceptions HK385 p8, HK336 p15), while GS and GBM39 lines were less than 10 passages. All cells were authenticated by short-tandem repeat (STR) analysis Reagents and Antibodies Chemical inhibitors from the following sources were dissolved in DMSO for in vitro studies: Erlotinib (Chemietek), Nutlin-3A (Selleck Chemicals), WEHI-539 (APExBIO), Pictilisib (Selleck Chemicals), Oligomycin (Sigma), Rotenone (Sigma). 2DG (Sigma) was dissolved freshly in media prior to usage. Antibodies used for immunoblotting were obtained from the listed sources: β-actin (Cell signaling, 3700), tubulin (Cell signaling, 3873), p-EGFR Y1086 (Thermo Fischer Scientific, 36-9700), t-EGFR (Millipore, 06-847), t-AKT (Cell Signaling, 4685), p-AKT T308 (Cell Signaling, 13038), p-AKT 5473 (Cell Signaling, 4060), t-ERK (Cell Signaling, 4695), p-ERK T202/Y204 (Cell Signaling, 4370), t-S6 (Cell Signaling, 2217), p-S6 S235/236 (Cell Signaling, 4858), t-4EBP1 (Cell Signaling, 9644), p-4EBP1 S65 (Cell Signaling 9451), Glut3 (Abcam, ab15311), Glut1 (Millipore, 07-1401), p53 (Santa Cruz Biotechnology, SC-126), BAX (Cell Signaling, 5023), BIM (Cell Signaling, 2933), Bcl-2 (Cell Signaling, 2870), Bcl-xL (Cell Signaling, 2764), Mcl-1 (Cell Signaling, 5453), Cytochrome c (Cell Signaling, 4272), and Cleaved Caspase-3 (Cell Signaling, 9661). Antibodies used for immunoprecipitation were obtained from the listed sources: p53 (Cell Signaling, 12450) and Bcl-xL (Cell Signaling, 2764). Secondary antibodies were obtained from the listed sources: Anti-rabbit IgG HRP-linked (Cell Signaling, 7074) and Anti-mouse IgG HRP-linked (Cell Signaling, 7076). All immunoblotting antibodies were used at a dilution of 1:1000, except β-actin and tubulin, which were used at 1:10,000 Immunoprecipitation antibodies were diluted according to manufacturer's instructions (1:200 for p53 and 1:100 for Bcl-xL). Secondary antibodies were used at a dilution of 1:5000.

$^{18}$F-Fluorodeoxyglucose (18F-FDG) Uptake Assay

Cells were plated at $5\times10^4$ cells/ml and treated with designated drugs for indicated time points. Following appropriate treatment, cells were collected and resuspended in glucose-free DMEM/F12 (USBiological) containing $^{18}$F-FDG (radioactivity 1 μCi/mL). Cells were incubated at 37° C. for 1 hr and then washed three times with ice cold PBS. Radioactivity of each sample was then measured using a gamma counter.

Glucose, Glutamine, and Lactate Measurements

Cellular glucose consumption and lactate production were measured using a Nova Biomedical BioProfile Basic Analyzer. Briefly, cells were plated in $1\times10^5$ cells/ml in 2 mL of gliomasphere conditions and appropriate drug conditions (n=5). 12 hrs following drug treatment, 1 ml of media was removed from each sample and analyzed in the Nova BioProfile analyzer. Measurements were normalized to cell number.

Annexin V Apoptosis Assay

Cells were collected and analyzed for Annexin V and PI staining according to manufacturer's protocol (BD Biosciences). Briefly, cells were plated at $5\times10^4$ cells/ml and treated with appropriate drugs. Following indicated time points, cells were collected, trypsinized, washed with PBS, and stained with Annexin V and PI for 15 minutes. Samples were then analyzed using the BD LSRII flow cytometer.

Immunoblotting

Cells were collected and lysed in RIPA buffer (Boston BioProducts) containing Halt Protease and Phosphatase Inhibitor (Thermo Fischer Scientific). Lysates were centrifuged at 14,000×g for 15 min at 4° C. Protein samples were then boiled in NuPAGE LDS Sample Buffer (Invitrogen) and NuPAGE Sample Reducing Agent (Invitrogen) and separated using SDS-PAGE on 12% Bis-Tris gels (Invitrogen) and transferred to nitrocellulose membrane (GE Healthcare) Immunoblotting was performed per antibody's manufacturer's specifications and as mentioned previously. Membranes were developed using the SuperSignal system (Thermo Fischer Scientific).

Immunoprecipitation

Cells were collected, washed once with PBS, and incubated in IP lysis buffer (25 mM Tris-HCL pH 7.4, 150 mM NaCl, 1 mM EDTA, 1% NP-40, 5% Glycerol) at 4° C. for 15 minutes. 300-500 μg of each sample was then pre-cleared in Protein A/G Plus Agarose Beads (Thermo Fischer Scientific) for one hour. Following pre-clear, samples were then incubated with antibody-bead conjugates overnight according to manufacturer's specifications and as mentioned previously. The samples were then centrifuged at 1000 g for 1 mM, and the beads were washed with 500 μL of IP lysis buffer for five times. Proteins were eluted from the beads by boiling in 2× LDS Sample Buffer (Invitrogen) at 95° C. for 5 min. Samples analyzed by immunoblotting as previously described Immunoprecipitation antibodies were diluted according to manufacturer's instructions (1:200 for p53 and 1:100 for Bcl-xL).

Dynamic BH3 Profiling

GBM gliomaspheres were first disassociated to single-cell suspensions with TrypLE (Gibco) and resuspended in MEB buffer (150 mM Mannitol 10 mM HEPES-KOH, 50 mM KCl, 0.02 mM EGTA, 0.02 mM EDTA, 0.1% BSA, 5 mM Succinate). 50 μl of cell suspension ($3\times10^4$ cells/well) were plated in wells holding 50 μL MEB buffer containing 0.002% digitonin and indicated peptides in 96-well plates. Plates were then incubated at 25° C. for 50 min. Cells were then fixed with 4% paraformaldehyde for 10 min, followed by neutralization with N2 buffer (1.7M Tris, 1.25M Glycine pH 9.1) for 5 min. Samples were stained overnight with 20 μL of staining solution (10% BSA, 2% Tween 20 in PBS) containing DAPI and anti-cytochrome c (BioLegend). The following day, cytochrome c release was quantified using BD LSRII flow cytometer. Measurements were normalized to appropriate controls that do not promote cytochrome c release (DMSO and inactive PUMA2A peptide). Delta priming refers to the difference in amount of cytochrome c release between vehicle treated cells and drug treated cells.

BAX Oligomerization $7.5\times10^5$ cells were treated with indicated drugs. Following 24 hr of treatment, cells were collected, washed once with ice cold PBS, and re-suspended in 1 mM bismaleimidohexane (BMH) in PBS for 30 min. Cells were then pelleted and lysed for immunoblotting, as described above.

Cytochrome c Detection 5 million cells were plated at a concentration of $1\times10^5$ cells/mL and treated with indicated drugs. Following 24 hr of treatment, cells were collected, washed once with ice cold PBS. Subcellular fractionation was then performed using a mitochondrial isolation kit (Thermo Fischer Scientific, 89874). Both cytoplasmic and mitochondrial fractions were subjected to immunoblotting and cytochrome c was detected using cytochrome c antibody at a dilution of 1:1000 (Cell Signaling, 4272).

Mouse Xenograft Studies

For intracranial experiments, GBM39, HK336, HK393, and GS025 cells were injected ($4\times10^5$ cells per injection) into the right striatum of the brain of female NSG mice (6-8 weeks old). Injection coordinates were 2 mm lateral and 1 mm posterior to bregma, at a depth of 2 mm. Tumor burden was monitored by secreted gaussia luciferase and following three consecutive growth measurements, mice were randomized into four treatment arms consisting of appropriate vehicles, 75 mg/kg erlotinib, 50 mg/kg Idasanutlin, or a combination of both drugs. Vehicle consisted of 0.5% methylcellulose in water, which is used to dissolve erlotinib, and a proprietary formulation obtained from Roche, which is used to dissolve Idasanutlin. Tumor burden was assessed twice per week by secreted gaussia luciferase. When possible, mice were treated for 25 days and taken off treatment and monitored for survival. Drugs were administered through oral gavage. Sample sizes were chosen based off estimates from pilot experiments and results from previous literature[12]. Investigators were not blinded to group allocation or assessment of outcome. All studies were in accordance with UCLA OARO protocol guidelines.

Intracranial Delayed PET/CT Mouse Imaging

Mice were treated with indicated dose and time of erlotinib then pre-warmed, anesthetized with 2% isoflurane, and intravenously injected with 70 μCi of $^{18}$F-FDG. Following 1 hr unconscious uptake, mice were taken off anesthesia but kept warm for another 5 hr of uptake. 6 hr after the initial administration of $^{18}$F-FDG, mice were imaged using G8 PET/CT scanner (Sofie Biosciences). Per above, quantification was performed by drawing 3D regions of interest (ROI) using the AMIDE software.

Immunohistochemistry

Immunohistochemistry was performed on 4 μm sections that were cut from FFPE (formalin-fixed, paraffin-embedded) blocks. Sections were then deparaffinised with xylene and rehydrated through graded ethanol. Antigen retrieval was achieved with a pH 9.5 Nuclear Decloaker (Biocare Medical) in a Decloaking pressure cooker at 95° C. for 40 min. Tissue sections were then treated with 3% hydrogen peroxide (LOT 161509; Fisher Chemical) and with Background Sniper (Biocare Medical, Concord, Calif., USA) to reduce nonspecific background staining. Primary antibody for p53 (Cell Signaling, 2527) was applied in a 1:150 dilution for 80 min followed by detection with the MACH 3 Rabbit HRP-Polymer Detection kit (Biocare Medical). Visualization was achieved using VECTOR NovaRED (SK-4800; Vector Laboratories, Inc.) as chromogen. Lastly, sections were counterstained with Tacha's Automated Hematoxylin (Biocare Medical).

Quantitative RT-PCR

RNA was extracted from all cells using Purelink RNA Kit (Invitrogen). cDNA was synthesized with iScript cDNA Synthesis Kit (Bio-Rad) as per manufacturer's instructions. Quantitative PCR (qPCR) was conducted on the Roche LightCycler 480 using SYBRGreen Master Mix (Kapa Biosciences). Relative expression values are normalized to control gene (GAPDH). Primer sequences are as listed (5' to 3'): P21 (forward GACTTTGTCACCGA GACACC (SEQ ID NO: 1), reverseGACAGGTCCACATGGTCTTC (SEQ ID NO: 2)), PUMA (forward ACGACCTCAACGCACAGTACG (SEQ ID NO: 3), reverse GTAAG GGCAGGAGTCCCATGATG (SEQ ID NO: 4)), GAPDH (forward TGCCATGTAGACC CCTTGAAG (SEQ ID NO: 5), reverse ATGGTACATGACAAGGTGCGG (SEQ ID NO: 6)), MDM2 (forward CTGTGTTCAGTGGCGATTGG (SEQ ID NO: 7), reverse AGGGT CTCTTGTTCCGAAGC (SEQ ID NO: 8)), TIGAR (forward GGAAGAGTGCCCTGTG TTTAC (SEQ ID NO: 9), reverse GACTCAAGACTTCGGGAAAGG (SEQ ID NO: 10)), PIG3 (forward GCAGCTGCTGGATTCAATTA (SEQ ID NO: 11), reverse TCCCAGT AGGATCCGCCTAT (SEQ ID NO: 12)).

P53 Reporter Activity

Cells were first infected with lentivirus synthesized from a p53 reporter plasmid which codes for luciferase under the control of a p53 responsive element: TACAGAA-CATGTCTAAGCATGCTGTGCCTTGCCTGGACTTGC-CTGGCCTTGCCTT GGG (SEQ ID NO: 13). Infected cells were then plated into a 96-well plate at 5,000 cells/50 μL and treated with indicated drugs for 24 hr and then incubated with 1 mM D-luciferin for two hours. Bioluminescence was measured using IVIS Lumina II (Perkin Elmer).

Genetic Manipulation

In general, lentivirus used for genetic manipulation were produced by transfecting 293-FT cells (Thermo) using Lipofectamine 2000 (Invitrogen). Virus was collected 48 hours after transfection. The lentiviral sgp53 vector and sgControl vector contained the following guide RNA, respectively: CCGGTTCATGCCGCCCATGC (SEQ ID NO: 14) and GTAATCCTAGCACTTTTAGG (SEQ ID NO: 15). LentiCRISPR-v2 was used as the backbone. Glut1 and Glut3 cDNA was cloned from commercially available vectors and incorporated into pLenti-GLuc-IRES-EGFP lentiviral backbone containing a CMV promoter (Glut1 was a gift from Wolf Frommer (Addgene #18085[44]), Glut3 was obtained from OriGene #SC115791, and the lentiviral backbone was obtained from Targeting Systems #GL-GFP). pMIG Bcl-xL was a gift from Stanley Korsmeyer (Addgene #8790[45]) and cloned into the lentiviral backbone mentioned above (Targeting Systems). Cytoplasmic (K305A and R306A) and wild-type p53 constructs were a kind gift from R. Agami and G. Lahav. The genes of interest were cloned into a lentiviral vector containing a PGK promoter. Constructs for p53 DNA binding domain mutants (R175H and R273H) as well as the nuclear mutant (L348A and L350A) were generated using site-directed mutagenesis (New England Biolabs #E0554S) on the wild-type p53 construct.

For EGFR knockdown experiments, siRNA against EGFR (Thermo Fischer Scientific, s563) was transfected into cells using DharmaFECT 4 (Dharmacon). Following 48 hours, cells were harvested and used for indicated experiments.

Immunofluorescence

For immunofluorescence, gliomaspheres were first disassociated to single cell and adhered to the 96-well plates using Cell-Tak (Corning) according to manufacturer instructions. Adhered cells were then fixed with ice-cold methanol for 10 min then washed three times with PBS. Cells were then incubated with blocking solution containing 10% FBS and 3% BSA in PBS for 1 hr and subsequently incubated with p53 (Santa Cruz, SC-126, dilution of 1:50) antibody overnight at 4° C. The following day, cells were incubated with secondary antibody (Alexa Fluor 647, dilution 1:2000) for an hour and DAPI staining for 10 min, then imaged using a Nikon TI Eclipse microscope equipped with a Cascade II fluorescent camera (Roper Scientific). Cells were imaged with emissions at 461 nM and 647 nM and then processed using NIS-Elements AR analysis software.

Oxygen Consumption Rate (OCR) and Extracellular Acidification Rate (ECAR) Measurements For metabolic measurements involving OCR and ECAR, gliomaspheres treated with indicated drugs were first disassociated to single cell suspensions and adhered to XF24 plates (Seahorse Bioscience) using Cell-Tak (Corning) according to manufacturer instructions. Prior to the assay, cells were supplemented with unbuffered DMEM, and incubated at 37° C. for 30 min before starting OCR and ECAR measurements. Basal ECAR measurements between control and erlotinib treated cells are shown.

Mass-Spectroscopy Sample Preparation

Male CD-1 mice (6-8 weeks old) were treated with 50 mg/kg Idasanutlin in duplicate through oral gavage. At 0.5, 1, 2, 4, 6, 8, 12, and 24 hr after administration, mice were sacrificed, blood was harvested by retro-orbital bleeding, and brain tissue was collected. Whole blood from mice was centrifuged to isolate plasma. Idasanutlin was isolated by liquid-liquid extraction from plasma: 50 μL plasma was added to 2 μL internal standard and 100 μL acetonitrile. Mouse brain tissue was washed with 2 mL cold PBS and homogenized using a tissue homogenizer with fresh 2 mL cold PBS. Idasanutlin was then isolated and reconstituted in a similar manner by liquid-liquid extraction: 100 μL brain homogenate was added to 2 μL internal standard and 200 μL acetonitrile. After vortex mixing, the samples was centrifuged. The supernatant was removed and evaporated by a rotary evaporator and reconstituted in 100 μL 50:50 water:acetonitrile.

Idasanutlin Detection by Mass-Spectrometry

Chromatographic separations were performed on a 100× 2.1 mm Phenomenex Kinetex C18 column (Kinetex) using the 1290 Infinity LC system (Agilent). The mobile phase was composed of solvent A: 0.1% formic acid in Milli-Q water, and B: 0.1% formic acid in acetonitrile. Analytes were eluted with a gradient of 5% B (0-4 min), 5-99% B (4-32 min), 99% B (32-36 min), and then returned to 5% B for 12 min to re-equilibrate between injections. Injections of 20 μL into the chromatographic system were used with a solvent flow rate of 0.10 mL/min Mass spectrometry was performed on the 6460 triple quadrupole LC/MS system (Agilent). Ionization was achieved by using electrospray in the positive mode and data acquisition was made in multiple reactions monitoring (MRM) mode. The MRM transition used for Idasanutlin detection was m/z 616.2→421.2 with fragmentor voltage of 114V, and collision energy of 20 eV. Analyte signal was normalized to the internal standard and concentrations were determined by comparison to the calibration curve (0.5, 5, 50, 250, 500, 2000 nM). Idasanutlin brain concentrations were adjusted by 1.4% of the mouse brain weight for the residual blood in the brain vasculature.

Secreted Gaussia Luciferase Measurements

Cells were infected with a lentiviral vector containing secreted gaussia luciferase (sGluc) reporter gene (Targeting Systems #GL-GFP) and intracranially implanted into the right striatum of mice ($4\times10^5$ cells/mouse). To measure the levels of secreted Gaussia luciferase (sGluc), 6 μL of blood was collected from the tail vein of the mice and immediately mixed with 50 mM EDTA to prevent coagulation. Gluc activity was obtained by measuring chemiluminescence following injection of 100 μL of 100 μM coelentarazine (Nanolight) in a 96 well plate.

Synergy Score Calculations $1.0\times10^5$ GBM cells were plated in triplicate and treated with erlotinib, nutlin, or combination at multiple concentrations using a matrix where each drug was added to the cells at six concentrations (0-10 μM). Annexin V staining was measured following 72 hrs of treatment. Using the Chalice software, the response of the combination was compared to its single agents. The combinatorial effects were calculated using the synergy score.

DNA Sequencing

Targeted sequencing was performed for samples HK206, HK217, HK250, HK296 for the following genes BCL11A, BCL11B, BRAF, CDKN2A, CHEK2, EGFR, ERBB2, IDH1, IDH2, MSH6, NF1, PIK3CA, PIK3R1, PTEN, RB1, TP53 using Illumina Miseq. There were 1 to 2 million reads per sample with average coverage of 230 per gene. Copy number variants were determined for these samples using a whole genome SNP array. The genetic profile of GBM39 has been previously reported in the literature.

Whole exome sequencing was performed for samples HK157, HK229, HK248, HK250, HK254, HK296, HK301, HK336, HK350, HK390, HK393 and carried out at SeqWright. Samples were grouped into 2 pools with separate capture reactions. Nextera Rapid capture and library preparation were used and sequencing performed on a HiSeq 2500, 2×100 bp with 100× on-target coverage, 2 full rapid runs, each with 1 normal diploid control. Copy number analysis for these samples was carried out using EXCAVATOR software.

Annotation of TCGA Samples

273 GBM samples from the TCGA were analyzed for genetic alterations in EGFR, p53 and p53-regulated pathways. Co-occurrences of mutations were examined and only significant interactions are displayed. Data was analyzed using cBioPortal as previously described.

Fluorescence In Situ Hybridization (FISH)

Fluorescence in situ hybridization (FISH) was performed using commercially available fluorescently labeled dual-color EGFR (red)/CEP 7 (green) probe (Abbott-Molecular). FISH hybridization and analyses were performed on cell lines, following the manufacturer's suggested protocols. The cells were counterstained with DAPI and the fluorescent probe signals were imaged under a Zeiss (Axiophot) Fluorescent Microscope equipped with dual- and triple-color filters.

Statistical Analysis.

Comparisons were made using two-tailed unpaired Student's t-tests and p values <0.05 were considered statistically significant. All data from multiple independent experiments were assumed to be of normal variance. Data represent means±s.e.m. values. All statistical analyses were calculated using Prism 6.0 (GraphPad). For all in vitro and in vivo experiments, no statistical method was used to predetermine sample size and no samples were excluded. For in vivo tumor measurements, the last data sets were used for comparisons between groups. As described above, all mice were randomized before studies.

Example 15

Exemplary Design Rational for Certain Compounds of the JGK Series

Certain Compounds of the present disclosure were designed according to Scheme 1.

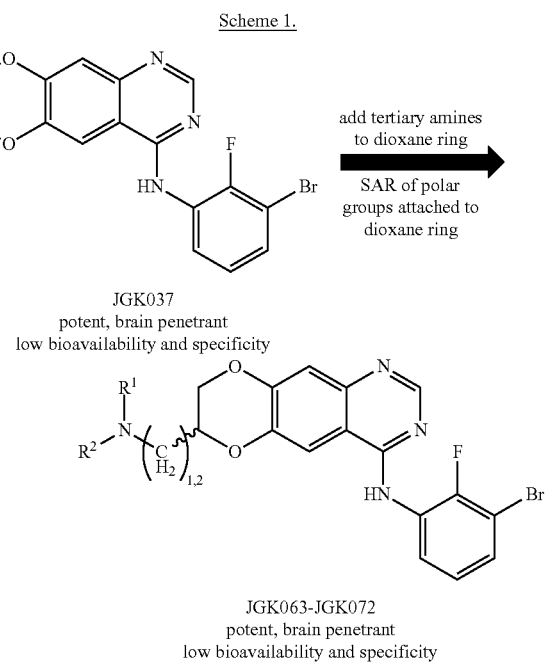

Example 16
Preparation of Further Exemplary Compounds of the JGK Series
Exemplary compounds of the present disclosure were prepared according to the following methods.
Scheme 1. Synthesis of monoprotected quinazoline intermediate 3.
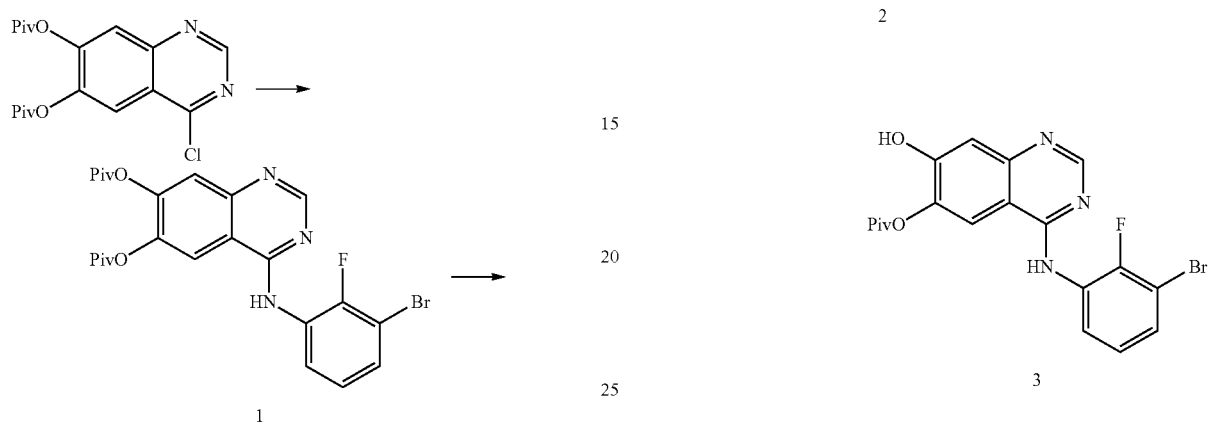

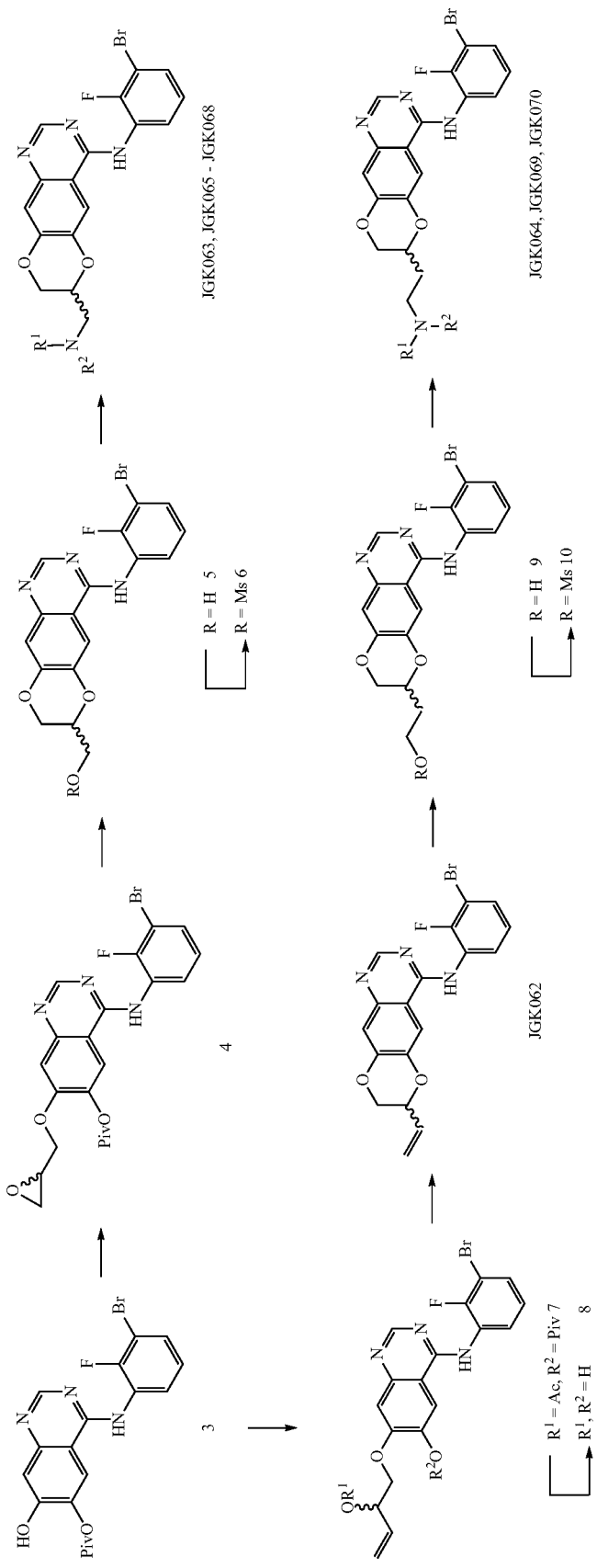
Scheme 2. Synthesis of JGK063 - HGK070.

Scheme 3. Synthesis of JGK068S ((S)-JGK068). The synthesis was performed in the same way as for the racemic sample of JGK068 ((±)-JGK068), but with enantiomerically pure (S)-(—)-glycidol. The other enantiomer JGK068R ((R)-JGK068) was prepared using (R)-(+)-glycidol (not shown).

Scheme 4. The enantiomeric purity of the synthetic intermediate 5 was determined by chiral SFC (Chiralpak AD-3 column, 40% MeOH) and by comparison of the $^{19}$F NMR spectra of the Mosher ester derivatives of 5 (FIG. 39).

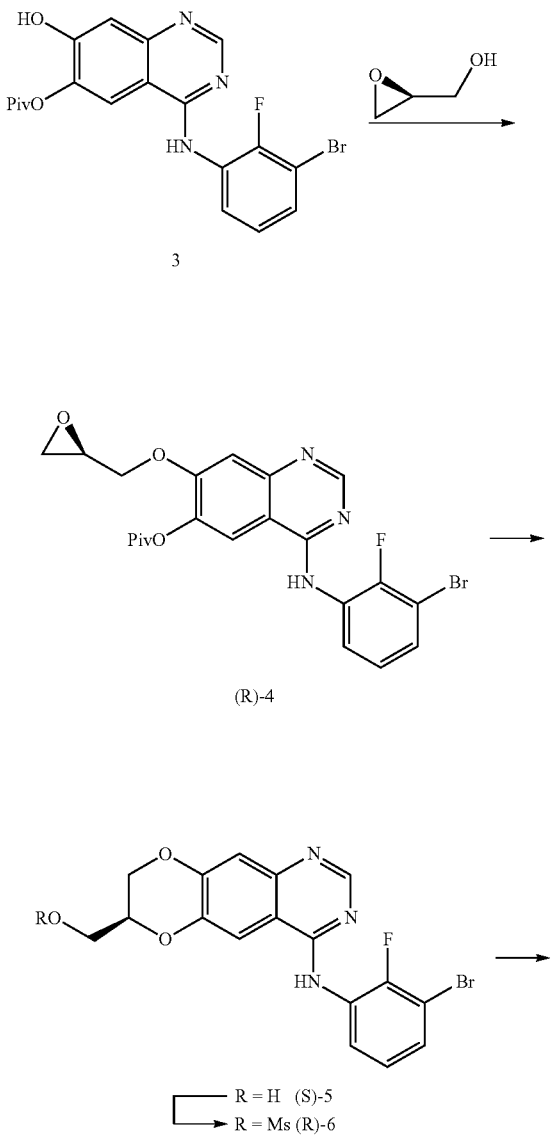

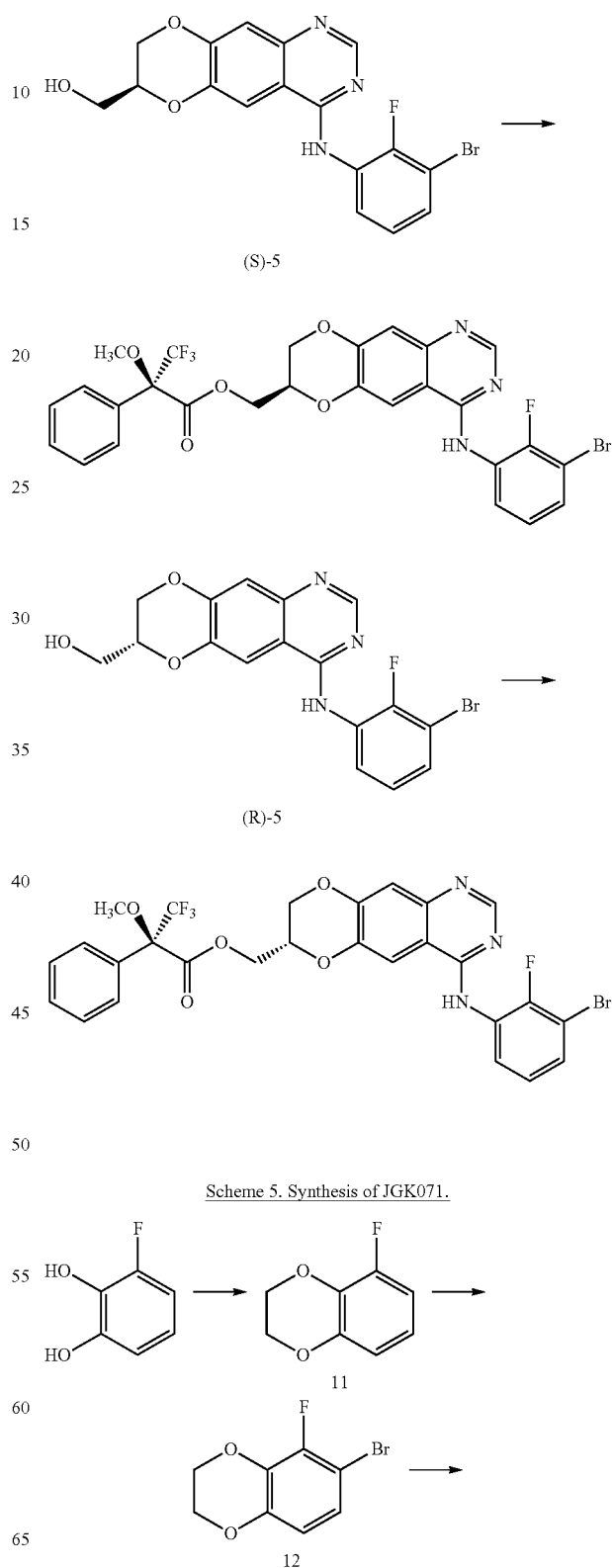

Scheme 5. Synthesis of JGK071.

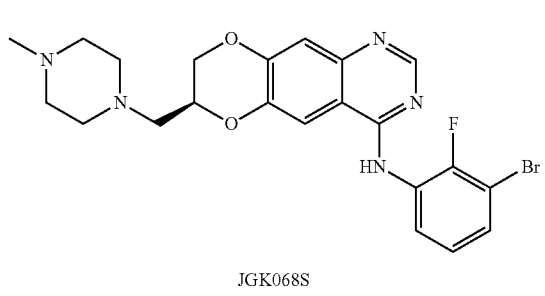

-continued
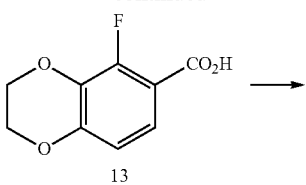
13
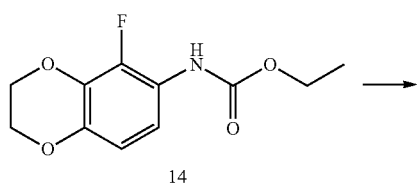
14
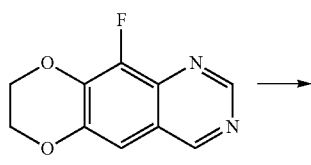
15
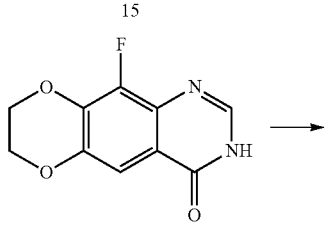
16
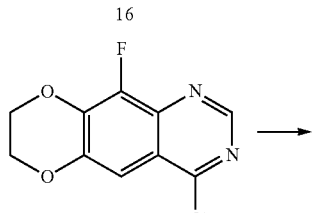
17
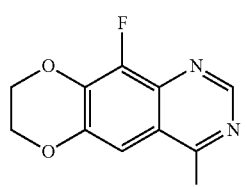
JGK071
Scheme 6. Synthesis of JGK072.
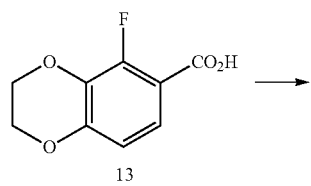
13
-continued
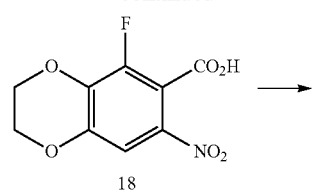
18
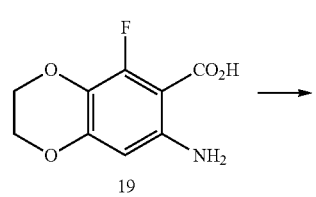
19
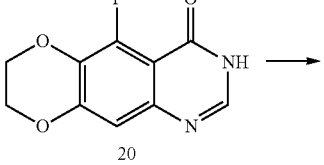
20
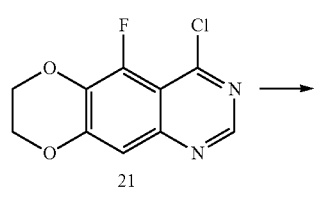
21
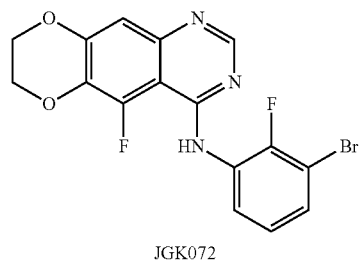
JGK072
Scheme 7. Synthesis of JGK076-JGK080.
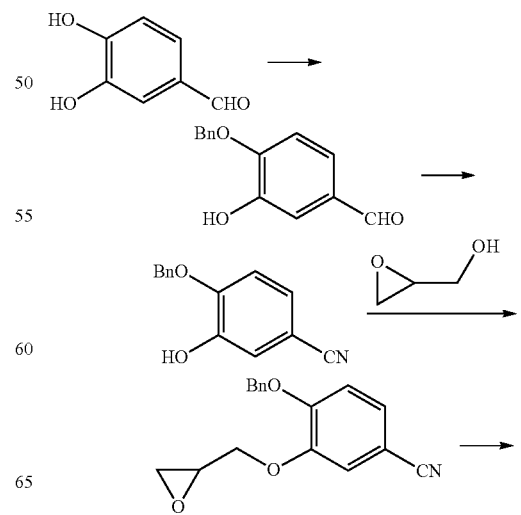

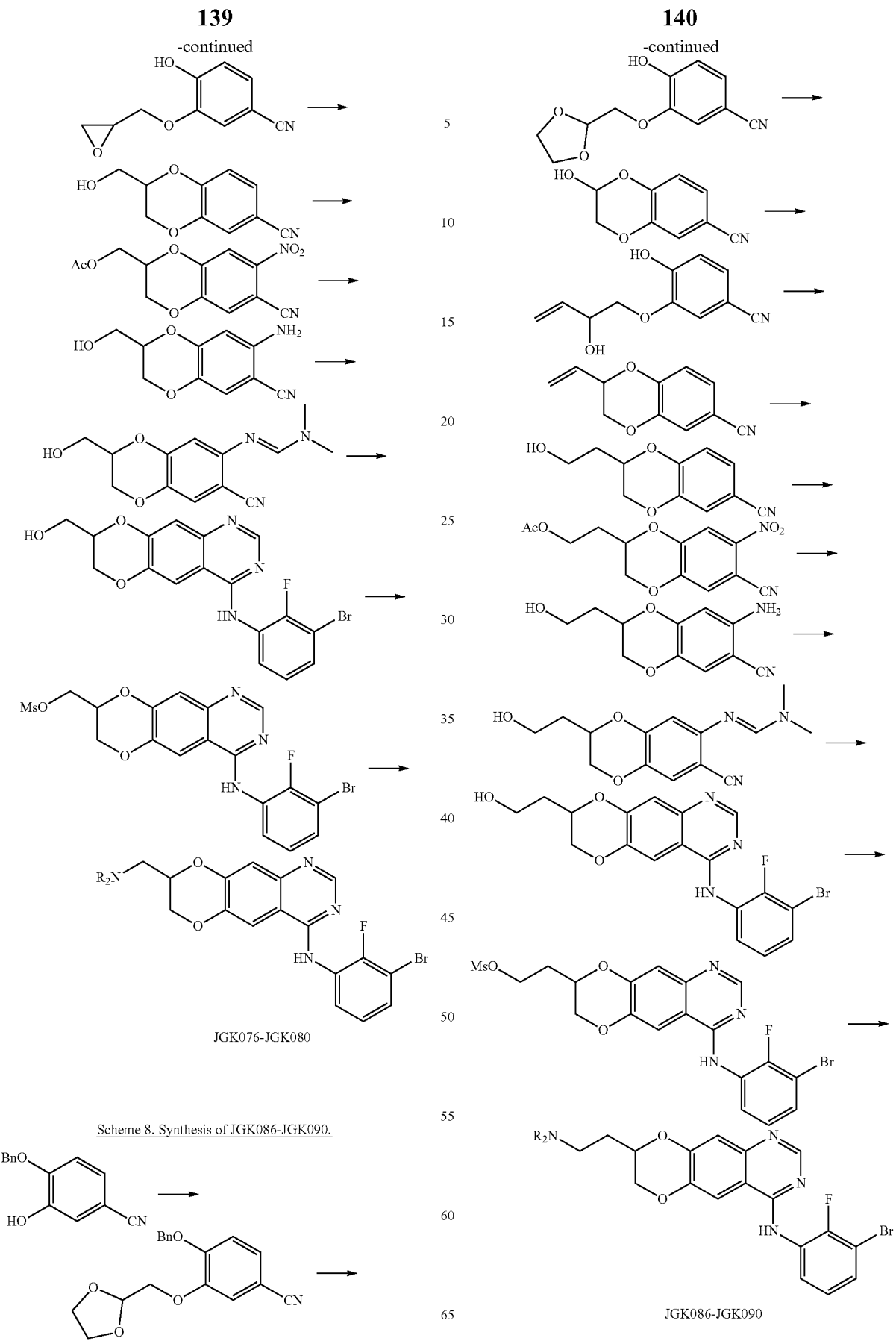

General Chemistry Information

All chemicals, reagents, and solvents were purchased from commercial sources when available and were used as received. When necessary, reagents and solvents were purified and dried by standard methods. Air- and moisture-sensitive reactions were carried out under an inert atmosphere of argon in oven-dried glassware. Microwave-irradiated reactions were carried out in a single mode reactor CEM Discover microwave synthesizer. Room temperature (RT) reactions were carried out at ambient temperature (approximately 23° C.). All reactions were monitored by thin layer chromatography (TLC) on precoated Merck 60 $F_{254}$ silica gel plates with spots visualized by UV light ($\lambda$=254, 365 nm) or by using an alkaline $KMnO_4$ solution. Flash column chromatography (FC) was carried out on $SiO_2$ 60 (particle size 0.040-0.063 mm, 230-400 mesh). Preparative thin-layer chromatography (PTLC) was carried out with Merck 60 $F_{254}$ silica gel plates (20×20 cm, 210-270 mm) or Analtech Silica Gel GF TLC plates (20×20 cm, 1000 mm). Concentration under reduced pressure (in vacuo) was performed by rotary evaporation at 23-50° C. Purified compounds were further dried under high vacuum or in a desiccator. Yields correspond to purified compounds, and were not further optimized. Proton nuclear magnetic resonance ($^1$H NMR) spectra were recorded on Bruker spectrometers (operating at 300, 400, or 500 MHz). Carbon NMR ($^{13}$C NMR) spectra were recorded on Bruker spectrometers (either at 400 or 500 MHz). NMR chemical shifts ($\delta$ppm) were referenced to the residual solvent signals. $^1$H NMR data are reported as follows: chemical shift in ppm; multiplicity (s=singlet, d=doublet, t=triplet, q=quartet, quint=quintet, m=multiplet/complex pattern, td=triplet of doublets, ddd=doublet of doublet of doublets, br=broad signal); coupling constants (J) in Hz, integration. Data for $^{13}$C NMR spectra are reported in terms of chemical shift, and if applicable coupling constants. High resolution mass (HRMS) spectra were recorded on a Thermo Fisher Scientific Exactive Plus with IonSense ID-CUBE DART source mass spectrometer, or on a Waters LCT Premier mass spectrometer with ACQUITY UPLC with autosampler.

General Procedures (GP). GP-1: Nucleophilic Substitution of Quinazolinyl Mesylates with Secondary Amines. A mixture of quinazolinyl mesylate (1 equiv) in DMF (0.05 M) was treated with the secondary amine (5 equiv) and triethylamine (2 equiv), and the mixture was stirred at 85° C. for 24 h. The mixture was cooled to 23° C., and evaporated. The residue was dissolved in EtOAc (20 mL), washed with 10 mm NaOH (4×5 mL), brine (5 mL), dried ($Na_2SO_4$), filtered, and evaporated. Purification by FC or PTLC afforded the desired products typically as off-white, friable foams.

GP-2: Nucleophilic Aromatic Substitution of 4-Chloroquinazoline with Anilines. A mixture of 4-chloroquinazoline (1 equiv) in acetonitrile (0.1 M) was treated with aniline (2 equiv), and with a 4 M solution of HCl in dioxane (1 equiv). The mixture was heated at 80° C. under microwave irradiation for 30 min. The mixture was either concentrated under reduced pressure, or the precipitated 4-anilinoquinazoline hydrochloride salt was isolated by filtration (washings with $Et_2O$). The residue was suspended in sat. aq. $NaHCO_3$, and extracted with $CH_2Cl_2$ (3×). The combined organic extracts were washed with water, brine, dried ($Na_2SO_4$), filtered, and concentrated. Purification by FC (elution with a gradient of $CH_2Cl_2$/EtOAc or hexanes/EtOAc) afforded the desired products typically as white to off-white, or pale-yellow solids.

4-(3-Bromo-2-fluoroanilino)quinazoline-6,7-diyl bis(2,2-dimethylpropanoate) (1)

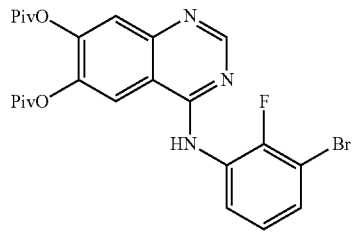

A mixture of 4-chloroquinazoline-6,7-diyl bis(2,2-dimethylpropanoate)[1] (41.08 g, 113 mmol) in iPrOH (450 mL) was treated with 3-bromo-2-fluoroaniline (17.05 mL, 152 mmol) and stirred at 80° C. for 3.5 h. The mixture was cooled to 23° C. and evaporated. The residue was several times resuspended in hexanes (50 mL) and concentrated, and then dried under HV. The residue was recrystallized from EtOH to give a yellow solid, which was suspended in sat. aq. $NaHCO_3$ (1 L), and extracted with DCM (3×550 mL). The combined organics were washed with water (400 mL), brine (400 mL), dried ($MgSO_4$), filtered, and evaporated to afford the title compound 1 (35.057 g, 60%) as a yellow friable foam.

$^1$H NMR (500 MHz, $CDCl_3$): $\delta$=8.76 (s, 1H), 8.46 (t, J=7.5 Hz, 1H), 7.72 (s, 1H), 7.68 (s, 1H), 7.56 (br, 1H), 7.32 (ddd, J=8.0, 6.4, 1.5 Hz, 1H), 7.11 (td, J=8.2, 1.5 Hz, 1H), 1.40 (s, 9H), 1.39 ppm (s, 9H). $^{13}$C NMR (126 MHz, $CDCl_3$): $\delta$=176.13, 175.55, 156.71, 154.96, 150.69 (d, $J_{CF}$=243.7 Hz), 148.75, 147.83, 142.45, 128.27, 127.86 (d, $J_{CF}$=10.8 Hz), 125.29 (d, $J_{CF}$=4.7 Hz), 122.70, 122.51, 114.43, 113.21, 108.84 (d, $J_{CF}$=19.4 Hz), 39.54, 39.51, 27.40, 27.32 ppm. HRMS (DART): m/z [M+H]$^+$ calcd for $C_{24}H_{26}BrFN_3O_4^+$, 518.1085; found, 518.1072.

4-(3-Bromo-2-fluoroanilino)quinazoline-6,7-diol (2)

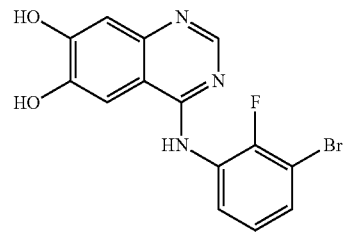 [SMILES: Oc1cc2ncnc(Nc3cccc(Br)c3F)c2cc1O]

A stirred slurry of 1 (34.988 g, 67.5 mmol) was treated at 0° C. with 7 M solution of $NH_3$ in MeOH (241 mL, 1.69 mol). The mixture was stirred at 0° C. for 15 min, and then at 23° C. for 4.5 h. The mixture was evaporated, and the residue suspended in water (400 mL), stirred overnight, and filtered. The residue was washed with water (500 mL), acetonitrile (100 mL), DCM (4×150 mL), $Et_2O$ (2×150 mL), and dried in a desiccator to afford the title compound 2 (23.68 g, quant.) as a pale-yellow powder.

$^1$H NMR (500 MHz, DMSO-$d_6$): $\delta$=8.18 (s, 1H), 7.59-7.47 (m, 2H), 7.51 (s, 1H), 7.16 (t, J=8.0 Hz, 1H), 6.87 ppm (s, 1H). $^{13}$C NMR (126 MHz, DMSO-$d_6$): $\delta$=156.43, 156.12, 153.06 (d, $J_{CF}$=246.7 Hz), 151.34, 148.39, 146.80, 129.23, 129.01, 127.12, 125.23 (d, $J_{CF}$=4.3 Hz), 108.47, 108.32, 107.09, 103.04 ppm. HRMS (DART): m/z [M+H]$^+$ calcd for C$_{14}$H$_{10}$BrFN$_3$O$_2$$^+$, 349.9935; found, 349.9923.

4-(3-Bromo-2-fluoroanilino)-7-hydroxyquinazolin-6-yl 2,2-dimethylpropanoate (3)

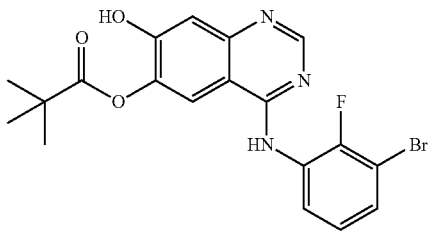 [SMILES: CC(C)(C)C(=O)Oc1cc2c(Nc3cccc(Br)c3F)ncnc2cc1O]

A stirred suspension of 2 (3500 mg, 10.0 mmol) in DMF (52.6 mL) was treated with Et$_3$N (5.57 mL, 40.0 mmol), cooled to −40° C., and treated dropwise with Piv$_2$O (3.14 mL, 15.5 mmol). The mixture was stirred at −40° C. for 1 h, after which the cooling bath was removed, and stirring was continued for 2.5 h. The reaction mixture was diluted with DCM (500 mL), washed with 10% citric acid (2×50 mL), dried (Na$_2$SO$_4$), filtered, and evaporated. FC (DCM/EtOAc 1:1→0:1) afforded a solid, which was redissolved in EtOAc (750 mL), and washed with half-sat. aq. NH$_4$Cl (4×75 mL), dried (Na$_2$SO$_4$), filtered, and evaporated to afford the title compound 3 (2.844 g, 66%) as a beige-yellow solid.

$^1$H NMR (500 MHz, DMSO-d$_6$): δ=11.00 (br, 1H), 9.70 (s, 1H), 8.39 (s, 1H), 8.14 (s, 1H), 7.59 (ddd, J=8.0, 6.2, 1.6 Hz, 1H), 7.53 (ddd, J=8.3, 7.1, 1.6 Hz, 1H), 7.21 (td, J=8.1, 1.2 Hz, 1H), 7.17 (s, 1H), 1.36 ppm (s, 9H). $^{13}$C NMR (126 MHz, DMSO-d$_6$): δ=175.93, 157.68, 154.61, 154.53, 153.34 (d, J$_{CF}$=247.3 Hz), 149.80, 139.65, 130.14, 127.92 (d, J$_{CF}$=12.9 Hz), 127.62, 125.47 (d, J$_{CF}$=4.4 Hz), 116.36, 111.00, 108.55 (d, J=20.0 Hz), 107.77, 38.64, 26.93 ppm. HRMS (DART): m/z [M+H]$^+$ calcd for C$_{19}$H$_{18}$BrFN$_3$O$_3$$^+$, 434.0510; found, 434.0489.

(±)-4-(3-Bromo-2-fluoroanilino)-7-[(oxiran-2-yl)methoxy]quinazolin-6-yl 2,2-dimethylpropanoate ((±)-4)

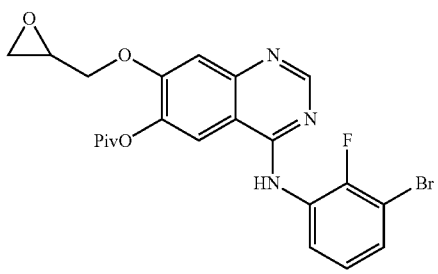

A mixture of 3 (1350 mg, 3.11 mmol) and PPh$_3$ (2038 mg, 7.77 mmol) in THF (21 mL) was treated with glycidol (495 µL, 7.46 mmol), cooled to 0° C., and treated with DIAD (1.47 mL, 7.46 mmol) during 10 min. The mixture was stirred at 23° C. for 2.5 h, and concentrated. FC (DCM/EtOAc 9:1→4:6) afforded the title compound (±)-4 (848 mg, 56%) as an off-white solid.

$^1$H NMR (500 MHz, CDCl$_3$): δ=8.73 (s, 1H), 8.54 (ddd, J=8.6, 7.3, 1.6 Hz, 1H), 7.54 (s, 1H), 7.45 (br, 1H), 7.30 (ddd, J=8.2, 6.4, 1.5 Hz, 1H), 7.28 (s, 1H), 7.11 (td, J=8.2, 1.6 Hz, 1H), 4.34 (dd, J=10.8, 3.0 Hz, 1H), 3.99 (dd, J=10.8, 6.2 Hz, 1H), 3.35 (ddt, J=6.2, 4.1, 2.8 Hz, 1H), 2.92 (dd, J=4.8, 4.1 Hz, 1H), 2.74 (dd, J=4.8, 2.6 Hz, 1H), 1.45 ppm (s, 9H). $^{13}$C NMR (126 MHz, CDCl$_3$): δ=176.87, 156.46, 155.10, 154.93, 150.41 (d, J$_{CF}$=243.3 Hz), 150.27, 140.99, 128.25 (d, J$_{CF}$=10.5 Hz), 127.75, 125.28 (d, J$_{CF}$=4.7 Hz), 122.22, 114.02, 109.72, 109.49, 108.74 (d, J$_{CF}$=19.1 Hz), 70.05, 49.55, 44.56, 39.45, 27.38 ppm. HRMS (DART): m/z [M+H]$^+$ calcd for C$_{22}$H$_{22}$BrFN$_3$O$_4$$^+$, 490.0772; found, 490.0764.

(±)-N-(3-Bromo-2-fluorophenyl)-7-ethenyl-7,8-dihydro[1,4]dioxino[2,3-g]quinazolin-4-amine ((±)-JGK062).

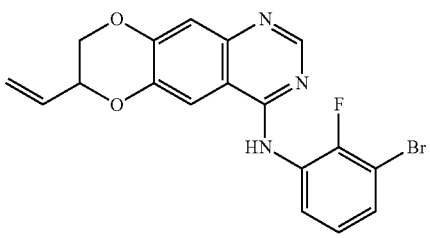 [SMILES: C=CC1COc2cc3ncnc(Nc4cccc(Br)c4F)c3cc2O1]

A solution of PPh$_3$ (832 mg, 3.17 mmol) and DIAD (624 µL, 3.17 mmol) in THF (23 mL) was stirred at 0° C. for 15 min, and then added dropwise to a solution of (±)-8 (1149 mg, 2.73 mmol) in THF (27 mL) during 10 min at 0° C. The mixture was stirred at 0° for 2 h, and evaporated. FC (hexanes/EtOAc 9:1→4:6) followed by another FC (DCM/EtOAc 1:0→6:4) afforded the title compound (±)-JGK062 (1115 mg, quant.) as an off-white friable foam. $^1$H NMR (500 MHz, CDCl$_3$): δ=8.68 (s, 1H), 8.65 (ddd, J=8.2, 7.3, 1.5 Hz, 1H), 7.40 (s, 1H), 7.37 (br, 1H), 7.35 (s, 1H), 7.27 (ddd, J=8.0, 6.4, 1.5 Hz, 1H), 7.10 (td, J=8.2, 1.6 Hz, 1H), 5.95 (ddd, J=17.3, 10.7, 5.8 Hz, 1H), 5.60 (dt, J=17.3, 1.2 Hz, 1H), 5.48 (dt, J=10.7, 1.1 Hz, 1H), 4.82-4.74 (m, 1H), 4.42 (dd, J=11.5, 2.5 Hz, 1H), 4.09 ppm (dd, J=11.6, 8.1 Hz, 1H). $^{13}$C NMR (126 MHz, CDCl$_3$): 67 =155.90, 153.38, 150.14 (d, J=242.4 Hz), 149.12, 146.70, 144.12, 131.48, 128.64 (d, J=10.3 Hz), 127.24, 125.30 (d, J=4.7 Hz), 121.76, 120.43, 114.29, 110.69, 108.58 (d, J=19.3 Hz), 106.06, 74.03, 67.84 ppm. HRMS (DART): m/z [M+H]$^+$ calcd for C$_{18}$H$_{14}$BrFN$_3$O$_2$$^+$, 402.0248; found, 402.0233.

(±)-[4-(3-Bromo-2-fluoroanilino)-7,8-dihydro[1,4]dioxino[2,3-g]quinazolin-7-yl]methanol ((±)-5)

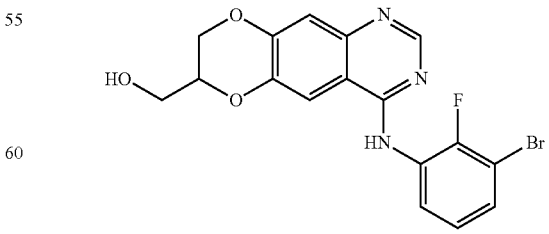

A mixture of (±)-4 (842 mg, 1.72 mmol) in MeOH (31 mL) was treated with K$_2$CO$_3$ (482 mg, 3.49 mmol), stirred at 23° C. for 10.5 h, and concentrated. The residue was suspended in half-sat. aq. NH₄Cl (130 mL), and extracted with EtOAc (3×20 mL). The combined organics were washed with water (20 mL), brine (20 mL), dried (Na₂SO₄), filtered, and concentrated to afford the title compound (±)-5 (720 mg, quant.) as a yellow solid.

$^1$H NMR (500 MHz, DMSO-d₆): δ=9.59 (s, 1H), 8.34 (s, 1H), 7.95 (s, 1H), 7.59 (ddd, J=8.0, 6.2, 1.6 Hz, 1H), 7.55 (ddd, J=8.4, 7.0, 1.6 Hz, 1H), 7.24-7.18 (m, 1H), 7.21 (s, 1H), 5.16 (t, J=5.6 Hz, 1H), 4.49 (dd, J=11.5, 2.4 Hz, 1H), 4.34 (dtd, J=7.6, 5.2, 2.3 Hz, 1H), 4.21 (dd, J=11.5, 7.4 Hz, 1H), 3.76-3.64 ppm (m, 2H). $^{13}$C NMR (126 MHz, DMSO-d₆): δ=157.20, 153.35 (d, $J_{CF}$=247.5 Hz), 153.10, 148.88, 145.95, 143.39, 130.11, 128.05 (d, $J_{CF}$=13.0 Hz), 127.73, 125.44 (d, $J_{CF}$=4.4 Hz), 112.33, 109.79, 108.56 (d, $J_{CF}$=20.0 Hz), 108.37, 73.78, 65.50, 59.78 ppm. HRMS (DART): m/z [M+H]⁺ calcd for $C_{17}H_{14}BrFN_3O_3^+$, 406.0197; found, 406.0185.

(±)-[4-(3-Bromo-2-fluoroanilino)-7,8-dihydro[1,4]dioxino[2,3-g]quinazolin-7-yl]methyl methanesulfonate ((±)-6)

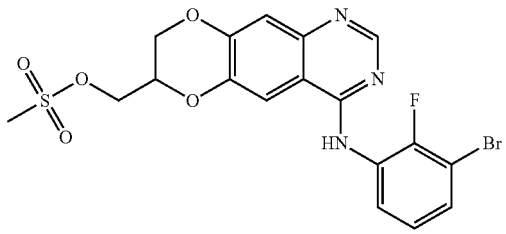 [SMILES: CS(=O)(=O)OCC1COc2cc3ncnc(Nc4cccc(Br)c4F)c3cc2O1]

A solution of (±)-5 (688 mg, 1.69 mmol) in THF (14 mL) was treated with Et₃N (357 μL, 2.56 mmol), cooled to 0° C., and treated dropwise with MsCl (174 μL, 2.24 mmol). The mixture was stirred at 23° C. for 16 h, cooled to 0° C., treated with sat. aq. NaHCO₃ (120 mL), and extracted with DCM (3×120 mL). The combined organics were washed with water (100 mL), brine (100 mL), dried (Na₂SO₄), filtered and evaporated. FC (DCM/EtOAc 8:2→3:7) afforded the title compound (±)-6 (496 mg, 61%) as an off-white solid.

$^1$H NMR (500 MHz, CDCl₃): δ=8.69 (s, 1H), 8.60 (ddd, J=8.5, 7.2, 1.4 Hz, 1H), 7.43 (s, 1H), 7.39 (br, 1H), 7.37 (s, 1H), 7.29 (ddd, J=8.1, 6.5, 1.5 Hz, 1H), 7.11 (td, J=8.2, 1.5 Hz, 1H), 4.63 (dtd, J=7.2, 4.9, 2.5 Hz, 1H), 4.52 (dd, J=4.9, 0.9 Hz, 2H), 4.49 (dd, J=11.8, 2.5 Hz, 1H), 4.29 (dd, J=11.8, 7.1 Hz, 1H), 3.13 ppm (s, 3H). $^{13}$C NMR (126 MHz, CDCl₃): δ=156.02, 153.66, 150.28 (d, $J_{CF}$=242.9 Hz), 148.65, 146.80, 143.09, 128.43 (d, $J_{CF}$=10.4 Hz), 127.54, 125.32 (d, $J_{CF}$=4.7 Hz), 122.01, 114.77, 110.90, 108.66 (d, $J_{CF}$=19.4 Hz), 106.44, 71.10, 66.46, 64.77, 38.02 ppm. HRMS (DART): m/z [M+H]⁺ calcd for $C_{18}H_{15}BrFN_3O_5S^+$, 483.9973; found, 483.9950.

(±)-4-(3-Bromo-2-fluoroanilino)-7-{[2-(acetoxy)but-3-en-1-yl]oxy}quinazolin-6-yl 2,2-dimethylpropanoate ((±)-7)

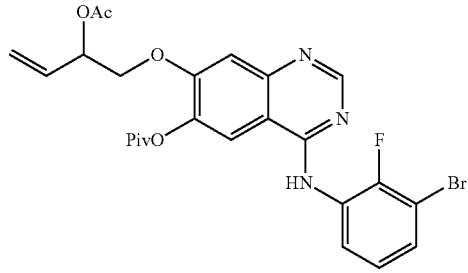

A mixture of 3 (2639 mg, 6.08 mmol) and PPh₃ (3986 mg, 15.2 mmol) in THF (41 mL) was treated with racemic 1-hydroxybut-3-en-2-yl acetate[2] (1.7 mL, 13.7 mmol), cooled to 0° C., and treated dropwise with DIAD (2.7 mL, 13.7 mmol). The mixture was stirred at 23° C. for 3 h, and concentrated. FC (DCM/EtOAc 1:0→6:4) afforded the crude (±)-7 (5.508 g, estimated yield 60%) as an off-white solid, which was contaminated with remaining Ph₃PO. The material was used in the next step without any further purification.

$^1$H NMR (400 MHz, CDCl₃): δ=8.74 (s, 1H), 8.53 (t, J=7.9 Hz, 1H), 7.53 (s, 1H), 7.45 (br, 1H), 7.33 (s, 1H), 7.30 (t, J=7.7 Hz, 1H), 7.11 (t, J=8.0 Hz, 1H), 5.90 (ddd, J=17.0, 10.6, 6.2 Hz, 1H), 5.65 (q, J=6.0 Hz, 1H), 5.49-5.29 (m, 2H), 4.31-4.08 (m, 2H), 2.11 (s, 3H), 1.41 ppm (s, 9H). $^{13}$C NMR (126 MHz, CDCl₃): δ=176.51, 170.08, 156.49, 155.24, 154.88, 150.46 (d, $J_{CF}$=243.2 Hz), 150.17, 140.90, 132.16, 128.18 (d, $J_{CF}$=11.0 Hz), 127.86, 125.31 (d, $J_{CF}$=4.8 Hz), 122.27, 119.64, 114.00, 109.56, 109.39, 108.76 (d, $J_{CF}$=19.4 Hz), 72.18, 69.81, 39.34, 27.33, 21.19 ppm. HRMS (DART): m/z [M+H]⁺ calcd for $C_{25}H_{26}BrFN_3O_5^+$, 546.1034; found, 546.1018.

(±)-4-(3-Bromo-2-fluoroanilino)-7-[(2-hydroxybut-3-en-1-yl)oxy]quinazolin-6-ol ((±)-8)

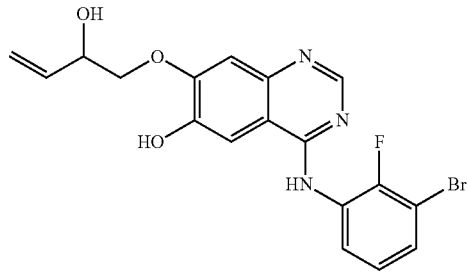 [SMILES: C=CC(O)COc1cc2ncnc(Nc3cccc(Br)c3F)c2cc1O]

A mixture of crude (±)-7 (5508 mg, contaminated with remaining Ph3PO from the last step) in MeOH (61 mL) was treated with K₂CO₃ (4198 mg, 30.4 mmol), stirred at 23° C. for 1 h, and concentrated. The residue was suspended in half-sat. aq. NH₄Cl (1 L), and extracted with EtOAc (3×600 mL). The combined organics were dried (Na₂SO₄), filtered, and evaporated. FC (DCM/EtOAc 1:1→0:1) afforded the title compound (±)-8 (1154 mg, 45% over two steps) as an off-white solid.

$^1$H NMR (500 MHz, DMSO-d$_6$): δ=9.46 (s, 1H), 9.40 (br, 1H), 8.33 (s, 1H), 7.71 (s, 1H), 7.59-7.52 (m, 2H), 7.203 (s), 7.197 (td, J=8.1, 1.1 Hz, 1H), 6.01 (ddd, J=17.4, 10.7, 4.9 Hz, 1H), 5.42 (dt, J=17.3, 1.9 Hz, 1H), 5.36 (br, 1H), 5.20 (dt, J=10.6, 1.8 Hz, 1H), 4.49 (br, 1H), 4.20 (dd, J=9.8, 3.8 Hz, 1H), 3.95 ppm (dd, J=9.8, 7.5 Hz, 1H). $^{13}$C NMR (126 MHz, DMSO-d$_6$): δ=156.77, 153.30 (d, J$_{CF}$=244.9 Hz), 152.77, 152.31, 146.66, 146.11, 137.61, 129.75, 128.46 (d, J$_{CF}$=13.0 Hz), 127.49, 125.38 (d, J$_{CF}$=4.3 Hz), 115.58, 109.42, 108.50 (d, J$_{CF}$=19.8 Hz), 107.68, 105.14, 72.56, 69.26 ppm. HRMS (DART): m/z [M+H]$^+$ calcd for C$_{18}$H$_{16}$BrFN$_3$O$_3$$^+$, 420.0354; found, 420.0340.

(±)-2-[4-(3-Bromo-2-fluoroanilino)-7,8-dihydro[1,4]dioxino[2,3-g]quinazolin-7-yl]ethan-1-ol ((±)-9)

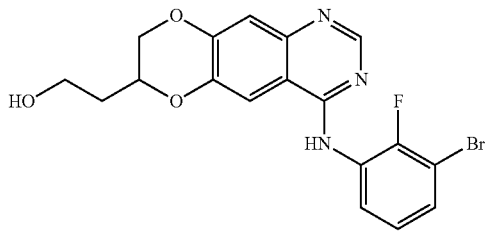 [SMILES: OCCC1COc2cc3ncnc(Nc4cccc(Br)c4F)c3cc2O1]

A mixture of (±)-JGK062 (480 mg, 1.19 mmol) in THF (4.8 mL) was treated with a 0.5 M solution of 9-BBN in THF (4.8 mL, 2.39 mmol), and the mixture was stirred at 68° C. for 16 h. The mixture was cooled to 0° C., diluted with THF (2.4 mL), and treated with 3 N NaOH (3 mL, 8.95 mmol), and 30% H$_2$O$_2$ (474 μL, 8.95 mmol), and stirred at 23° C. for 6 h. The mixture was concentrated to about half of the original volume of THF, diluted with water (100 mL) and brine (40 mL), and extracted with EtOAc (3×100 mL). The combined organics were washed with water (70 mL), brine (70 mL), dried (Na$_2$SO$_4$), filtered, and evaporated to afford the title compound (±)-9 (912 mg) as a yellow foam, which was directly used in the next step without further purification.

$^1$H NMR (500 MHz, CDCl$_3$): δ=8.66 (s, 1H), 8.62 (ddd, J=8.8, 7.4, 1.6 Hz, 1H), 7.35 (s, 1H), 7.33 (br, 1H), 7.2 (ddd, J=8.0, 6.5, 1.6 Hz, 1H), 7.16 (s, 1H), 7.09 (td, J=8.2, 1.6 Hz, 1H), 4.50 (dtd, J=8.4, 6.4, 2.3 Hz, 1H), 4.43 (dd, J=11.5, 2.3 Hz, 1H), 4.09 (dd, J=11.5, 8.2 Hz, 1H), 4.01-3.91 (m, 2H), 1.95 ppm (td, J=6.5, 5.3 Hz, 2H). $^{13}$C NMR (126 MHz, CDCl$_3$): δ=155.84, 153.28, 150.08 (d, J$_{CF}$=242.6 Hz), 149.42, 146.47, 144.20, 128.51 (d, J$_{CF}$=10.2 Hz), 127.31, 125.30 (d, J$_{CF}$=4.7 Hz), 121.69, 113.95, 110.50, 108.58 (d, J$_{CF}$=19.2 Hz), 105.83, 71.33, 68.49, 58.23, 33.61 ppm. HRMS (ESI): m/z [M+H]$^+$ calcd for C$_{18}$H$_{16}$BrFN$_3$O$_3$$^+$, 420.0354; found, 420.0370.

(±)-2-[4-(3-Bromo-2-fluoroanilino)-7,8-dihydro[1,4]dioxino[2,3-g]quinazolin-7-yl]ethyl methanesulfonate ((±)-10)

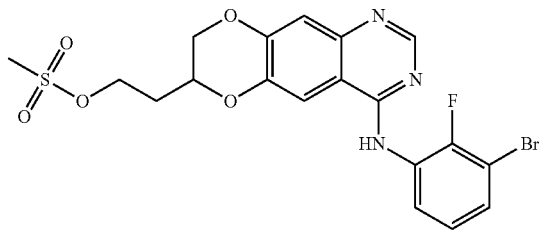 [SMILES: CS(=O)(=O)OCCC1COc2cc3ncnc(Nc4cccc(Br)c4F)c3cc2O1]

A solution of crude (±)-9 (912 mg) in THF (11.9 mL) was treated with Et$_3$N (931 mL, 6.68 mmol), cooled to 0° C., and treated dropwise with MsCl (462 μL, 5.97 mmol). The mixture was stirred at 0° C. for 15 min, and then at 23° C. for 21 h. The mixture was cooled to 0° C., treated dropwise with sat. aq. NaHCO$_3$ (120 mL), and extracted with DCM (3×120 mL). The combined organics were washed with water (100 mL), brine (100 mL), dried (Na$_2$SO$_4$), filtered, and evaporated. FC (DCM/EtOAc 9:1→4:6) afforded the title compound (±)-10 (112 mg, 19% over two steps) as an off-white, friable foam.

$^1$H NMR (500 MHz, CDCl$_3$): δ=8.68 (s, 1H), 8.60 (ddd, J=8.6, 7.3, 1.5 Hz, 1H), 7.44 (br, 1H), 7.42 (s, 1H), 7.35 (s, 1H), 7.29 (ddd, J=8.1, 6.5, 1.6 Hz, 1H), 7.11 (td, J=8.2, 1.5 Hz, 1H), 4.60-4.48 (m, 3H), 4.44 (dd, J=11.6, 2.4 Hz, 1H), 4.12 (dd, J=11.6, 7.6 Hz, 1H), 3.08 (s, 3H), 2.24-2.10 ppm (m, 2H). $^{13}$C NMR (126 MHz, CDCl$_3$): δ=156.03, 153.39, 150.31 (d, J$_{CF}$=242.9 Hz), 149.11, 146.54, 143.60, 128.47 (d, J$_{CF}$=10.5 Hz), 127.52, 125.32 (d, J$_{CF}$=4.6 Hz), 122.02, 114.30, 110.68, 108.66 (d, J$_{CF}$=19.2 Hz), 106.32, 69.78, 67.82, 65.05, 37.75, 30.90 ppm. HRMS (ESI): m/z [M+H]$^+$ calcd for C$_{19}$H$_{18}$BrFN$_3$O$_5$S$^+$, 498.0129; found, 498.0144.

(±)-N-(3-Bromo-2-fluorophenyl)-7-[(morpholin-4-yl)methyl]-7,8-dihydro[1,4]dioxino[2,3-g]quinazolin-4-amine ((±)-JGK063)

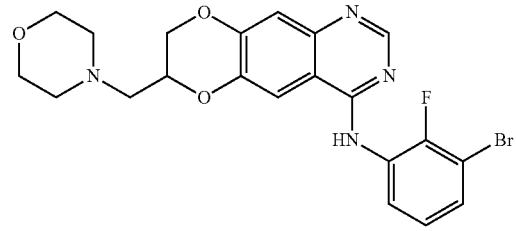 [SMILES: Fc1c(Br)cccc1Nc1ncnc2cc3c(cc12)OC(CN1CCOCC1)CO3]

Following general procedure GP-1, compound (±)-JGK063 was prepared from (±)-6 (20 mg, 0.04 mmol) and morpholine (18 μL, 0.21 mmol) in DMF (826 μL). PTLC (DCM/EtOAc 1:9) afforded (±)-JGK063 (15 mg, 76%) as an off-white, friable foam.

$^1$H NMR (500 MHz, CDCl$_3$): δ=8.67 (s, 1H), 8.63 (ddd, J=8.6, 7.3, 1.5 Hz, 1H), 7.38 (s, 1H), 7.37 (br, 1H), 7.31 (s, 1H), 7.27 (ddd, J=8.0, 6.3, 1.5 Hz, 1H), 7.10 (td, J=8.2, 1.5 Hz, 1H), 4.50-4.41 (m, 2H), 4.21-4.12 (m, 1H), 3.75 (t, J=4.7 Hz, 4H), 2.77 (dd, J=13.4, 5.9 Hz, 1H), 2.69-2.54 ppm (m, 5H). $^{13}$C NMR (126 MHz, CDCl$_3$): δ=155.89, 153.36, 150.15 (d, J$_{CF}$=242.5 Hz), 149.35, 146.66, 144.02, 128.60

(d, $J_{CF}$=10.4 Hz), 127.27, 125.30 (d, $J_{CF}$=4.6 Hz), 121.80, 114.29, 110.63, 108.58 (d, $J_{CF}$=19.5 Hz), 106.06, 71.61, 67.18, 67.01, 58.94, 54.56 ppm. HRMS (ESI): m/z [M−H]⁻ calcd for $C_{21}H_{19}BrFN_4O_3^-$, 473.0630; found, 473.0630.

(±)-N-(3-Bromo-2-fluorophenyl)-7-[2-(morpholin-4-yl)ethyl]-7,8-dihydro[1,4]dioxino[2,3-g]quinazolin-4-amine ((±)-JGK064)

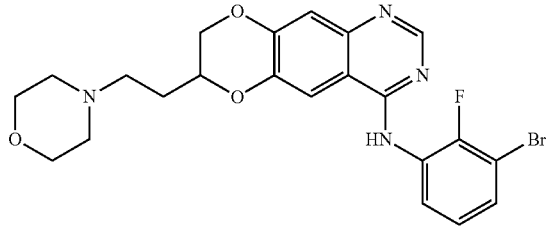 [SMILES: Fc1c(Br)cccc1Nc1ncnc2cc3c(cc12)OC(CCN1CCOCC1)CO3]

Following general procedure GP-1, compound (±)-JGK064 was prepared from (±)-10 (35 mg, 0.07 mmol) and morpholine (31 μL, 0.35 mmol) in DMF (1.4 mL). PTLC (EtOAc, 0.5% acetonitrile, 1.5% aq. NH₄OH) followed by another PTLC (EtOAc) afforded (±)-JGK064 (25 mg, 73%) as an off-white, friable foam.

¹H NMR (500 MHz, CDCl₃): δ=8.68 (s, 1H), 8.65 (ddd, J=8.3, 7.4, 1.5 Hz, 1H), 7.39 (s, 1H), 7.36 (br, 1H), 7.28 (s, 1H), 7.30-7.25 (m, 1H), 7.11 (td, J=8.2, 1.5 Hz, 1H), 4.44 (dd, J=11.3, 2.3 Hz, 1H), 4.43-4.37 (m, 1H), 4.10 (dd, J=11.3, 7.7 Hz, 1H), 3.73 (t, J=4.7 Hz, 4H), 2.62 (ddt, J=12.5, 8.4, 3.9 Hz, 2H), 2.57-2.42 (m, 4H), 2.00-1.82 ppm (m, 2H). ¹³C NMR (126 MHz, CDCl₃): δ=155.86, 153.31, 150.13 (d, $J_{CF}$=242.3 Hz), 149.40, 146.67, 144.33, 128.66 (d, $J_{CF}$=10.4 Hz), 127.22, 125.33 (d, $J_{CF}$=4.6 Hz), 121.75, 114.21, 110.63, 108.58 (d, $J_{CF}$=19.2 Hz), 105.87, 72.20, 68.33, 67.06, 54.23, 53.86, 28.15 ppm. HRMS (ESI): m/z [M+H]⁺ calcd for $C_{22}H_{23}BrFN_4O_3^+$, 489.0932; found, 489.0935.

(±)-N-(3-Bromo-2-fluorophenyl)-7-[(piperidin-1-yl)methyl]-7,8-dihydro[1,4]dioxino[2,3-g]quinazolin-4-amine ((±)-JGK065)

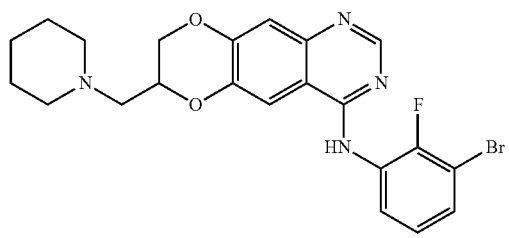 [SMILES: Fc1c(Br)cccc1Nc1ncnc2cc3c(cc12)OC(CN1CCCCC1)CO3]

Following general procedure GP-1, compound (±)-JGK065 was prepared from (±)-6 (40 mg, 0.08 mmol) and piperidine (41 μL, 0.41 mmol) in DMF (1.65 mL). PTLC (EtOAc) afforded (±)-JGK065 (24 mg, 61%) as an off-white, friable foam.

¹H NMR (500 MHz, CDCl₃): δ=8.66 (s, 1H), 8.63 (ddd, J=8.7, 7.3, 1.5 Hz, 1H), 7.369 (s, 1H), 7.368 (br, 1H), 7.30 (s, 1H), 7.26 (ddd, J=8.1, 6.5, 1.5 Hz, 1H), 7.09 (td, J=8.2, 1.5 Hz, 1H), 4.46 (dd, J=11.3, 2.3 Hz, 1H), 4.43 (ddd, J=8.3, 5.8, 2.0 Hz, 1H), 4.12 (dd, J=11.2, 7.5 Hz, 1H), 2.71 (dd, J=13.3, 5.9 Hz, 1H), 2.58 (dd, J=13.4, 6.2 Hz, 1H), 2.59-2.42 (m, 4H), 1.65-1.57 (m, 4H), 1.49-1.41 ppm (m, 2H). ¹³C NMR (126 MHz, CDCl₃): δ=155.86, 153.26, 150.12 (d, $J_{CF}$=242.6 Hz), 149.49, 146.62, 144.23, 128.65 (d, $J_{CF}$=10.3 Hz), 127.18, 125.27 (d, $J_{CF}$=4.5 Hz), 121.76, 114.16, 110.57, 108.56 (d, $J_{CF}$=19.4 Hz), 106.00, 71.87, 67.46, 59.34, 55.59, 26.07, 24.20 ppm. HRMS (ESI): [M+H]⁺ calcd for $C_{22}H_{23}BrFN_4O_2^+$, 473.0983; found, 473.0991.

(±)-N-(3-Bromo-2-fluorophenyl)-7-[(dimethylamino)methyl]-7,8-dihydro[1,4]dioxino[2,3-g]quinazolin-4-amine ((±)-JGK066)

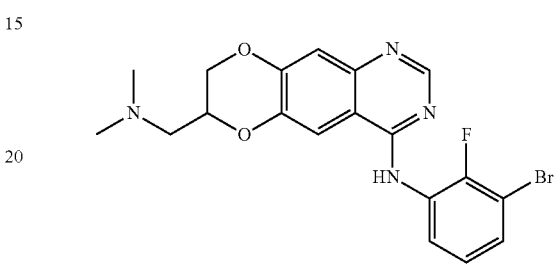

Following general procedure GP-1, compound (±)-JGK066 was prepared from (±)-6 (45 mg, 0.09 mmol) and a 2 M solution of Me₂NH in THF (232 μL, 0.46 mmol) in DMF (1.85 mL). PTLC (EtOAc, 0.5% acetonitrile, 1.5% aq. NH₄OH) afforded (±)-JGK066 (39 mg, 97%) as an off-white, friable foam.

¹H NMR (500 MHz, CDCl₃): δ=8.680 (s, 1H), 8.675 (ddd, J=8.2, 7.5, 1.5 Hz, 1H), 7.39 (s, 1H), 7.38 (s, 1H), 7.37 (br, 1H), 7.27 (ddd, J=8.0, 6.4, 1.5 Hz, 1H), 7.10 (d, J=1.6 Hz, 1H), 4.46-4.41 (m, 1H), 4.45 (dd, J=11.8, 2.3 Hz, 1H), 4.12 (dd, J=11.9, 8.1 Hz, 1H), 2.73 (dd, J=13.2, 7.1 Hz, 1H), 2.55 (dd, J=13.1, 5.0 Hz, 1H), 2.38 ppm (s, 6H). ¹³C NMR (126 MHz, CDCl₃): δ=155.89, 153.34, 150.07 (d, $J_{CF}$=242.3 Hz), 149.38, 146.67, 144.06, 128.70 (d, $J_{CF}$=10.4 Hz), 127.16, 125.29 (d, $J_{CF}$=4.7 Hz), 121.65, 114.27, 110.67, 108.56 (d, $J_{CF}$=19.4 Hz), 106.15, 71.70, 67.20, 59.78, 46.41 ppm. HRMS (ESI): m/z [M+H]⁺ calcd for $C_{19}H_{19}BrFN_4O_2^+$, 433.0670; found, 433.0677.

(±)-N-(3-Bromo-2-fluorophenyl)-7-[(pyrrolidin-1-yl)methyl]-7,8-dihydro[1,4]dioxino[2,3-g]quinazolin-4-amine ((±)-JGK067)

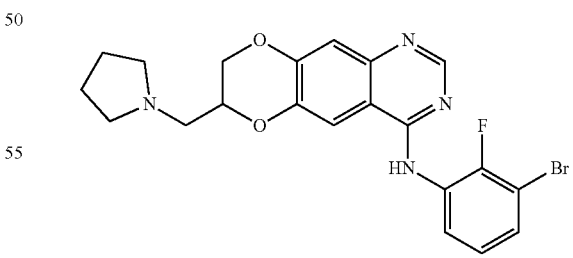

Following general procedure GP-1, compound (±)-JGK067 was prepared from (±)-6 (35 mg, 0.07 mmol) and pyrrolidine (30 μL, 0.36 mmol) in DMF (1.45 mL). PTLC (EtOAc, 1.5% iPrOH, 1.5% aq. NH₄OH) afforded (±)-JGK067 (31 mg, 93%) as an off-white, friable foam.

¹H NMR (500 MHz, CDCl₃): δ=8.68 (s, 1H), 8.67 (ddd, J=8.7, 7.5, 1.6 Hz, 2H), 7.39 (s, 1H), 7.36 (br, 1H), 7.35 (s, 1H), 7.27 (ddd, J=8.0, 6.4, 1.5 Hz, 2H), 7.10 (td, J=8.2, 1.5 Hz, 1H), 4.49-4.42 (m, 1H), 4.48 (dd, J=11.6, 2.0 Hz, 1H), 4.15 (dd, J=11.7, 8.0 Hz, 1H), 2.88 (dd, J=12.9, 6.5 Hz, 1H), 2.80 (dd, J=12.6, 5.5 Hz, 1H), 2.72-2.60 (m, 4H), 1.90-1.79 ppm (m, 4H). $^{13}$C NMR (126 MHz, CDCl$_3$): δ=155.87, 153.32, 150.09 (d, $J_{CF}$=242.6 Hz), 149.45, 146.68, 144.18, 128.71 (d, $J_{CF}$=10.3 Hz), 127.15, 125.30 (d, $J_{CF}$=4.7 Hz), 121.67, 114.26, 110.65, 108.56 (d, $J_{CF}$=19.4 Hz), 106.06, 72.73, 67.35, 56.57, 55.15, 23.75 ppm. HRMS (ESI): m/z [M+H]$^+$ calcd for $C_{21}H_{21}BrFN_4O_2^+$, 459.0826; found, 459.0845.

(±)-N-(3-Bromo-2-fluorophenyl)-7-[(4-methylpiperazin-1-yl)methyl]-7,8-dihydro[1,4]dioxino[2,3-g]quinazolin-4-amine ((±)-JGK068)

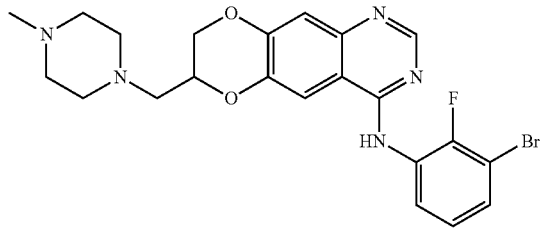

Following general procedure GP-1, compound (±)-JGK068 was prepared from (±)-6 (35 mg, 0.07 mmol) and 1-methylpiperazine (40 µL, 0.36 mmol) in DMF (1.45 mL). PTLC (EtOAc/iPrOH 85:15, 1.5% aq. NH$_4$OH) afforded (±)-JGK068 (29 mg, 82%) as an off-white, friable foam.

$^1$H NMR (500 MHz, CDCl$_3$): δ=8.68 (s, 1H), 8.64 (ddd, J=8.3, 7.3, 1.5 Hz, 1H), 7.39 (s, 1H), 7.36 (br d, J=3.8 Hz, 1H), 7.32 (s, 1H), 7.27 (ddd, J=8.0, 6.5, 1.6 Hz, 1H), 7.10 (td, J=8.2, 1.5 Hz, 1H), 4.48-4.41 (m, 2H), 4.15 (dd, J=11.5, 8.6 Hz, 1H), 2.78 (dd, J=13.4, 6.0 Hz, 1H), 2.661 (dd, J=13.4, 5.8 Hz, 1H), 2.656 (br, 4H), 2.51 (br, 4H), 2.32 ppm (s, 3H). $^{13}$C NMR (126 MHz, CDCl$_3$): δ=155.89, 153.35, 150.15 (d, $J_{CF}$=242.6 Hz), 149.40, 146.69, 144.11, 128.64 (d, $J_{CF}$=10.3 Hz), 127.24, 125.30 (d, $J_{CF}$=4.7 Hz), 121.78, 114.27, 110.63, 108.59 (d, $J_{CF}$=19.2 Hz), 106.07, 71.80, 67.27, 58.43, 55.10, 53.96, 46.06 ppm. HRMS (ESI): m/z [M+H]$^+$ calcd for $C_{22}H_{24}BrFN_5O_2^+$, 488.1092; found, 488.1109.

(±)-N-(3-Bromo-2-fluorophenyl)-7-[2-(dimethylamino)ethyl]-7,8-dihydro[1,4]dioxino[2,3-g]quinazolin-4-amine ((±)-JGK069)

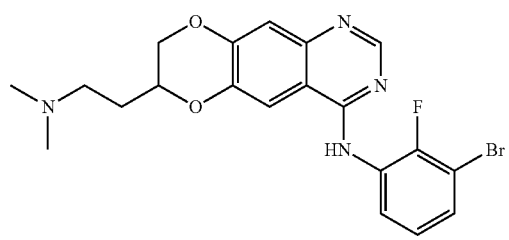 [SMILES: CN(C)CCC1COc2cc3ncnc(Nc4cccc(Br)c4F)c3cc2O1]

Following general procedure GP-1, compound (±)-JGK069 was prepared from (±)-10 (32 mg, 0.06 mmol) and a 2 M solution of Me$_2$NH in THF (161 µL, 0.32 mmol) in DMF (1.3 mL). PTLC (EtOAc, 5% iPrOH, 1.5% aq. NH$_4$OH) afforded (±)-JGK069 (19 mg, 66%) as an off-white friable foam.

$^1$H NMR (500 MHz, CDCl$_3$): δ=8.67 (s, 1H), 8.63 (ddd, J=8.7, 7.4, 1.6 Hz, 1H), 7.373 (br, 1H), 7.371 (s, 1H), 7.28 (s, 1H), 7.28-7.24 (m, 1H), 7.10 (td, J=8.2, 1.5 Hz, 1H), 4.42 (dd, J=11.4, 2.3 Hz, 1H), 4.38 (tdd, J=7.7, 5.1, 2.3 Hz, 1H), 4.08 (dd, J=11.3, 7.8 Hz, 1H), 2.56 (t, J=7.2 Hz, 2H), 2.29 (s, 6H), 1.93 (dq, J=14.2, 7.4 Hz, 1H), 1.84 ppm (dtd, J=14.2, 7.5, 5.1 Hz, 1H). $^{13}$C NMR (126 MHz, CDCl$_3$): δ=155.86, 153.26, 150.14 (d, $J_{CF}$=242.4 Hz), 149.42, 146.65, 144.36, 128.67 (d, $J_{CF}$=10.5 Hz), 127.18, 125.30 (d, $J_{CF}$=4.7 Hz), 121.77, 114.14, 110.60, 108.56 (d, $J_{CF}$=19.2 Hz), 105.88, 72.19, 68.34, 55.06, 45.58, 29.16 ppm. HRMS (ESI): m/z [M+H]$^+$ calcd for $C_{20}H_{21}BrFN_4O_2^+$, 447.0826; found, 447.0820.

(±)-N-(3-Bromo-2-fluorophenyl)-7-[2-(4-methylpiperazin-1-yl)ethyl]-7,8-dihydro[1,4]dioxino[2,3-g]quinazolin-4-amine ((±)-JGK070)

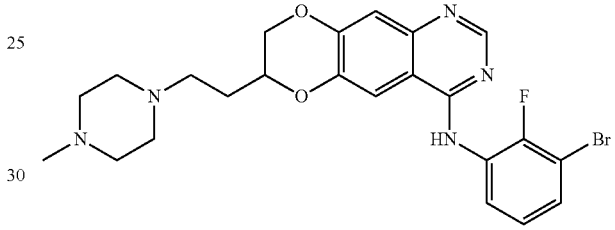

Following general procedure GP-1, compound (±)-JGK070 was prepared from (±)-10 (32 mg, 0.06 mmol) and 1-methylpiperazine (36 µL, 0.32 mmol) in DMF (1.3 mL). PTLC (EtOAc/iPrOH 8:2, 1.5% aq. NH$_4$OH) afforded (±)-JGK070 (21 mg, 65%) as an off-white friable foam.

$^1$H NMR (500 MHz, CDCl$_3$): δ=8.66 (s, 1H), 8.62 (ddd, J=8.5, 7.3, 1.5 Hz, 1H), 7.373 (br, 1H), 7.367 (s, 1H), 7.29-7.24 (m, 1H), 7.28 (s, 1H), 7.09 (td, J=8.2, 1.5 Hz, 1H), 4.43 (dd, J=11.4, 2.3 Hz, 1H), 4.37 (tdd, J=7.7, 5.4, 2.3 Hz, 1H), 4.08 (dd, J=11.4, 7.9 Hz, 1H), 2.68-2.54 (m, 2H), 2.50 (br, 8H), 2.30 (s, 3H), 1.94 (dtd, J=13.6, 7.5, 6.0 Hz, 1H), 1.86 ppm (dtd, J=14.2, 7.3, 5.3 Hz, 1H). $^{13}$C NMR (126 MHz, CDCl$_3$): δ=155.86, 153.27, 150.16 (d, $J_{CF}$=242.5 Hz), 149.41, 146.64, 144.37, 128.64 (d, $J_{CF}$=10.3 Hz), 127.22, 125.28 (d, $J_{CF}$=4.6 Hz), 121.81, 114.13, 110.60, 108.57 (d, $J_{CF}$=19.4 Hz), 105.88, 72.38, 68.36, 55.20, 53.77, 53.25, 46.11, 28.50 ppm. HRMS (ESI): m/z [M+H]$^+$ calcd for $C_{23}H_{26}BrFN_5O_2^+$, 502.1248; found, 502.1261.

5-Fluoro-2,3-dihydro-1,4-benzodioxine (11)

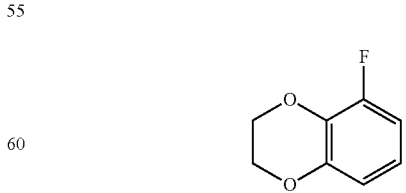

A mixture of 3-fluorobenzene-1,2-diol (7233 mg, 56.5 mmol) in DMF (113 mL) was treated with K$_2$CO$_3$ (19514 mg, 141 mmol), stirred for 10 min at 23° C., and treated with 1-bromo-2-chloroethane (9.4 mL, 113 mmol). The mixture was stirred at 23° C. for 1 h, and then at 95° C. for 16 h. The mixture was cooled to 23° C., diluted with water (150 mL), and extracted with EtOAc (3×150 mL). The combined organics were washed with water (90 mL), brine (90 mL), dried (Na$_2$SO$_4$), filtered, and evaporated. FC (hexanes/EtOAc 30:1→10:1) afforded the title compound 11 (7973 mg, 92%) as a clear, colorless oil.

$^1$H NMR (400 MHz, CDCl$_3$): δ=6.78-6.63 (m, 3H), 4.34-4.26 ppm (m, 4H). $^{13}$C NMR (101 MHz, CDCl$_3$): δ=152.05 (d, J$_{CF}$=244.3 Hz), 145.27 (d, J$_{CF}$=3.8 Hz), 132.78 (d, J$_{CF}$=13.9 Hz), 120.02 (d, J$_{CF}$=8.9 Hz), 112.74 (d, J$_{CF}$=3.1 Hz), 108.52 (d, J$_{CF}$=18.1 Hz), 64.50, 64.45 ppm. HRMS (DART): m/z [M]$^{·+}$ calcd for C$_8$H$_7$FO$_2$$^{·+}$, 154.0425; found, 154.0420.

6-Bromo-5-fluoro-2,3-dihydro-1,4-benzodioxine (12)

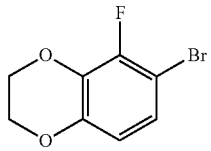 [SMILES: Fc1c(Br)ccc2c1OCCO2]

A solution of 11 (7812 mg, 50.7 mmol) in MeOH (101 mL) was treated with NBS (9022 mg, 50.7 mmol), and heated at 70° C. for 30 min. The mixture was cooled to 23° C., and concentrated. The residue was dissolved in DCM (700 mL), washed with water (300 mL), dried (MgSO$_4$), filtered, and evaporated. FC (hexanes/EtOAc 30:1→20:1) followed by drying under HV at 100° C. to remove any remaining starting material, afforded the title compound 12 (8807 mg, 75%, containing about 15% of the regioisomer) as a clear, colorless oil, which solidified in the freezer to give an off-white solid.

$^1$H NMR (400 MHz, CDCl$_3$): δ=6.96 (dd, J=9.0, 7.0 Hz, 1H), 6.59 (dd, J=9.0, 2.0 Hz, 1H), 4.35-4.24 ppm (m, 4H). $^{13}$C NMR (101 MHz, CDCl$_3$): δ=148.87 (d, J$_{CF}$=245.1 Hz), 144.53 (d, J$_{CF}$=3.5 Hz), 133.81 (d, J$_{CF}$=14.6 Hz), 123.31, 113.39 (d, J$_{CF}$=3.6 Hz), 109.17 (d, J$_{CF}$=19.3 Hz), 64.51, 64.34 ppm. HRMS (DART): m/z [M]$^{·+}$ calcd for C$_8$H$_6$BrFO$_2$$^{·+}$, 231.9530; found, 231.9525.

5-Fluoro-2,3-dihydro-1,4-benzodioxine-6-carboxylic acid (13)

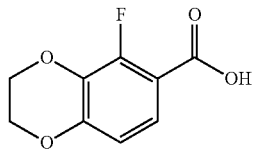 [SMILES: O=C(O)c1ccc2c(c1F)OCCO2]

A mixture of 12 (7.0 g, 30.0 mmol) in THF (108 mL) was cooled to −78° C., and treated dropwise with a 2.5 M solution of nBuLi in hexanes (12.02 mL, 30.0 mmol) during 10 min. The mixture was stirred at −78° C. for 30 min, and then transferred via cannula onto crushed dry ice (rinsed the cannula with 10 mL of THF). The mixture was allowed to warm to 23° C., and concentrated. Water (200 mL) and 1 M NaOH (50 mL) were added to the residue, and the aq. phase was extracted with Et$_2$O (3×60 mL). The aq. phase was acidified with 6 M HCl (15 mL), and extracted with DCM (3×150 mL). The combined organics were washed with brine (150 mL), dried (MgSO$_4$), filtered, and evaporated. FC (hexanes/EtOAc 7:3→3:7) afforded the title compound 13 (3591 mg, 60%) as a white solid.

$^1$H NMR (400 MHz, DMSO-d$_6$): δ=12.90 (br, 1H), 7.33 (dd, J=8.9, 7.7 Hz, 1H), 6.78 (dd, J=8.9, 1.7 Hz, 1H), 4.39-4.29 ppm (m, 4H). $^{13}$C NMR (101 MHz, DMSO-d$_6$): δ=164.65 (d, J$_{CF}$=3.0 Hz), 151.21 (d, J$_{CF}$=257.5 Hz), 148.50 (d, J$_{CF}$=4.4 Hz), 132.68 (d, J$_{CF}$=13.6 Hz), 122.44 (d, J$_{CF}$=1.4 Hz), 112.12 (d, J$_{CF}$=3.4 Hz), 111.97 (d, J$_{CF}$=7.3 Hz), 64.42, 63.91 ppm. HRMS (DART): m/z [M−H]$^-$ calcd for C$_9$H$_6$FO$_4$$^-$, 197.0256; found, 197.0250.

Ethyl (5-fluoro-2,3-dihydro-1,4-benzodioxin-6-yl)carbamate (14)

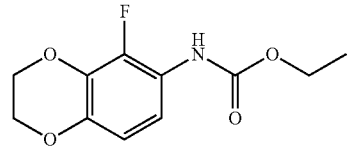 [SMILES: CCOC(=O)Nc1ccc2c(c1F)OCCO2]

A mixture of 13 (650 mg, 3.28 mmol) in toluene (13.1 mL) was treated with Et$_3$N (1.4 mL, 9.84 mmol), and at 10° C. with DPPA (780 μL, 3.62 mmol). The mixture was stirred at 23° C. for 30 min, then at 85° C. for 1.5 h. The mixture was cooled to 23° C., treated with EtOH (5 mL), stirred for 1.5 h at 23° C., and concentrated. The residue was dissolved in Et$_2$O (150 mL), washed with sat. aq. NaHCO$_3$ (40 mL), water (40 mL), brine (40 mL), dried (MgSO$_4$), filtered, and evaporated. FC (hexanes/DCM 7:3→1:9) afforded the title compound 14 (512 mg, 65%) as a white solid.

$^1$H NMR (500 MHz, CDCl$_3$): δ=7.42 (br, 1H), 6.64 (dd, J=9.2, 2.2 Hz, 1H), 6.56 (br, 1H), 4.32-4.24 (m, 4H), 4.22 (q, J=7.1 Hz, 2H), 1.31 ppm (t, J=7.1 Hz, 3H). $^{13}$C NMR (126 MHz, CDCl$_3$): δ=153.80, 142.61 (d, J$_{CF}$=246.0 Hz), 140.82, 132.66 (d, J$_{CF}$=12.4 Hz), 120.36 (d, J$_{CF}$=6.9 Hz), 112.36, 111.81 (d, J$_{CF}$=3.7 Hz), 64.72, 64.29, 61.61, 14.66 ppm. HRMS (DART): m/z [M+H]$^+$ calcd for C$_{11}$H$_{13}$FNO$_4$$^+$, 242.0823; found, 242.0816.

10-Fluoro-7,8-dihydro[1,4]dioxino[2,3-g]quinazoline (15)

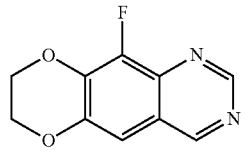

A mixture of 14 (450 mg, 1.87 mmol) and HMTA (263 mg, 1.87 mmol) in TFA (5.7 mL) was irradiated in the microwave at 110° C. for 10 min. The mixture was cooled to 23° C., diluted with water (60 mL), treated with 6 M NaOH (12 mL), and extracted with DCM (3×60 mL). The combined organics were washed with water (50 mL), brine (50 mL), dried (Na$_2$SO$_4$), filtered, and evaporated to give a foamy, yellow oil.

A mixture of the oil in 10% KOH in dioxane/water 1:1 (15.5 mL) was treated with [K$_3$Fe(CN)$_6$] (614 mg, 1.87 mmol), and irradiated in the microwave at 100° C. for 10 min. This procedure was repeated a total of four times (4 cycles of addition of 1 equiv of potassium ferricyanide followed by microwave irradiation). The resulting mixture was diluted with water (160 mL), and extracted with DCM (3×120 mL). The combined organics were washed with water (100 mL), brine (100 mL), dried (Na$_2$SO$_4$), filtered, and evaporated to afford the title compound 15 (330 mg, 86%) as a yellow solid, which was used in the next step without any further purification.

$^1$H NMR (500 MHz, CDCl$_3$): δ=9.21 (br, 1H), 9.19 (s, 1H), 7.18 (d, J=2.0 Hz, 1H), 4.53-4.41 ppm (m, 4H). $^{13}$C NMR (126 MHz, CDCl$_3$): δ=158.06 (d, J$_{CF}$=2.9 Hz), 153.81 (d, J$_{CF}$=1.8 Hz), 145.76 (d, J$_{CF}$=2.9 Hz), 144.40 (d, J$_{CF}$=256.1 Hz), 138.56 (d, J$_{CF}$=11.0 Hz), 136.73 (d, J$_{CF}$=10.1 Hz), 119.81 (d, J$_{CF}$=2.7 Hz), 106.55 (d, J$_{CF}$=4.3 Hz), 64.78, 64.34 ppm. HRMS (DART): m/z [M+H]$^+$ calcd for C$_{10}$H$_8$FN$_2$O$_2$$^+$, 207.0564; found, 207.0563.

10-Fluoro-7,8-dihydro[1,4]dioxino[2,3-g]quinazolin-4(3H)-one (16)

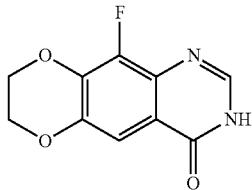 [SMILES: O=c1[nH]cnc2c(F)c3c(cc12)OCCO3]

A solution of 15 (306 mg, 1.48 mmol) in AcOH (1 mL) was treated dropwise with a 0.833 M solution of CAN in water (7.12 mL, 5.94 mmol), and stirred at 23° C. for 15 min. The white precipitate was collected by filtration, and washed with water (2×2 mL), acetonitrile (2×2 mL), DCM (2 mL), and Et$_2$O (2 mL) to afford a first batch of the title compound. The aq. filtrate was neutralized to pH ~7 with 1 M NaOH, and the white precipitate was collected as before by filtration, followed by washings to afford a second batch of the title compound 16 (81 mg, 25%) as a white solid.

$^1$H NMR (500 MHz, DMSO-d$_6$): δ=12.19 (br, 1H), 7.98 (d, J=3.3 Hz, 1H), 7.32 (s, 1H), 4.52-4.28 ppm (m, 4H). $^{13}$C NMR (126 MHz, DMSO-d$_6$): δ=159.31, 144.58 (d, J$_{CF}$=251.8 Hz), 144.28, 143.80 (d, J$_{CF}$=3.4 Hz), 137.86 (d, J$_{CF}$=11.1 Hz), 132.94 (d, J$_{CF}$=8.9 Hz), 115.75, 106.62 (d, J$_{CF}$=3.7 Hz), 64.57, 64.02 ppm. HRMS (DART): m/z [M+H]$^+$ calcd for C$_{10}$H$_8$FN$_2$O$_3$$^+$, 223.0513; found, 223.0503.

4-Chloro-10-fluoro-7,8-dihydro[1,4]dioxino[2,3-g]quinazoline (17)

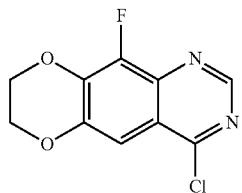 [SMILES: Fc1c2c(cc3c(Cl)ncnc13)OCCO2]

A stirred suspension of 16 (92 mg, 0.41 mmol) in toluene (1.2 mL) was treated with DIPEA (220 μL, 1.26 mmol), followed by dropwise addition of POCl$_3$ (103 μL, 1.12 mmol) at 10° C. The mixture was stirred at 23° C. for 1 h, then at 90° C. for 5 h, and concentrated. The residue was treated with sat. aq. NaHCO$_3$ (10 mL) at 0° C. for 5 min, diluted with water (5 mL), and extracted with DCM (3×7 mL). The combined organics were washed with half-sat. aq. NaHCO$_3$ (7 mL), brine (7 mL), dried (Na$_2$SO$_4$), filtered, and evaporated to afford the title compound 17 (51 mg, 51%) as a light-brown solid, which was used in the next step without any further purification.

$^1$H NMR (500 MHz, CDCl$_3$): δ=8.90 (s, 1H), 7.51 (d, J=2.0 Hz, 1H), 4.55-4.43 ppm (m, 4H). $^{13}$C NMR (126 MHz, CDCl$_3$): δ=160.48 (d, J$_{CF}$=4.3 Hz), 152.31, 146.29 (d, J$_{CF}$=3.3 Hz), 144.63 (d, J$_{CF}$=256.2 Hz), 138.95 (d, J$_{CF}$=11.3 Hz), 137.68 (d, J$_{CF}$=10.2 Hz), 118.56 (d, J$_{CF}$=2.4 Hz), 105.82 (d, J$_{CF}$=4.2 Hz), 64.81, 64.41 ppm. HRMS (DART): m/z [M+H]$^+$ calcd for C$_{10}$H$_7$ClFN$_2$O$_2$$^+$, 241.0175; found, 241.0174.

5-Fluoro-7-nitro-2,3-dihydro-1,4-benzodioxine-6-carboxylic acid (18)

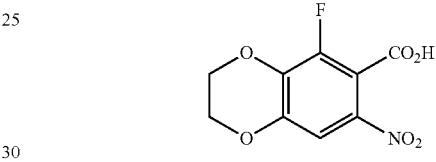

A mixture of 13 (1500 mg, 7.57 mmol) in AcOH (7.5 mL) was treated dropwise with H$_2$SO$_4$ (2.02 mL) at 10° C. The vigorously stirred mixture was treated dropwise with 65% HNO$_3$ (2.6 mL) at 0° C. during 10 min. The resulting mixture was stirred at 0° C. for 30 min, and then at 23° C. for 16 h. The mixture was poured into ice-water (40 mL), and the white precipitate was collected by filtration (washings with cold water, 40 mL), and dried in a desiccator to afford the title compound 18 (1280 mg, 70%) as a white solid.

$^1$H NMR (500 MHz, DMSO-d$_6$): δ=14.09 (br, 1H), 7.62 (d, J=1.7 Hz, 1H), 4.52-4.40 ppm (m, 4H). $^{13}$C NMR (126 MHz, DMSO-d$_6$): δ=162.71, 147.16 (d, J$_{CF}$=248.7 Hz), 144.72 (d, J$_{CF}$=5.1 Hz), 138.15 (d, J$_{CF}$=13.7 Hz), 137.10 (d, J$_{CF}$=6.6 Hz), 113.44 (d, J$_{CF}$=20.3 Hz), 109.52 (d, J$_{CF}$=2.3 Hz), 64.97, 64.48 ppm. HRMS (DART): m/z [M–H]$^-$ calcd for C$_9$H$_5$FNO$_6$$^-$, 242.0106; found, 242.0124.

7-Amino-5-fluoro-2,3-dihydro-1,4-benzodioxine-6-carboxylic acid (19)

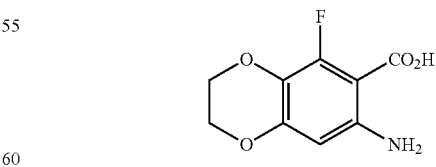

A mixture of 18 (500 mg, 2.06 mmol) and 5% Pd/C (223 mg, 0.10 mmol) in MeOH (21 mL) was stirred under an atmosphere of H$_2$ at 23° C. for 13.5 h. The mixture was filtered through Celite (washings with EtOH), and evaporated to give the title compound 19 (418 mg, 95%) as a grey solid, which did not seem to be very stable.

¹H NMR (500 MHz, DMSO-d₆): δ=8.35 (br, 2H), 6.04 (d, J=1.9 Hz, 1H), 4.29-4.24 (m, 2H), 4.19-4.14 ppm (m, 2H). ¹³C NMR (126 MHz, DMSO-d₆): δ=167.36 (d, $J_{CF}$=2.9 Hz), 151.36 (d, $J_{CF}$=252.0 Hz), 148.86 (d, $J_{CF}$=7.0 Hz), 145.81 (d, $J_{CF}$=5.7 Hz), 122.88 (d, $J_{CF}$=15.4 Hz), 97.19 (d, $J_{CF}$=2.9 Hz), 95.37 (d, $J_{CF}$=10.9 Hz), 64.95, 63.58 ppm. HRMS (DART): m/z [M+H]⁺ calcd for $C_9H_9FNO_4^+$, 214.0510; found, 214.0508.

5-Fluoro-7,8-dihydro[1,4]dioxino[2,3-g]quinazolin-4(3H)-one (20)

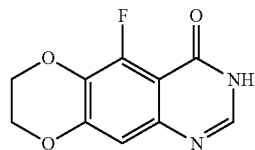

A mixture of 19 (417 mg, 1.96 mmol) in formamide (2.3 mL, 58.7 mmol) was stirred at 120-125° C. for 16 h. The mixture was cooled to 0° C., and treated with water (4 mL), stirred for 30 min, diluted with water (4 mL), and filtered. The residue was washed with cold water (3×5 mL), and dried over Drierite under HV to afford the title compound 20 (249 mg, 57%) as an off-white solid.

¹H NMR (400 MHz, DMSO-d₆): δ=12.00 (br, 1H), 7.90 (d, J=3.6 Hz, 1H), 6.93 (d, J=1.9 Hz, 1H), 4.45-4.35 ppm (m, 4H). ¹³C NMR (126 MHz, DMSO-d₆): δ=157.64 (d, $J_{CF}$=3.0 Hz), 149.70 (d, $J_{CF}$=6.0 Hz), 148.45 (d, $J_{CF}$=261.3 Hz), 144.60, 142.99, 131.47 (d, $J_{CF}$=12.7 Hz), 108.76 (d, $J_{CF}$=3.5 Hz), 106.38 (d, $J_{CF}$=3.8 Hz), 64.69, 63.98 ppm. HRMS (DART): m/z [M+H]⁺ calcd for $C_{10}H_8FN_2O_3^+$, 223.0513; found, 223.0510.

4-Chloro-5-fluoro-7,8-dihydro[1,4]dioxino[2,3-g]quinazoline (21)

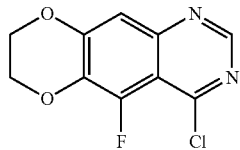 [SMILES: Fc1c2c(cc3ncnc(Cl)c13)OCCO2]

A stirred suspension of 20 (90 mg, 0.41 mmol) in toluene (1.2 mL) was treated with DIPEA (215 μL, 1.24 mmol), followed by dropwise addition of POCl₃ (100 μL, 1.09 mmol) at 10° C. The mixture was stirred at 23° C. for 1 h, then at 88° C. for 5 h, and concentrated. The residue was treated with sat. aq. NaHCO₃ (10 mL) at 0° C., diluted with water (5 mL), and extracted with DCM (3×7 mL). The combined organics were washed with half-sat. aq. NaHCO₃ (7 mL), brine (7 mL), dried (Na₂SO₄), filtered, and evaporated to afford the title compound 21 (96 mg, 99%) as a light-orange solid, which was used in the next step without any further purification.

¹H NMR (500 MHz, CDCl₃): δ=8.83 (s, 1H), 7.35 (d, J=2.0 Hz, 1H), 4.51-4.45 ppm (m, 4H). ¹³C NMR (126 MHz, CDCl₃): δ=156.76 (d, $J_{CF}$=4.5 Hz), 152.70 (d, $J_{CF}$=2.3 Hz), 151.66 (d, $J_{CF}$=4.9 Hz), 146.08, 144.51 (d, $J_{CF}$=261.8 Hz), 134.04 (d, $J_{CF}$=14.0 Hz), 110.85 (d, $J_{CF}$=7.7 Hz), 109.43 (d, $J_{CF}$=4.0 Hz), 64.89, 64.37 ppm. HRMS (DART): m/z [M++H]⁺ calcd for $C_{10}H_7ClFN_2O_2^+$, 241.0175; found, 241.0176.

N-(3-Bromo-2-fluorophenyl)-10-fluoro-7,8-dihydro[1,4]dioxino[2,3-g]quinazolin-4-amine (JGK071)

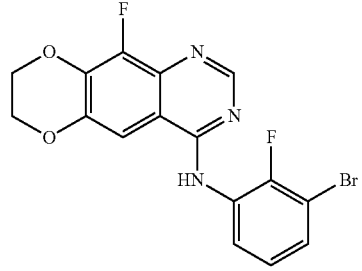 [SMILES: Fc1c(Br)cccc1Nc1ncnc2c(F)c3c(cc12)OCCO3]

Following general procedure GP-2, compound JGK071 was prepared from chloroquinazoline 17 (35 mg, 0.15 mmol) and 3-bromo-2-fluoroaniline. FC (DCM/EtOAc 1:0→8:2) afforded JGK071 (44 mg, 77%) as a white solid.

¹H NMR (500 MHz, DMSO-d₆): δ=9.76 (s, 1H), 8.38 (s, 1H), 7.80 (d, J=1.8 Hz, 1H), 7.62 (ddd, J=8.0, 6.3, 1.6 Hz, 1H), 7.54 (ddd, J=8.5, 7.1, 1.6 Hz, 1H), 7.22 (td, J=8.0, 1.2 Hz, 1H), 4.53-4.40 ppm (m, 4H). ¹³C NMR (126 MHz, DMSO-d₆): δ=156.93 (d, $J_{CF}$=3.7 Hz), 153.44 (d, $J_{CF}$=247.5 Hz), 153.12, 144.04 (d, $J_{CF}$=250.0 Hz), 143.97 (d, $J_{CF}$=3.2 Hz), 137.04 (d, $J_{CF}$=10.9 Hz), 135.62 (d, $J_{CF}$=9.9 Hz), 130.48, 127.89, 127.62 (d, $J_{CF}$=13.1 Hz), 125.51 (d, $J_{CF}$=4.5 Hz), 108.58 (d, $J_{CF}$=23.4 Hz), 108.51, 103.25 (d, $J_{CF}$=3.9 Hz), 64.63, 64.21 ppm. HRMS (DART): m/z [M+H]⁺ calcd for $C_{16}H_{11}BrF_2N_3O_2^+$, 393.9997; found, 393.9999.

N-(3-Bromo-2-fluorophenyl)-5-fluoro-7,8-dihydro[1,4]dioxino[2,3-g]quinazolin-4-amine (JGK072)

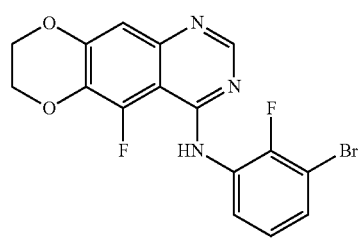 [SMILES: Fc1c(Br)cccc1Nc1ncnc2cc3c(c(F)c12)OCCO3]

Following general procedure GP-2, compound JGK072 was prepared from chloroquinazoline 21 (35 mg, 0.15 mmol) and 3-bromo-2-fluoroaniline. FC (DCM/EtOAc 1:0→8:2) afforded JGK072 (47 mg, 82%) as a white solid.

¹H NMR (500 MHz, CDCl₃): δ=8.67 (ddd, J=8.6, 7.2, 1.5 Hz, 1H), 8.62 (s, 1H), 8.52 (dd, J=19.6, 2.2 Hz, 1H), 7.29 (ddd, J=8.1, 6.4, 1.5 Hz, 1H), 7.23 (d, J=2.0 Hz, 1H), 7.10 (td, J=8.2, 1.6 Hz, 1H), 4.48-4.42 ppm (m, 4H). ¹³C NMR (126 MHz, CDCl₃): δ=155.27 (d, $J_{CF}$=5.2 Hz), 153.90, 150.34 (d, $J_{CF}$=243.9 Hz), 149.93 (d, $J_{CF}$=6.2 Hz), 145.75 (d, $J_{CF}$=250.3 Hz), 144.78, 131.96 (d, $J_{CF}$=15.6 Hz), 128.43 (d, $J_{CF}$=10.4 Hz), 127.71, 125.20 (d, $J_{CF}$=4.7 Hz), 122.48, 109.69 (d, $J_{CF}$=3.3 Hz), 108.63 (d, $J_{CF}$=19.2 Hz), 101.42 (d, $J_{CF}$=7.2 Hz), 64.84, 64.48 ppm. HRMS (DART): m/z [M+H]⁺ calcd for $C_{16}H_{11}BrF_2N_3O_2^+$, 393.9997; found, 393.9996.

Example 17

Brain Penetration of Exemplary Compounds of the Disclosure

Disclosed in table 5 Brain to plasma percentages and unbound ratios of drugs in brain to plasma of indicated drugs in non-tumor bearing mice

TABLE 5

Brain Penetration of Exemplary Compounds of the Disclsoure

| Compound | Brain Penetration (% of plasma) | Kpuu (Avg) |
|---|---|---|
| Erlotinib | 8.50 | 0.051 |
| JGK005 | 64.8 | 0.491 |
| JGK038 | 84.3 | 0.575 |
| JGK028 | 106.2 | 1.037 |
| JGK010 | 106.4 | 1.045 |
| JGK037 | 212.1 | 1.301 |
| JGK042 | 167.6 | 1.033 |
| JGK063 | 72.5 | 0.341 |
| JGK066 | 274.3 | 1.175 |
| JGK068 | 354.5 | 1.184 |
| JGK068S | 378.3 | 1.181 |
| JGK074 | 166.2 | n.d. |
| JGK083S | 231.3 | 0.798 |

Example 18

Preparation of Exemplary Compounds of the JGK Series

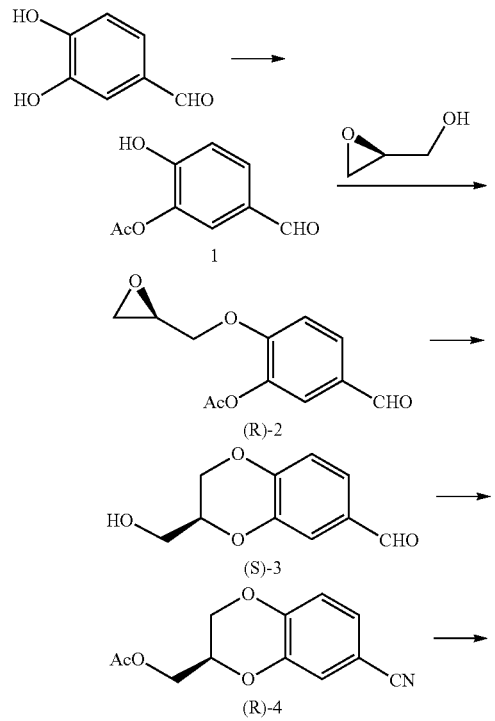

Scheme 1. Synthesis of JGK068S.

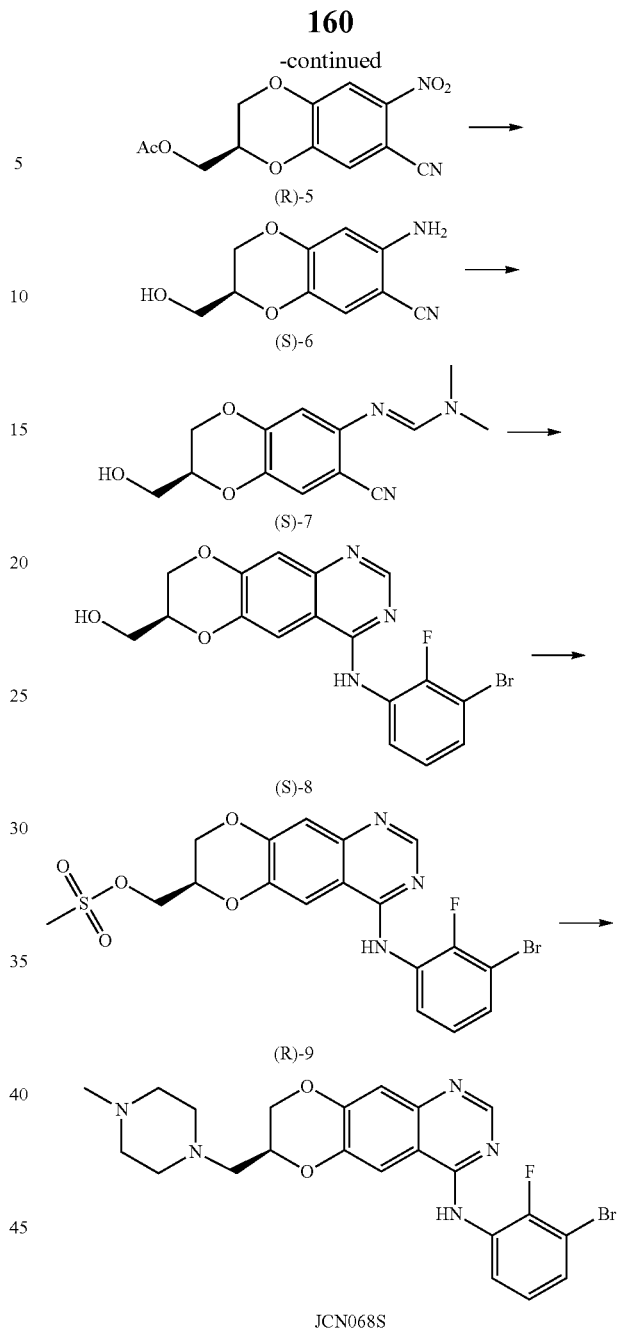

Scheme 2. The preparation of the (R)-enantiomer JGK068R or of racemic mixtures (JGK068) follows the same route as shown in Scheme 1, but employs (R)- or racemic glycidol, respectively.

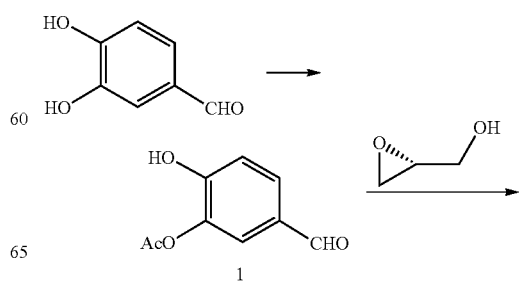

161
-continued

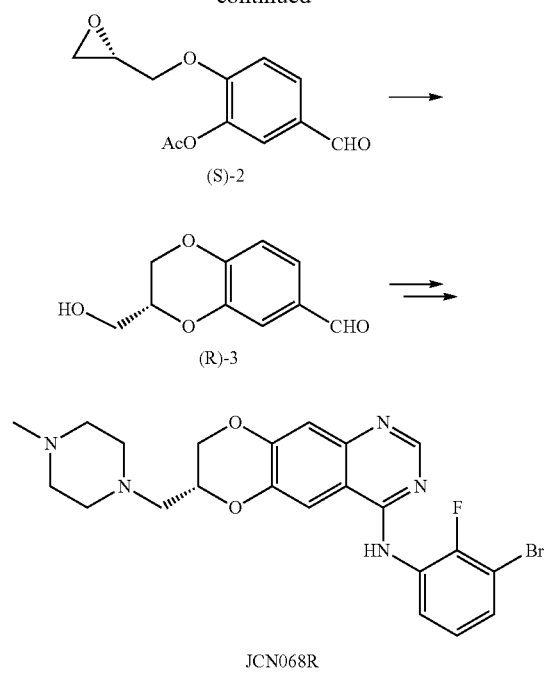

162

Scheme 3. Synthesis of benzodioxane carbaldehyde (R)-10 in one step from benzaldehyde 1 with chiral glycidyl tosylate. This route avoids the Mitsunobu reaction in Scheme 1 (preparation of 2 from 1). Compound (R)-10 can be used in the route shown in Scheme 1 for the preparation of JGK068S.

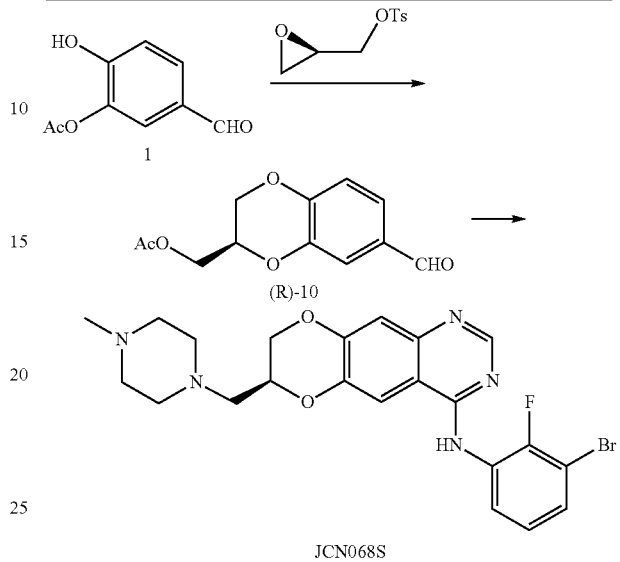

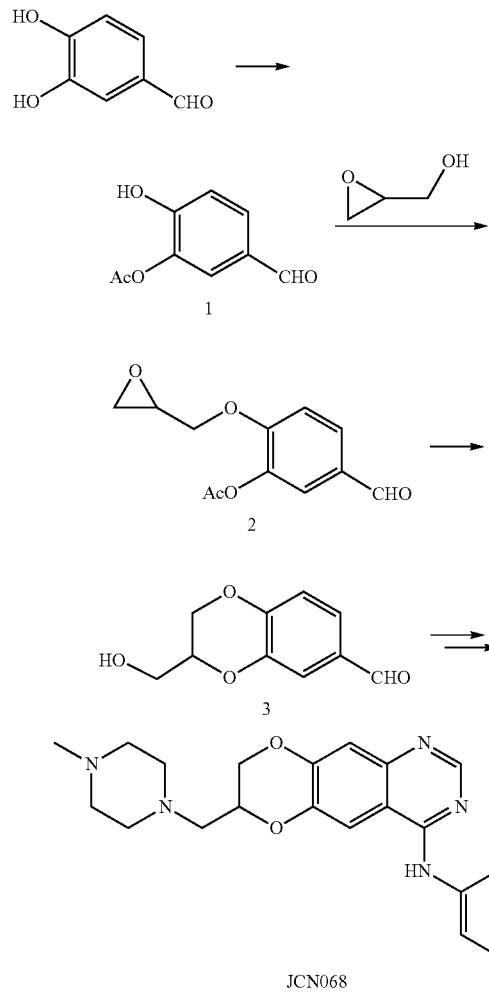

General Chemistry Information

All chemicals, reagents, and solvents were purchased from commercial sources when available and were used as received. When necessary, reagents and solvents were purified and dried by standard methods. Air- and moisture-sensitive reactions were carried out under an inert atmosphere of argon in oven-dried glassware. Microwave-irradiated reactions were carried out in a single mode reactor CEM Discover microwave synthesizer. Room temperature (RT) reactions were carried out at ambient temperature (approximately 23° C.). All reactions were monitored by thin layer chromatography (TLC) on precoated Merck 60 $F_{254}$ silica gel plates with spots visualized by UV light ($\lambda$=254, 365 nm) or by using an alkaline $KMnO_4$ solution. Flash column chromatography (FC) was carried out on $SiO_2$ 60 (particle size 0.040-0.063 mm, 230-400 mesh). Preparative thin-layer chromatography (PTLC) was carried out with Merck 60 $F_{254}$ silica gel plates (20×20 cm, 210-270 mm) or Analtech Silica Gel GF TLC plates (20×20 cm, 1000 mm). Concentration under reduced pressure (in vacuo) was performed by rotary evaporation at 23-50° C. Purified compounds were further dried under high vacuum or in a desiccator. Yields correspond to purified compounds, and were not further optimized. Proton nuclear magnetic resonance ($^1$H NMR) spectra were recorded on Bruker spectrometers (operating at 300, 400, or 500 MHz). Carbon NMR ($^{13}$C NMR) spectra were recorded on Bruker spectrometers (either at 400 or 500 MHz). NMR chemical shifts ($\delta$ ppm) were referenced to the residual solvent signals. $^1$H NMR data are reported as follows: chemical shift in ppm; multiplicity (s=singlet, d=doublet, t=triplet, q=quartet, quint=quintet, m=multiplet/complex pattern, td=triplet of doublets, ddd=doublet of doublet of doublets, br=broad signal); coupling constants (J) in Hz, integration. Data for $^{13}$C NMR spectra are reported in terms of chemical shift, and if applicable coupling constants. High resolution mass spectra (HRMS) were recorded on a Thermo Fisher Scientific Exactive Plus with IonSense ID-CUBE DART source mass spectrometer, or on a Waters LCT Premier mass spectrometer with ACQUITY UPLC with autosampler.

5-Formyl-2-hydroxyphenyl acetate (1)

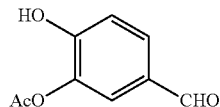

A mixture of 3,4-dihydroxybenzaldehyde (100 g, 0.724 mol) in THF (965 mL) was cooled to 0° C., and treated with 10% aq. NaOH (724 mL, 1.81 mol) over 4-5 min. After the reaction mixture was stirred at 0° C. for 15 min, acetic anhydride ($Ac_2O$, 82.1 mL, 0.869 mol) was added dropwise over 20 min. The mixture was stirred for 30 min at the same temperature, and then poured into a mixture of EtOAc (1.25 L) and 2 M HCl (1.13 L) at 0° C. The phases were separated, and the aq. phase was extracted with EtOAc (4×250 mL). The combined organics were washed with water (2×500 mL), brine (500 mL), dried ($Na_2SO_4$), filtered, and evaporated. The residue was treated with a small amount of n-heptane and evaporated (3×). Recrystallization from EtOAc (275 mL; crystals washed with $Et_2O$) gave a first crop of the title compound 1 (66.96 g, 51%) as light-brown crystals. Recrystallization of the mother liquor from EtOAc gave a second crop of the title compound 1 (29.436 g, 23%) as a light-brown solid. $^1$H NMR (500 MHz, $CDCl_3$): δ 9.85 (s, 1H), 7.73-7.65 (m, 2H), 7.11 (d, J=8.8 Hz, 1H), 6.34 (br, 1H), 2.39 (s, 3H). $^{13}$C NMR (126 MHz, $CDCl_3$): δ 190.40, 168.99, 152.96, 138.81, 130.24, 129.72, 124.13, 117.87, 21.09. HRMS (DART): m/z [M+H]$^+$ calcd for $C_9H_9O_4^+$, 181.0495; found, 181.0488.

5-Formyl-2-{[(2R)-oxiran-2-yl]methoxy}phenyl acetate ((R)-2)

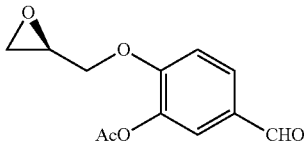 [SMILES: CC(=O)Oc1cc(C=O)ccc1OC[C@H]1CO1]

A mixture of 1 (32.5 g, 0.18 mol) and triphenylphosphine ($PPh_3$, 70.976 g, 0.27 mol) in THF (905 mL) was treated with (S)-glycidol (17.95 mL, 0.27 mol), cooled to 0° C., and treated dropwise with diisopropyl azodicarboxylate (DIAD, 56.8 mL, 0.289 mmol) over 30 min. The mixture was stirred for an additional 10 min at 0° C., after which the cooling bath was removed, and stirring was continued at 23° C. for 15.5 h. All volatiles were evaporated, and crude (R)-2, obtained as a brown oil, was used without any further purification in the next step.

(3S)-3-(Hydroxymethyl)-2,3-dihydro-1,4-benzodioxine-6-carbaldehyde ((S)-3)

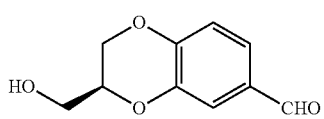 [SMILES: O=Cc1ccc2c(c1)O[C@@H](CO)CO2]

A mixture of crude (R)-2 in MeOH (1.564 L) was treated with $K_2CO_3$ (49.87 g, 0.36 mol) and stirred at 23° C. for 18.5 h, and then the solvent was evaporated. The residue was suspended in half-sat. $NH_4Cl$ (750 mL), and extracted with EtOAc (3×500 mL). The combined organics were washed with water (250 mL), brine (250 mL), dried ($Na_2SO_4$), filtered, and evaporated. The crude material was purified by several rounds of flash chromatography (hexanes/EtOAc 9:1→1:1) as well as by precipitation from hexanes/$Et_2O$ 1:1 (to remove triphenylphospine oxide $Ph_3PO$), to afford the title compound (S)-3 (17.322 g, 49% over two steps) as a white solid. $^1$H NMR (500 MHz, $CDCl_3$): δ 9.81 (s, 1H), 7.43 (d, J=1.8 Hz, 1H), 7.41 (dd, J=8.1, 1.9 Hz, 1H), 7.00 (d, J=8.2 Hz, 1H), 4.39 (dd, J=11.4, 2.3 Hz, 1H), 4.31-4.25 (m, 1H), 4.20 (dd, J=11.3, 7.9 Hz, 1H), 3.95 (dd, J=12.1, 4.3 Hz, 1H), 3.87 (dd, J=12.1, 4.9 Hz, 1H), 2.18 (br, 1H). $^{13}$C NMR (126 MHz, $CDCl_3$): δ 190.79, 148.76, 143.46, 130.79, 124.46, 118.33, 117.70, 73.31, 65.61, 61.54. HRMS (DART): m/z [M+H]$^+$ calcd for $C_{10}H_{11}O_4^+$, 195.0652; found, 195.0650.

[(2R)-7-Cyano-2,3-dihydro-1,4-benzodioxin-2-yl]methyl acetate ((R)-4)

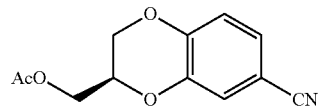 [SMILES: CC(=O)OC[C@H]1COc2ccc(C#N)cc2O1]

A mixture of (S)-3 (17.322 g, 0.089 mol) in AcOH (189 mL) was treated with KOAc (22.944 g, 0.234 mol), stirred at 23° C. for 10 min, and then treated with $NH_2OH \cdot HCl$ (16.233 g, 0.234 mol). The resulting mixture was stirred at 120-125° C. for 18.5 h. The mixture was cooled to 23° C., poured into water (1 L), and extracted with EtOAc (4×250 mL). The combined organics were treated with 3.5 M NaOH (400 mL) and sat. aq. $NaHCO_3$ (100 mL) to obtain a final pH of ~8, and the emulsion was stirred at 23° C. for 1 h. The organic layer was separated, and washed with sat. aq. $NaHCO_3$ (300 mL), water (300 mL), brine (300 mL), dried ($Na_2SO_4$), filtered, and evaporated. Purification by flash chromatography (hexanes/EtOAc 10:1→6:4) afforded the title compound (R)-4 (13.513 g, 65%) as a clear, colorless oil. $^1$H NMR (500 MHz, $CDCl_3$): δ 7.20 (d, J=2.0 Hz, 1H), 7.16 (dd, J=8.4, 2.0 Hz, 1H), 6.94 (d, J=8.4 Hz, 1H), 4.43-4.38 (m, 1H), 4.36 (dd, J=11.6, 2.4 Hz, 1H), 4.34 (dd, J=11.1, 4.5 Hz, 1H), 4.30 (dd, J=11.6, 4.6 Hz, 1H), 4.11 (dd, J=11.5, 7.2 Hz, 1H), 2.12 (s, 3H). $^{13}$C NMR (126 MHz, $CDCl_3$): δ 170.64, 147.13, 143.11, 126.28, 121.56, 118.85, 118.32, 105.13, 71.11, 65.45, 62.24, 20.83. HRMS (DART): m/z [M+H]$^+$ calcd for $C_{12}H_{12}NO_4^+$, 234.0761; found, 234.0759.

[(2R)-7-Cyano-6-nitro-2,3-dihydro-1,4-benzodioxin-2-yl]methyl acetate ((R)-5)

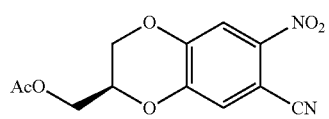 [SMILES: CC(=O)OC[C@H]1COc2cc([N+](=O)[O-])c(C#N)cc2O1]

A mixture of (R)-4 (13.345 g, 57.2 mmol) in Ac$_2$O (74.3 mL) was treated with H$_2$SO$_4$ (3.05 mL, 57.2 mmol), cooled to 0° C., and treated dropwise with 70% HNO$_3$ (19.63 mL, 286 mmol) at 0° C. over 35 min. The mixture was stirred for another 2 h at 0° C., and then at 23° C. for 3.5 h. The mixture was poured into ice-water (850 mL), and the pH was adjusted to ~7 with 6 M NaOH (320 mL). Sat. aq. NaHCO$_3$ (200 mL) was added, and the mixture was extracted with CH$_2$Cl$_2$ (3×500 mL). The combined organics were washed with sat. aq. NaHCO$_3$ (400 mL), water (400 mL), brine (400 mL), dried (Na$_2$SO$_4$), filtered, and evaporated to afford the title compound (R)-5 (15.696 g, 99%) as a yellow oil, which was used in the next step without any further purification. $^1$H NMR (500 MHz, DMSO-d$_6$): δ 7.96 (s, 1H), 7.80 (s, 1H), 4.73-4.67 (m, 1H), 4.58 (dd, J=11.8, 2.6 Hz, 1H), 4.36 (dd, J=12.5, 3.7 Hz, 1H), 4.31 (dd, J=12.5, 5.7 Hz, 1H), 4.27 (dd, J=11.8, 7.0 Hz, 1H), 2.05 (s, 3H). $^{13}$C NMR (126 MHz, DMSO-d$_6$): δ 170.11, 147.75, 146.26, 142.23, 123.77, 115.21, 115.17, 100.06, 72.00, 64.98, 61.72, 20.52. HRMS (DART): m/z [M+H]$^+$ calcd for C$_{12}$H$_{11}$N$_2$O$_6$$^+$, 279.0612; found, 279.0601.

(3S)-7-Amino-3-(hydroxymethyl)-2,3-dihydro-1,4-benzodioxine-6-carbonitrile ((S)-6)

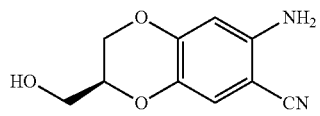 [SMILES: N#Cc1cc2c(cc1N)OC[C@H](CO)O2]

A suspension of (R)-5 (15.591 g, 56 mmol) in water/ethanol 1:1 (250 mL) was treated with Na$_2$S$_2$O$_4$ (39.266 g, 185 mmol), and the mixture was stirred at 50° C. for 105 min, and then heated to 70° C. for 2 h while treated portionwise with conc. HCl (73.6 mL, 0.897 mol) during that time. The mixture was cooled to 23° C., poured on ice, and the pH was adjusted to ~10 with 6 M NaOH (200 mL) and half-sat. NaHCO$_3$ (500 mL). The mixture was extracted with EtOAc (3×500 mL). The combined organics were washed with water (500 mL), brine (500 mL), dried (Na$_2$SO$_4$), filtered, and evaporated to afford crude (S)-6 (9.483 g, 82%) as an orange-yellow solid, which was used in the next step without any further purification. $^1$H NMR (500 MHz, DMSO-d$_6$): δ 6.92 (s, 1H), 6.29 (s, 1H), 5.50 (br, 2H), 5.04 (t, J=5.7 Hz, 1H), 4.32 (dd, J=10.7, 1.6 Hz, 1H), 4.07-3.99 (m, 1H), 4.00 (dd, J=11.2, 8.3 Hz, 1H), 3.64-3.51 (m, 2H). $^{13}$C NMR (126 MHz, DMSO-d$_6$): δ 148.50, 147.29, 134.39, 119.04, 118.04, 102.45, 86.72, 73.25, 65.92, 59.77. HRMS (DART): m/z [M+H]$^+$ calcd for C$_{10}$H$_{10}$N$_2$O$_3$$^{·+}$, 206.0686; found, 206.0685.

N'-[(2S)-7-Cyano-2-(hydroxymethyl)-2,3-dihydro-1,4-benzodioxin-6-yl]-N,N-dimethylmethan-imidamide ((S)-7)

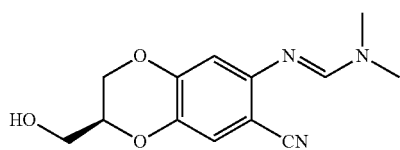 [SMILES: CN(C)/C=N/c1cc2c(cc1C#N)O[C@@H](CO)CO2]

A mixture of (S)-6 (9.38 g, 45.5 mmol) in toluene (117 mL) was treated with AcOH (143 µL, 2.5 mmol) and DMF-DMA (13.1 mL, 98.9 mmol), and the mixture was stirred at 105° C. for 3 h. The evaporated MeOH (~4-5 mL) was collected in a Dean-Stark trap to monitor the progress of the reaction. The mixture was cooled to 23° C. and evaporated to obtain crude (S)-7 (14.243 g, quant.) as a viscous, brown oil, which was used in the next step without any further purification. $^1$H NMR (500 MHz, CDCl$_3$): δ 7.51 (s, 1H), 7.05 (s, 1H), 6.48 (s, 1H), 4.33 (dd, J=11.2, 2.0 Hz, 1H), 4.23-4.17 (m, 1H), 4.13 (dd, J=11.2, 8.1 Hz, 1H), 3.90 (dd, J=12.1, 4.2 Hz, 1H), 3.83 (dd, J=12.1, 4.8 Hz, 1H), 3.07 (s, 3H), 3.05 (s, 3H). $^{13}$C NMR (126 MHz, CDCl$_3$): δ 160.40, 153.78, 147.68, 138.63, 121.08, 118.64, 108.16, 99.31, 73.34, 65.83, 61.67, 40.51, 34.82. HRMS (DART): m/z [M+H]$^+$ calcd for C$_{13}$H$_{16}$N$_3$O$_3$$^+$, 262.1186; found, 262.1183.

[(7S)-4-(3-Bromo-2-fluoroanilino)-7,8-dihydro[1,4]dioxino[2,3-g]quinazolin-7-yl]methanol ((S)-8)

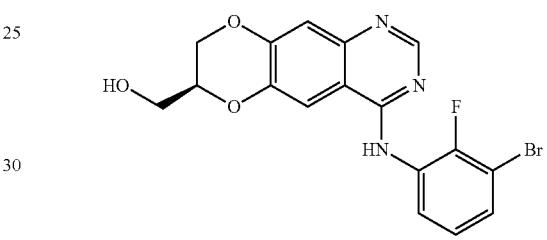

A mixture of (S)-7 in AcOH (152 mL) was treated with 3-bromo-2-fluoroaniline (6.63 mL, 59.1 mmol), and the mixture was stirred at 125-130° C. for 3 h. The mixture was cooled to 23° C., poured into ice-water (500 mL), and the pH was adjusted to ~9 with sat. aq. NH$_4$OH (185 mL) and half-sat. aq. NaHCO$_3$ (200 mL). The mixture was extracted with EtOAc (3×400 mL), and the combined organics were washed with half-sat. aq. NaHCO$_3$ (400 mL), water (400 mL), brine (400 mL), dried (Na$_2$SO$_4$), filtered, and evaporated. The residue was dissolved in MeOH (272 mL), and treated with K$_2$CO$_3$ (12.579 g, 91 mmol), stirred at 23° C. for 1 h, and evaporated. The residue was suspended in half-sat. aq. NH$_4$Cl (700 mL), and extracted with EtOAc (3×400 mL). The combined organics were washed with water (400 mL), brine (400 mL), dried (Na$_2$SO$_4$), filtered, and evaporated. The orange-yellow residue was suspended in EtOAc, warmed to 65° C., and then let slowly cool down to 23° C. overnight. Filtration, and washing of the residue with cold hexanes (2×15 mL) and Et$_2$O (2×15 mL), and drying under high vacuum afforded the title compound (S)-8 (9.407 g, 50.9% over two steps) as a fine, yellow powder. $^1$H NMR (500 MHz, DMSO-d$_6$): δ 9.69 (s, 1H), 8.33 (s, 1H), 7.99 (s, 1H), 7.59 (ddd, J=8.0, 6.2, 1.6 Hz, 1H), 7.54 (ddd, J=8.4, 7.0, 1.6 Hz, 1H), 7.24-7.17 (m, 1H), 7.20 (s, 1H), 5.20 (t, J=5.6 Hz, 1H), 4.49 (dd, J=11.5, 2.4 Hz, 1H), 4.37-4.29 (m, 1H), 4.21 (dd, J=11.6, 7.4 Hz, 1H), 3.76-3.64 (m, 2H). $^{13}$C NMR (126 MHz, DMSO-d$_6$): δ 157.22, 153.38 (d, J$_{CF}$=247.0 Hz), 153.09, 148.87, 145.94, 143.37, 130.08, 128.09 (d, J$_{CF}$=12.9 Hz), 127.75, 125.43 (d, J$_{CF}$=4.5 Hz), 112.29, 109.81, 108.54 (d, J$_{CF}$=20.0 Hz), 73.77, 65.52, 59.76. HRMS (DART): m/z [M+H]$^+$ calcd for C$_{17}$H$_{14}$BrFN$_3$O$_3$$^+$, 406.0197; found, 406.0185.

[(7R)-4-(3-Bromo-2-fluoroanilino)-7,8-dihydro[1,4]dioxino[2,3-g]quinazolin-7-yl]methyl methanesulfonate ((R)-9)

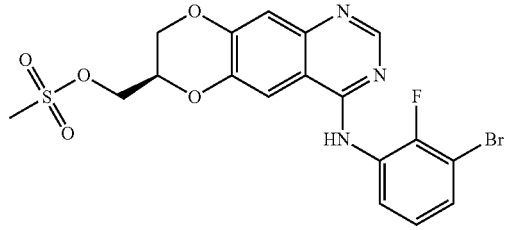 [SMILES: CS(=O)(=O)OC[C@H]1COc2cc3ncnc(Nc4cccc(Br)c4F)c3cc2O1]

A mixture of (S)-8 (9.01 g, 22.2 mmol) and Me$_3$N.HCl (234 mg, 2.45 mmol) in acetonitrile (148 mL) was treated with Et$_3$N (6.18 mL, 44.4 mmol), cooled to 0-5° C., and treated dropwise with a solution of MsCl (2.57 mL, 33.2 mmol) in acetonitrile (17 mL; rinsed with 3 mL) over 10 min. The mixture was stirred at 0° C. for 1 h. Water (100 mL) was added, and most of the acetonitrile was evaporated in vacuo. Additional water (700 mL) was added, and the mixture was extracted with EtOAc (3×400 mL). The combined organics were washed with water (400 mL), brine (400 mL), dried (Na$_2$SO$_4$), filtered, and evaporated to afford the title compound (R)-9 (10.33 g, 96%) as a yellow, friable foam, which was used in the next step without any further purification. $^1$H NMR (500 MHz, CDCl$_3$): δ 8.70 (s, 1H), 8.62 (ddd, J=8.7, 7.3, 1.6 Hz, 1H), 7.44 (s, 1H), 7.362 (s, 1H), 7.360 (br, 1H), 7.29 (ddd, J=8.1, 6.5, 1.5 Hz, 1H), 7.11 (td, J=8.2, 1.6 Hz, 1H), 4.67-4.61 (m, 1H), 4.54-4.51 (m, 2H), 4.50 (dd, J=11.7, 2.4 Hz, 1H), 4.29 (dd, J=11.8, 7.1 Hz, 1H), 3.13 (s, 3H).

(7S)—N-(3-Bromo-2-fluorophenyl)-7-[(4-methylpiperazin-1-yl)methyl]-7,8-dihydro[1,4]dioxino[2,3-g]quinazolin-4-amine (JGK068S)

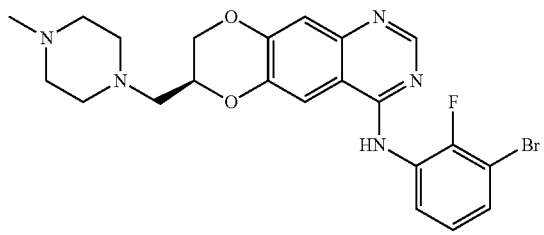 [SMILES: CN1CCN(C[C@H]2COc3cc4ncnc(Nc5cccc(Br)c5F)c4cc3O2)CC1]

A mixture of (R)-9 in DMF (427 mL) was treated with 1-methylpiperazine (11.83 mL, 107 mmol) and Et$_3$N (5.95 mL, 42.7 mmol), and the mixture was stirred at 85° C. for 24 h. The mixture was cooled to 23° C., and evaporated. The residue was dissolved in EtOAc (1.2 L), and washed with 0.5 M NaOH (4×250 mL), brine (250 mL), dried (Na$_2$SO$_4$), filtered, and evaporated. Purification by flash chromatography (CH$_2$Cl$_2$/MeOH 1:0→8:2) afforded the title compound JGK068S (6.013 g, 58% over two steps) as an off-white, friable foam. $^1$H NMR (500 MHz, CDCl$_3$): δ 8.67 (s, 1H), 8.63 (ddd, J=8.7, 7.3, 1.6 Hz, 1H), 7.374 (s, 1H), 7.372 (br, 1H), 7.32 (s, 1H), 7.26 (ddd, J=8.1, 6.5, 1.5 Hz, 1H), 7.09 (td, J=8.2, 1.6 Hz, 1H), 4.48-4.40 (m, 2H), 4.14 (dd, J=11.8, 8.0 Hz, 1H), 2.77 (dd, J=13.4, 6.0 Hz, 1H), 2.653 (dd, J=13.4, 5.8 Hz, 1H), 2.648 (br, 4H), 2.51 (br, 4H), 2.32 (s, 3H).

Scheme 4. Synthesis of JGK083S.

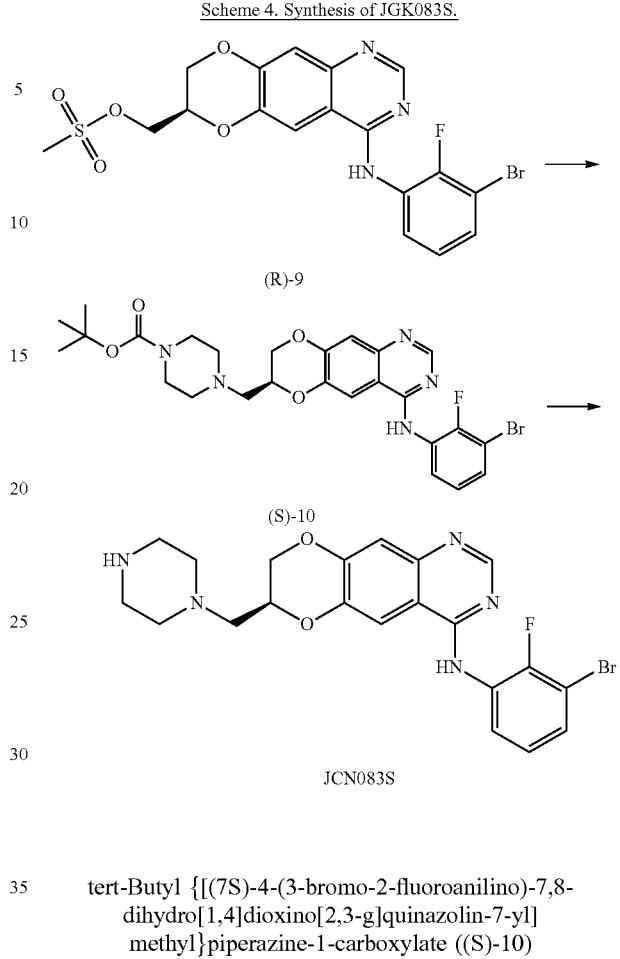

tert-Butyl {[(7S)-4-(3-bromo-2-fluoroanilino)-7,8-dihydro[1,4]dioxino[2,3-g]quinazolin-7-yl]methyl}piperazine-1-carboxylate ((S)-10)

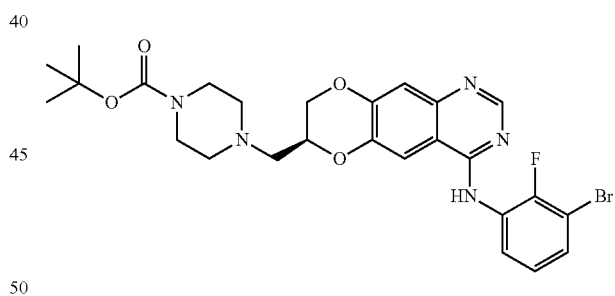

Following general procedure GP-1 of Example 16, compound (S)-10 was prepared from R-9 (91 mg, 0.188 mmol) and tert-butyl piperazine-1-carboxylate (175 mg, 0.94 mmol) in DMF (3.8 mL), and stirred at 85° C. for 15 h. PTLC (CH$_2$Cl$_2$/EtOAc 4:6) afforded (S)-10 (50 mg, 46%) as an off-white, friable foam. $^1$H NMR (500 MHz, CDCl$_3$): δ 8.68 (s, 1H), 8.65 (ddd, J=8.3, 7.4, 1.5 Hz, 1H), 7.39 (s, 1H), 7.36 (br, 1H), 7.31 (s, 1H), 7.27 (ddd, J=8.0, 6.5, 1.5 Hz, 1H), 7.11 (td, J=8.2, 1.5 Hz, 1H), 4.50-4.42 (m, 2H), 4.17 (dd, J=12.1, 8.2 Hz, 1H), 3.47 (t, J=5.1 Hz, 4H), 2.78 (dd, J=13.4, 5.9 Hz, 1H), 2.67 (dd, J=13.5, 5.9 Hz, 1H), 2.62-2.47 (m, 4H), 1.47 (s, 9H). $^{13}$C NMR (126 MHz, CDCl$_3$): δ 155.89, 154.83, 153.39, 150.15 (d, J$_{CF}$=242.4 Hz), 149.36, 146.72, 144.02, 128.63 (d, J$_{CF}$=10.3 Hz), 127.27, 125.34, 121.78, 114.34, 110.66, 108.60 (d, J$_{CF}$=19.5 Hz), 106.06, 79.97, 71.76, 67.18, 58.56, 53.96, 28.57, one carbon signal

(7S)—N-(3-Bromo-2-fluorophenyl)-7-[(piperazin-1-yl)methyl]-7,8-dihydro[1,4]dioxino [2,3-g]quinazolin-4-amine (JGK083S)

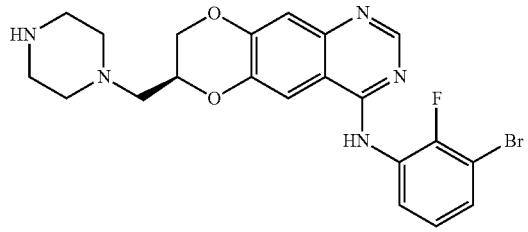 [SMILES: Fc1c(Br)cccc1Nc1ncnc2cc3c(cc12)O[C@@H](CN1CCNCC1)CO3]

A mixture of (S)-10 (42 mg, 0.073 mmol) in CH$_2$Cl$_2$ (500 μL) and TFA (250 μL) was stirred at 23° C. for 12 h. The mixture was diluted with 1 M HCl (20 mL), and washed with CH$_2$Cl$_2$ (3×7 mL). The aqueous phase was diluted with 6 M NaOH (4 mL) to pH>12, and extracted with EtOAc (3×8 mL). The combined organics were washed with brine (8 mL), dried (Na$_2$SO$_4$), filtered, and evaporated. Purification by PTLC (CH$_2$CL$_2$/MeOH 8:2) afforded the title compound JGK083S (18 mg, 52%) as a white, friable foam. $^1$H NMR (500 MHz, CDCl$_3$): δ 8.68 (s, 1H), 8.66 (ddd, J=8.2, 7.3, 1.6 Hz, 1H), 7.39 (s, 1H), 7.35 (br d, J=4.0 Hz, 1H), 7.32 (s, 1H), 7.27 (ddd, J=8.1, 6.5, 1.6 Hz, 1H), 7.11 (td, J=8.2, 1.5 Hz, 1H), 4.50-4.42 (m, 2H), 4.19-4.13 (m, 1H), 2.93 (t, J=4.9 Hz, 4H), 2.76 (dd, J=13.4, 5.9 Hz, 1H), 2.63 (dd, J=13.4, 6.0 Hz, 1H), 2.63-2.50 (m, 4H). $^{13}$C NMR (126 MHz, CDCl$_3$): δ 155.88, 153.35, 150.12 (d, J$_{CF}$=242.3 Hz), 149.45, 146.71, 144.17, 128.67 (d, J$_{CF}$=10.4 Hz), 127.21, 125.32 (d, J$_{CF}$=4.7 Hz), 121.74, 114.30, 110.64, 108.58 (d, J$_{CF}$=19.3 Hz), 106.02, 71.70, 67.32, 59.19, 55.54, 46.23. HRMS (DART): m/z [M−H]$^−$ calcd for C$_{21}$H$_{20}$BrFN$_5$O$_2^−$, 472.0790; found, 472.0773.

[(2R)-7-Formyl-2,3-dihydro-1,4-benzodioxin-2-yl]methyl acetate ((R)-10)

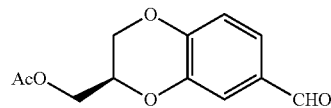 [SMILES: CC(=O)OC[C@H]1COc2ccc(C=O)cc2O1]

A mixture of 1 (150 mg, 0.833 mmol) and (2R)-glycidyl tosylate (203 mg, 0.891 mmol) in DMF (2 mL) was treated with K$_2$CO$_3$ (181 mg, 1.31 mmol), and the mixture was stirred at 60° C. for 15 h. The mixture was cooled to 23° C., water (30 mL) was added, and the mixture was extracted with EtOAc (3×15 mL). The combined organics were washed with water (15 mL), brine (15 mL), dried (Na$_2$SO$_4$), filtered, and evaporated. Purification by preparative thin layer chromatography (hexanes/EtOAc 7:3) afforded the title compound (R)-10 (111 mg, 56%) as a clear, colorless oil. $^1$H NMR (400 MHz, CDCl$_3$): δ=9.82 (s, 1H), 7.44 (d, J=1.8 Hz, 1H), 7.42 (dd, J=8.2, 1.9 Hz, 1H), 7.00 (d, J=8.1 Hz, 1H), 4.46-4.39 (m, 1H), 4.37 (dd, J=11.5, 2.4 Hz, 1H), 4.35 (dd, J=11.7, 4.9 Hz, 1H), 4.31 (dd, J=11.9, 5.1 Hz, 1H), 4.13 (dd, J=11.5, 7.1 Hz, 1H), 2.11 (s, 3H). $^{13}$C NMR (101 MHz, CDCl$_3$): δ 190.72, 170.67, 148.57, 143.22, 131.15, 124.38, 118.76, 117.85, 70.94, 65.54, 62.36, 20.83. HRMS (DART): m/z [M+H]$^+$ calcd for C$_{12}$H$_{13}$O$_5^+$, 237.0757; found, 237.0745.

(±)-N-(3-Chloro-2-fluorophenyl)-7-[(4-methylpiperazin-1-yl)methyl]-7,8-dihydro[1,4]dioxino [2,3-g]quinazolin-4-amine (JGK075)

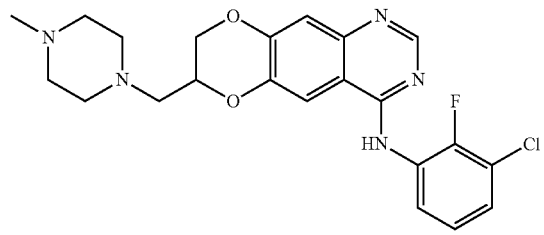 [SMILES: CN1CCN(CC2COc3cc4ncnc(Nc5cccc(Cl)c5F)c4cc3O2)CC1]

$^1$H NMR (500 MHz, CDCl$_3$): δ 8.68 (s, 1H), 8.61 (td, J=7.3, 2.2 Hz, 1H), 7.39 (s, 1H), 7.35 (br d, J=3.4 Hz, 1H), 7.32 (s, 1H), 7.16 (td, J=8.1, 1.2 Hz, 1H), 7.13 (td, J=8.2, 1.9 Hz, 1H), 4.49-4.41 (m, 2H), 4.15 (dd, J=11.8, 8.1 Hz, 1H), 2.78 (dd, J=13.4, 5.9 Hz, 1H), 2.66 (dd, J=13.4, 5.9 Hz, 1H), 2.64 (br, 4H), 2.48 (br, 4H), 2.31 (s, 3H). $^{13}$C NMR (126 MHz, CDCl$_3$): δ 155.89, 153.35, 149.44, 149.30 (d, J$_{CF}$=244.2 Hz), 146.72, 144.15, 128.76 (d, J$_{CF}$=9.3 Hz), 124.71 (d, J$_{CF}$=4.7 Hz), 124.45, 121.01, 120.85 (d, J$_{CF}$=16.1 Hz), 114.30, 110.63, 106.05, 71.81, 67.31, 58.50, 55.17, 54.15, 46.19. HRMS (DART): m/z [M+H]$^+$ calcd for C$_{22}$H$_{24}$ClFN$_5$O$_2^+$, 444.1597; found, 444.1582.

(±)-N-(3-Bromo-2-fluorophenyl)-8-[(morpholin-4-yl)methyl]-7,8-dihydro[1,4]dioxino[2,3-g]quinazolin-4-amine (JGK076)

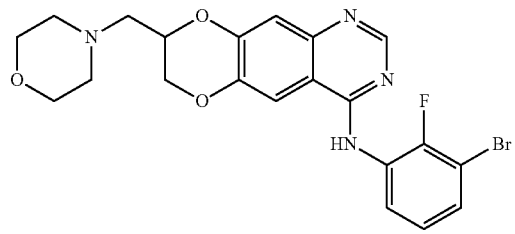 [SMILES: Fc1c(Br)cccc1Nc1ncnc2cc3c(cc12)OCC(CN1CCOCC1)O3]

$^1$H NMR (500 MHz, DMSO-d$_6$): δ 9.62 (s, 1H), 8.33 (s, 1H), 7.94 (s, 1H), 7.59 (ddd, J=8.0, 6.2, 1.6 Hz, 1H), 7.54 (ddd, J=8.5, 7.1, 1.6 Hz, 1H), 7.21 (td, J=8.1, 1.2 Hz, 1H), 7.19 (s, 1H), 4.63-4.56 (m, 1H), 4.46 (dd, J=11.6, 2.5 Hz, 1H), 4.17 (dd, J=11.6, 7.1 Hz, 1H), 3.59 (t, J=4.6 Hz, 4H), 2.71-2.59 (m, 2H), 2.57-2.44 (m, 4H). $^{13}$C NMR (126 MHz, DMSO-d$_6$): δ 157.22, 153.37 (d, J$_{CF}$=247.3 Hz), 153.13, 148.75, 146.16, 143.28, 130.14, 128.02 (d, J$_{CF}$=13.0 Hz), 127.74, 125.45 (d, J$_{CF}$=4.7 Hz), 112.57, 109.61, 108.55 (d, $J_{CF}$=19.9 Hz), 108.23, 71.41, 66.29, 66.18, 57.97, 53.89. HRMS (DART): m/z [M–H]⁻ calcd for $C_{21}H_{19}BrFN_4O_3^-$, 473.0630; found, 473.0608.

(±)-N-(3-Bromo-2-fluorophenyl)-8-[(dimethylamino)methyl]-7,8-dihydro[1,4]dioxino[2,3-g]quinazolin-4-amine (JGK077)

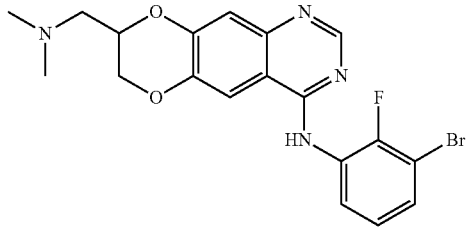 [SMILES: CN(C)CC1COc2cc3c(Nc4cccc(Br)c4F)ncnc3cc2O1]

¹H NMR (500 MHz, DMSO-d₆): δ 9.62 (s, 1H), 8.33 (s, 1H), 7.94 (s, 1H), 7.59 (ddd, J=8.0, 6.2, 1.6 Hz, 1H), 7.54 (ddd, J=8.5, 7.1, 1.6 Hz, 1H), 7.21 (td, J=8.1, 1.2 Hz, 1H), 7.17 (s, 1H), 4.57-4.51 (m, 1H), 4.44 (dd, J=11.6, 2.5 Hz, 1H), 4.14 (dd, J=11.7, 7.1 Hz, 1H), 2.58 (s, 1H), 2.57 (s, 1H), 2.25 (s, 6H). ¹³C NMR (126 MHz, DMSO-d₆): δ 157.22, 153.38 (d, $J_{CF}$=247.4 Hz), 153.12, 148.78, 146.16, 143.29, 130.14, 128.02 (d, $J_{CF}$=13.1 Hz), 127.75, 125.45 (d, $J_{CF}$=4.4 Hz), 112.54, 109.59, 108.55 (d, $J_{CF}$=19.8 Hz), 108.20, 71.76, 66.31, 58.73, 45.92. HRMS (DART): m/z [M–H]⁻ calcd for $C_{19}H_{17}BrFN_4O_2^-$, 431.0524; found, 431.0503.

(±)-N-(3-Bromo-2-fluorophenyl)-8-[(4-methylpiperazin-1-yl)methyl]-7,8-dihydro[1,4]dioxino[2,3-g]quinazolin-4-amine (JGK078)

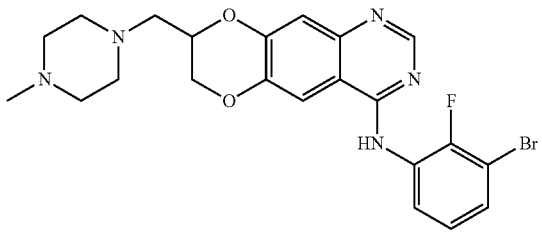 [SMILES: CN1CCN(CC2COc3cc4c(Nc5cccc(Br)c5F)ncnc4cc3O2)CC1]

¹H NMR (500 MHz, DMSO-d₆): δ 9.61 (s, 1H), 8.33 (s, 1H), 7.94 (s, 1H), 7.59 (ddd, J=8.0, 6.2, 1.6 Hz, 1H), 7.54 (ddd, J=8.5, 7.1, 1.6 Hz, 1H), 7.21 (td, J=8.1, 1.2 Hz, 1H), 7.19 (s, 1H), 4.60-4.53 (m, 1H), 4.44 (dd, J=11.6, 2.5 Hz, 1H), 4.14 (dd, J=11.7, 7.1 Hz, 1H), 2.68-2.59 (m, 2H), 2.53 (br, 4H), 2.34 (br, 4H), 2.16 (s, 3H). ¹³C NMR (126 MHz, DMSO-d₆): δ 157.22, 153.38 (d, $J_{CF}$=247.4 Hz), 153.12, 148.78, 146.15, 143.29, 130.13, 128.02 (d, $J_{CF}$=13.1 Hz), 127.74, 125.45 (d, $J_{CF}$=4.5 Hz), 112.55, 109.60, 108.55 (d, $J_{CF}$=19.8 Hz), 108.22, 71.57, 66.34, 57.52, 54.68, 53.29, 45.72. HRMS (DART): m/z [M–H]⁻ calcd for $C_{22}H_{22}BrFN_5O_2^-$, 486.0946; found, 486.0928.

(±)-N-(3-Bromo-2-fluorophenyl)-8-[(pyrrolidin-1-yl)methyl]-7,8-dihydro[1,4]dioxino[2,3-g]quinazolin-4-amine (JGK079)

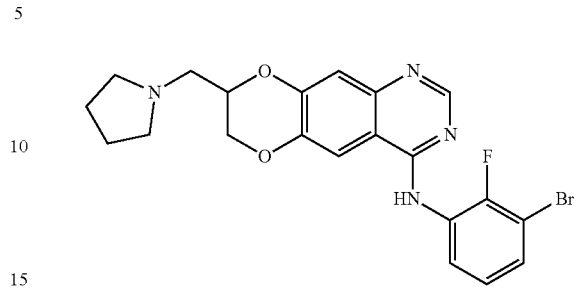

¹H NMR (500 MHz, DMSO-d₆): δ 9.61 (s, 1H), 8.33 (s, 1H), 7.94 (s, 1H), 7.59 (ddd, J=8.0, 6.3, 1.6 Hz, 1H), 7.54 (ddd, J=8.5, 7.1, 1.6 Hz, 1H), 7.21 (td, J=8.0, 1.2 Hz, 1H), 7.19 (s, 1H), 4.57-4.49 (m, 1H), 4.46 (dd, J=11.6, 2.5 Hz, 1H), 4.16 (dd, J=11.6, 7.1 Hz, 1H), 2.80 (dd, J=12.8, 6.0 Hz, 1H), 2.73 (dd, J=12.8, 6.2 Hz, 1H), 2.62-2.48 (m, 4H), 1.74-1.66 (m, 4H). ¹³C NMR (126 MHz, DMSO-d₆): δ 157.22, 153.37 (d, $J_{CF}$=247.5 Hz), 153.12, 148.79, 146.17, 143.29, 130.13, 128.02 (d, $J_{CF}$=12.9 Hz), 127.74, 125.45 (d, $J_{CF}$=4.5 Hz), 112.54, 109.58, 108.55 (d, $J_{CF}$=20.0 Hz), 108.19, 72.65, 66.32, 55.42, 54.31, 23.23. HRMS (DART): m/z [M–H]⁻ calcd for $C_{21}H_{19}BrFN_4O_2^-$, 457.0681; found, 457.0660.

(±)-N-(3-Bromo-2-fluorophenyl)-8-[(piperidin-1-yl)methyl]-7,8-dihydro[1,4]dioxino[2,3-g]quinazolin-4-amine (JGK080)

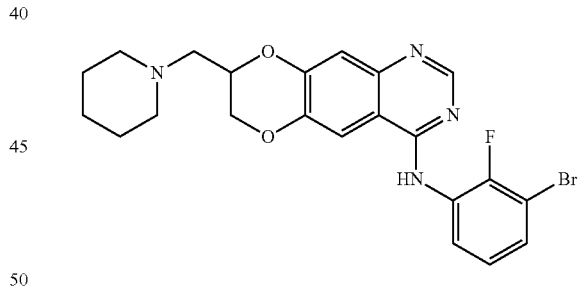

¹H NMR (500 MHz, DMSO-d₆): δ 9.61 (s, 1H), 8.33 (s, 1H), 7.94 (s, 1H), 7.59 (ddd, J=8.0, 6.3, 1.6 Hz, 1H), 7.54 (ddd, J=8.4, 7.0, 1.6 Hz, 1H), 7.21 (td, J=8.1, 1.2 Hz, 1H), 7.18 (s, 1H), 4.59-4.52 (m, 1H), 4.44 (dd, J=11.6, 2.5 Hz, 1H), 4.14 (dd, J=11.7, 7.1 Hz, 1H), 2.65-2.54 (m, 2H), 2.53-2.37 (m, 4H), 1.55-1.47 (m, 4H), 1.43-1.34 (m, 2H). ¹³C NMR (126 MHz, DMSO-d₆): δ 157.21, 153.37 (d, $J_{CF}$=247.1 Hz), 153.11, 148.83, 146.15, 143.32, 130.12, 128.03 (d, $J_{CF}$=13.1 Hz), 127.73, 125.45 (d, $J_{CF}$=4.5 Hz), 112.53, 109.57, 108.55 (d, $J_{CF}$=19.8 Hz), 108.19, 71.63, 66.42, 58.35, 54.74, 25.61, 23.83. HRMS (DART): m/z [M–H]⁻ calcd for $C_{22}H_{21}BrFN_4O_2^-$, 471.0837; found, 471.0814.

173

N-(3-Bromo-2-fluorophenyl)(7,7,8,8-$^2$H$_4$)-7,8-dihydro[1,4]dioxino[2,3-g]quinazolin-4-amine (JGK081)

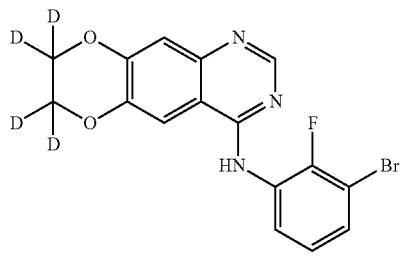 [SMILES: [2H]C1([2H])Oc2cc3ncnc(Nc4cccc(Br)c4F)c3cc2OC1([2H])[2H]]

$^1$H NMR (500 MHz, DMSO-d$_6$): δ 9.61 (s, 1H), 8.33 (s, 1H), 7.93 (s, 1H), 7.59 (ddd, J=7.9, 6.3, 1.6 Hz, 1H), 7.54 (ddd, J=8.4, 7.1, 1.6 Hz, 1H), 7.21 (td, J=8.1, 1.2 Hz, 1H), 7.19 (s, 1H). $^{13}$C NMR (126 MHz, DMSO-d$_6$): δ 157.19, 153.37 (d, J$_{CF}$=247.2 Hz), 153.10, 149.27, 146.03, 143.67, 130.12, 128.03 (d, J$_{CF}$=13.0 Hz), 127.74, 125.44 (d, J$_{CF}$=4.2 Hz), 112.47, 109.63, 108.55 (d, J$_{CF}$=19.9 Hz), 108.35. HRMS (DART): m/z [M+H]$^+$ calcd for C$_{16}$H$_8$D$_4$BrFN$_3$O$_2$$^+$, 380.0342; found, 380.0327.

(±)-N-(3-Bromo-2-fluorophenyl)-7-[2-(pyrrolidin-1-yl)ethyl]-7,8-dihydro[1,4]dioxino[2,3-g]quinazolin-4-amine (JGK084)

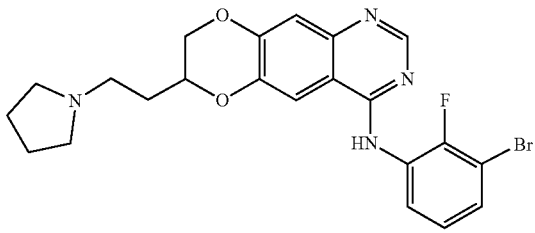 [SMILES: Fc1c(Br)cccc1Nc1ncnc2cc3c(cc12)OC(CCN1CCCC1)CO3]

$^1$H NMR (500 MHz, DMSO-d$_6$): δ 9.60 (s, 1H), 8.33 (s, 1H), 7.95 (s, 1H), 7.58 (ddd, J=8.0, 6.2, 1.6 Hz, 1H), 7.53 (ddd, J=8.4, 7.0, 1.6 Hz, 1H), 7.21 (td, J=8.1, 1.1 Hz, 2H), 7.20 (s, 1H), 4.50 (dd, J=11.5, 2.3 Hz, 1H), 4.42-4.36 (m, 1H), 4.12 (dd, J=11.5, 7.7 Hz, 1H), 2.70-2.56 (m, 2H), 2.49-2.40 (m, 4H), 1.89-1.78 (m, 2H), 1.73-1.64 (m, 4H). $^{13}$C NMR (126 MHz, DMSO-d$_6$): δ 157.21, 153.33 (d, J$_{CF}$=247.5 Hz), 153.13, 148.95, 146.02, 143.37, 130.08, 128.07 (d, J$_{CF}$=13.1 Hz), 127.64, 125.48 (d, J$_{CF}$=4.6 Hz), 112.26, 109.78, 108.58 (d, J$_{CF}$=19.8 Hz), 108.44, 71.76, 67.78, 53.63, 51.03, 29.53, 23.16. HRMS (DART): m/z [M+H]$^+$ calcd for C$_{22}$H$_{23}$BrFN$_4$O$_2$$^+$, 473.0983; found, 473.0976.

174

(±)-N-(3-Bromo-2-fluorophenyl)-7-[2-(piperidin-1-yl)ethyl]-7,8-dihydro[1,4]dioxino[2,3-g]quinazolin-4-amine (JGK085)

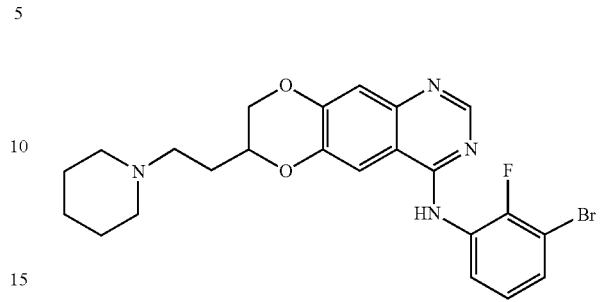

$^1$H NMR (500 MHz, DMSO-d$_6$): δ 9.60 (s, 1H), 8.33 (s, 1H), 7.94 (s, 1H), 7.58 (ddd, J=8.0, 6.2, 1.6 Hz, 1H), 7.53 (ddd, J=8.4, 7.1, 1.6 Hz, 1H), 7.204 (td, J=8.2, 1.3 Hz, 1H), 7.198 (s, 1H), 4.51 (dd, J=11.5, 2.4 Hz, 1H), 4.39-4.33 (m, 1H), 4.11 (dd, J=11.6, 7.8 Hz, 1H), 2.50-2.44 (m, 2H), 2.42-2.27 (m, 4H), 1.90-1.76 (m, 2H), 1.55-1.45 (m, 4H), 1.42-1.34 (m, 2H). $^{13}$C NMR (126 MHz, DMSO-d$_6$): δ 157.20, 153.33 (d, J$_{CF}$=247.4 Hz), 153.12, 148.95, 146.02, 143.39, 130.08, 128.07 (d, J$_{CF}$=13.1 Hz), 127.64, 125.48 (d, J$_{CF}$=4.5 Hz), 112.25, 109.77, 108.58 (d, J$_{CF}$=20.0 Hz), 108.43, 71.97, 67.80, 54.08, 53.96, 27.69, 25.61, 24.12. HRMS (DART): m/z [M+H]$^+$ calcd for C$_{23}$H$_{25}$BrFN$_4$O$_2$$^+$, 487.1139; found, 487.1137.

(±)-N-(3-Bromo-2-fluorophenyl)-8-[2-(morpholin-4-yl)ethyl]-7,8-dihydro[1,4]dioxino[2,3-g]quinazolin-4-amine (JGK086)

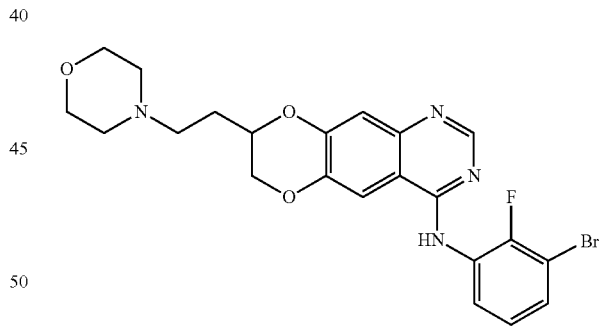

$^1$H NMR (500 MHz, DMSO-d$_6$): δ 9.63 (s, 1H), 8.32 (s, 1H), 7.93 (s, 1H), 7.58 (ddd, J=8.0, 6.3, 1.5 Hz, 1H), 7.53 (t, J=7.0 Hz, 1H), 7.21 (td, J=8.1, 1.2 Hz, 1H), 4.50 (dd, J=11.5, 2.4 Hz, 1H), 4.47-4.40 (m, 1H), 4.10 (dd, J=11.6, 7.4 Hz, 1H), 3.58 (t, J=4.7 Hz, 4H), 2.55-2.46 (m, 2H), 2.45-2.33 (m, 4H), 1.92-1.79 (m, 2H). $^{13}$C NMR (126 MHz, DMSO-d$_6$): δ 157.20, 153.33 (d, J$_{CF}$=248.3 Hz), 153.06, 148.94, 146.06, 143.26, 130.03, 128.12 (d, J$_{CF}$=9.8 Hz), 127.69, 125.44 (d, J$_{CF}$=4.4 Hz), 112.47, 109.64, 108.55 (d, J$_{CF}$=19.9 Hz), 108.18, 72.30, 67.35, 66.22, 53.53, 53.28, 27.25. HRMS (DART): m/z [M+H]$^+$ calcd for C$_{22}$H$_{23}$BrFN$_4$O$_3$$^+$, 489.0932; found, 489.0926.

175

(±)-N-(3-Bromo-2-fluorophenyl)-8-[2-(dimethylamino)ethyl]-7,8-dihydro[1,4]dioxino[2,3-g]quinazolin-4-amine (JGK087)

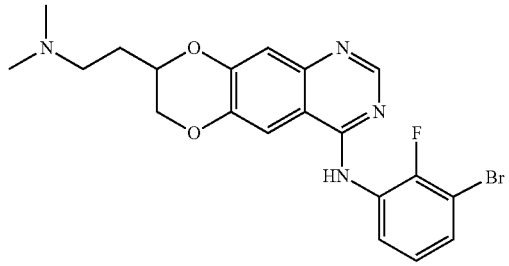 [SMILES: CN(C)CCC1COc2cc3c(Nc4cccc(Br)c4F)ncnc3cc2O1]

¹H NMR (500 MHz, DMSO-d₆): δ 9.61 (s, 1H), 8.33 (s, 1H), 7.93 (s, 1H), 7.59 (t, J=6.9 Hz, 1H), 7.54 (t, J=7.5 Hz, 1H), 7.21 (t, J=8.1 Hz, 1H), 7.18 (s, 1H), 4.49 (dd, J=11.6, 2.3 Hz, 1H), 4.45-4.38 (m, 1H), 4.09 (dd, J=11.6, 7.5 Hz, 1H), 2.47-2.38 (m, 2H), 2.17 (s, 6H), 1.86-1.78 (m, 2H). ¹³C NMR (126 MHz, DMSO-d₆): δ 157.20, 153.37 (d, $J_{CF}$=247.6 Hz), 153.08, 148.99, 146.14, 143.29, 130.10, 128.07 (d, $J_{CF}$=15.6 Hz), 127.72, 125.44 (d, $J_{CF}$=4.4 Hz), 112.50, 109.58, 108.54 (d, $J_{CF}$=19.7 Hz), 108.13, 72.30, 67.36, 54.43, 45.17, 28.27. HRMS (DART): m/z [M+H]⁺ calcd for $C_{20}H_{21}BrFN_4O_2^+$, 447.0826; found, 447.0818.

(±)-N-(3-Bromo-2-fluorophenyl)-8-[2-(4-methylpiperazin-1-yl)ethyl]-7,8-dihydro[1,4]dioxino[2,3-g]quinazolin-4-amine (JGK088)

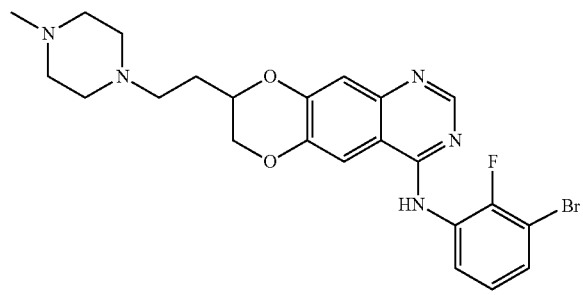 [SMILES: CN1CCN(CCC2COc3cc4c(Nc5cccc(Br)c5F)ncnc4cc3O2)CC1]

¹H NMR (500 MHz, DMSO-d₆): δ 9.62 (s, 1H), 8.33 (s, 1H), 7.93 (s, 1H), 7.59 (t, J=7.1 Hz, 1H), 7.54 (t, J=7.5 Hz, 1H), 7.21 (t, J=8.0 Hz, 1H), 7.17 (s, 1H), 4.49 (dd, J=11.5, 2.4 Hz, 1H), 4.45-4.38 (m, 1H), 4.10 (dd, J=11.6, 7.4 Hz, 1H), 2.48-2.21 (m, 10H), 2.14 (s, 3H), 1.91-1.76 (m, 2H). ¹³C NMR (126 MHz, DMSO-d₆): δ 157.20, 153.36 (d, $J_{CF}$=246.9 Hz), 153.08, 148.98, 146.13, 143.28, 130.09, 128.05 (d, $J_{CF}$=11.7 Hz), 127.72, 125.44 (d, $J_{CF}$=4.3 Hz), 112.50, 109.58, 108.55 (d, $J_{CF}$=19.8 Hz), 108.13, 72.40, 67.37, 54.78, 53.11, 52.65, 45.76, 27.61. HRMS (DART): m/z [M+H]⁺ calcd for $C_{23}H_{26}BrFN_5O_2^+$, 502.1248; found, 502.1240.

176

(±)-N-(3-Bromo-2-fluorophenyl)-8-[2-(pyrrolidin-1-yl)ethyl]-7,8-dihydro[1,4]dioxino[2,3-g]quinazolin-4-amine (JGK089)

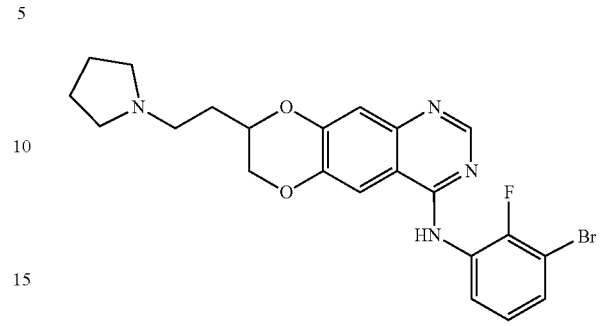

¹H NMR (500 MHz, DMSO-d₆): δ 9.62 (s, 1H), 8.33 (s, 1H), 7.93 (s, 1H), 7.59 (t, J=7.2 Hz, 1H), 7.53 (t, J=7.5 Hz, 1H), 7.21 (t, J=8.0 Hz, 1H), 7.17 (s, 1H), 4.49 (dd, J=11.5, 2.4 Hz, 1H), 4.47-4.41 (m, 1H), 4.10 (dd, J=11.5, 7.4 Hz, 1H), 2.68-2.53 (m, 2H), 2.50-2.40 (m, 4H), 1.89-1.81 (m, 2H), 1.73-1.65 (m, 4H). ¹³C NMR (126 MHz, DMSO-d₆): 157.20, 153.36 (d, $J_{CF}$=246.9 Hz), 153.07, 148.98, 146.13, 143.28, 130.07, 128.10, 127.71, 125.44 (d, $J_{CF}$=4.6 Hz), 112.48, 109.60, 108.55 (d, $J_{CF}$=19.8 Hz), 108.15, 72.31, 67.37, 53.57, 50.97, 29.58, 23.14. HRMS (DART): m/z [M+H]⁺ calcd for $C_{22}H_{23}BrFN_4O_2^+$, 473.0983; found, 473.0976.

(±)-N-(3-Bromo-2-fluorophenyl)-8-[2-(piperidin-1-yl)ethyl]-7,8-dihydro[1,4]dioxino[2,3-g]quinazolin-4-amine (JGK090)

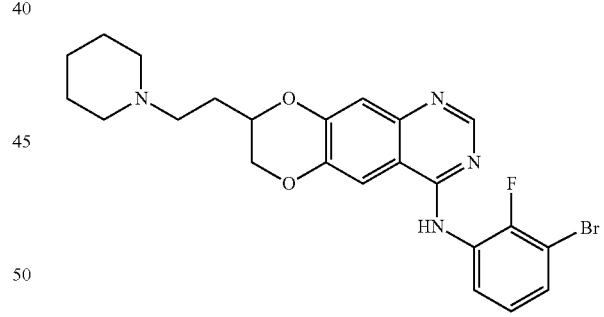

¹H NMR (500 MHz, DMSO-d₆): δ 9.62 (s, 1H), 8.32 (s, 1H), 7.93 (s, 1H), 7.59 (t, J=7.1 Hz, 1H), 7.53 (t, J=7.5 Hz, 1H), 7.21 (td, J=8.0, 1.2 Hz, 1H), 7.17 (s, 1H), 4.49 (dd, J=11.5, 2.4 Hz, 1H), 4.44-4.37 (m, 1H), 4.10 (dd, J=11.6, 7.4 Hz, 1H), 2.48-2.43 (m, 2H), 2.41-2.27 (m, 4H), 1.90-1.77 (m, 2H), 1.54-1.45 (m, 4H), 1.42-1.34 (m, 2H). ¹³C NMR (126 MHz, DMSO-d₆): δ 157.19, 153.34 (d, $J_{CF}$=246.7 Hz), 153.07, 149.00, 146.11, 143.29, 130.07, 128.10, 127.71, 125.44 (d, $J_{CF}$=4.3 Hz), 112.48, 109.60, 108.55 (d, $J_{CF}$=19.9 Hz), 108.14, 72.50, 67.40, 54.02, 53.87, 27.70, 25.63, 24.13. HRMS (DART): m/z [M+H]⁺ calcd for $C_{23}H_{25}BrFN_4O_2^+$, 487.1139; found, 487.1133.

N-(3-Bromo-2-fluorophenyl)-8,9-dihydro-7H-[1,4]dioxepino[2,3-g]quinazolin-4-amine (JGK091)

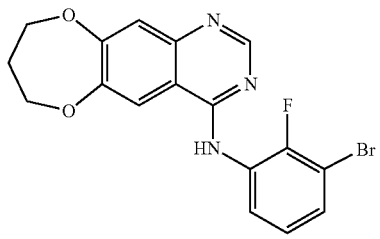 [SMILES: Fc1c(Br)cccc1Nc1ncnc2cc3c(cc12)OCCCO3]

$^1$H NMR (500 MHz, CDCl$_3$): δ 8.71 (s, 1H), 8.65 (ddd, J=8.3, 7.3, 1.5 Hz, 1H), 7.48 (s, 1H), 7.43 (s, 1H), 7.39 (br, 1H), 7.28 (ddd, J=8.1, 6.5, 1.5 Hz, 1H), 7.11 (td, J=8.2, 1.6 Hz, 1H), 4.41 (t, J=5.7 Hz, 1H), 4.38 (t, J=5.8 Hz, 1H), 2.32 (p, J=5.8 Hz, 1H). $^{13}$C NMR (126 MHz, CDCl$_3$): δ 157.06, 156.08, 153.93, 151.62, 150.19 (d, J$_{CF}$=242.7 Hz), 147.83, 128.53 (d, J$_{CF}$=10.4 Hz), 127.39, 125.32 (d, J$_{CF}$=4.7 Hz), 121.84, 119.15, 111.47, 110.85, 108.62 (d, J$_{CF}$=19.3 Hz), 70.86, 70.51, 31.03. HRMS (DART): m/z [M+H]$^+$ calcd for C$_{17}$H$_{14}$BrFN$_3$O$_2$$^+$, 390.0248; found, 390.0236.

N-(3-Bromo-2-fluorophenyl)-2H-[1,3]dioxolo[4,5-g]quinazolin-8-amine (JGK092)

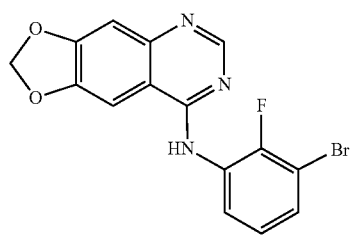 [SMILES: Fc1c(Br)cccc1Nc1ncnc2cc3c(cc12)OCO3]

$^1$H NMR (500 MHz, CDCl$_3$): δ 8.69 (s, 1H), 8.58 (ddd, J=8.3, 7.3, 1.5 Hz, 1H), 7.28 (ddd, J=8.1, 6.5, 1.6 Hz, 1H), 7.25 (br, 1H), 7.14 (s, 1H), 7.11 (td, J=8.2, 1.6 Hz, 1H), 6.17 (s, 2H), signal of one proton missing (probably hidden by the chloroform signal). $^{13}$C NMR (126 MHz, CDCl$_3$): δ 156.10, 153.37, 153.22, 150.22 (d, J$_{CF}$=242.3 Hz), 149.37, 148.43, 128.67 (d, J$_{CF}$=10.4 Hz), 127.28, 125.30 (d, J$_{CF}$=4.7 Hz), 121.84, 110.75, 108.64 (d, J$_{CF}$=19.4 Hz), 106.29, 102.48, 96.49. HRMS (DART): m/z [M+H]$^+$ calcd for C$_{15}$H$_{10}$BrFN$_3$O$_2$$^+$, 361.9935; found, 361.9925.

Example 19

Metabolic Studies of Exemplary Compounds of the JGK Series

Figure 47:
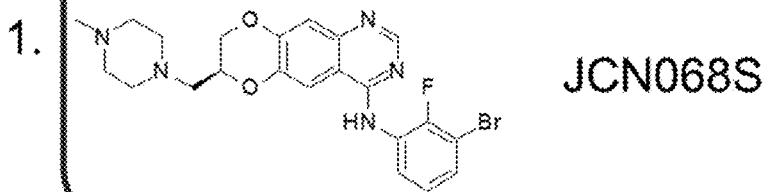
FIG. 47 depicts certain metabolites of exemplary compounds of the disclosure.
Figure 47:
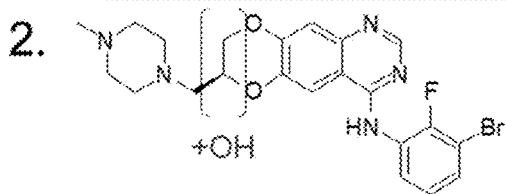
Figure 47:
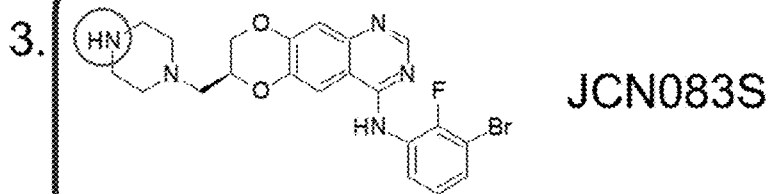
Figure 47:
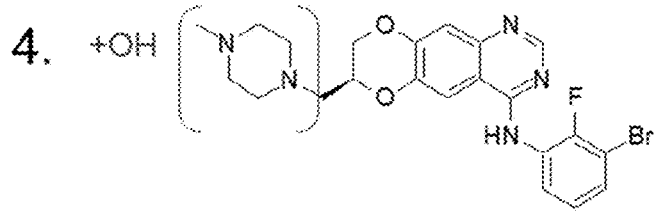
Figure 47:
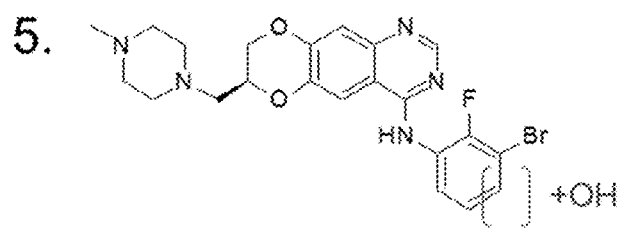
Figure 47:
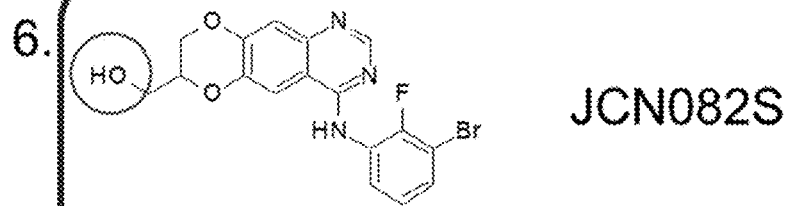
Figure 48A:
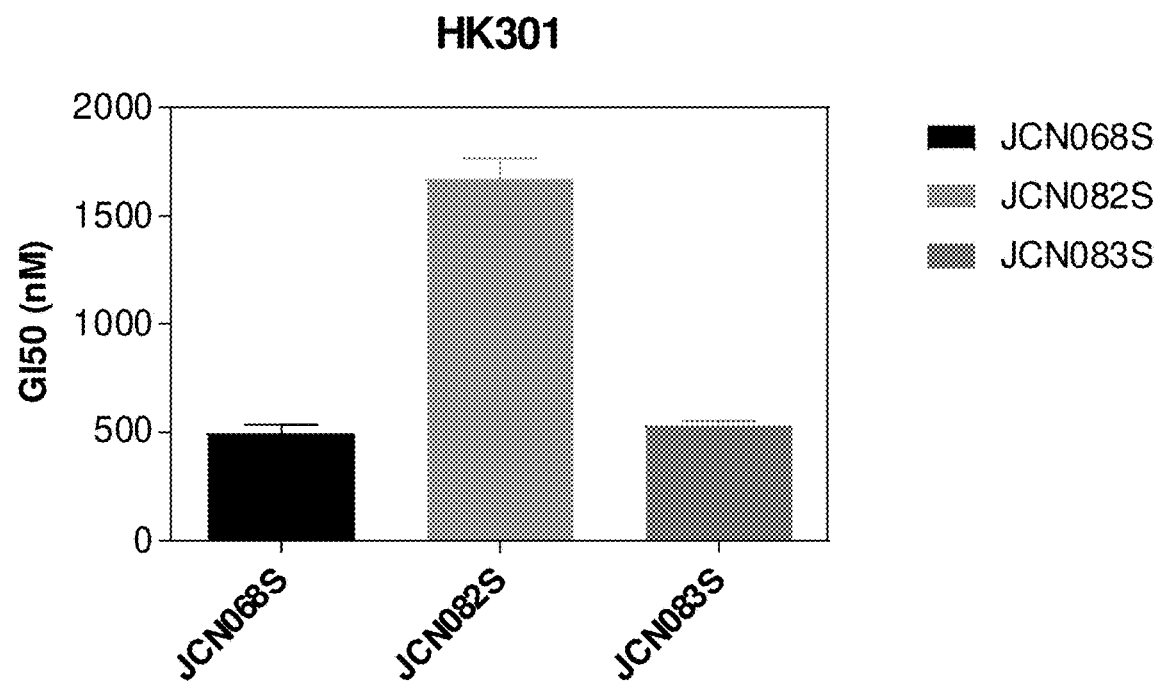
FIG. 48A depicts the activite of exemplary compounds of the disclosure against HK301.
Figure 48B:
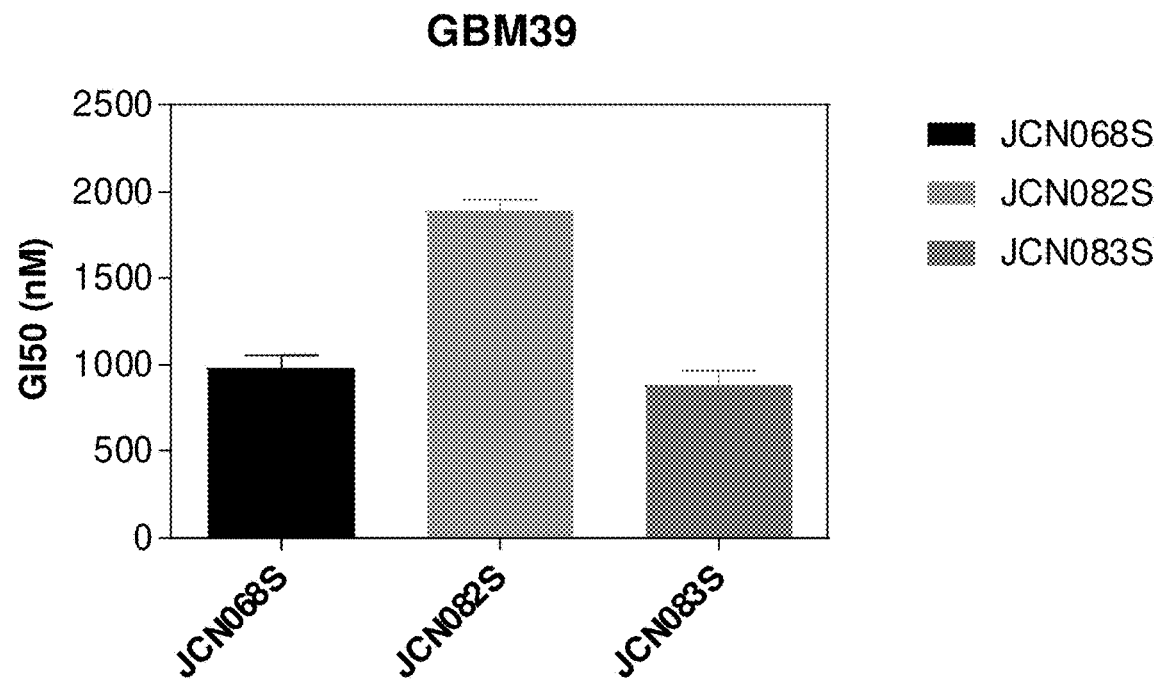
FIG. 48B depicts the activite of exemplary compounds of the disclosure against GBM39.
Figure 48C:
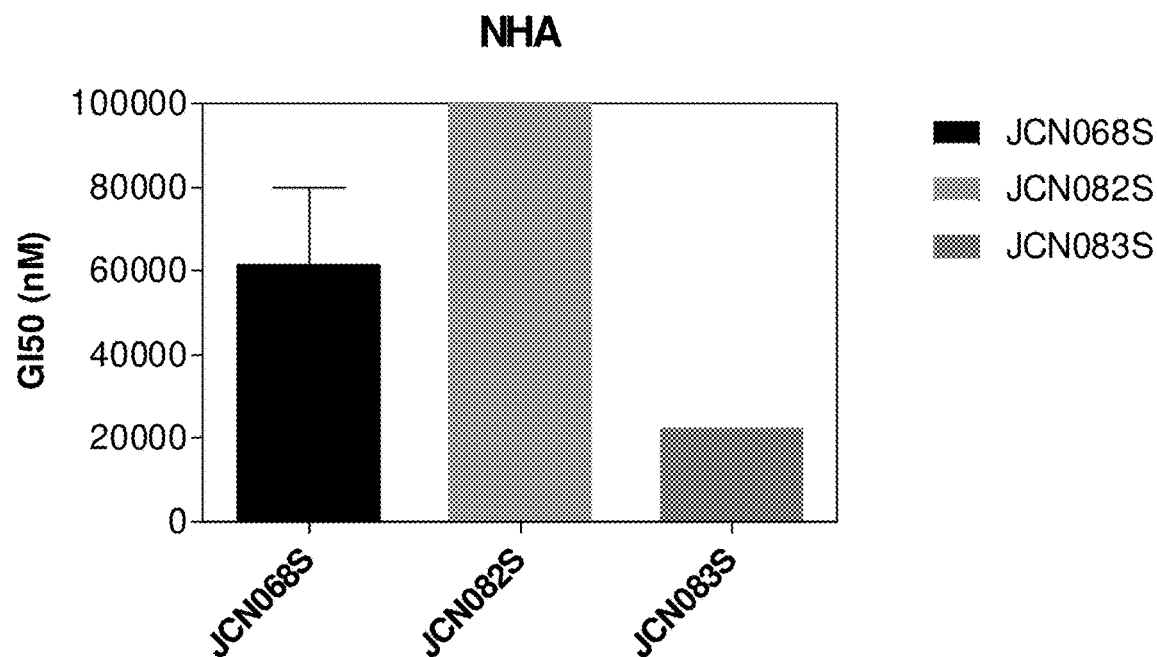
FIG. 48C depicts the activite of exemplary compounds of the disclosure against NHA.
Figure 49A:
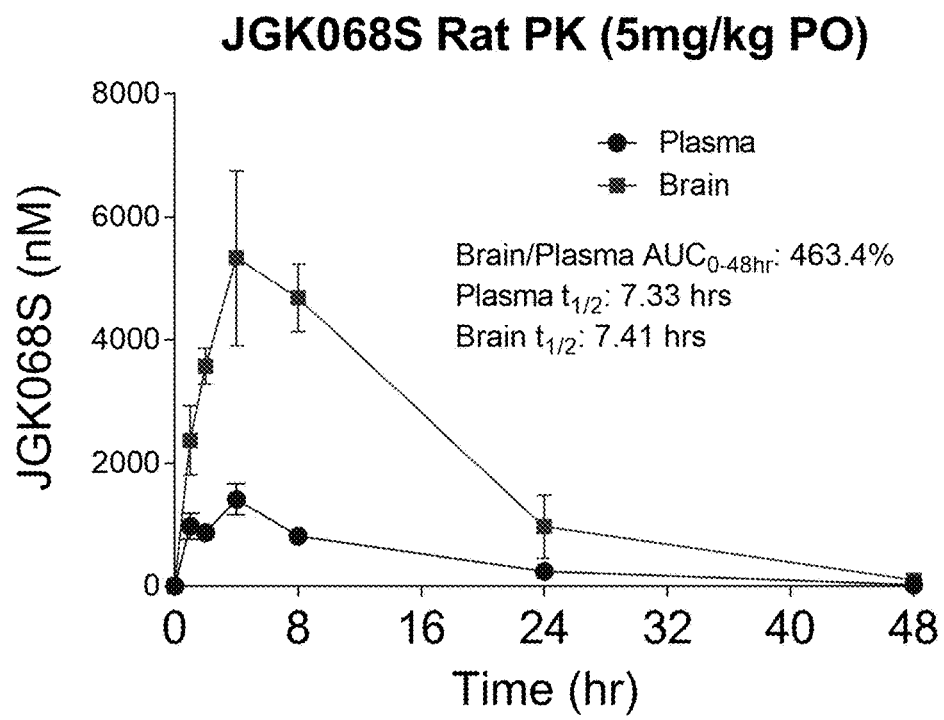
FIG. 49A depicts the ADME characteristics of an exemplary compound of the disclosure in rats following PO administration.
Figure 49B:
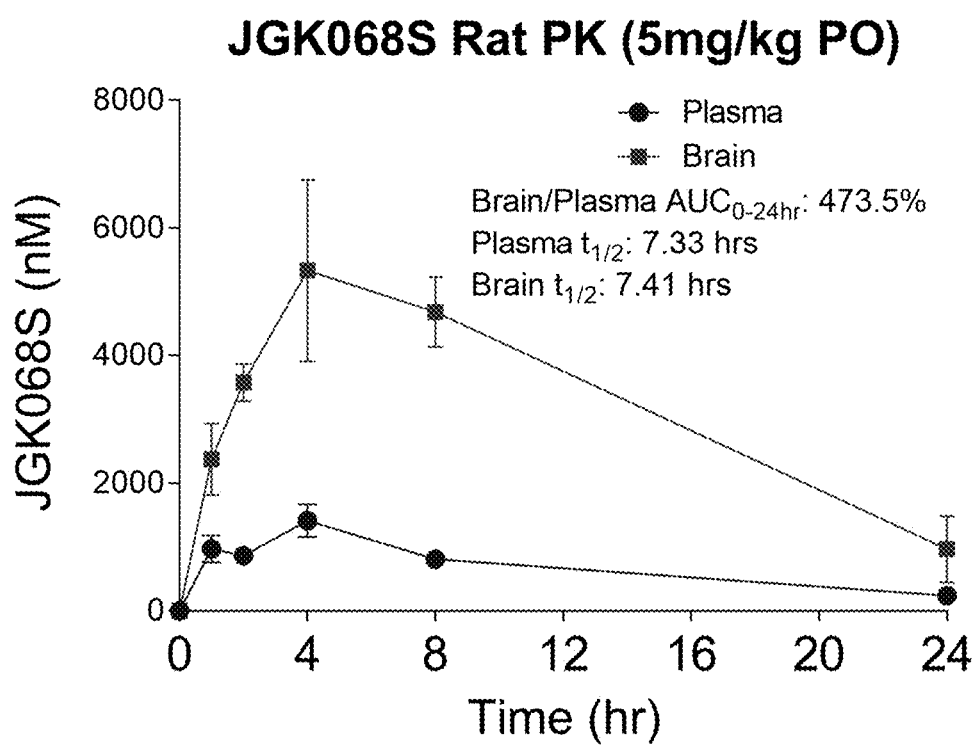
FIG. 49B depicts the ADME characteristics of an exemplary compound of the disclosure in rats following PO administration.
Figure 50A:
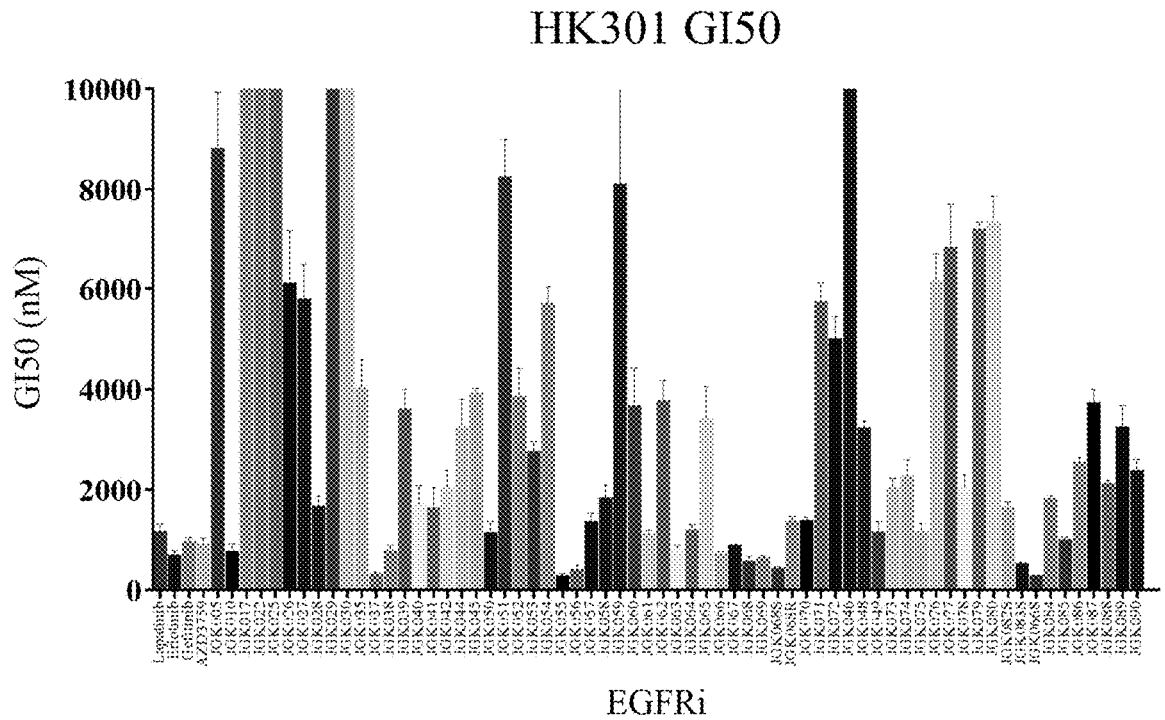
FIG. 50A depicts the activity of certain compounds of the disclosure as compared against the current standard of care (i.e., Labpatinib, Erlotinib, Gefitinib, and AZD3759) against HK301, a patient derived, EGFRvIII mutant GBM gliomasphere.
Figure 50B:
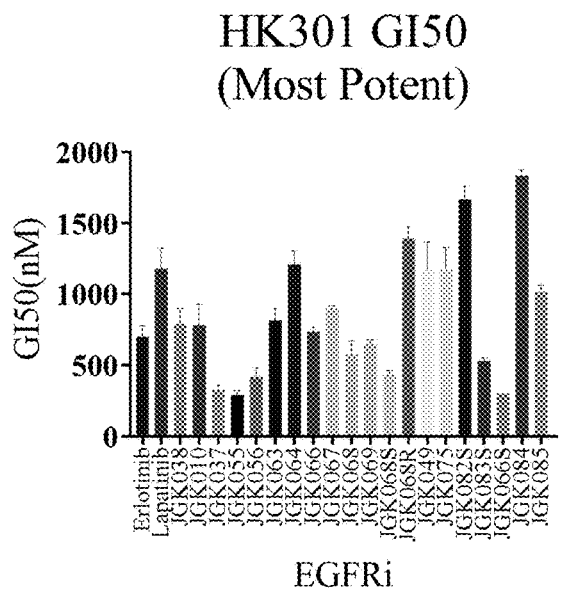
FIG. 50B depicts the activity of certain compounds of the disclosure as compared against the current standard of care (i.e., Labpatinib, Erlotinib, Gefitinib, and AZD3759) against HK301, a patient derived, EGFRvIII mutant GBM gliomasphere.
Figure 51A:
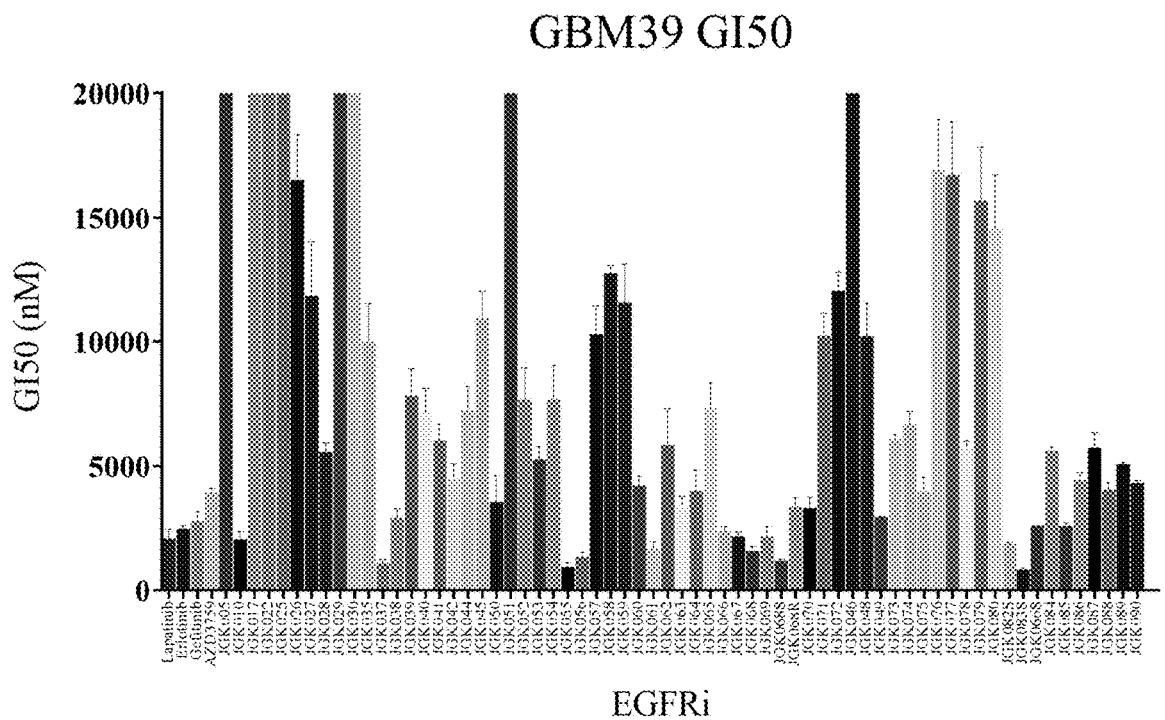
FIG. 51A depicts the activity of certain compounds of the disclosure as compared against the current standard of care (i.e., Labpatinib, Erlotinib, Gefitinib, and AZD3759) against GBM39, a patient derived, EGFRvIII mutant GBM gliomasphere.
Figure 51B:
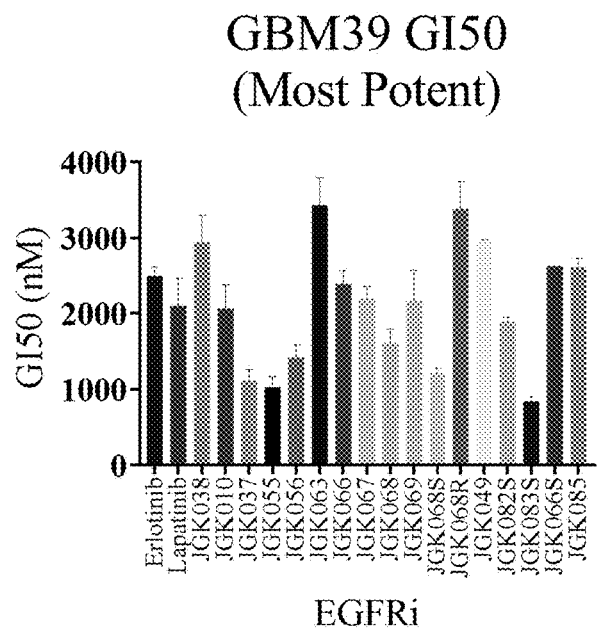
FIG. 51B depicts the activity of certain compounds of the disclosure as compared against the current standard of care (i.e., Labpatinib, Erlotinib, Gefitinib, and AZD3759) against GBM39, a patient derived, EGFRvIII mutant GBM gliomasphere.
Figure 52A:
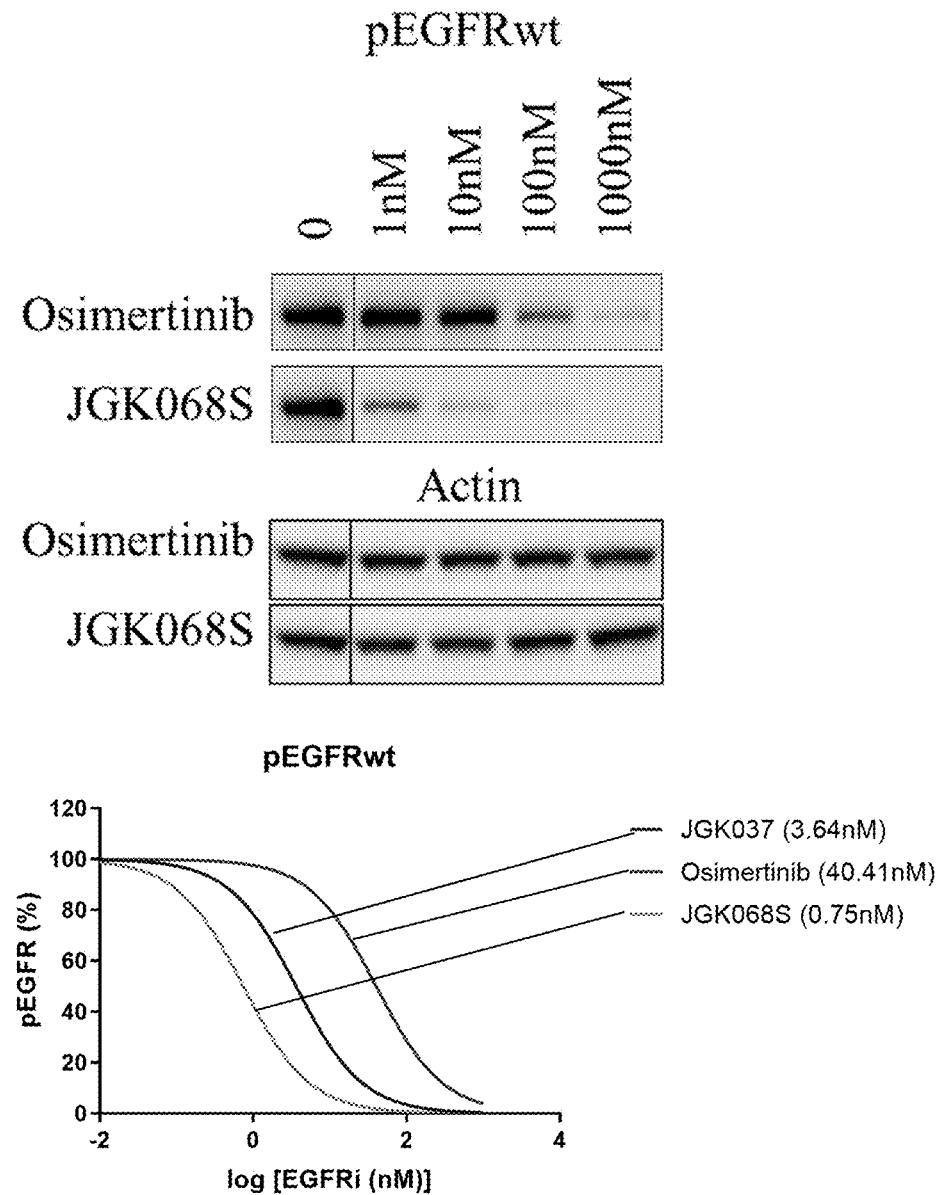
FIG. 52A depicts the activity of osimertinib and JGK068S against pEGFRwt.
Figure 52B:
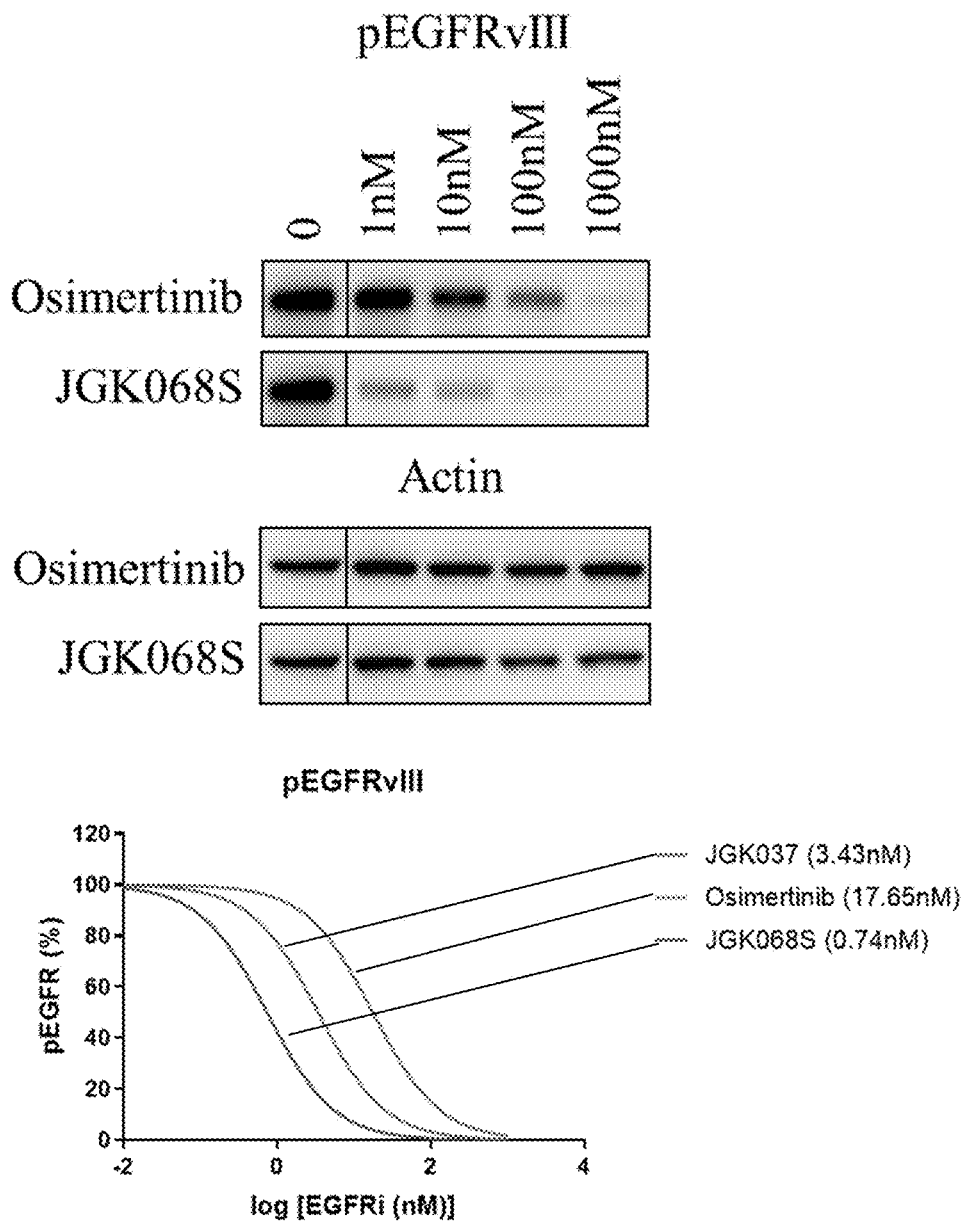
FIG. 52B depicts the activity of osimertinib and JGK068S against pEGFRvIII.
Figure 53A:
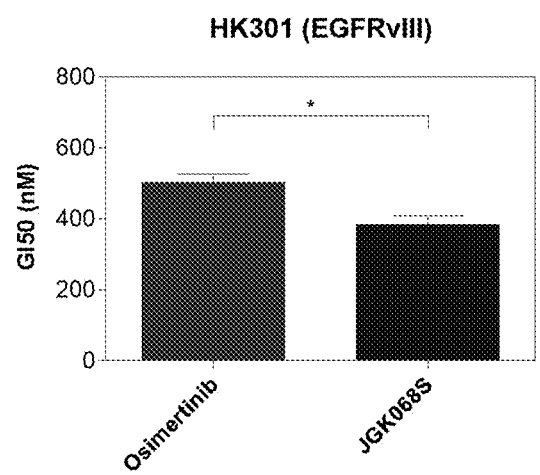
FIG. 53A depicts the activity of osimertinib and JGK068S against HK301.
Figure 53B:
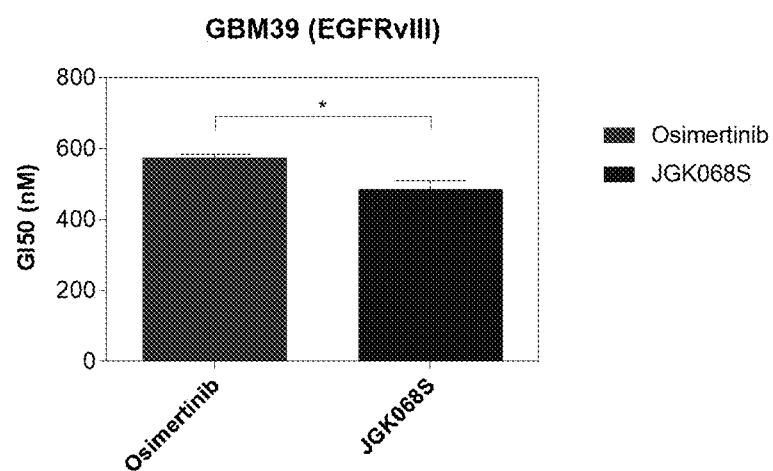
FIG. 53B depicts the activity of osimertinib and JGK068S against GBM39.
Figure 54A:
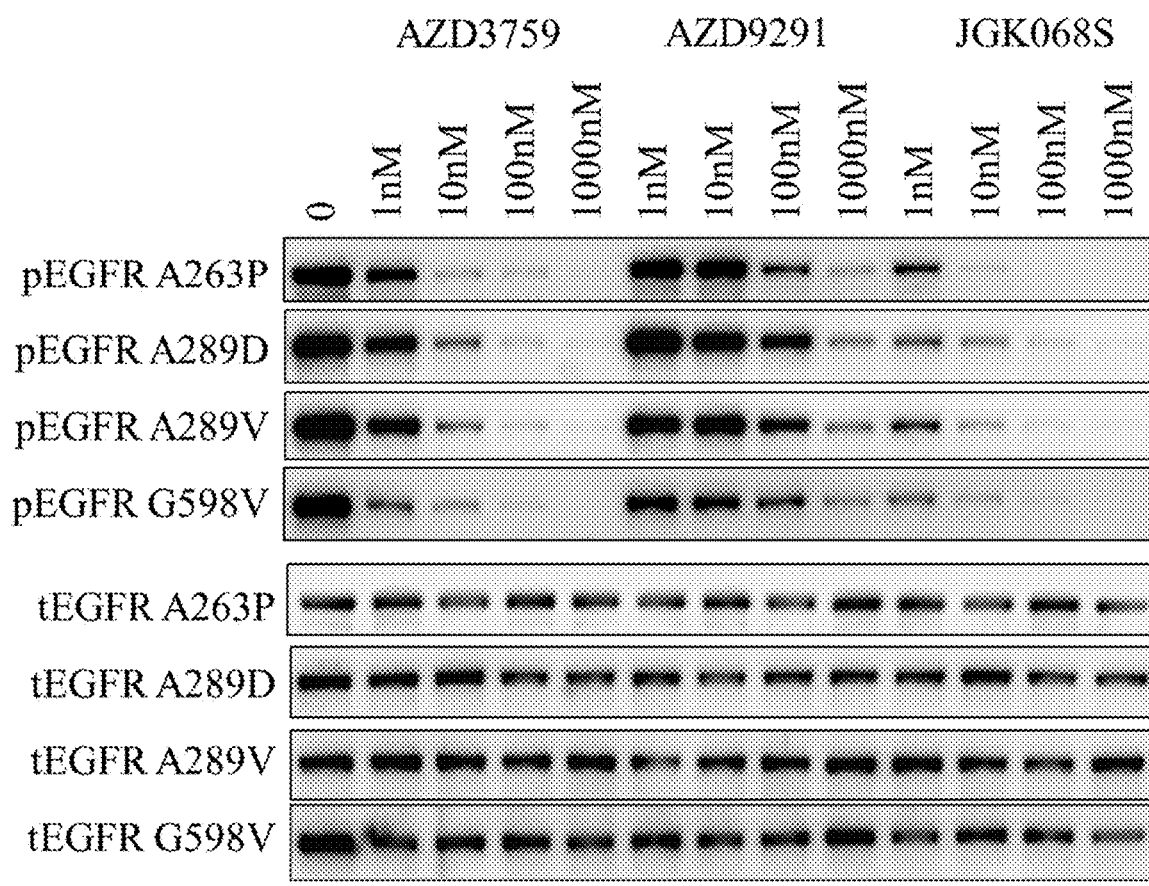
FIG. 54A depicts the activity of AZD3759, AZD9291, and JGK068S against certain EGFR mutants.
Figure 54B:
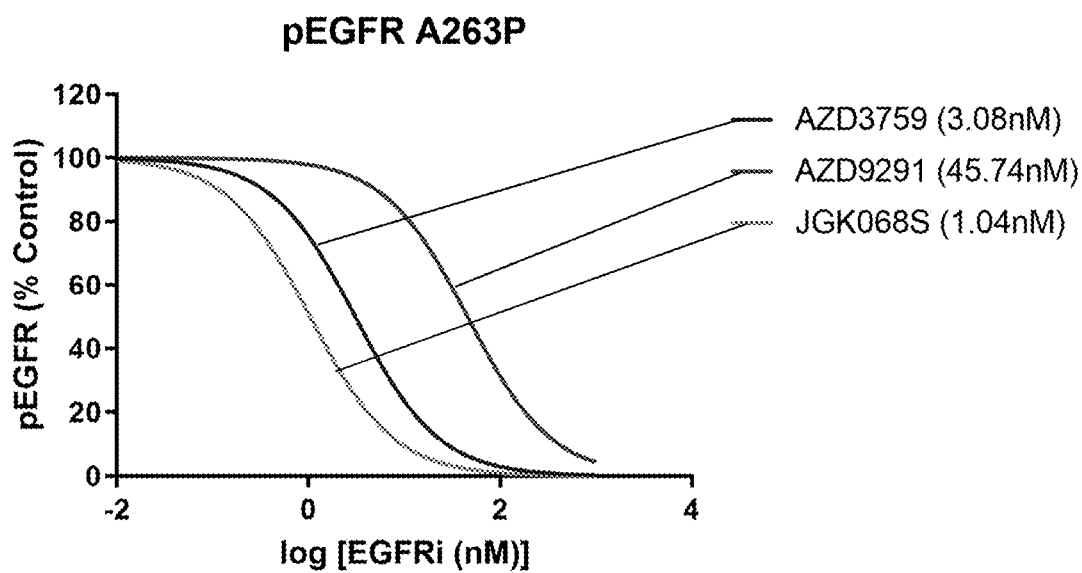
FIG. 54B depicts the activity of AZD3759, AZD9291, and JGK068S against pEGFR A263P.
Figure 54C:
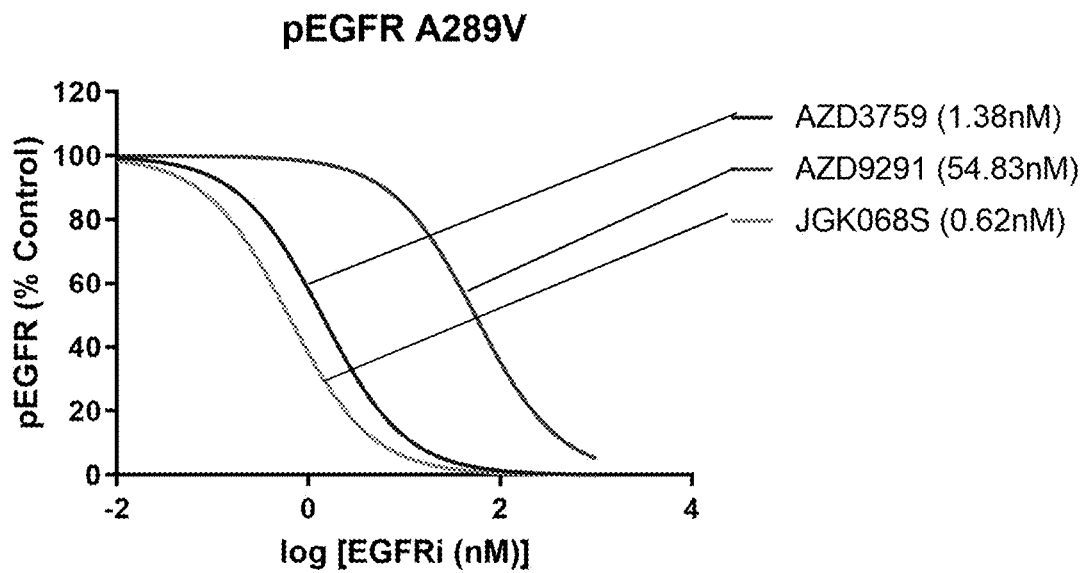
FIG. 54C depicts the activity of AZD3759, AZD9291, and JGK068S against pEGFR A289V.
Figure 54D:
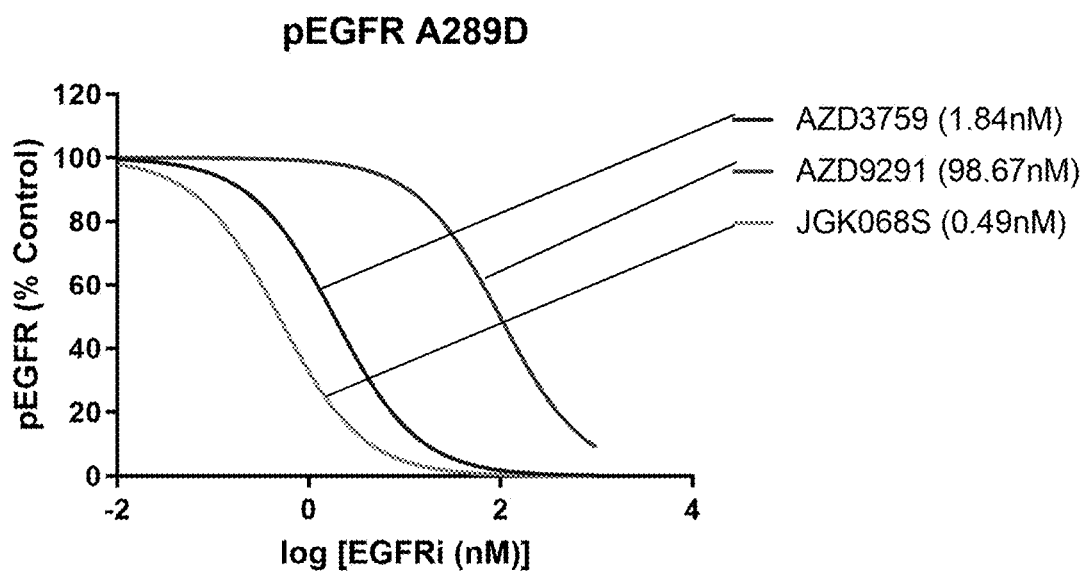
FIG. 54D depicts the activity of AZD3759, AZD9291, and JGK068S against pEGFR A289D.
Figure 54E:
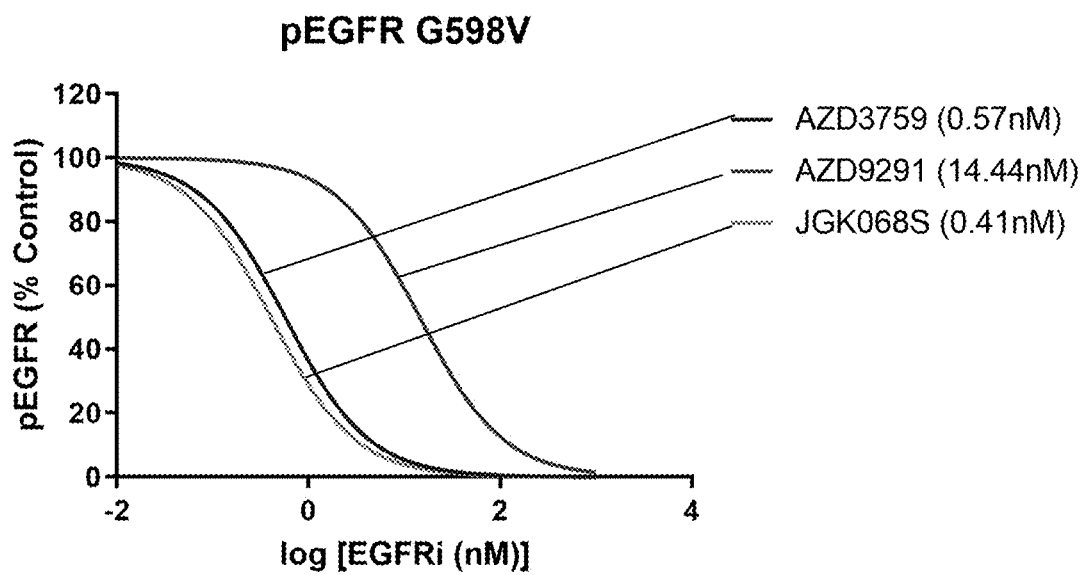
FIG. 54E depicts the activity of AZD3759, AZD9291, and JGK068S against pEGFR G598V.

Exemplary compounds (10 mM) were incubated in human, dog, mouse, or rat liver microsomes (1 mg/mL) for up to 90 minutes at 37° C. Reactions were stopped by the addition of acetonitrile. Controls (compound free) microsome studies were run in parallel. LCMS Studies were performed on a Waters Xevo G2 QTof equipped with a Luna Omega Polar C18, 1.6 m, 2.1×30 mm column. Structures of exemplary metabolites are depicted in FIG. 47,

| Modification | Human (%) | Dog (%) | Mouse (%) | Rat (%) |
|---|---|---|---|---|
| 1. Parent | 67.0 | 3.5 | 59.9 | 70.2 |
| 2. Hydroxylation | 6.0 | 0.0 | 0.0 | 4.8 |
| 3. N-demethylation | 13.7 | 0.9 | 5.4 | 8.2 |
| 4. Hydroxylation | 4.2 | 61.9 | 22.0 | 21.9 |
| 5. Hydroxylation | 0.7 | 0.0 | 0.0 | 0.6 |
| 6. N-dealkylation | 6.5 | 0.0 | 1.3 | 2.7 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound selected from the group consisting of:

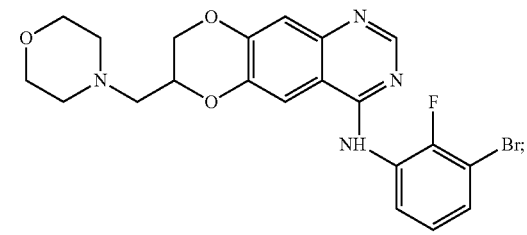

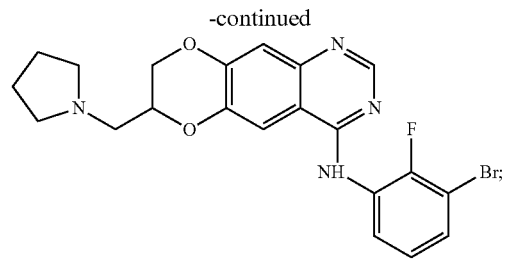

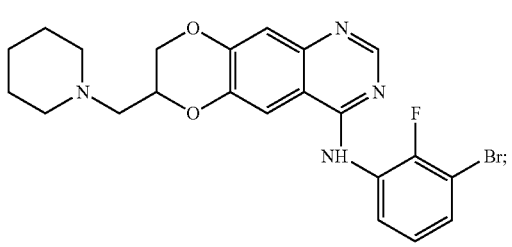

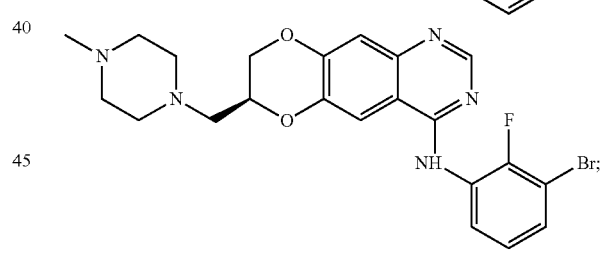

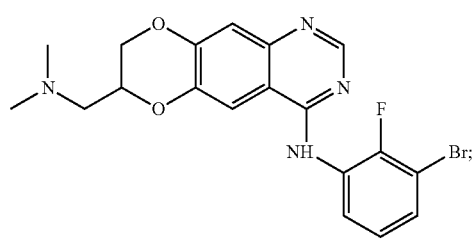

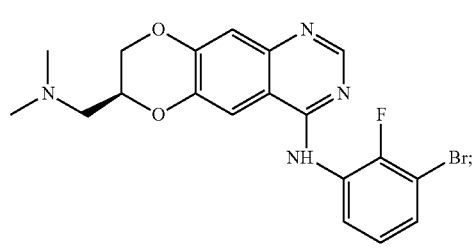

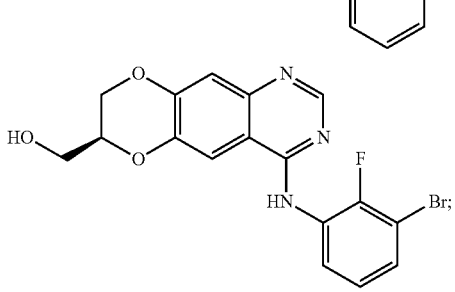

-continued

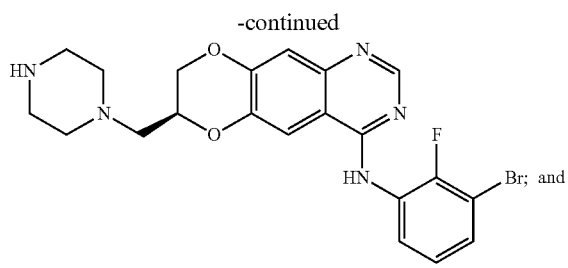

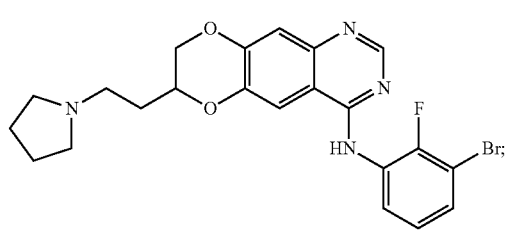 [SMILES: Fc1c(Br)cccc1Nc1ncnc2cc3c(cc12)OC(CCN1CCCC1)CO3]

or a pharmaceutically acceptable salt thereof.

2. The compound of claim 1, wherein the compound is

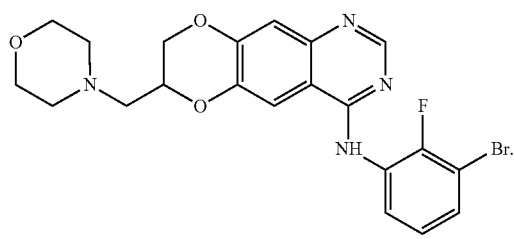 [SMILES: Fc1c(Br)cccc1Nc1ncnc2cc3c(cc12)OC(CN1CCOCC1)CO3]

3. The compound of claim 1, wherein the compound is

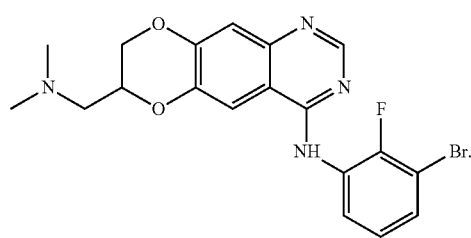 [SMILES: CN(C)CC1COc2cc3ncnc(Nc4cccc(Br)c4F)c3cc2O1]

4. The compound of claim 1, wherein the compound is

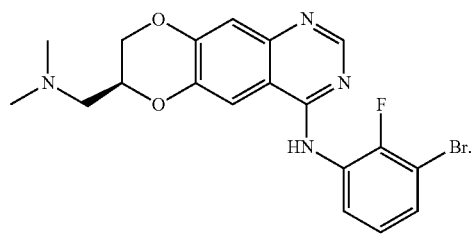 [SMILES: CN(C)C[C@H]1COc2cc3ncnc(Nc4cccc(Br)c4F)c3cc2O1]

5. The compound of claim 1, wherein the compound is

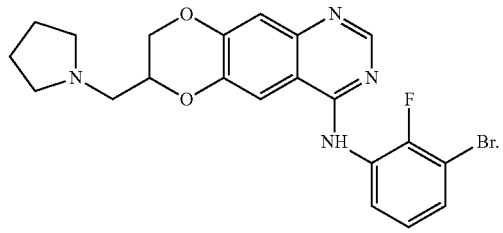 [SMILES: Fc1c(Br)cccc1Nc1ncnc2cc3c(cc12)OC(CN1CCCC1)CO3]

6. The compound of claim 1, wherein the compound is

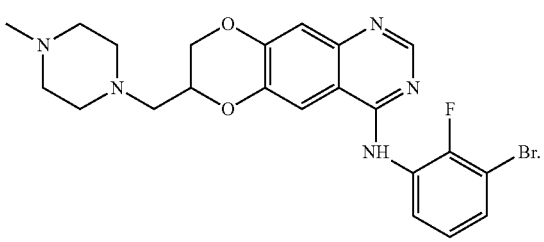 [SMILES: CN1CCN(CC2COc3cc4ncnc(Nc5cccc(Br)c5F)c4cc3O2)CC1]

7. The compound of claim 1, wherein the compound is

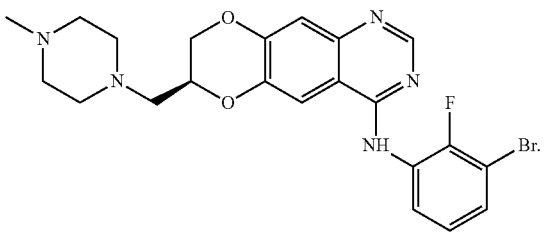 [SMILES: CN1CCN(C[C@H]2COc3cc4ncnc(Nc5cccc(Br)c5F)c4cc3O2)CC1]

8. The compound of claim 1, wherein the compound is

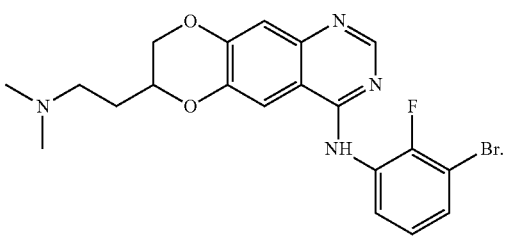 [SMILES: CN(C)CCC1COc2cc3ncnc(Nc4cccc(Br)c4F)c3cc2O1]

9. The compound of claim 1, wherein the compound is

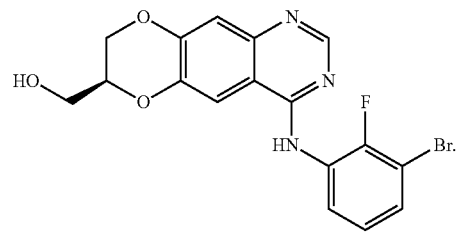 [SMILES: OC[C@H]1COc2cc3ncnc(Nc4cccc(Br)c4F)c3cc2O1]

10. The compound of claim 1, wherein the compound is

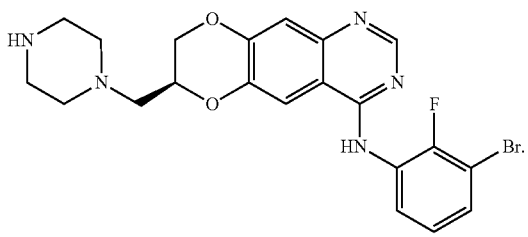 [SMILES: Fc1c(Br)cccc1Nc1ncnc2cc3c(cc12)O[C@@H](CN1CCNCC1)CO3]

11. The compound of claim 1, wherein the compound is

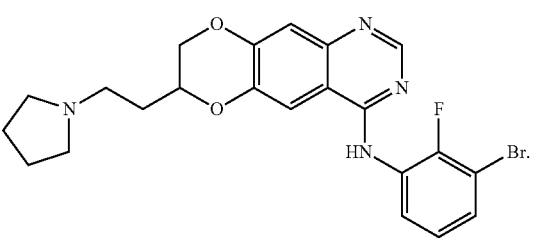 [SMILES: Fc1c(Br)cccc1Nc1ncnc2cc3c(cc12)OC(CCN1CCCC1)CO3]

12. The compound of claim 1, wherein the compound is a pharmaceutically acceptable salt of the compound which is

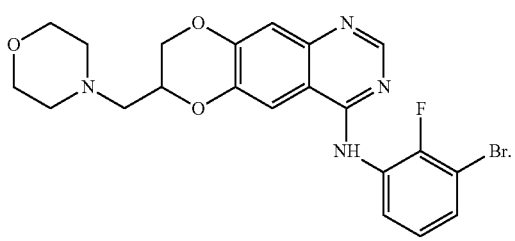 [SMILES: Fc1c(Br)cccc1Nc1ncnc2cc3c(cc12)OC(CN1CCOCC1)CO3]

13. The compound of claim 1, wherein the compound is a pharmaceutically acceptable salt of the compound which is

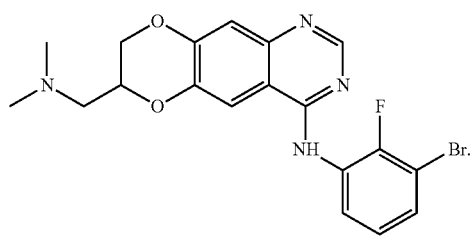 [SMILES: CN(C)CC1COc2cc3ncnc(Nc4cccc(Br)c4F)c3cc2O1]

14. The compound of claim 1, wherein the compound is a pharmaceutically acceptable salt of the compound which is

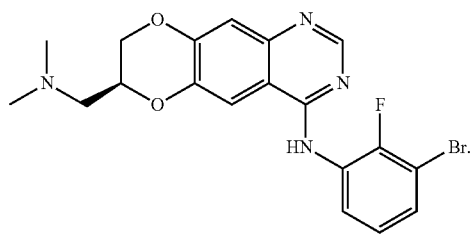 [SMILES: CN(C)C[C@H]1COc2cc3ncnc(Nc4cccc(Br)c4F)c3cc2O1]

15. The compound of claim 1, wherein the compound is a pharmaceutically acceptable salt of the compound which is

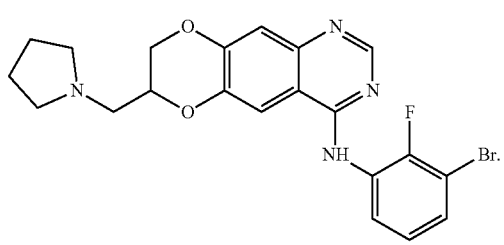 [SMILES: Fc1c(Br)cccc1Nc1ncnc2cc3c(cc12)OC(CN1CCCC1)CO3]

16. The compound of claim 1, wherein the compound is a pharmaceutically acceptable salt of the compound which is

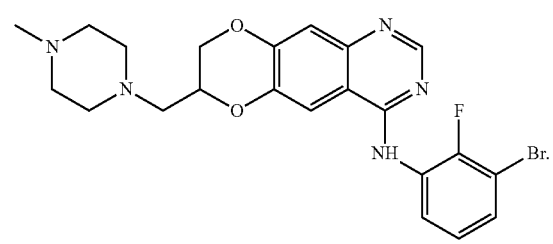 [SMILES: CN1CCN(CC2COc3cc4ncnc(Nc5cccc(Br)c5F)c4cc3O2)CC1]

17. The compound of claim 1, wherein the compound is a pharmaceutically acceptable salt of the compound which is

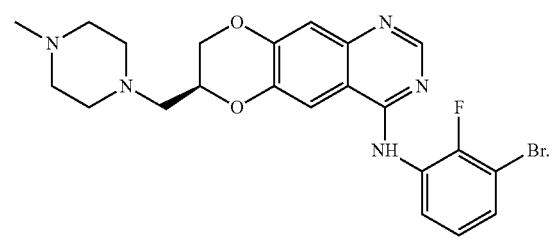 [SMILES: CN1CCN(C[C@H]2COc3cc4ncnc(Nc5cccc(Br)c5F)c4cc3O2)CC1]

18. The compound of claim 1, wherein the compound is a pharmaceutically acceptable salt of the compound which is

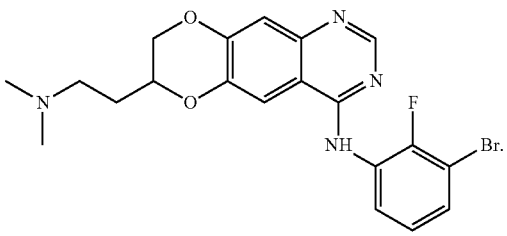 [SMILES: CN(C)CCC1COc2cc3ncnc(Nc4cccc(Br)c4F)c3cc2O1]

19. The compound of claim 1, wherein the compound is a pharmaceutically acceptable salt of the compound which is 20. The compound of claim 1, wherein the compound is a pharmaceutically acceptable salt of the compound which is

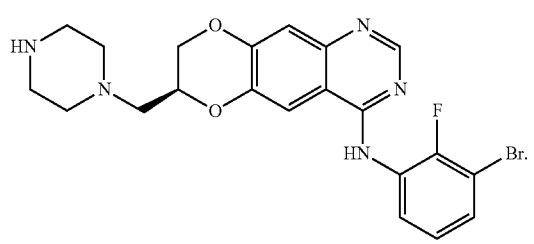

21. The compound of claim 1, wherein the compound is a pharmaceutically acceptable salt of the compound which is

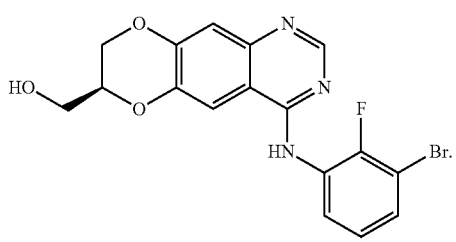 [SMILES: OC[C@H]1COc2cc3ncnc(Nc4cccc(Br)c4F)c3cc2O1]

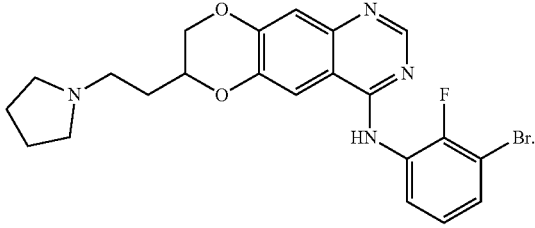 [SMILES: Fc1c(Br)cccc1Nc1ncnc2cc3c(cc12)OC(CCN1CCCC1)CO3]

22. A pharmaceutical composition comprising a compound, or pharmaceutically acceptable salt thereof, of claim 1 and a pharmaceutically acceptable excipient.

* * * * *

SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gactttgtca ccgagacacc          20

<210> SEQ ID NO 2
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gacaggtcca catggtcttc                                              20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgacctcaa cgcacagtac g                                            21

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtaagggcag gagtcccatg atg                                          23

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgccatgtag accccttgaa g                                            21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atggtacatg acaaggtgcg g                                            21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctgtgttcag tggcgattgg                                              20

<210> SEQ ID NO 8
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 8
agggtctctt gttccgaagc                                                  20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggaagagtgc cctgtgttta c                                                21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gactcaagac ttcgggaaag g                                                21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcagctgctg gattcaatta                                                  20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcccagtagg atccgcctat                                                  20

<210> SEQ ID NO 13
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tacagaacat gtctaagcat gctgtgcctt gcctggactt gcctggcctt gccttggg       58

<210> SEQ ID NO 14
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 14
ccggttcatg ccgcccatgc                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtaatcctag cacttttagg                                              20
```